(12) United States Patent
Goudar et al.

(10) Patent No.: US 12,227,571 B2
(45) Date of Patent: Feb. 18, 2025

(54) CONTINUOUS MANUFACTURING PROCESS FOR BISPECIFIC ANTIBODY PRODUCTS

(71) Applicant: AMGEN INC., Thousand Oaks, CA (US)

(72) Inventors: Chetan Goudar, Newbury Park, CA (US); Rohini Deshpande, Camarillo, CA (US); Natalia Gomez, Playa Vista, CA (US); Hedieh Barkhordarian, Newbury Park, CA (US); Yan Wang, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 921 days.

(21) Appl. No.: 16/770,441

(22) PCT Filed: Dec. 11, 2018

(86) PCT No.: PCT/US2018/064901
§ 371 (c)(1),
(2) Date: Jun. 5, 2020

(87) PCT Pub. No.: WO2019/118426
PCT Pub. Date: Jun. 20, 2019

(65) Prior Publication Data
US 2021/0163592 A1   Jun. 3, 2021

Related U.S. Application Data

(60) Provisional application No. 62/597,250, filed on Dec. 11, 2017.

(51) Int. Cl.
| | | |
|---|---|---|
| C07K 16/28 | (2006.01) | |
| C07K 16/30 | (2006.01) | |
| C12M 1/00 | (2006.01) | |
| C12N 5/00 | (2006.01) | |
| B01F 101/44 | (2022.01) | |
| C12M 3/00 | (2006.01) | |

(52) U.S. Cl.
CPC ...... *C07K 16/2809* (2013.01); *C07K 16/2863* (2013.01); *C07K 16/2878* (2013.01); *C07K 16/3069* (2013.01); *C12M 29/10* (2013.01); *C12N 5/0018* (2013.01); *B01F 2101/44* (2022.01); *B01J 2219/00725* (2013.01); *B01J 2219/2446* (2013.01); *B01J 2219/2466* (2013.01); *C07K 2317/14* (2013.01); *C07K 2317/31* (2013.01); *C07K 2317/565* (2013.01); *C07K 2317/94* (2013.01); *C12M 3/00* (2013.01); *C12M 21/00* (2013.01); *C12N 2521/00* (2013.01)

(58) Field of Classification Search
CPC ............ C07K 16/2809; C07K 16/2863; C07K 16/2878; C07K 16/3069; C07K 2317/14; C07K 2317/31; C07K 2317/565; C07K 2317/94; C12N 5/0018; C12N 2521/00; B01F 2101/44; B01J 2219/00725; B01J 2219/2446; B01J 2219/2466; C12M 3/00; C12M 21/00
See application file for complete search history.

(56) References Cited

U.S. PATENT DOCUMENTS

| | | | |
|---|---|---|---|
| 3,691,016 A | 9/1972 | Patel | |
| 3,773,919 A | 11/1973 | Boswell et al. | |
| 3,969,287 A | 7/1976 | Jaworek et al. | |
| 4,179,337 A | 12/1979 | Davis et al. | |
| 4,195,128 A | 3/1980 | Gribnau et al. | |
| 4,229,537 A | 10/1980 | Hodgins et al. | |
| 4,247,642 A | 1/1981 | Hirohara et al. | |
| 4,301,144 A | 11/1981 | Washita et al. | |
| 4,330,440 A | 5/1982 | Ayers et al. | |
| 4,439,196 A | 3/1984 | Higuchi | |
| 4,447,224 A | 5/1984 | Decant et al. | |
| 4,447,233 A | 5/1984 | Mayfield | |

(Continued)

FOREIGN PATENT DOCUMENTS

| | | | |
|---|---|---|---|
| EP | 0088046 A2 | 9/1983 | |
| EP | 0133988 A2 | 3/1985 | |

(Continued)

OTHER PUBLICATIONS

Altschul et al., Basic local alignment search tool, J. Mol. Biol., 215(3):403-410 (1990).

(Continued)

*Primary Examiner* — Catherine S Hibbert
(74) *Attorney, Agent, or Firm* — MARSHALL, GERSTEIN & BORUN LLP

(57) ABSTRACT

The present invention provides a continuous upstream manufacturing process for the production of bispecific antibody products, which comprise at least two binding domains. The process comprises at least the steps of (i) providing in a perfusion bioreactor at least one mammalian cell culture, which is capable of expressing the bispecific antibody product, (ii) growing the mammalian cell culture at a first perfusion rate until a set point viable cell density is reached, and (iii) maintaining perfusion culture at a second perfusion rate, wherein the bispecific antibody product concentration in the bioreactor is kept below a threshold value. The bispecific antibody product is then subject to subsequent downstream processing. Moreover, the invention provides a bispecific antibody product produced by the continuous upstream manufacturing process.

23 Claims, 15 Drawing Sheets
Specification includes a Sequence Listing.

(56) References Cited

U.S. PATENT DOCUMENTS

| | | |
|---|---|---|
| 4,475,196 A | 10/1984 | La Zor |
| 4,485,045 A | 11/1984 | Regen |
| 4,486,194 A | 12/1984 | Ferrara |
| 4,487,603 A | 12/1984 | Harris |
| 4,496,689 A | 1/1985 | Mitra |
| 4,544,545 A | 10/1985 | Ryan et al. |
| 4,596,556 A | 6/1986 | Morrow et al. |
| 4,640,835 A | 2/1987 | Shimizu et al. |
| 4,670,417 A | 6/1987 | Iwasaki et al. |
| 4,694,778 A | 9/1987 | Learn et al. |
| 4,751,180 A | 6/1988 | Cousens et al. |
| 4,790,824 A | 12/1988 | Morrow et al. |
| 4,791,192 A | 12/1988 | Nakagawa et al. |
| 4,816,397 A | 3/1989 | Boss et al. |
| 4,816,567 A | 3/1989 | Cabilly et al. |
| 4,935,233 A | 6/1990 | Bell et al. |
| 4,941,880 A | 7/1990 | Burns |
| 4,946,778 A | 8/1990 | Adner et al. |
| 5,013,556 A | 5/1991 | Woodle et al. |
| 5,064,413 A | 11/1991 | Mckinnon et al. |
| 5,223,409 A | 6/1993 | Ladner et al. |
| 5,225,539 A | 7/1993 | Winter |
| 5,260,203 A | 11/1993 | Ladner et al. |
| 5,292,658 A | 3/1994 | Cormier et al. |
| 5,312,335 A | 5/1994 | Mckinnon et al. |
| 5,383,851 A | 1/1995 | Mckinnon et al. |
| 5,399,163 A | 3/1995 | Peterson et al. |
| 5,418,155 A | 5/1995 | Cormier et al. |
| 5,476,996 A | 12/1995 | Wilson et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Onberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,648,260 A | 7/1997 | Winter et al. |
| 5,661,016 A | 8/1997 | Lonberg et al. |
| 5,683,888 A | 11/1997 | Campbell |
| 5,693,761 A | 12/1997 | Queen et al. |
| 5,693,762 A | 12/1997 | Queen et al. |
| 5,698,767 A | 12/1997 | Wilson et al. |
| 5,721,367 A | 2/1998 | Kay et al. |
| 5,741,668 A | 4/1998 | Ward et al. |
| 5,770,429 A | 6/1998 | Lonberg et al. |
| 5,777,079 A | 7/1998 | Tsien et al. |
| 5,789,215 A | 8/1998 | Berns et al. |
| 5,789,650 A | 8/1998 | Lonberg et al. |
| 5,804,387 A | 9/1998 | Cormack et al. |
| 5,814,318 A | 9/1998 | Lonberg et al. |
| 5,859,205 A | 1/1999 | Adair et al. |
| 5,874,299 A | 2/1999 | Lonberg et al. |
| 5,874,304 A | 2/1999 | Zolotukhin et al. |
| 5,876,995 A | 3/1999 | Bryan |
| 5,877,397 A | 3/1999 | Lonberg et al. |
| 5,925,558 A | 7/1999 | Tsien et al. |
| 5,939,598 A | 8/1999 | Kucherlapati et al. |
| 5,958,765 A | 9/1999 | Brams et al. |
| 5,981,175 A | 11/1999 | Loring et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg et al. |
| 6,300,064 B1 | 10/2001 | Knappik et al. |
| 6,407,213 B1 | 6/2002 | Carter et al. |
| 6,673,986 B1 | 1/2004 | Kucherlapati et al. |
| 2003/0070185 A1 | 4/2003 | Jakobovits et al. |
| 2005/0076395 A1 | 4/2005 | Kucherlapati et al. |
| 2014/0302037 A1 | 10/2014 | Borges et al. |
| 2014/0308285 A1 | 10/2014 | Yan et al. |
| 2017/0204446 A1 | 7/2017 | Cattaneo et al. |
| 2020/0332251 A1* | 10/2020 | Lin ............ C12N 5/0018 |

FOREIGN PATENT DOCUMENTS

| | | |
|---|---|---|
| EP | 0171496 A2 | 2/1986 |
| EP | 0173494 A2 | 3/1986 |
| EP | 0183070 A2 | 6/1986 |
| EP | 0058481 B1 | 10/1986 |
| EP | 0244234 A2 | 11/1987 |
| EP | 0143949 B1 | 10/1988 |
| EP | 0036676 B2 | 9/1990 |
| EP | 0402226 A1 | 12/1990 |
| EP | 0463151 A1 | 1/1992 |
| EP | 0239400 B1 | 8/1994 |
| EP | 0773288 A2 | 5/1997 |
| EP | 0546073 B1 | 9/1997 |
| EP | 0843961 A1 | 5/1998 |
| GB | 2177096 A | 1/1987 |
| JP | 3068180 B2 | 7/2000 |
| JP | 3068506 B2 | 7/2000 |
| JP | 3068507 B2 | 7/2000 |
| WO | 1987/05330 A1 | 9/1987 |
| WO | 1988/01649 A1 | 3/1988 |
| WO | 1988/09344 A1 | 12/1988 |
| WO | 1991/10741 A1 | 7/1991 |
| WO | 1992/03918 A1 | 3/1992 |
| WO | 1992/15673 A1 | 9/1992 |
| WO | 1992/22645 A1 | 12/1992 |
| WO | 1992/22647 A1 | 12/1992 |
| WO | 1992/22670 A1 | 12/1992 |
| WO | 1993/12227 A1 | 6/1993 |
| WO | 1993/15722 A1 | 8/1993 |
| WO | 1994/00569 A1 | 1/1994 |
| WO | 1994/02602 A1 | 2/1994 |
| WO | 1994/25585 A1 | 11/1994 |
| WO | 1995/07463 A1 | 3/1995 |
| WO | 1996/14436 A1 | 5/1996 |
| WO | 1996/33735 A1 | 10/1996 |
| WO | 1996/34096 A1 | 10/1996 |
| WO | 1997/13852 A1 | 4/1997 |
| WO | 1997/38731 A1 | 10/1997 |
| WO | 1998/14605 A1 | 4/1998 |
| WO | 1998/24884 A1 | 6/1998 |
| WO | 1998/24893 A2 | 6/1998 |
| WO | 1998/26277 A2 | 6/1998 |
| WO | 1998/52976 A1 | 11/1998 |
| WO | 1999/49019 A2 | 9/1999 |
| WO | 1999/54440 A1 | 10/1999 |
| WO | 2000/06605 A2 | 2/2000 |
| WO | 2000/34317 A2 | 6/2000 |
| WO | 2000/76310 A1 | 12/2000 |
| WO | 2003/47336 A2 | 6/2003 |
| WO | 2005/040220 A1 | 5/2005 |
| WO | 2006/138181 A2 | 12/2006 |
| WO | 2007/042261 A2 | 4/2007 |
| WO | 2008/119567 A2 | 10/2008 |
| WO | 2010/037838 A2 | 4/2010 |
| WO | 2010/052014 A1 | 5/2010 |
| WO | 2010/060719 A1 | 6/2010 |
| WO | 2013/026833 A1 | 2/2013 |
| WO | 2013/026837 A1 | 2/2013 |
| WO | 2014/144722 A2 | 9/2014 |
| WO | 2014/151910 A1 | 9/2014 |
| WO | 2015/048272 A1 | 4/2015 |
| WO | 2017/072201 A2 | 5/2017 |
| WO | 2017/134140 A1 | 8/2017 |

OTHER PUBLICATIONS

Altschul et al., Gapped BLAST and PSI-BLAST: a new generation of protein database search programs, Nucl. Acids Res., 25(17):3389-3402 (1993).

Altschul et al., Gapped blast and PSI-BLAST: a new generation of protein database search programs, Nucleic Acids Res., 25(17):3389-3402 (1997).

(56) References Cited

OTHER PUBLICATIONS

Altschul et al., Local alignment statistics, Meth. Enz., 266:460-480 (1996).
Aplin et al., Preparation, properties, and applications of carbohydrate conjugates of proteins and lipids, CRC Crit. Rev. Biochem., 10(4):259-306 (1981).
Arakawa et al., Protein-solvent interactions in pharmaceutical formulations, Pharm. Res., 8(3):285-91 (1991).
Artsaenko et al., Expression of a single-chain Fv antibody against abscisic acid creates a willy phenotype in transgenic tobacco, Plant J., 8(5):745-750 (1995).
Bird et al., Single-chain antigen-binding proteins, Science, 242(4877):423-442 (1988).
Bratt et al., Therapeutic IgG-Like Bispecific Antibodies: Modular Versatility and Manufacturing Challenges, Part 2, BioProcess International, pp. 1-14 (2018).
Briihl et al., Depletion of CCR5-expressing cells with bispecific antibodies and chemokine toxins: a new strategy in the treatment of chronic inflammatory diseases and HIV, Immunol., 166(4):2420-2426 (2001).
Carter et al., High level *Escherichia coli* expression and production of a bivalent humanized antibody fragment, BioTechnology, 10(2):163-167 (1992).
Carvalho et al., Production Processes for Monoclonal Antibodies, In: Ferm. Proc., XP055562271 (2017).
Chalfie et al., Green fluorescent protein as a marker for gene expression, Science, 263:802-805 (1994).
Cheadle et al., Cloning and expression of the variable regions of mouse myeloma protein MOPC315 in *E. coli*: recovery of active FV fragments, Mol Immunol., 29(1):21-30 (1992).
Cheson et al., Report of an international workshop to standardize response criteria for non-Hodgkin's lymphomas. NCI Sponsored International Working Group, J. Clin. Oncol., 7(4):1244 (1999).
Chi et al., Physical stability of proteins in aqueous solution: mechanism and driving forces in nonnative protein aggregation, Phann. Res., 20(9):1325-1336 (2003).
Chothia et al., Canonical structures for the hypervariable regions of immunoglobulins, J. Mol. Biol., 196(4):901-917 (1987).
Chothia et al., Conformations of immunoglobulin hypervariable regions, Nature, 342:877-83 (1989).
Christopher, Therapeutic protein aggregation: mechanisms, design, and control, Trends Biotechnol., 32(7):372-80 (2014).
Clackson et al., Making antibody fragments using phage display libraries, Nature, 352:624-628 (1991).
Cole et al., Monoclonal antibodies and cancer therapy, Alan R. Liss, Inc., 77-96 (1985).
Cook et al., The human immunoglobulin VH repertoire, Immunol. Today, 16(5):237-242 (1995).
Creighton, Proteins: Structure and molecular properties, W. H Freeman & Co., San Francisco, 79-86 (1983).
Cunningham et al., High-resolution epitope mapping of hGH-receptor interactions by alanine-scanning mutagenesis, Science, 244:1081-1085 (1989).
Current Methods in Sequence Comparison and Analysis, Macromolecule Sequencing and Synthesis, Selected Methods and Applications, 127-149 (1988).
Dall'Acqua et al., Contribution of domain interface residues to the stability of antibody CH3 domain homodimers, Biochem., 37(26):9266-9273 (1998).
Devereux et al., A comprehensive set of sequence analysis programs for the VAX, Nucl. Acid. Res., 12:387-395 (1984).
Duskin et al., Relationship of the structure and biological activity of the natural homologues of tunicamycin, J. Biol. Chem., 257(6):3105-9(1982).
Edge et al., Deglycosylation of glycoproteins by trifluoromethanesulfonic acid, Anal. Biochem., 118(1):131-7 (1981).
Eppstein et al., Biological activity of liposome-encapsulated murine interferon gamma is mediated by a cell membrane receptor, Proc. Natl. Acad. Sci. USA., 82(11):3688-3692 (1985).

Fan et al., Bispecific antibodies and their applications, Journal of Hematology & Oncology, 8:130 (2015).
Feng et al., Progressive sequence alignment as a prerequisite to correct phylogenetic trees, J. Mol. Evol., 25(4):351-360 (1987).
Gabizon et al., Pharmacokinetics and tissue distribution of doxorubicin encapsulated in stable liposomes with long circulation times, J. National Cancer Inst., 81(19):1484-8 (1989).
Graham et al., Characteristics of a human cell line transformed by DNA from human adenovirus type 5, J. Gen. Virol., 36(1):59-74 (1977).
Green et al., Antigen-specific human monoclonal antibodies from mice engineered with human Ig heavy and light chain YACs, Nat. Gene., 7(1):13-21 (1994).
Green et al., Regulation of B cell development by variable gene complexity in mice reconstituted with human immunoglobulin yeast artificial chromosomes, J. Exp. Med., 188:483-495 (1998).
Hakimuddin et al., A chemical method for the deglycosylation of proteins, Arch. Biochem. Biophys., 259(1):52-57 (1987).
Hawkins et al., Selection of phage antibodies by binding affinity. Mimicking affinity maturation, J. Mol. Biol., 226(3):889-896 (1992).
Hein et al., Engineering green fluorescent protein for improved brightness, longer wavelengths and fluorescence resonance energy transfer, Curr. Biol., 6(2):178-182 (1996).
Hiatt et al., Production of antibodies in transgenic plants, Nature, 342:76-78 (1989).
Higgins et al., Fast and sensitive multiple sequence alignments on a microcomputer, Comput. Appl. Biosci., 5(2):151-3 (1989).
Hollinger et al., "Diabodies": small bivalent and bispecific antibody fragments, Proc. Natl. Acad. Sci. USA., 90(14):6444-8 (1993).
Huston et al., Protein engineering of antibody binding sites: recovery of specific activity in an anti-digoxin single-chain Fv analogue produced in *Escherichia coli*, Proc. Natl. Acad. Sci. USA., 85(16):5879-5883 (1988).
Hwang et al., Hepatic uptake and degradation of unilamellar sphingomyelin/cholesterol liposomes: a kinetic study, Proc. Natl. Acad. Sci. USA., 77(7):4030-4 (1980).
Hwang et al., Immunogenicity of engineered antibodies, Methods, 36(1):3-10 (2005).
Ichiki et al., Regulation of the expression of human C epsilon germline transcript. Identification of a novel IL-4 responsive element, J. Immunol., 150(12):5408-5417 (1993).
International Application No. PCT/US2018/064901, International Search Report and Written Opinion, mailed on Mar. 21, 2019.
International Application No. PCT/US2018/064901, International Preliminary Report on Patentability, mailed Jun. 25, 2020.
Jones et al., Replacing the complementarity-determining regions in a human antibody with those from a mouse, Nature, 321:522-525 (1986).
Karin et al., Applications and statistics for multiple high-scoring segments in molecular sequences, Proc. Natl. Acad. Sci. USA., 90(12):5873-5787 (1993).
Kendrick et al., Physical stabilization of proteins in aqueous solution, Pharmaceutical Biotechnology, 13:61-84 (2002).
Kipriyanov et al., Bispecific tandem diabody for tumor therapy with improved antigen binding and pharmacokinetics, J. Mol. Biol., 293(1):41-56 (1999).
Koehler et al., Continuous cultures of fused cells secreting antibody of predefined specificity, Nature, 256:495-7 (1975).
Kozbor et al., The production of monoclonal antibodies from human lymphocytes, Immunology Today, 4(3):72-9 (1983).
Kufer et al., A revival of bispecific antibodies, Trends in Biotechnol., 22(5):238-244 (2004).
Kufer et al., Construction and biological activity of a recombinant bispecific single-chain antibody designed for therapy of minimal residual colorectal cancer, Cancer Immunol. Immunother., 45:193-197 (1997).
Lachmann, Bispecific antibody: a tool for diagnosis and treatment of disease, Clin. Exp. Immunol., 79(3):315-321 (1990).
Langer et al., Biocompatibility of polymeric delivery systems for macromolecules, J. Biomed. Mater. Res., 15(2):267-277 (1981).
Langer, Controlled release of macromolecules, Chem. Tech., 12(2):98-105 (1982).

(56) References Cited

OTHER PUBLICATIONS

Leader et al., Protein therapeutics: a summary and pharmacological classification, Nat. Rev. Drug Discovery, 7(1):21-39 (2008).
Loffler et al., A recombinant bispecific single-chain antibody, CD19 x CD3, induces rapid and high lymphoma-directed cytotoxicity by unstimulated T lymphocytes, Blood, 95(6):2098-2103 (2000).
Lowman et al., Selecting high-affinity binding proteins by monovalent phage display, Biochemistry, 30(45):10832-10837 (1991).
Maccallum et al., Antibody-antigen interactions: contact analysis and binding site topography, J. Mol. Biol., 262(5):732-45 (1996).
Mack et al., A small bispecific antibody construct expressed as a functional single-chain molecule with high tumor cell cytotoxicity, PNAS, 92(15):7021-7025 (1995).
Mack et al., Biologic properties of a bispecific single-chain antibody directed against 17-1A (EpCAM) and CD3: tumor cell-dependent T cell stimulation and cytotoxic activity, J. Immunol., 158(8):3965-3970 (1997).
Malmborg et al., BIAcore as a tool in antibody engineering, J. Immunol. Methods, 183(1):7-13 (1995).
Marks et al., By-passing immunization. Human antibodies from V-gene libraries displayed on phage, J. Mol. Biol., 222(3):581-597 (1991).
Martin et al., Irreversible coupling of immunoglobulin fragments to preformed vesicles. an improved method for liposome targeting, J. Biol. Chem., 257(1):286-288 (1982).
Martin et al., Structural families in loops of homologous proteins: automatic classification, modelling and application to antibodies, J. Mol. Biol., 263(5):800-15 (1996).
Mather et al., Culture of testicular cells in hormone-supplemented serum-free medium, Annals N. Y. Acad. Sci., 383:44-68 (1982).
Mather, Establishment and characterization of two distinct mouse testicular epithelial cell lines, Biol. Reprod., 23(1):243-251 (1980).
Mendez et al., Functional transplant of megabase human immunoglobulin loci recapitulates human antibody response in mice, Nat. Gen., 15(2):146-156 (1997).
Morrison et al., Chimeric human antibody molecules: mouse antigen-binding domains with human constant region domains, Proc. Natl. Acad. Sci. USA., 81(21):6851-6855 (1984).
Morrison et al., Combinatorial alanine-scanning, Cur. Opin. Chem. Biol., 5(3):302-307 (2001).
Morrison, Transfectomas provide novel chimeric antibodies, Science, 229:1202-1207 (1985).
Needleman et al., A general method applicable to the search for similarities in the amino acid sequence of two proteins, J. Mol. Biol., 48(3):443-53 (1970).
Nolan et al., Fluorescence-activated cell analysis and sorting of viable mammalian cells based on beta-D-galactosidase activity after transduction of Escherichia coli lacZ, Proc. Natl. Acad. Sci. USA., 85(8):2603-2607 (1988).
Oi et al., Chimeric antibodies, BioTechniques, 4(3):214-221 (1986).
Olsson et al., Human—human monoclonal antibody-producing hybridomas: technical aspects, Meth. Enzymol., 92:3-16 (1982).
Owen et al., Synthesis of a functional anti-phytochrome single-chain Fv protein in transgenic tobacco, BioTechnology, 10(7):790-794 (1992).
Padlan, Anatomy of the antibody molecule, Mol. Immunol., 31(3):169-217 (1993).
Pearson et al., Improved tools for biological sequence comparison, Proc. Nat. Acad. Sci. USA., 85(8):2444-8 (1988).
Pecker et al., Expression of single-chain antibody fragments (scFv) specific for beet necrotic yellow vein virus coat protein or 25 kDa protein in Escherichia coli and Nicotiana benthamiana, Plant Mol. Biol., 32(5):979-986 (1996).
Presta, Current opinion in structural biology, Curr. Op. Struct. Biol., 2(4):593-596 (1992).
Raag et al., Single-chain Fvs, FASEB, 9(1):73-80 (1995).
Randolph et al., Surfactant-protein interactions, Pharm. Biotechnol., 13:159-75 (2002).
Reichmann et al., Reshaping human antibodies for therapy, Nature, 332:323-329 (1988).
Schier et al., Efficient in vitro affinity maturation of phage antibodies using BIAcore guided selections, Human Antibodies Hybridomas, 7(3):97-105 (1996).
Schlereth et al., T-cell activation and B-cell depletion in chimpanzees treated with a bispecific anti-CD19/anti-CD3 single-chain antibody construct, Cancer Immunol. Immunother., 55(5):503-14 (2006).
Sherman et al., Continuous Cell Culture Operation at 2,000-L Scale, Bioprocess International, 14(10):22-28 (2016).
Shukla et al., Evolving trends in mAb production processes, Bioeng. Transl. Med., 2(1):58-69 (2017).
Sidman et al., Controlled release of macromolecules and pharmaceuticals from synthetic polypeptides based on glutamic acid, Biopolymers, 2(1):547-556 (1983).
Single chain antibodies are discussed in detail by pluckthun in The pharmacology of monoclonal antibodies, Rosenburg and Moore eds. Springer-Verlag, New York, 113:269-315 (1994).
Skerra et al., Assembly of a functional immunoglobulin Fv fragment in Escherichia coli, Science, 240(4855):1038-1041 (1988).
Smith et al., Comparison of biosequences, Adv. Appl. Math., 2(4):482-489 (1981).
Smith, Filamentous fusion phage: novel expression vectors that display cloned antigens on the virion surface, Science, 228:1315-1317 (1985).
Stauber et al., Development and applications of enhanced green fluorescent protein mutants, Biotechniques, 24(3):462-471 (1998).
Takeda et al., Construction of chimaeric processed immunoglobulin genes containing mouse variable and human constant region sequences, Nature, 314:452-54 (1985).
Teng et al., Construction and testing of mouse—human heteromyelomas for human monoclonal antibody production, Proc. Natl. Acad. Sci. USA., 80(23):7308-7312 (1983).
Thotakura et al., Enzymatic deglycosylation of glycoproteins, Meth. Enzymol., 138:350-9 (1987).
Tomlinson et al., The repertoire of human germline VH sequences reveals about fifty groups of VH segments with different hypervariable loops, J. Mol. Biol., 227(3):776-798 (1992).
Tomlinson et al., The structural repertoire of the human V kappa domain, EMBO J., 14(18):4628-4638 (1995).
Tsuneo et al., Fed-batch techniques in microbial processes, Bioprocess Parameter Control, 30:147-194 (2005).
U.S. Patent Application filed Apr. 27, 1995, by Kucherlapati et al., U.S. Appl. No. 08/430,938.
U.S. Patent Application filed Apr. 28, 1994, by Kucherlapati et al., 08/234, 145.
U.S. Patent Application filed Aug. 27, 1993, by Kucherlapati et al., U.S. Appl. No. 08/112,848.
U.S. Patent Application filed Aug. 31, 1990, by Lonberg et al., U.S. Appl. No. 07/575,962.
U.S. Patent Application filed Dec. 3, 1996, by Jakobovits et al., U.S. Appl. No. 08/759,620.
U.S. Patent Application filed Jan. 12, 1990, by Kucherpatali et al., U.S. Appl. No. 07/466,008.
U.S. Patent Application filed Jul. 24, 1992, by Kucherlapati et al., U.S. Appl. No. 07/919,297.
U.S. Patent Application filed Jun. 5, 1995, by Kucherlapati et al., U.S. Appl. No. 07/574,748.
U.S. Patent Application filed Jun. 5, 1995, by Kucherlapati et al., U.S. Appl. No. 08/463,191.
U.S. Patent Application filed Jun. 23, 1992, by Lonberg et al., U.S. Appl. No. 07/904,068.
U.S. Patent Application filed Mar. 9, 1994, by Lonberg et al., U.S. Appl. No. 08/209,741.
U.S. Patent Application filed Nov. 8, 1990, by Kucherlapati et al., U.S. Appl. No. 07/610,515.
U.S. Appl. No. 08/155,301.
U.S. Appl. No. 08/161,739.
U.S. Appl. No. 08/165,699.
U.S. Appl. No. 08/376,279.
U.S. Appl. No. 08/462,837.
U.S. Appl. No. 08/464,584.
U.S. Appl. No. 08/486,853.
U.S. Appl. No. 08/486,859.

(56) References Cited

OTHER PUBLICATIONS

Urlaub et al., Isolation of chinese hamster cell mutants deficient in dihydrofolate reductase activity, Proc. Natl. Acad. Sci. USA., 77(7):4216-20 (1980).
Wang, Instability, stabilization, and formulation of liquid protein pharmaceuticals, Int. J. Phann., 185(2):129-88 (1999).
Ward et al., Binding activities of a repertoire of single immunoglobulin variable domains secreted from *Escherichia coli*, Nature, 341:544-546 (1989).
Yang et al., Bispecific antibodies as a development platform for new concepts and treatment strategies, Int. J. Mol. Sciences, 18(1):48 (2016).
Scanlan et al., "Challenges and Strategies for the Downstream Processing of BiSpecific Antibodies (BsAbs)," ADC Review/ Journal of Antibody-drug Conjugates (2014).

\* cited by examiner

Fig. 15
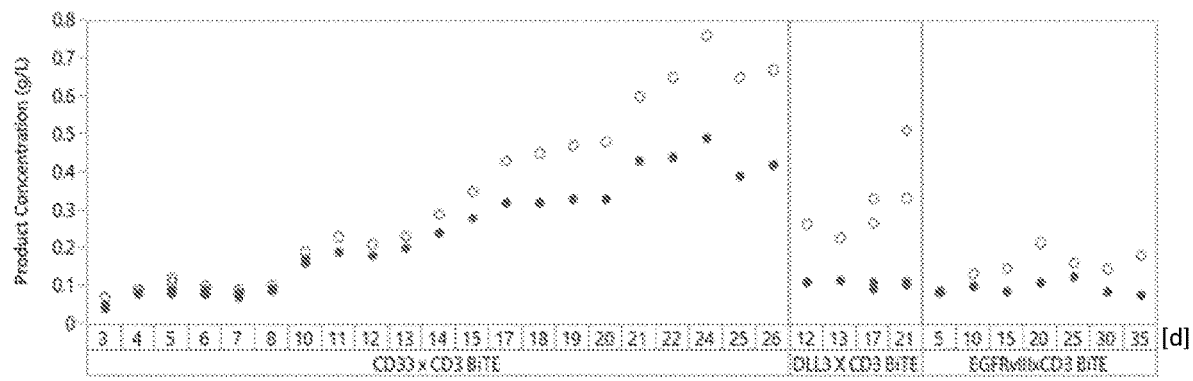
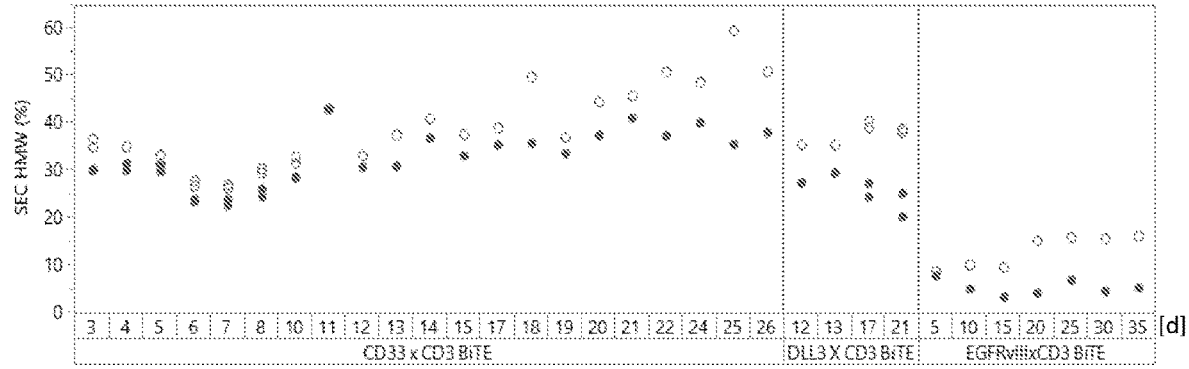

SEQUENCE LISTING

```
<160> NUMBER OF SEQ ID NOS: 202

<210> SEQ ID NO 1
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL CDR1

<400> SEQUENCE: 1

Lys Ala Ser Gln Ser Val Asp Tyr Asp Gly Asp Ser Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL CDR2

<400> SEQUENCE: 2

Asp Ala Ser Asn Leu Val Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: CD19 VL CDR3

<400> SEQUENCE: 3

Gln Gln Ser Thr Glu Asp Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR1

<400> SEQUENCE: 4

Ser Tyr Trp Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR2

<400> SEQUENCE: 5

Gln Ile Trp Pro Gly Asp Gly Asp Thr Asn Tyr Asn Gly Lys Phe Lys
1               5                   10                  15

Gly

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR3

<400> SEQUENCE: 6

Arg Glu Thr Thr Thr Val Gly Arg Tyr Tyr Tyr Ala Met Asp Tyr
1               5                   10                  15

<210> SEQ ID NO 7
<211> LENGTH: 111
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL

<400> SEQUENCE: 7

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
```

```
                35                  40                  45
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110
```

<210> SEQ ID NO 8
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH

<400> SEQUENCE: 8

```
Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
             35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH CDR1

<400> SEQUENCE: 9

```
Arg Tyr Thr Met His
 1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH CDR2

<400> SEQUENCE: 10

```
Tyr Ile Asn Pro Ser Arg Gly Tyr Thr Asn Tyr Asn Gln Lys Phe Lys
1               5                   10                  15

Asp

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH CDR3

<400> SEQUENCE: 11

Tyr Tyr Asp Asp His Tyr Cys Leu Asp Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR1

<400> SEQUENCE: 12

Arg Ala Ser Ser Ser Val Ser Tyr Met Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR2

<400> SEQUENCE: 13

Asp Thr Ser Lys Val Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR3

<400> SEQUENCE: 14

Gln Gln Trp Ser Ser Asn Pro Leu Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

<223> OTHER INFORMATION: CD3 VH

<400> SEQUENCE: 15

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL

<400> SEQUENCE: 16

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105

<210> SEQ ID NO 17
<211> LENGTH: 504
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19xCD3 scFv BLINCYTO incl linker and his-tag

<400> SEQUENCE: 17

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp

```
                20              25              30
Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                      55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                    85                  90                  95

Glu Asp Pro Trp Thr Phe Gly Gly Thr Lys Leu Glu Ile Lys Gly
                100                 105             110

Gly Gly Gly Ser Gly Gly Gly Gly Ser Gly Gly Gly Ser Gln Val
            115                 120                 125

Gln Leu Gln Gln Ser Gly Ala Glu Leu Val Arg Pro Gly Ser Ser Val
        130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
            195                 200                 205

Leu Ser Ser Leu Ala Ser Glu Asp Ser Ala Val Tyr Phe Cys Ala Arg
        210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
                260                 265                 270

Val Lys Met Ser Cys Lys Thr Ser Gly Tyr Thr Phe Thr Arg Tyr Thr
            275                 280                 285

Met His Trp Val Lys Gln Arg Pro Gly Gln Gly Leu Glu Trp Ile Gly
        290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445
```

```
Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys His His His His His His
            500

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L1 of I2C

<400> SEQUENCE: 18

Gly Ser Ser Thr Gly Ala Val Thr Ser Gly Asn Tyr Pro Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L2 of I2C

<400> SEQUENCE: 19

Gly Thr Lys Phe Leu Ala Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L3 of I2C

<400> SEQUENCE: 20

Val Leu Trp Tyr Ser Asn Arg Trp Val
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H1 of I2C

<400> SEQUENCE: 21

Lys Tyr Ala Met Asn
1               5

<210> SEQ ID NO 22
```

```
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H2 of I2C

<400> SEQUENCE: 22

Arg Ile Arg Ser Lys Tyr Asn Asn Tyr Ala Thr Tyr Tyr Ala Asp Ser
1               5                   10                  15

Val Lys Asp

<210> SEQ ID NO 23
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H3 of I2C

<400> SEQUENCE: 23

His Gly Asn Phe Gly Asn Ser Tyr Ile Ser Tyr Trp Ala Tyr
1               5                   10

<210> SEQ ID NO 24
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH of I2C

<400> SEQUENCE: 24

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 25
<211> LENGTH: 109
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL of I2C
```

<400> SEQUENCE: 25

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105
```

<210> SEQ ID NO 26
<211> LENGTH: 249
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-VL of I2C

<400> SEQUENCE: 26

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220
```

```
Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245
```

<210> SEQ ID NO 27
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 ccVH of E11

<400> SEQUENCE: 27

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120
```

<210> SEQ ID NO 28
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 VH of E11

<400> SEQUENCE: 28

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120
```

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HCDR1 of E11

<400> SEQUENCE: 29

Asn Tyr Gly Met Asn
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HCDR2 of E11

<400> SEQUENCE: 30

Trp Ile Asn Thr Tyr Thr Gly Glu Pro Thr Tyr Ala Asp Lys Phe Gln
1               5                   10                  15

Gly

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HCDR3 of E11

<400> SEQUENCE: 31

Trp Ser Trp Ser Asp Gly Tyr Tyr Val Tyr Phe Asp Tyr
1               5                   10

<210> SEQ ID NO 32
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 CC VL of E11

<400> SEQUENCE: 32

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

```
Ile Asp Ser Pro Gln Pro Glu Asp Ser Ala Thr Tyr Tyr Cys Gln Gln
                85                  90                  95

Ser Ala His Phe Pro Ile Thr Phe Gly Cys Gly Thr Arg Leu Glu Ile
            100                 105                 110

Lys

<210> SEQ ID NO 33
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 VL of E11

<400> SEQUENCE: 33

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Thr Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80

Ile Asp Ser Pro Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 34
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR1 of E11

<400> SEQUENCE: 34

Lys Ser Ser Gln Ser Val Leu Asp Ser Ser Thr Asn Lys Asn Ser Leu
1               5                   10                  15

Ala

<210> SEQ ID NO 35
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR2 of E11

<400> SEQUENCE: 35

Trp Ala Ser Thr Arg Glu Ser
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR3 of E11

<400> SEQUENCE: 36

Gln Gln Ser Ala His Phe Pro Ile Thr
1               5

<210> SEQ ID NO 37
<211> LENGTH: 250
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HL CC of E11

<400> SEQUENCE: 37

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys
                245                 250

<210> SEQ ID NO 38
<211> LENGTH: 250
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HL of E11

<400> SEQUENCE: 38

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 39
<211> LENGTH: 505
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 CC E11 HL x I2C HL Bispecific molecule

<400> SEQUENCE: 39

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45
```

Gly Trp Ile Asn Thr Tyr Thr Gly Glu Pro Thr Tyr Ala Asp Lys Phe
                50                  55                  60

Gln Gly Arg Val Thr Met Thr Thr Asp Thr Ser Thr Ser Thr Ala Tyr
 65                  70                  75                  80

Met Glu Ile Arg Asn Leu Gly Gly Asp Asp Thr Ala Val Tyr Tyr Cys
                    85                  90                  95

Ala Arg Trp Ser Trp Ser Asp Gly Tyr Val Tyr Phe Asp Tyr Trp
                100                 105                 110

Gly Gln Gly Thr Ser Val Thr Val Ser Ser Gly Gly Gly Ser Gly
            115                 120                 125

Gly Gly Gly Ser Gly Gly Gly Ser Asp Ile Val Met Thr Gln Ser
130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
                180                 185                 190

Trp Ala Ser Thr Arg Glu Ser Gly Ile Pro Asp Arg Phe Ser Gly Ser
                195                 200                 205

Gly Ser Gly Thr Asp Phe Thr Leu Thr Ile Asp Ser Pro Gln Pro Glu
            210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
                340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
                420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
            485                 490                 495

Gly Gly Gly Thr Lys Leu Thr Val Leu
            500                 505

<210> SEQ ID NO 40
<211> LENGTH: 511
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 E11 HL x I2C HL

<400> SEQUENCE: 40

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
            405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
            485                 490                 495

Gly Gly Gly Thr Lys Leu Thr Val Leu His His His His His His
            500                 505                 510

<210> SEQ ID NO 41
<211> LENGTH: 993
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 CC x I2C-scFc Bispecific HLE molecule

<400> SEQUENCE: 41

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

```
Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Ser Lys Asn Thr
                325                 330                 335

Ala Tyr Leu Gln Met Asn Asn Leu Lys Thr Glu Asp Thr Ala Val Tyr
    340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu Gly Gly Gly Asp Lys Thr
            500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
    530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
```

```
                565                 570                 575
Lys Thr Lys Pro Cys Glu Glu Gln Tyr Gly Ser Thr Tyr Arg Cys Val
                580                 585                 590

Ser Val Leu Thr Val Leu His Gln Asp Trp Leu Asn Gly Lys Glu Tyr
                595                 600                 605

Lys Cys Lys Val Ser Asn Lys Ala Leu Pro Ala Pro Ile Glu Lys Thr
        610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
                645                 650                 655

Leu Val Lys Gly Phe Tyr Pro Ser Asp Ile Ala Val Glu Trp Glu Ser
                660                 665                 670

Asn Gly Gln Pro Glu Asn Asn Tyr Lys Thr Thr Pro Pro Val Leu Asp
                675                 680                 685

Ser Asp Gly Ser Phe Phe Leu Tyr Ser Lys Leu Thr Val Asp Lys Ser
        690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
                725                 730                 735

Gly Gly Gly Gly Ser Gly Gly Gly Gly Ser Gly Gly Gly Gly Ser Gly
                740                 745                 750

Gly Gly Gly Ser Gly Gly Gly Gly Ser Gly Gly Gly Ser Gly Asp Lys
        755                 760                 765

Thr His Thr Cys Pro Pro Cys Pro Ala Pro Glu Leu Leu Gly Gly Pro
770                 775                 780

Ser Val Phe Leu Phe Pro Pro Lys Pro Lys Asp Thr Leu Met Ile Ser
785                 790                 795                 800

Arg Thr Pro Glu Val Thr Cys Val Val Val Asp Val Ser His Glu Asp
                805                 810                 815

Pro Glu Val Lys Phe Asn Trp Tyr Val Asp Gly Val Glu Val His Asn
                820                 825                 830

Ala Lys Thr Lys Pro Cys Glu Glu Gln Tyr Gly Ser Thr Tyr Arg Cys
                835                 840                 845

Val Ser Val Leu Thr Val Leu His Gln Asp Trp Leu Asn Gly Lys Glu
        850                 855                 860

Tyr Lys Cys Lys Val Ser Asn Lys Ala Leu Pro Ala Pro Ile Glu Lys
865                 870                 875                 880

Thr Ile Ser Lys Ala Lys Gly Gln Pro Arg Glu Pro Gln Val Tyr Thr
                885                 890                 895

Leu Pro Pro Ser Arg Glu Glu Met Thr Lys Asn Gln Val Ser Leu Thr
                900                 905                 910

Cys Leu Val Lys Gly Phe Tyr Pro Ser Asp Ile Ala Val Glu Trp Glu
                915                 920                 925

Ser Asn Gly Gln Pro Glu Asn Asn Tyr Lys Thr Thr Pro Pro Val Leu
        930                 935                 940

Asp Ser Asp Gly Ser Phe Phe Leu Tyr Ser Lys Leu Thr Val Asp Lys
945                 950                 955                 960

Ser Arg Trp Gln Gln Gly Asn Val Phe Ser Cys Ser Val Met His Glu
                965                 970                 975

Ala Leu His Asn His Tyr Thr Gln Lys Ser Leu Ser Leu Ser Pro Gly
                980                 985                 990
```

Lys

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR1

<400> SEQUENCE: 42

Asn Tyr Gly Met His
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR2

<400> SEQUENCE: 43

Val Ile Trp Tyr Asp Gly Ser Asp Lys Tyr Tyr Ala Asp Ser Val Arg
1               5                   10                  15

Gly

<210> SEQ ID NO 44
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR3

<400> SEQUENCE: 44

Asp Gly Tyr Asp Ile Leu Thr Gly Asn Pro Arg Asp Phe Asp Tyr
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VL CDR1

<400> SEQUENCE: 45

Arg Ser Ser Gln Ser Leu Val His Ser Asp Gly Asn Thr Tyr Leu Ser
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VL CDR2

<400> SEQUENCE: 46

Arg Ile Ser Arg Arg Phe Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VL CDR3

<400> SEQUENCE: 47

Met Gln Ser Thr His Val Pro Arg Thr
1               5

<210> SEQ ID NO 48
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc VH

<400> SEQUENCE: 48

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Cys Leu Glu Trp Val
        35                  40                  45

Ala Val Ile Trp Tyr Asp Gly Ser Asp Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
            100                 105                 110

Tyr Trp Gly Gln Gly Thr Leu Val Thr Val Ser Ser
        115                 120

<210> SEQ ID NO 49
<211> LENGTH: 112
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc VL

<400> SEQUENCE: 49

Asp Thr Val Met Thr Gln Thr Pro Leu Ser Ser His Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro

```
                35                  40                  45
Pro Arg Leu Leu Ile Tyr Arg Ile Ser Arg Arg Phe Ser Gly Val Pro
 50                  55                  60

Asp Arg Phe Ser Gly Ser Gly Ala Gly Thr Asp Phe Thr Leu Glu Ile
 65                  70                  75                  80

Ser Arg Val Glu Ala Glu Asp Val Gly Val Tyr Tyr Cys Met Gln Ser
                 85                  90                  95

Thr His Val Pro Arg Thr Phe Gly Cys Gly Thr Lys Val Glu Ile Lys
            100                 105                 110

<210> SEQ ID NO 50
<211> LENGTH: 251
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc scFv

<400> SEQUENCE: 50

Gln Val Gln Leu Val Glu Ser Gly Gly Gly Val Val Gln Ser Gly Arg
 1               5                  10                  15

Ser Leu Arg Leu Ser Cys Ala Ala Ser Gly Phe Thr Phe Arg Asn Tyr
             20                  25                  30

Gly Met His Trp Val Arg Gln Ala Pro Gly Lys Cys Leu Glu Trp Val
         35                  40                  45

Ala Val Ile Trp Tyr Asp Gly Ser Asp Lys Tyr Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Tyr Asp Ile Leu Thr Gly Asn Pro Arg Asp Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Thr Val Met Thr
130                 135                 140

Gln Thr Pro Leu Ser Ser His Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Pro Arg Leu Leu Ile
            180                 185                 190

Tyr Arg Ile Ser Arg Arg Phe Ser Gly Val Pro Asp Arg Phe Ser Gly
        195                 200                 205

Ser Gly Ala Gly Thr Asp Phe Thr Leu Glu Ile Ser Arg Val Glu Ala
    210                 215                 220

Glu Asp Val Gly Val Tyr Tyr Cys Met Gln Ser Thr His Val Pro Arg
225                 230                 235                 240

Thr Phe Gly Cys Gly Thr Lys Val Glu Ile Lys
                245                 250

<210> SEQ ID NO 51
<211> LENGTH: 506
<212> TYPE: PRT
```

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc Bispecific molecule

<400> SEQUENCE: 51

```
Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Cys Leu Glu Trp Val
        35                  40                  45

Ala Val Ile Trp Tyr Asp Gly Ser Asp Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Thr Val Met Thr
    130                 135                 140

Gln Thr Pro Leu Ser Ser His Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Arg Leu Leu Ile
            180                 185                 190

Tyr Arg Ile Ser Arg Arg Phe Ser Gly Val Pro Asp Arg Phe Ser Gly
        195                 200                 205

Ser Gly Ala Gly Thr Asp Phe Thr Leu Glu Ile Ser Arg Val Glu Ala
    210                 215                 220

Glu Asp Val Gly Val Tyr Tyr Cys Met Gln Ser Thr His Val Pro Arg
225                 230                 235                 240

Thr Phe Gly Cys Gly Thr Lys Val Glu Ile Lys Ser Gly Gly Gly Gly
                245                 250                 255

Ser Glu Val Gln Leu Val Glu Ser Gly Gly Gly Leu Val Gln Pro Gly
            260                 265                 270

Gly Ser Leu Lys Leu Ser Cys Ala Ala Ser Gly Phe Thr Phe Asn Lys
        275                 280                 285

Tyr Ala Met Asn Trp Val Arg Gln Ala Pro Gly Lys Gly Leu Glu Trp
    290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
        355                 360                 365

Trp Ala Tyr Trp Gly Gln Gly Thr Leu Val Thr Val Ser Ser Gly Gly
```

```
                370              375              380
Gly Gly Ser Gly Gly Gly Ser Gly Gly Gly Ser Gln Thr Val
385              390              395              400

Val Thr Gln Glu Pro Ser Leu Thr Val Ser Pro Gly Gly Thr Val Thr
            405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
            435                 440                 445

Gly Thr Lys Phe Leu Ala Pro Gly Thr Pro Ala Arg Phe Ser Gly Ser
            450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
            485                 490                 495

Phe Gly Gly Gly Thr Lys Leu Thr Val Leu
            500                 505

<210> SEQ ID NO 52
<211> LENGTH: 994
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc Bispecific HLE molecule

<400> SEQUENCE: 52

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Cys Leu Glu Trp Val
        35                  40                  45

Ala Val Ile Trp Tyr Asp Gly Ser Asp Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Thr Val Met Thr
130                 135                 140

Gln Thr Pro Leu Ser Ser His Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Pro Arg Leu Leu Ile
            180                 185                 190

Tyr Arg Ile Ser Arg Arg Phe Ser Gly Val Pro Asp Arg Phe Ser Gly
        195                 200                 205

Ser Gly Ala Gly Thr Asp Phe Thr Leu Glu Ile Ser Arg Val Glu Ala
```

-continued

```
            210                 215                 220
Glu Asp Val Gly Val Tyr Tyr Cys Met Gln Ser Thr His Val Pro Arg
225                 230                 235                 240

Thr Phe Gly Cys Gly Thr Lys Val Glu Ile Lys Ser Gly Gly Gly Gly
                245                 250                 255

Ser Glu Val Gln Leu Val Glu Ser Gly Gly Leu Val Gln Pro Gly Gly
                260                 265                 270

Ser Leu Lys Leu Ser Cys Ala Ala Ser Gly Phe Thr Phe Asn Lys Tyr
            275                 280                 285

Tyr Ala Met Asn Trp Val Arg Gln Ala Pro Gly Lys Gly Leu Glu Trp
290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
                340                 345                 350

Tyr Tyr Cys Val Arg His Gly Asn Phe Gly Asn Ser Tyr Ile Ser Tyr
            355                 360                 365

Trp Ala Tyr Trp Gly Gln Gly Thr Leu Val Thr Val Ser Ser Gly Gly
370                 375                 380

Gly Gly Ser Gly Gly Gly Ser Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
                420                 425                 430

Asn Trp Val Gln Gln Lys Pro Gly Gln Ala Pro Arg Gly Leu Ile Gly
                435                 440                 445

Gly Thr Lys Phe Leu Ala Pro Gly Thr Pro Ala Arg Phe Ser Gly Ser
            450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu Gly Gly Gly Gly Asp Lys
                500                 505                 510

Thr His Thr Cys Pro Pro Cys Pro Ala Pro Glu Leu Leu Gly Gly Pro
            515                 520                 525

Ser Val Phe Leu Phe Pro Pro Lys Pro Lys Asp Thr Leu Met Ile Ser
            530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
                565                 570                 575

Ala Lys Thr Lys Pro Cys Glu Glu Gln Tyr Gly Ser Thr Tyr Arg Cys
                580                 585                 590

Val Ser Val Leu Thr Val Leu His Gln Asp Trp Leu Asn Gly Lys Glu
            595                 600                 605

Tyr Lys Cys Lys Val Ser Asn Lys Ala Leu Pro Ala Pro Ile Glu Lys
            610                 615                 620

Thr Ile Ser Lys Ala Lys Gly Gln Pro Arg Glu Pro Gln Val Tyr Thr
625                 630                 635                 640
```

```
Leu Pro Pro Ser Arg Glu Glu Met Thr Lys Asn Gln Val Ser Leu Thr
                645                 650                 655

Cys Leu Val Lys Gly Phe Tyr Pro Ser Asp Ile Ala Val Glu Trp Glu
            660                 665                 670

Ser Asn Gly Gln Pro Glu Asn Asn Tyr Lys Thr Thr Pro Pro Val Leu
        675                 680                 685

Asp Ser Asp Gly Ser Phe Phe Leu Tyr Ser Lys Leu Thr Val Asp Lys
    690                 695                 700

Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
                725                 730                 735

Lys Gly Gly Gly Gly Ser Gly Gly Gly Ser Gly Gly Gly Gly Gly Ser
            740                 745                 750

Gly Gly Gly Gly Ser Gly Gly Gly Ser Gly Gly Gly Gly Gly Ser Asp
        755                 760                 765

Lys Thr His Thr Cys Pro Pro Cys Pro Ala Pro Glu Leu Leu Gly Gly
    770                 775                 780

Pro Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Cys Glu Glu Gln Tyr Gly Ser Thr Tyr Arg
        835                 840                 845

Cys Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Glu Glu Met Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
                965                 970                 975

Glu Ala Leu His Asn His Tyr Thr Gln Lys Ser Leu Ser Leu Ser Pro
            980                 985                 990

Gly Lys

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR1
```

-continued

<400> SEQUENCE: 53

Asp Tyr Tyr Met Thr
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR2

<400> SEQUENCE: 54

Tyr Ile Ser Ser Ser Gly Ser Thr Ile Tyr Tyr Ala Asp Ser Val Lys
1               5                   10                  15

Gly

<210> SEQ ID NO 55
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR3

<400> SEQUENCE: 55

Asp Arg Asn Ser His Phe Asp Tyr
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL CDR1

<400> SEQUENCE: 56

Arg Ala Ser Gln Gly Ile Asn Thr Trp Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL CDR2

<400> SEQUENCE: 57

Gly Ala Ser Gly Leu Gln Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<223> OTHER INFORMATION: MSLN_5 VL CDR3

<400> SEQUENCE: 58

Gln Gln Ala Lys Ser Phe Pro Arg Thr
1               5

<210> SEQ ID NO 59
<211> LENGTH: 117
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN _5 VH

<400> SEQUENCE: 59

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
            100                 105                 110

Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL

<400> SEQUENCE: 60

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Thr Trp
            20                  25                  30

Leu Ala Trp Tyr Gln Gln Lys Pro Gly Lys Ala Pro Lys Leu Leu Ile
        35                  40                  45

Tyr Gly Ala Ser Gly Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Arg
                85                  90                  95

Thr Phe Gly Gln Gly Thr Lys Val Glu Ile Lys
            100                 105
```

<210> SEQ ID NO 61
<211> LENGTH: 239
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 scFv

<400> SEQUENCE: 61

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Gly Ser Thr Ile Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Ile Gln Met Thr Gln Ser Pro Ser Ser Val Ser
    130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Lys
    210                 215                 220

Ser Phe Pro Arg Thr Phe Gly Gln Gly Thr Lys Val Glu Ile Lys
225                 230                 235

<210> SEQ ID NO 62
<211> LENGTH: 494
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5xI2C0 bispecific molecule

<400> SEQUENCE: 62

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu

```
                35                  40                  45
Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Arg Asn Ser His Phe Asp Tyr Trp Gly Gln Gly Thr Leu
                100                 105                 110

Val Thr Val Ser Ser Gly Gly Gly Ser Gly Gly Gly Ser Gly
            115                 120                 125

Gly Gly Gly Ser Asp Ile Gln Met Thr Gln Ser Pro Ser Ser Val Ser
            130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
                180                 185                 190

Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Ala Lys
                210                 215                 220

Ser Phe Pro Arg Thr Phe Gly Gln Gly Thr Lys Val Glu Ile Lys Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
                260                 265                 270

Thr Phe Asn Lys Tyr Ala Met Asn Trp Val Arg Gln Ala Pro Gly Lys
                275                 280                 285

Gly Leu Glu Trp Val Ala Arg Ile Arg Ser Lys Tyr Asn Asn Tyr Ala
                290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Ser
                340                 345                 350

Tyr Ile Ser Tyr Trp Ala Tyr Trp Gly Gln Gly Thr Leu Val Thr Val
                355                 360                 365

Ser Ser Gly Gly Gly Gly Ser Gly Gly Gly Ser Gly Gly Gly
                370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
                405                 410                 415

Gly Asn Tyr Pro Asn Trp Val Gln Lys Pro Gly Gln Ala Pro Arg
                420                 425                 430

Gly Leu Ile Gly Gly Thr Lys Phe Leu Ala Pro Gly Thr Pro Ala Arg
                435                 440                 445

Phe Ser Gly Ser Leu Leu Gly Gly Lys Ala Ala Leu Thr Leu Ser Gly
                450                 455                 460
```

-continued

```
Val Gln Pro Glu Asp Glu Ala Glu Tyr Tyr Cys Val Leu Trp Tyr Ser
465                 470                 475                 480

Asn Arg Trp Val Phe Gly Gly Gly Thr Lys Leu Thr Val Leu
            485                 490

<210> SEQ ID NO 63
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5xCD3-scFc Bispecific HLE molecule

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Val Ser
130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Lys
    210                 215                 220

Ser Phe Pro Arg Thr Phe Gly Gln Gly Thr Lys Val Glu Ile Lys Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
            260                 265                 270

Thr Phe Asn Lys Tyr Ala Met Asn Trp Val Arg Gln Ala Pro Gly Lys
        275                 280                 285

Gly Leu Glu Trp Val Ala Arg Ile Arg Ser Lys Tyr Asn Asn Tyr Ala
    290                 295                 300

Thr Tyr Tyr Ala Asp Ser Val Lys Asp Arg Phe Thr Ile Ser Arg Asp
305                 310                 315                 320
```

```
Asp Ser Lys Asn Thr Ala Tyr Leu Gln Met Asn Asn Leu Lys Thr Glu
            325                 330                 335

Asp Thr Ala Val Tyr Tyr Cys Val Arg His Gly Asn Phe Gly Asn Ser
            340                 345                 350

Tyr Ile Ser Tyr Trp Ala Tyr Trp Gly Gln Gly Thr Leu Val Thr Val
            355                 360                 365

Ser Ser Gly Gly Gly Gly Ser Gly Gly Gly Gly Ser Gly Gly Gly Gly
            370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
            405                 410                 415

Gly Asn Tyr Pro Asn Trp Val Gln Gln Lys Pro Gly Gln Ala Pro Arg
            420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
            450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Gly Thr Lys Leu Thr Val Leu Gly Gly
            485                 490                 495

Gly Gly Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
            515                 520                 525

Leu Met Ile Ser Arg Thr Pro Glu Val Thr Cys Val Val Val Asp Val
            530                 535                 540

Ser His Glu Asp Pro Glu Val Lys Phe Asn Trp Tyr Val Asp Gly Val
545                 550                 555                 560

Glu Val His Asn Ala Lys Thr Lys Pro Cys Glu Glu Gln Tyr Gly Ser
            565                 570                 575

Thr Tyr Arg Cys Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
            595                 600                 605

Pro Ile Glu Lys Thr Ile Ser Lys Ala Lys Gly Gln Pro Arg Glu Pro
            610                 615                 620

Gln Val Tyr Thr Leu Pro Pro Ser Arg Glu Glu Met Thr Lys Asn Gln
625                 630                 635                 640

Val Ser Leu Thr Cys Leu Val Lys Gly Phe Tyr Pro Ser Asp Ile Ala
            645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
            675                 680                 685

Thr Val Asp Lys Ser Arg Trp Gln Gln Gly Asn Val Phe Ser Cys Ser
            690                 695                 700

Val Met His Glu Ala Leu His Asn His Tyr Thr Gln Lys Ser Leu Ser
705                 710                 715                 720

Leu Ser Pro Gly Lys Gly Gly Gly Gly Ser Gly Gly Gly Gly Ser Gly
            725                 730                 735
```

Gly Gly Gly Ser Gly Gly Gly Ser Gly Gly Gly Ser Gly Gly
                740                 745                 750

Gly Gly Ser Asp Lys Thr His Thr Cys Pro Pro Cys Pro Ala Pro Glu
            755                 760                 765

Leu Leu Gly Gly Pro Ser Val Phe Leu Phe Pro Pro Lys Pro Lys Asp
770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
            805                 810                 815

Val Glu Val His Asn Ala Lys Thr Lys Pro Cys Glu Glu Gln Tyr Gly
            820                 825                 830

Ser Thr Tyr Arg Cys Val Ser Val Leu Thr Val Leu His Gln Asp Trp
            835                 840                 845

Leu Asn Gly Lys Glu Tyr Lys Cys Lys Val Ser Asn Lys Ala Leu Pro
850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
            915                 920                 925

Thr Pro Pro Val Leu Asp Ser Asp Gly Ser Phe Phe Leu Tyr Ser Lys
930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980

<210> SEQ ID NO 64
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5_CCxCD3-scFc Bispecific HLE molecule

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Cys Leu Glu Trp Phe
        35                  40                  45

Ser Tyr Ile Ser Ser Ser Gly Gly Ile Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Arg Asp Val Gly Ser His Phe Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Ile Gln Met Thr Gln Ser Pro Ser Ser Val Ser
130                 135                 140

Ala Ser Val Gly Asp Arg Val Thr Ile Thr Cys Arg Ala Ser Gln Asp
145                 150                 155                 160

Ile Ser Arg Trp Leu Ala Trp Tyr Gln Gln Lys Pro Gly Lys Ala Pro
                165                 170                 175

Lys Leu Leu Ile Ser Ala Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Ile Tyr Tyr Cys Gln Gln Ala Lys
    210                 215                 220

Ser Phe Pro Arg Thr Phe Gly Cys Gly Thr Lys Val Glu Ile Lys Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
        260                 265                 270

Thr Phe Asn Lys Tyr Ala Met Asn Trp Val Arg Gln Ala Pro Gly Lys
        275                 280                 285

Gly Leu Glu Trp Val Ala Arg Ile Arg Ser Lys Tyr Asn Asn Tyr Ala
290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Ser
            340                 345                 350

Tyr Ile Ser Tyr Trp Ala Tyr Trp Gly Gln Gly Thr Leu Val Thr Val
        355                 360                 365

Ser Ser Gly Gly Gly Gly Ser Gly Gly Gly Gly Ser Gly Gly Gly Gly
370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
                405                 410                 415

Gly Asn Tyr Pro Asn Trp Val Gln Gln Lys Pro Gly Gln Ala Pro Arg
            420                 425                 430

Gly Leu Ile Gly Gly Thr Lys Phe Leu Ala Pro Gly Thr Pro Ala Arg
        435                 440                 445

Phe Ser Gly Ser Leu Leu Gly Gly Lys Ala Ala Leu Thr Leu Ser Gly
    450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Thr Lys Leu Thr Val Leu Gly Gly
                485                 490                 495

Gly Gly Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
```

```
                515                 520                 525
Leu Met Ile Ser Arg Thr Pro Glu Val Thr Cys Val Val Asp Val
    530                 535                 540

Ser His Glu Asp Pro Glu Val Lys Phe Asn Trp Tyr Val Asp Gly Val
545                 550                 555                 560

Glu Val His Asn Ala Lys Thr Lys Pro Cys Glu Glu Gln Tyr Gly Ser
                565                 570                 575

Thr Tyr Arg Cys Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Glu Glu Met Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly Lys Gly Gly Gly Gly Ser Gly Gly Gly Gly Ser Gly
                725                 730                 735

Gly Gly Gly Ser Gly Gly Gly Gly Ser Gly Gly Gly Gly Ser Gly Gly
            740                 745                 750

Gly Gly Ser Asp Lys Thr His Thr Cys Pro Pro Cys Pro Ala Pro Glu
        755                 760                 765

Leu Leu Gly Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Cys Glu Glu Gln Tyr Gly
            820                 825                 830

Ser Thr Tyr Arg Cys Val Ser Val Leu Thr Val Leu His Gln Asp Trp
        835                 840                 845

Leu Asn Gly Lys Glu Tyr Lys Cys Lys Val Ser Asn Lys Ala Leu Pro
    850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940
```

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
            965                 970                 975

Ser Leu Ser Pro Gly Lys
            980

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H1 of CDH19 65254.007

<400> SEQUENCE: 65

Ser Tyr Gly Met His
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H2 of CDH19 65254.007

<400> SEQUENCE: 66

Phe Ile Trp Tyr Glu Gly Ser Asn Lys Tyr Tyr Ala Glu Ser Val Lys
1               5                   10                  15

Asp

<210> SEQ ID NO 67
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H3 of CDH19 65254.007

<400> SEQUENCE: 67

Arg Ala Gly Ile Ile Gly Thr Ile Gly Tyr Tyr Tyr Gly Met Asp Val
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L1 of CDH19 65254.007

<400> SEQUENCE: 68

Ser Gly Asp Arg Leu Gly Glu Lys Tyr Thr Ser
1               5                   10

<210> SEQ ID NO 69
<211> LENGTH: 7

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L2 of CDH19 65254.007

<400> SEQUENCE: 69

Gln Asp Thr Lys Arg Pro Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L3 of CDH19 65254.007

<400> SEQUENCE: 70

Gln Ala Trp Glu Ser Ser Thr Val Val
1               5

<210> SEQ ID NO 71
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH of CDH19 65254.007

<400> SEQUENCE: 71

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Arg Ala Gly Ile Ile Gly Thr Ile Gly Tyr Tyr Tyr Gly Met
        100                 105                 110

Asp Val Trp Gly Gln Gly Thr Thr Val Thr Val Ser Ser
        115                 120                 125

<210> SEQ ID NO 72
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL of CDH19 65254.007

<400> SEQUENCE: 72
```

```
Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Glu Lys Tyr Thr
            20                  25                  30

Ser Trp Tyr Gln Gln Arg Pro Gly Gln Ser Pro Leu Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Glu Ser Ser Thr Val Val
                85                  90                  95

Phe Gly Gly Gly Thr Lys Leu Thr Val Leu Ser
            100                 105
```

<210> SEQ ID NO 73
<211> LENGTH: 247
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-VL of CDH19 65254.007

<400> SEQUENCE: 73

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Gly Gly
225                 230                 235                 240
```

```
Thr Lys Leu Thr Val Leu Ser
            245
```

```
<210> SEQ ID NO 74
<211> LENGTH: 507
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C

<400> SEQUENCE: 74

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Gly Gly
225                 230                 235                 240

Thr Lys Leu Thr Val Leu Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335
```

```
Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu His His His His His His
            500                 505

<210> SEQ ID NO 75
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C scFc Bispecific HLE
      molecule

<400> SEQUENCE: 75

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175
```

```
Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
            195                 200                 205

Thr Ala Thr Leu Thr Ile Ser Gly Thr Gln Ala Met Asp Glu Ala Asp
210                 215                 220

Tyr Tyr Cys Gln Ala Trp Glu Ser Ser Thr Val Val Phe Gly Gly Gly
225                 230                 235                 240

Thr Lys Leu Thr Val Leu Ser Gly Gly Gly Ser Glu Val Gln Leu
            245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
        290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
            405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
            485                 490                 495

Lys Leu Thr Val Leu Gly Gly Gly Gly Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
        530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
            565                 570                 575

Cys Glu Glu Gln Tyr Gly Ser Thr Tyr Arg Cys Val Ser Val Leu Thr
            580                 585                 590
```

```
Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
        675                 680                 685

Phe Phe Leu Tyr Ser Lys Leu Thr Val Asp Lys Ser Arg Trp Gln Gln
690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
                725                 730                 735

Ser Gly Gly Gly Gly Ser Gly Gly Gly Gly Ser Gly Gly Gly Gly Ser
            740                 745                 750

Gly Gly Gly Gly Ser Gly Gly Gly Gly Ser Asp Lys Thr His Thr Cys
        755                 760                 765

Pro Pro Cys Pro Ala Pro Glu Leu Leu Gly Gly Pro Ser Val Phe Leu
770                 775                 780

Phe Pro Pro Lys Pro Lys Asp Thr Leu Met Ile Ser Arg Thr Pro Glu
785                 790                 795                 800

Val Thr Cys Val Val Val Asp Val Ser His Glu Asp Pro Glu Val Lys
                805                 810                 815

Phe Asn Trp Tyr Val Asp Gly Val Glu Val His Asn Ala Lys Thr Lys
            820                 825                 830

Pro Cys Glu Glu Gln Tyr Gly Ser Thr Tyr Arg Cys Val Ser Val Leu
        835                 840                 845

Thr Val Leu His Gln Asp Trp Leu Asn Gly Lys Glu Tyr Lys Cys Lys
850                 855                 860

Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
            900                 905                 910

Gly Phe Tyr Pro Ser Asp Ile Ala Val Glu Trp Glu Ser Asn Gly Gln
        915                 920                 925

Pro Glu Asn Asn Tyr Lys Thr Thr Pro Pro Val Leu Asp Ser Asp Gly
930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 76
<211> LENGTH: 987
<212> TYPE: PRT
```

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C scFc_delGK Bispecific HLE molecule

<400> SEQUENCE: 76

```
Gln Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Phe Ile Trp Tyr Glu Gly Ser Asn Lys Tyr Tyr Ala Glu Ser Val
    50                  55                  60
Lys Asp Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Ala Gly Ile Ile Gly Thr Ile Tyr Tyr Tyr Gly Met
            100                 105                 110
Asp Val Trp Gly Gln Gly Thr Thr Val Thr Val Ser Ser Gly Gly Gly
        115                 120                 125
Gly Ser Gly Gly Gly Gly Ser Gly Gly Gly Gly Ser Ser Tyr Glu Leu
    130                 135                 140
Thr Gln Pro Pro Ser Val Ser Val Ser Pro Gly Gln Thr Ala Ser Ile
145                 150                 155                 160
Thr Cys Ser Gly Asp Arg Leu Gly Glu Lys Tyr Thr Ser Trp Tyr Gln
                165                 170                 175
Gln Arg Pro Gly Gln Ser Pro Leu Leu Val Ile Tyr Gln Asp Thr Lys
            180                 185                 190
Arg Pro Ser Gly Ile Pro Glu Arg Phe Ser Gly Ser Asn Ser Gly Asn
        195                 200                 205
Thr Ala Thr Leu Thr Ile Ser Gly Thr Gln Ala Met Asp Glu Ala Asp
    210                 215                 220
Tyr Tyr Cys Gln Ala Trp Glu Ser Ser Thr Val Val Phe Gly Gly Gly
225                 230                 235                 240
Thr Lys Leu Thr Val Leu Ser Gly Gly Gly Ser Glu Val Gln Leu
                245                 250                 255
Val Glu Ser Gly Gly Gly Leu Val Gln Pro Gly Gly Ser Leu Lys Leu
            260                 265                 270
Ser Cys Ala Ala Ser Gly Phe Thr Phe Asn Lys Tyr Ala Met Asn Trp
        275                 280                 285
Val Arg Gln Ala Pro Gly Lys Gly Leu Glu Trp Val Ala Arg Ile Arg
    290                 295                 300
Ser Lys Tyr Asn Asn Tyr Ala Thr Tyr Tyr Ala Asp Ser Val Lys Asp
305                 310                 315                 320
Arg Phe Thr Ile Ser Arg Asp Asp Ser Lys Asn Thr Ala Tyr Leu Gln
                325                 330                 335
Met Asn Asn Leu Lys Thr Glu Asp Thr Ala Val Tyr Tyr Cys Val Arg
            340                 345                 350
His Gly Asn Phe Gly Asn Ser Tyr Ile Ser Tyr Trp Ala Tyr Trp Gly
        355                 360                 365
```

```
Gln Gly Thr Leu Val Thr Val Ser Ser Gly Gly Gly Ser Gly Gly
    370             375             380
Gly Gly Ser Gly Gly Gly Ser Gln Thr Val Thr Gln Glu Pro
385             390             395             400
Ser Leu Thr Val Ser Pro Gly Gly Thr Val Thr Leu Thr Cys Gly Ser
            405             410             415
Ser Thr Gly Ala Val Thr Ser Gly Asn Tyr Pro Asn Trp Val Gln Gln
            420             425             430
Lys Pro Gly Gln Ala Pro Arg Gly Leu Ile Gly Gly Thr Lys Phe Leu
            435             440             445
Ala Pro Gly Thr Pro Ala Arg Phe Ser Gly Ser Leu Leu Gly Gly Lys
450             455             460
Ala Ala Leu Thr Leu Ser Gly Val Gln Pro Glu Asp Glu Ala Glu Tyr
465             470             475             480
Tyr Cys Val Leu Trp Tyr Ser Asn Arg Trp Val Phe Gly Gly Gly Thr
            485             490             495
Lys Leu Thr Val Leu Gly Gly Gly Asp Lys Thr His Thr Cys Pro
            500             505             510
Pro Cys Pro Ala Pro Glu Leu Leu Gly Gly Pro Ser Val Phe Leu Phe
    515             520             525
Pro Pro Lys Pro Lys Asp Thr Leu Met Ile Ser Arg Thr Pro Glu Val
530             535             540
Thr Cys Val Val Val Asp Val Ser His Glu Asp Pro Glu Val Lys Phe
545             550             555             560
Asn Trp Tyr Val Asp Gly Val Glu Val His Asn Ala Lys Thr Lys Pro
            565             570             575
Cys Glu Glu Gln Tyr Gly Ser Thr Tyr Arg Cys Val Ser Val Leu Thr
            580             585             590
Val Leu His Gln Asp Trp Leu Asn Gly Lys Glu Tyr Lys Cys Lys Val
            595             600             605
Ser Asn Lys Ala Leu Pro Ala Pro Ile Glu Lys Thr Ile Ser Lys Ala
    610             615             620
Lys Gly Gln Pro Arg Glu Pro Gln Val Tyr Thr Leu Pro Pro Ser Arg
625             630             635             640
Glu Glu Met Thr Lys Asn Gln Val Ser Leu Thr Cys Leu Val Lys Gly
            645             650             655
Phe Tyr Pro Ser Asp Ile Ala Val Glu Trp Glu Ser Asn Gly Gln Pro
            660             665             670
Glu Asn Asn Tyr Lys Thr Thr Pro Pro Val Leu Asp Ser Asp Gly Ser
            675             680             685
Phe Phe Leu Tyr Ser Lys Leu Thr Val Asp Lys Ser Arg Trp Gln Gln
    690             695             700
Gly Asn Val Phe Ser Cys Ser Val Met His Glu Ala Leu His Asn His
705             710             715             720
Tyr Thr Gln Lys Ser Leu Ser Leu Ser Pro Gly Gly Gly Gly Ser Gly
            725             730             735
Gly Gly Ser Gly Gly Gly Ser Gly Gly Gly Ser Gly Gly Gly Ser Gly
            740             745             750
Gly Ser Gly Gly Gly Gly Ser Asp Lys Thr His Thr Cys Pro Pro
            755             760             765
Cys Pro Ala Pro Glu Leu Leu Gly Gly Pro Ser Val Phe Leu Phe Pro
    770             775             780
Pro Lys Pro Lys Asp Thr Leu Met Ile Ser Arg Thr Pro Glu Val Thr
```

```
                785                 790                 795                 800
Cys Val Val Asp Val Ser His Glu Asp Pro Glu Val Lys Phe Asn
                    805                 810                 815
Trp Tyr Val Asp Gly Val Glu Val His Asn Ala Lys Thr Lys Pro Cys
                820                 825                 830
Glu Glu Gln Tyr Gly Ser Thr Tyr Arg Cys Val Ser Val Leu Thr Val
                835                 840                 845
Leu His Gln Asp Trp Leu Asn Gly Lys Glu Tyr Lys Cys Lys Val Ser
850                 855                 860
Asn Lys Ala Leu Pro Ala Pro Ile Glu Lys Thr Ile Ser Lys Ala Lys
865                 870                 875                 880
Gly Gln Pro Arg Glu Pro Gln Val Tyr Thr Leu Pro Pro Ser Arg Glu
                885                 890                 895
Glu Met Thr Lys Asn Gln Val Ser Leu Thr Cys Leu Val Lys Gly Phe
                900                 905                 910
Tyr Pro Ser Asp Ile Ala Val Glu Trp Glu Ser Asn Gly Gln Pro Glu
                915                 920                 925
Asn Asn Tyr Lys Thr Thr Pro Pro Val Leu Asp Ser Asp Gly Ser Phe
930                 935                 940
Phe Leu Tyr Ser Lys Leu Thr Val Asp Lys Ser Arg Trp Gln Gln Gly
945                 950                 955                 960
Asn Val Phe Ser Cys Ser Val Met His Glu Ala Leu His Asn His Tyr
                965                 970                 975
Thr Gln Lys Ser Leu Ser Leu Ser Pro Gly Lys
                980                 985

<210> SEQ ID NO 77
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc VH

<400> SEQUENCE: 77

Gln Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Cys Leu Glu Trp Val
            35                  40                  45
Ala Phe Ile Trp Tyr Glu Gly Ser Asn Lys Tyr Tyr Ala Glu Ser Val
        50                  55                  60
Lys Asp Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Ala Gly Ile Ile Gly Thr Ile Gly Tyr Tyr Tyr Gly Met
                100                 105                 110
Asp Val Trp Gly Gln Gly Thr Thr Val Thr Val Ser Ser
            115                 120                 125

<210> SEQ ID NO 78
<211> LENGTH: 106
<212> TYPE: PRT
```

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc VL

<400> SEQUENCE: 78

```
Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Glu Lys Tyr Thr
            20                  25                  30

Ser Trp Tyr Gln Gln Arg Pro Gly Gln Ser Pro Leu Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Glu Ser Ser Thr Val Val
                85                  90                  95

Phe Gly Cys Gly Thr Lys Leu Thr Val Leu
            100                 105
```

<210> SEQ ID NO 79
<211> LENGTH: 246
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc scFv

<400> SEQUENCE: 79

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190
```

```
Arg Pro Ser Gly Ile Pro Glu Arg Phe Ser Gly Ser Asn Ser Gly Asn
            195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Cys Gly
225                 230                 235                 240

Thr Lys Leu Thr Val Leu
                245

<210> SEQ ID NO 80
<211> LENGTH: 501
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc Bispecific
      molecule

<400> SEQUENCE: 80

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Cys Gly
225                 230                 235                 240

Thr Lys Leu Thr Val Leu Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285
```

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Ser Gly Gly
    370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu
            500

<210> SEQ ID NO 81
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc Bispecific HLE
      molecule

<400> SEQUENCE: 81

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly

```
            115                 120                 125
Gly Ser Gly Gly Gly Ser Gly Gly Gly Ser Ser Tyr Glu Leu
        130                 135                 140
Thr Gln Pro Pro Ser Val Ser Val Ser Pro Gly Gln Thr Ala Ser Ile
145                     150                  155                 160
Thr Cys Ser Gly Asp Arg Leu Gly Glu Lys Tyr Thr Ser Trp Tyr Gln
                    165                 170                  175
Gln Arg Pro Gly Gln Ser Pro Leu Leu Val Ile Tyr Gln Asp Thr Lys
                180                 185                 190
Arg Pro Ser Gly Ile Pro Glu Arg Phe Ser Gly Ser Asn Ser Gly Asn
            195                 200                 205
Thr Ala Thr Leu Thr Ile Ser Gly Thr Gln Ala Met Asp Glu Ala Asp
        210                 215                 220
Tyr Tyr Cys Gln Ala Trp Glu Ser Ser Thr Val Val Phe Gly Cys Gly
225                 230                 235                 240
Thr Lys Leu Thr Val Leu Ser Gly Gly Gly Ser Glu Val Gln Leu
                    245                 250                 255
Val Glu Ser Gly Gly Gly Leu Val Gln Pro Gly Gly Ser Leu Lys Leu
                260                 265                 270
Ser Cys Ala Ala Ser Gly Phe Thr Phe Asn Lys Tyr Ala Met Asn Trp
            275                 280                 285
Val Arg Gln Ala Pro Gly Lys Gly Leu Glu Trp Val Ala Arg Ile Arg
        290                 295                 300
Ser Lys Tyr Asn Asn Tyr Ala Thr Tyr Tyr Ala Asp Ser Val Lys Asp
305                 310                 315                 320
Arg Phe Thr Ile Ser Arg Asp Asp Ser Lys Asn Thr Ala Tyr Leu Gln
                    325                 330                 335
Met Asn Asn Leu Lys Thr Glu Asp Thr Ala Val Tyr Tyr Cys Val Arg
                340                 345                 350
His Gly Asn Phe Gly Asn Ser Tyr Ile Ser Tyr Trp Ala Tyr Trp Gly
            355                 360                 365
Gln Gly Thr Leu Val Thr Val Ser Ser Gly Gly Gly Ser Gly Gly
        370                 375                 380
Gly Gly Ser Gly Gly Gly Gly Ser Gln Thr Val Val Thr Gln Glu Pro
385                 390                 395                 400
Ser Leu Thr Val Ser Pro Gly Gly Thr Val Thr Leu Thr Cys Gly Ser
                    405                 410                 415
Ser Thr Gly Ala Val Thr Ser Gly Asn Tyr Pro Asn Trp Val Gln Gln
                420                 425                 430
Lys Pro Gly Gln Ala Pro Arg Gly Leu Ile Gly Gly Thr Lys Phe Leu
            435                 440                 445
Ala Pro Gly Thr Pro Ala Arg Phe Ser Gly Ser Leu Leu Gly Gly Lys
        450                 455                 460
Ala Ala Leu Thr Leu Ser Gly Val Gln Pro Glu Asp Glu Ala Glu Tyr
465                 470                 475                 480
Tyr Cys Val Leu Trp Tyr Ser Asn Arg Trp Val Phe Gly Gly Gly Thr
                    485                 490                 495
Lys Leu Thr Val Leu Gly Gly Gly Asp Lys Thr His Thr Cys Pro
                500                 505                 510
Pro Cys Pro Ala Pro Glu Leu Leu Gly Gly Pro Ser Val Phe Leu Phe
            515                 520                 525
Pro Pro Lys Pro Lys Asp Thr Leu Met Ile Ser Arg Thr Pro Glu Val
        530                 535                 540
```

```
Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Val Leu Asp Ser Asp Gly Ser
        675                 680                 685

Phe Phe Leu Tyr Ser Lys Leu Thr Val Asp Lys Ser Arg Trp Gln Gln
        690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
                725                 730                 735

Ser Gly Gly Gly Gly Ser Gly Gly Gly Gly Ser Gly Gly Gly Gly Ser
            740                 745                 750

Gly Gly Gly Gly Ser Gly Gly Gly Gly Ser Asp Lys Thr His Thr Cys
            755                 760                 765

Pro Pro Cys Pro Ala Pro Glu Leu Leu Gly Gly Pro Ser Val Phe Leu
770                 775                 780

Phe Pro Pro Lys Pro Lys Asp Thr Leu Met Ile Ser Arg Thr Pro Glu
785                 790                 795                 800

Val Thr Cys Val Val Val Asp Val Ser His Glu Asp Pro Glu Val Lys
                805                 810                 815

Phe Asn Trp Tyr Val Asp Gly Val Glu Val His Asn Ala Lys Thr Lys
                820                 825                 830

Pro Cys Glu Glu Gln Tyr Gly Ser Thr Tyr Arg Cys Val Ser Val Leu
            835                 840                 845

Thr Val Leu His Gln Asp Trp Leu Asn Gly Lys Glu Tyr Lys Cys Lys
        850                 855                 860

Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
            900                 905                 910

Gly Phe Tyr Pro Ser Asp Ile Ala Val Glu Trp Glu Ser Asn Gly Gln
        915                 920                 925

Pro Glu Asn Asn Tyr Lys Thr Thr Pro Val Leu Asp Ser Asp Gly
    930                 935                 940

Ser Phe Phe Leu Tyr Ser Lys Leu Thr Val Asp Lys Ser Arg Trp Gln
945                 950                 955                 960
```

-continued

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 82
<211> LENGTH: 987
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C scFc_delGK Bispecific
      HLE molecule

<400> SEQUENCE: 82

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Cys Gly
225                 230                 235                 240

Thr Lys Leu Thr Val Leu Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

```
Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
        340                 345                 350

His Gly Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Ser Gly Gly
        370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu Gly Gly Gly Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
        530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
        610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
            645                 650                 655

Phe Tyr Pro Ser Asp Ile Ala Val Glu Trp Glu Ser Asn Gly Gln Pro
        660                 665                 670

Glu Asn Asn Tyr Lys Thr Thr Pro Pro Val Leu Asp Ser Asp Gly Ser
        675                 680                 685

Phe Phe Leu Tyr Ser Lys Leu Thr Val Asp Lys Ser Arg Trp Gln Gln
        690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Gly Gly Gly Ser Gly
                725                 730                 735
```

```
Gly Gly Gly Ser Gly Gly Gly Ser Gly Gly Gly Ser Gly Gly
                740                 745                 750
Gly Gly Ser Gly Gly Gly Ser Asp Lys Thr His Thr Cys Pro Pro
        755                 760                 765
Cys Pro Ala Pro Glu Leu Leu Gly Gly Pro Ser Val Phe Leu Phe Pro
    770                 775                 780
Pro Lys Pro Lys Asp Thr Leu Met Ile Ser Arg Thr Pro Glu Val Thr
785                 790                 795                 800
Cys Val Val Val Asp Val Ser His Glu Asp Pro Glu Val Lys Phe Asn
                805                 810                 815
Trp Tyr Val Asp Gly Val Glu Val His Asn Ala Lys Thr Lys Pro Cys
                820                 825                 830
Glu Glu Gln Tyr Gly Ser Thr Tyr Arg Cys Val Ser Val Leu Thr Val
                835                 840                 845
Leu His Gln Asp Trp Leu Asn Gly Lys Glu Tyr Lys Cys Lys Val Ser
    850                 855                 860
Asn Lys Ala Leu Pro Ala Pro Ile Glu Lys Thr Ile Ser Lys Ala Lys
865                 870                 875                 880
Gly Gln Pro Arg Glu Pro Gln Val Tyr Thr Leu Pro Pro Ser Arg Glu
                885                 890                 895
Glu Met Thr Lys Asn Gln Val Ser Leu Thr Cys Leu Val Lys Gly Phe
                900                 905                 910
Tyr Pro Ser Asp Ile Ala Val Glu Trp Glu Ser Asn Gly Gln Pro Glu
            915                 920                 925
Asn Asn Tyr Lys Thr Thr Pro Pro Val Leu Asp Ser Asp Gly Ser Phe
930                 935                 940
Phe Leu Tyr Ser Lys Leu Thr Val Asp Lys Ser Arg Trp Gln Gln Gly
945                 950                 955                 960
Asn Val Phe Ser Cys Ser Val Met His Glu Ala Leu His Asn His Tyr
                965                 970                 975
Thr Gln Lys Ser Leu Ser Leu Ser Pro Gly Lys
                980                 985

<210> SEQ ID NO 83
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR1

<400> SEQUENCE: 83

Asn Ala Arg Met Gly Val Ser
1               5

<210> SEQ ID NO 84
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR2

<400> SEQUENCE: 84

His Ile Phe Ser Asn Asp Glu Lys Ser Tyr Ser Thr Ser Leu Lys Asn
1               5                   10                  15
```

```
<210> SEQ ID NO 85
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR3

<400> SEQUENCE: 85

Ile Val Gly Tyr Gly Ser Gly Trp Tyr Gly Phe Phe Asp Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR1

<400> SEQUENCE: 86

Arg Ala Ser Gln Gly Ile Arg Asn Asp Leu Gly
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR2

<400> SEQUENCE: 87

Ala Ala Ser Thr Leu Gln Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR3

<400> SEQUENCE: 88

Leu Gln His Asn Ser Tyr Pro Leu Thr
1               5

<210> SEQ ID NO 89
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH

<400> SEQUENCE: 89

Gln Val Thr Leu Lys Glu Ser Gly Pro Thr Leu Val Lys Pro Thr Glu
```

```
                1               5                  10                 15
            Thr Leu Thr Leu Thr Cys Thr Leu Ser Gly Phe Ser Leu Asn Asn Ala
                        20                  25                  30

Arg Met Gly Val Ser Trp Ile Arg Gln Pro Pro Gly Lys Cys Leu Glu
                        35                  40                  45

Trp Leu Ala His Ile Phe Ser Asn Asp Glu Lys Ser Tyr Ser Thr Ser
                        50                  55                  60

Leu Lys Asn Arg Leu Thr Ile Ser Lys Asp Ser Ser Lys Thr Gln Val
             65                  70                  75                  80

Val Leu Thr Met Thr Asn Val Asp Pro Val Asp Thr Ala Thr Tyr Tyr
                        85                  90                  95

Cys Ala Arg Ile Val Gly Tyr Gly Ser Gly Trp Tyr Gly Phe Phe Asp
                        100                 105                 110

Tyr Trp Gly Gln Gly Thr Leu Val Thr Val Ser Ser
                        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_ A8-scFc VL

<400> SEQUENCE: 90

Asp Ile Gln Met Thr Gln Ser Pro Ser Ser Leu Ser Ala Ser Val Gly
             1               5                  10                 15

Asp Arg Val Thr Ile Thr Cys Arg Ala Ser Gln Gly Ile Arg Asn Asp
                        20                  25                  30

Leu Gly Trp Tyr Gln Gln Lys Pro Gly Lys Ala Pro Lys Arg Leu Ile
                        35                  40                  45

Tyr Ala Ala Ser Thr Leu Gln Ser Gly Val Pro Ser Arg Phe Ser Gly
                        50                  55                  60

Ser Gly Ser Gly Thr Glu Phe Thr Leu Thr Ile Ser Ser Leu Gln Pro
             65                  70                  75                  80

Glu Asp Phe Ala Thr Tyr Tyr Cys Leu Gln His Asn Ser Tyr Pro Leu
                        85                  90                  95

Thr Phe Gly Cys Gly Thr Lys Val Glu Ile Lys
                        100                 105

<210> SEQ ID NO 91
<211> LENGTH: 246
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3- scFv

<400> SEQUENCE: 91

Gln Val Thr Leu Lys Glu Ser Gly Pro Thr Leu Val Lys Pro Thr Glu
             1               5                  10                 15

Thr Leu Thr Leu Thr Cys Thr Leu Ser Gly Phe Ser Leu Asn Asn Ala
                        20                  25                  30

Arg Met Gly Val Ser Trp Ile Arg Gln Pro Pro Gly Lys Cys Leu Glu
                        35                  40                  45
```

Trp Leu Ala His Ile Phe Ser Asn Asp Glu Lys Ser Tyr Ser Thr Ser
            50                  55                  60

Leu Lys Asn Arg Leu Thr Ile Ser Lys Asp Ser Ser Lys Thr Gln Val
 65                  70                  75                  80

Val Leu Thr Met Thr Asn Val Asp Pro Val Asp Thr Ala Thr Tyr Tyr
                 85                  90                  95

Cys Ala Arg Ile Val Gly Tyr Gly Ser Gly Trp Tyr Gly Phe Phe Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
                165                 170                 175

Gln Lys Pro Gly Lys Ala Pro Lys Arg Leu Ile Tyr Ala Ala Ser Thr
            180                 185                 190

Leu Gln Ser Gly Val Pro Ser Arg Phe Ser Gly Ser Gly Ser Gly Thr
        195                 200                 205

Glu Phe Thr Leu Thr Ile Ser Ser Leu Gln Pro Glu Asp Phe Ala Thr
    210                 215                 220

Tyr Tyr Cys Leu Gln His Asn Ser Tyr Pro Leu Thr Phe Gly Cys Gly
225                 230                 235                 240

Thr Lys Val Glu Ile Lys
                245

<210> SEQ ID NO 92
<211> LENGTH: 501
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3 Bispecific molecule

<400> SEQUENCE: 92

Gln Val Thr Leu Lys Glu Ser Gly Pro Thr Leu Val Lys Pro Thr Glu
 1               5                  10                  15

Thr Leu Thr Leu Thr Cys Thr Leu Ser Gly Phe Ser Leu Asn Asn Ala
                 20                  25                  30

Arg Met Gly Val Ser Trp Ile Arg Gln Pro Pro Gly Lys Cys Leu Glu
            35                  40                  45

Trp Leu Ala His Ile Phe Ser Asn Asp Glu Lys Ser Tyr Ser Thr Ser
        50                  55                  60

Leu Lys Asn Arg Leu Thr Ile Ser Lys Asp Ser Ser Lys Thr Gln Val
 65                  70                  75                  80

Val Leu Thr Met Thr Asn Val Asp Pro Val Asp Thr Ala Thr Tyr Tyr
                 85                  90                  95

Cys Ala Arg Ile Val Gly Tyr Gly Ser Gly Trp Tyr Gly Phe Phe Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Gly Ser Asp Ile Gln Met Thr
130                 135                 140

```
Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
            165                 170                 175

Gln Lys Pro Gly Lys Ala Pro Lys Arg Leu Ile Tyr Ala Ala Ser Thr
        180                 185                 190

Leu Gln Ser Gly Val Pro Ser Arg Phe Ser Gly Ser Gly Ser Gly Thr
    195                 200                 205

Glu Phe Thr Leu Thr Ile Ser Ser Leu Gln Pro Glu Asp Phe Ala Thr
210                 215                 220

Tyr Tyr Cys Leu Gln His Asn Ser Tyr Pro Leu Thr Phe Gly Cys Gly
225                 230                 235                 240

Thr Lys Val Glu Ile Lys Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu
            500

<210> SEQ ID NO 93
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc Bispecific HLE molecule
```

<400> SEQUENCE: 93

```
Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
                85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
                165                 170                 175

Gln Lys Pro Gly Lys Ala Pro Lys Arg Leu Ile Tyr Ala Ala Ser Thr
            180                 185                 190

Leu Gln Ser Gly Val Pro Ser Arg Phe Ser Gly Ser Gly Ser Gly Thr
        195                 200                 205

Glu Phe Thr Leu Thr Ile Ser Ser Leu Gln Pro Glu Asp Phe Ala Thr
    210                 215                 220

Tyr Tyr Cys Leu Gln His Asn Ser Tyr Pro Leu Thr Phe Gly Cys Gly
225                 230                 235                 240

Thr Lys Val Glu Ile Lys Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
```

```
            405                 410                 415
Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Ala Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu Gly Gly Gly Asp Lys Thr His Thr Cys Pro
                500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
            610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
            675                 680                 685

Phe Phe Leu Tyr Ser Lys Leu Thr Val Asp Lys Ser Arg Trp Gln Gln
            690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
                725                 730                 735

Ser Gly Gly Gly Gly Ser Gly Gly Gly Ser Gly Gly Gly Gly Ser
                740                 745                 750

Gly Gly Gly Gly Ser Gly Gly Gly Gly Ser Asp Lys Thr His Thr Cys
            755                 760                 765

Pro Pro Cys Pro Ala Pro Glu Leu Leu Gly Gly Pro Ser Val Phe Leu
            770                 775                 780

Phe Pro Pro Lys Pro Lys Asp Thr Leu Met Ile Ser Arg Thr Pro Glu
785                 790                 795                 800

Val Thr Cys Val Val Val Asp Val Ser His Glu Asp Pro Glu Val Lys
                805                 810                 815

Phe Asn Trp Tyr Val Asp Gly Val Glu Val His Asn Ala Lys Thr Lys
                820                 825                 830
```

```
Pro Cys Glu Glu Gln Tyr Gly Ser Thr Tyr Arg Cys Val Ser Val Leu
        835                 840                 845

Thr Val Leu His Gln Asp Trp Leu Asn Gly Lys Glu Tyr Lys Cys Lys
    850                 855                 860

Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
            900                 905                 910

Gly Phe Tyr Pro Ser Asp Ile Ala Val Glu Trp Glu Ser Asn Gly Gln
        915                 920                 925

Pro Glu Asn Asn Tyr Lys Thr Thr Pro Pro Val Leu Asp Ser Asp Gly
    930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 94
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 DLL3_1_CC_delGK

<400> SEQUENCE: 94

Ser Tyr Tyr Trp Ser
1               5

<210> SEQ ID NO 95
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 DLL3_1_CC_delGK

<400> SEQUENCE: 95

Tyr Val Tyr Tyr Ser Gly Thr Thr Asn Tyr Asn Pro Ser Leu Lys Ser
1               5                   10                  15

<210> SEQ ID NO 96
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR3 DLL3_1_CC_delGK

<400> SEQUENCE: 96

Ile Ala Val Thr Gly Phe Tyr Phe Asp Tyr
1               5                   10
```

<210> SEQ ID NO 97
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR1 DLL3_1_CC_delGK

<400> SEQUENCE: 97

```
Arg Ala Ser Gln Arg Val Asn Asn Tyr Leu Ala
1               5                   10
```

<210> SEQ ID NO 98
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 DLL3_1_CC_delGK

<400> SEQUENCE: 98

```
Gly Ala Ser Ser Arg Ala Thr
1               5
```

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR3 DLL3_1_CC_delGK

<400> SEQUENCE: 99

```
Gln Gln Tyr Asp Arg Ser Pro Leu Thr
1               5
```

<210> SEQ ID NO 100
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH DLL3_1_CC_delGK

<400> SEQUENCE: 100

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95
```

Ser Ile Ala Val Thr Gly Phe Tyr Phe Asp Tyr Trp Gly Gln Gly Thr
            100                 105                 110

Leu Val Thr Val Ser Ser
        115

<210> SEQ ID NO 101
<211> LENGTH: 108
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL DLL3_1_CC_delGK

<400> SEQUENCE: 101

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Arg Val Asn Asn Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Cys Gly Thr Lys Leu Glu Ile Lys
            100                 105

<210> SEQ ID NO 102
<211> LENGTH: 241
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CC_delGK

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

```
Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
        210                 215                 220

Tyr Asp Arg Ser Pro Leu Thr Phe Gly Cys Gly Thr Lys Leu Glu Ile
225                 230                 235                 240

Lys

<210> SEQ ID NO 103
<211> LENGTH: 496
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CCxCD3_delGK  Bispecific molecule

<400> SEQUENCE: 103

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
        210                 215                 220

Tyr Asp Arg Ser Pro Leu Thr Phe Gly Cys Gly Thr Lys Leu Glu Ile
225                 230                 235                 240
```

```
Lys Ser Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
        260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
        290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
            355                 360                 365

Thr Val Ser Ser Gly Gly Gly Gly Ser Gly Gly Gly Gly Ser Gly Gly
370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
            405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
        450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495
```

<210> SEQ ID NO 104
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CCxCD3-scFc_delGK Bispecific HLE
      molecule

<400> SEQUENCE: 104

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Ser Ile Ala Val Thr Gly Phe Tyr Phe Asp Tyr Trp Gly Gln Gly Thr
                100                 105                 110
Leu Val Thr Val Ser Ser Gly Gly Gly Ser Gly Gly Gly Ser
            115                 120                 125
Gly Gly Gly Gly Ser Glu Ile Val Leu Thr Gln Ser Pro Gly Thr Leu
            130                 135                 140
Ser Leu Ser Pro Gly Glu Arg Val Thr Leu Ser Cys Arg Ala Ser Gln
145                 150                 155                 160
Arg Val Asn Asn Asn Tyr Leu Ala Trp Tyr Gln Gln Arg Pro Gly Gln
                165                 170                 175
Ala Pro Arg Leu Leu Ile Tyr Gly Ala Ser Ser Arg Ala Thr Gly Ile
                180                 185                 190
Pro Asp Arg Phe Ser Gly Ser Gly Ser Gly Thr Asp Phe Thr Leu Thr
                195                 200                 205
Ile Ser Arg Leu Glu Pro Glu Asp Phe Ala Val Tyr Tyr Cys Gln Gln
                210                 215                 220
Tyr Asp Arg Ser Pro Leu Thr Phe Gly Cys Gly Thr Lys Leu Glu Ile
225                 230                 235                 240
Lys Ser Gly Gly Gly Gly Ser Glu Val Gln Leu Val Glu Ser Gly Gly
                245                 250                 255
Gly Leu Val Gln Pro Gly Gly Ser Leu Lys Leu Ser Cys Ala Ala Ser
                260                 265                 270
Gly Phe Thr Phe Asn Lys Tyr Ala Met Asn Trp Val Arg Gln Ala Pro
                275                 280                 285
Gly Lys Gly Leu Glu Trp Val Ala Arg Ile Arg Ser Lys Tyr Asn Asn
                290                 295                 300
Tyr Ala Thr Tyr Tyr Ala Asp Ser Val Lys Asp Arg Phe Thr Ile Ser
305                 310                 315                 320
Arg Asp Asp Ser Lys Asn Thr Ala Tyr Leu Gln Met Asn Asn Leu Lys
                325                 330                 335
Thr Glu Asp Thr Ala Val Tyr Tyr Cys Val Arg His Gly Asn Phe Gly
                340                 345                 350
Asn Ser Tyr Ile Ser Tyr Trp Ala Tyr Trp Gly Gln Gly Thr Leu Val
                355                 360                 365
Thr Val Ser Ser Gly Gly Gly Gly Ser Gly Gly Gly Gly Ser Gly Gly
                370                 375                 380
Gly Gly Ser Gln Thr Val Val Thr Gln Glu Pro Ser Leu Thr Val Ser
385                 390                 395                 400
Pro Gly Gly Thr Val Thr Leu Thr Cys Gly Ser Ser Thr Gly Ala Val
                405                 410                 415
Thr Ser Gly Asn Tyr Pro Asn Trp Val Gln Gln Lys Pro Gly Gln Ala
                420                 425                 430
Pro Arg Gly Leu Ile Gly Gly Thr Lys Phe Leu Ala Pro Gly Thr Pro
                435                 440                 445
Ala Arg Phe Ser Gly Ser Leu Leu Gly Gly Lys Ala Ala Leu Thr Leu
                450                 455                 460
Ser Gly Val Gln Pro Glu Asp Glu Ala Glu Tyr Tyr Cys Val Leu Trp
465                 470                 475                 480
Tyr Ser Asn Arg Trp Val Phe Gly Gly Gly Thr Lys Leu Thr Val Leu
                485                 490                 495
Gly Gly Gly Gly Asp Lys Thr His Thr Cys Pro Pro Cys Pro Ala Pro
                500                 505                 510
```

-continued

```
Glu Leu Leu Gly Gly Pro Ser Val Phe Leu Phe Pro Lys Pro Lys
            515                 520                 525

Asp Thr Leu Met Ile Ser Arg Thr Pro Glu Val Thr Cys Val Val
530                 535                 540

Asp Val Ser His Glu Asp Pro Glu Val Lys Phe Asn Trp Tyr Val Asp
545                 550                 555                 560

Gly Val Glu Val His Asn Ala Lys Thr Lys Pro Cys Glu Glu Gln Tyr
                565                 570                 575

Gly Ser Thr Tyr Arg Cys Val Ser Val Leu Thr Val Leu His Gln Asp
            580                 585                 590

Trp Leu Asn Gly Lys Glu Tyr Lys Cys Lys Val Ser Asn Lys Ala Leu
            595                 600                 605

Pro Ala Pro Ile Glu Lys Thr Ile Ser Lys Ala Lys Gly Gln Pro Arg
            610                 615                 620

Glu Pro Gln Val Tyr Thr Leu Pro Pro Ser Arg Glu Glu Met Thr Lys
625                 630                 635                 640

Asn Gln Val Ser Leu Thr Cys Leu Val Lys Gly Phe Tyr Pro Ser Asp
                645                 650                 655

Ile Ala Val Glu Trp Glu Ser Asn Gly Gln Pro Glu Asn Asn Tyr Lys
            660                 665                 670

Thr Thr Pro Pro Val Leu Asp Ser Asp Gly Ser Phe Phe Leu Tyr Ser
            675                 680                 685

Lys Leu Thr Val Asp Lys Ser Arg Trp Gln Gln Gly Asn Val Phe Ser
            690                 695                 700

Cys Ser Val Met His Glu Ala Leu His Asn His Tyr Thr Gln Lys Ser
705                 710                 715                 720

Leu Ser Leu Ser Pro Gly Gly Gly Gly Ser Gly Gly Gly Gly Ser Gly
                725                 730                 735

Gly Gly Gly Ser Gly Gly Gly Gly Ser Gly Gly Gly Gly Ser Gly Gly
            740                 745                 750

Gly Gly Ser Asp Lys Thr His Thr Cys Pro Pro Cys Pro Ala Pro Glu
            755                 760                 765

Leu Leu Gly Gly Pro Ser Val Phe Leu Phe Pro Lys Pro Lys Asp
            770                 775                 780

Thr Leu Met Ile Ser Arg Thr Pro Glu Val Thr Cys Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Cys Glu Glu Gln Tyr Gly
            820                 825                 830

Ser Thr Tyr Arg Cys Val Ser Val Leu Thr Val Leu His Gln Asp Trp
            835                 840                 845

Leu Asn Gly Lys Glu Tyr Lys Cys Lys Val Ser Asn Lys Ala Leu Pro
850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
            915                 920                 925

Thr Pro Pro Val Leu Asp Ser Asp Gly Ser Phe Phe Leu Tyr Ser Lys
```

```
              930                 935                 940
Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980

<210> SEQ ID NO 105
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 CD19 97-G1RE-C2

<400> SEQUENCE: 105

Ser Tyr Gly Met His
1               5

<210> SEQ ID NO 106
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 CD19 97-G1RE-C2

<400> SEQUENCE: 106

Val Ile Ser Tyr Glu Gly Ser Asn Lys Tyr Tyr Ala Glu Ser Val Lys
1               5                   10                  15

Gly

<210> SEQ ID NO 107
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR3 CD19 97-G1RE-C2

<400> SEQUENCE: 107

Asp Arg Gly Thr Ile Phe Gly Asn Tyr Gly Leu Glu Val
1               5                   10

<210> SEQ ID NO 108
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CD19 97-G1RE-C2 CC

<400> SEQUENCE: 108

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Cys Leu Glu Trp Val
        35                  40                  45

Ala Val Ile Ser Tyr Glu Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
            85                  90                  95

Ala Arg Asp Arg Gly Thr Ile Phe Gly Asn Tyr Gly Leu Glu Val Trp
                100                 105                 110

Gly Gln Gly Thr Thr Val Thr Val Ser Ser
        115                 120

<210> SEQ ID NO 109
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR1 CD19 97-G1RE-C2

<400> SEQUENCE: 109

Arg Ser Ser Gln Ser Leu Leu His Lys Asn Ala Phe Asn Tyr Leu Asp
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 CD19 97-G1RE-C2

<400> SEQUENCE: 110

Leu Gly Ser Asn Arg Ala Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR3 CD19 97-G1RE-C2

<400> SEQUENCE: 111

Met Gln Ala Leu Gln Thr Pro Phe Thr
1               5

<210> SEQ ID NO 112
<211> LENGTH: 112
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CD19 97-G1RE-C2 CC

<400> SEQUENCE: 112
```

```
Asp Ile Val Met Thr Gln Ser Pro Leu Ser Leu Pro Val Ile Ser Gly
1               5                   10                  15

Glu Pro Ala Ser Ile Ser Cys Arg Ser Ser Gln Ser Leu Leu His Lys
            20                  25                  30

Asn Ala Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Cys Gly Thr Lys Val Asp Ile Lys
            100                 105                 110
```

<210> SEQ ID NO 113
<211> LENGTH: 525
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 97-G1RE-C2 CC x I2C0

<400> SEQUENCE: 113

```
Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Ile Ser Gly Glu Pro Ala Ser Ile Ser Cys Arg Ser Ser
        35                  40                  45

Gln Ser Leu Leu His Lys Asn Ala Phe Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Phe Thr Phe Gly Cys Gly
        115                 120                 125

Thr Lys Val Asp Ile Lys Gly Gly Gly Ser Gly Gly Gly Gly Ser
    130                 135                 140

Gly Gly Gly Gly Ser Gln Val Gln Leu Val Glu Ser Gly Gly Gly Val
145                 150                 155                 160

Val Gln Pro Gly Arg Ser Leu Arg Leu Ser Cys Ala Ala Ser Gly Phe
                165                 170                 175

Thr Phe Ser Ser Tyr Gly Met His Trp Val Arg Gln Ala Pro Gly Lys
            180                 185                 190

Cys Leu Glu Trp Val Ala Val Ile Ser Tyr Glu Gly Ser Asn Lys Tyr
        195                 200                 205

Tyr Ala Glu Ser Val Lys Gly Arg Phe Thr Ile Ser Arg Asp Asn Ser
    210                 215                 220

Lys Asn Thr Leu Tyr Leu Gln Met Asn Ser Leu Arg Asp Glu Asp Thr
225                 230                 235                 240
```

Ala Val Tyr Tyr Cys Ala Arg Asp Arg Gly Thr Ile Phe Gly Asn Tyr
                245                 250                 255

Gly Leu Glu Val Trp Gly Gln Gly Thr Val Thr Val Ser Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Lys Leu Ser Cys Ala Ala Ser Gly Phe Thr
290                 295                 300

Phe Asn Lys Tyr Ala Met Asn Trp Val Arg Gln Ala Pro Gly Lys Gly
305                 310                 315                 320

Leu Glu Trp Val Ala Arg Ile Arg Ser Lys Tyr Asn Asn Tyr Ala Thr
                325                 330                 335

Tyr Tyr Ala Asp Ser Val Lys Asp Arg Phe Thr Ile Ser Arg Asp Asp
                340                 345                 350

Ser Lys Asn Thr Ala Tyr Leu Gln Met Asn Asn Leu Lys Thr Glu Asp
            355                 360                 365

Thr Ala Val Tyr Tyr Cys Val Arg His Gly Asn Phe Gly Asn Ser Tyr
        370                 375                 380

Ile Ser Tyr Trp Ala Tyr Trp Gly Gln Gly Thr Leu Val Thr Val Ser
385                 390                 395                 400

Ser Gly Gly Gly Ser Gly Gly Gly Ser Gly Gly Gly Ser
                405                 410                 415

Gln Thr Val Val Thr Gln Glu Pro Ser Leu Thr Val Ser Pro Gly Gly
            420                 425                 430

Thr Val Thr Leu Thr Cys Gly Ser Ser Thr Gly Ala Val Thr Ser Gly
        435                 440                 445

Asn Tyr Pro Asn Trp Val Gln Gln Lys Pro Gly Gln Ala Pro Arg Gly
    450                 455                 460

Leu Ile Gly Gly Thr Lys Phe Leu Ala Pro Gly Thr Pro Ala Arg Phe
465                 470                 475                 480

Ser Gly Ser Leu Leu Gly Gly Lys Ala Ala Leu Thr Leu Ser Gly Val
                485                 490                 495

Gln Pro Glu Asp Glu Ala Glu Tyr Tyr Cys Val Leu Tyr Ser Asn
            500                 505                 510

Arg Trp Val Phe Gly Gly Gly Thr Lys Leu Thr Val Leu
        515                 520                 525

<210> SEQ ID NO 114
<211> LENGTH: 1013
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 97-G1RE-C2 CC x I2C0-scFc

<400> SEQUENCE: 114

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Ile Ser Gly Glu Pro Ala Ser Ile Ser Cys Arg Ser Ser
        35                  40                  45

Gln Ser Leu Leu His Lys Asn Ala Phe Asn Tyr Leu Asp Trp Tyr Leu
    50                  55                  60

```
Gln Lys Pro Gly Gln Ser Pro Gln Leu Leu Ile Tyr Leu Gly Ser Asn
 65                  70                  75                  80

Arg Ala Ser Gly Val Pro Asp Arg Phe Ser Gly Ser Gly Ser Gly Thr
                 85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Phe Thr Phe Gly Cys Gly
            115                 120                 125

Thr Lys Val Asp Ile Lys Gly Gly Gly Ser Gly Gly Gly Gly Ser
            130                 135                 140

Gly Gly Gly Gly Ser Gln Val Gln Leu Val Glu Ser Gly Gly Gly Val
145                 150                 155                 160

Val Gln Pro Gly Arg Ser Leu Arg Leu Ser Cys Ala Ala Ser Gly Phe
                165                 170                 175

Thr Phe Ser Ser Tyr Gly Met His Trp Val Arg Gln Ala Pro Gly Lys
                180                 185                 190

Cys Leu Glu Trp Val Ala Val Ile Ser Tyr Glu Gly Ser Asn Lys Tyr
            195                 200                 205

Tyr Ala Glu Ser Val Lys Gly Arg Phe Thr Ile Ser Arg Asp Asn Ser
    210                 215                 220

Lys Asn Thr Leu Tyr Leu Gln Met Asn Ser Leu Arg Asp Glu Asp Thr
225                 230                 235                 240

Ala Val Tyr Tyr Cys Ala Arg Asp Arg Gly Thr Ile Phe Gly Asn Tyr
                245                 250                 255

Gly Leu Glu Val Trp Gly Gln Gly Thr Val Thr Val Ser Ser Gly
            260                 265                 270

Gly Gly Gly Ser Glu Val Gln Leu Val Glu Ser Gly Gly Gly Leu Val
    275                 280                 285

Gln Pro Gly Gly Ser Leu Lys Leu Ser Cys Ala Ala Ser Gly Phe Thr
290                 295                 300

Phe Asn Lys Tyr Ala Met Asn Trp Val Arg Gln Ala Pro Gly Lys Gly
305                 310                 315                 320

Leu Glu Trp Val Ala Arg Ile Arg Ser Lys Tyr Asn Asn Tyr Ala Thr
            325                 330                 335

Tyr Tyr Ala Asp Ser Val Lys Asp Arg Phe Thr Ile Ser Arg Asp Asp
        340                 345                 350

Ser Lys Asn Thr Ala Tyr Leu Gln Met Asn Asn Leu Lys Thr Glu Asp
        355                 360                 365

Thr Ala Val Tyr Tyr Cys Val Arg His Gly Asn Phe Gly Asn Ser Tyr
        370                 375                 380

Ile Ser Tyr Trp Ala Tyr Trp Gly Gln Gly Thr Leu Val Thr Val Ser
385                 390                 395                 400

Ser Gly Gly Gly Gly Ser Gly Gly Gly Gly Ser Gly Gly Gly Gly Ser
                405                 410                 415

Gln Thr Val Val Thr Gln Glu Pro Ser Leu Thr Val Ser Pro Gly Gly
            420                 425                 430

Thr Val Thr Leu Thr Cys Gly Ser Ser Thr Gly Ala Val Thr Ser Gly
            435                 440                 445

Asn Tyr Pro Asn Trp Val Gln Gln Lys Pro Gly Gln Ala Pro Arg Gly
        450                 455                 460

Leu Ile Gly Gly Thr Lys Phe Leu Ala Pro Gly Thr Pro Ala Arg Phe
465                 470                 475                 480
```

Ser Gly Ser Leu Leu Gly Gly Lys Ala Ala Leu Thr Leu Ser Gly Val
                485                 490                 495

Gln Pro Glu Asp Glu Ala Glu Tyr Tyr Cys Val Leu Trp Tyr Ser Asn
            500                 505                 510

Arg Trp Val Phe Gly Gly Gly Thr Lys Leu Thr Val Leu Gly Gly Gly
            515                 520                 525

Gly Asp Lys Thr His Thr Cys Pro Cys Pro Ala Pro Glu Leu Leu
    530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
            565                 570                 575

His Glu Asp Pro Glu Val Lys Phe Asn Trp Tyr Val Asp Gly Val Glu
            580                 585                 590

Val His Asn Ala Lys Thr Lys Pro Cys Glu Glu Gln Tyr Gly Ser Thr
        595                 600                 605

Tyr Arg Cys Val Ser Val Leu Thr Val Leu His Gln Asp Trp Leu Asn
610                 615                 620

Gly Lys Glu Tyr Lys Cys Lys Val Ser Asn Lys Ala Leu Pro Ala Pro
625                 630                 635                 640

Ile Glu Lys Thr Ile Ser Lys Ala Lys Gly Gln Pro Arg Glu Pro Gln
            645                 650                 655

Val Tyr Thr Leu Pro Pro Ser Arg Glu Glu Met Thr Lys Asn Gln Val
            660                 665                 670

Ser Leu Thr Cys Leu Val Lys Gly Phe Tyr Pro Ser Asp Ile Ala Val
            675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Lys Leu Thr
705                 710                 715                 720

Val Asp Lys Ser Arg Trp Gln Gln Gly Asn Val Phe Ser Cys Ser Val
            725                 730                 735

Met His Glu Ala Leu His Asn His Tyr Thr Gln Lys Ser Leu Ser Leu
            740                 745                 750

Ser Pro Gly Lys Gly Gly Gly Ser Gly Gly Gly Ser Gly Gly
            755                 760                 765

Gly Gly Ser Gly Gly Gly Ser Gly Gly Gly Ser Gly Gly Gly
        770                 775                 780

Gly Ser Asp Lys Thr His Thr Cys Pro Cys Pro Ala Pro Glu Leu
785                 790                 795                 800

Leu Gly Gly Pro Ser Val Phe Leu Phe Pro Pro Lys Pro Lys Asp Thr
            805                 810                 815

Leu Met Ile Ser Arg Thr Pro Glu Val Thr Cys Val Val Val Asp Val
            820                 825                 830

Ser His Glu Asp Pro Glu Val Lys Phe Asn Trp Tyr Val Asp Gly Val
    835                 840                 845

Glu Val His Asn Ala Lys Thr Lys Pro Cys Glu Glu Gln Tyr Gly Ser
    850                 855                 860

Thr Tyr Arg Cys Val Ser Val Leu Thr Val Leu His Gln Asp Trp Leu
865                 870                 875                 880

Asn Gly Lys Glu Tyr Lys Cys Lys Val Ser Asn Lys Ala Leu Pro Ala
            885                 890                 895

Pro Ile Glu Lys Thr Ile Ser Lys Ala Lys Gly Gln Pro Arg Glu Pro

```
                    900             905             910
Gln Val Tyr Thr Leu Pro Pro Ser Arg Glu Glu Met Thr Lys Asn Gln
         915                 920                 925

Val Ser Leu Thr Cys Leu Val Lys Gly Phe Tyr Pro Ser Asp Ile Ala
     930                 935                 940

Val Glu Trp Glu Ser Asn Gly Gln Pro Glu Asn Asn Tyr Lys Thr Thr
945                 950                 955                 960

Pro Pro Val Leu Asp Ser Asp Gly Ser Phe Phe Leu Tyr Ser Lys Leu
                965                 970                 975

Thr Val Asp Lys Ser Arg Trp Gln Gln Gly Asn Val Phe Ser Cys Ser
            980                 985                 990

Val Met His Glu Ala Leu His Asn  His Tyr Thr Gln Lys  Ser Leu Ser
        995                 1000                1005

Leu Ser  Pro Gly Lys
    1010
```

<210> SEQ ID NO 115
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 CDH3 G8A 6-B12

<400> SEQUENCE: 115

```
Ser Tyr Pro Ile Asn
1               5
```

<210> SEQ ID NO 116
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 CDH3 G8A 6-B12

<400> SEQUENCE: 116

```
Val Ile Trp Thr Gly Gly Gly Thr Asn Tyr Ala Ser Ser Val Lys Gly
1               5                   10                  15
```

<210> SEQ ID NO 117
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR3 CDH3 G8A 6-B12

<400> SEQUENCE: 117

```
Ser Arg Gly Val Tyr Asp Phe Asp Gly Arg Gly Ala Met Asp Tyr
1               5                   10                  15
```

<210> SEQ ID NO 118
<211> LENGTH: 17
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: MISC_FEATURE
<223> OTHER INFORMATION: VL CDR1 CDH3 G8A 6-B12

<400> SEQUENCE: 118

Lys Ser Ser Gln Ser Leu Leu Tyr Ser Ser Asn Gln Lys Asn Tyr Phe
1               5                   10                  15
Ala

<210> SEQ ID NO 119
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 CDH3 G8A 6-B12

<400> SEQUENCE: 119

Trp Ala Ser Thr Arg Glu Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR3 CDH3 G8A 6-B12

<400> SEQUENCE: 120

Gln Gln Tyr Tyr Ser Tyr Pro Tyr Thr
1               5

<210> SEQ ID NO 121
<211> LENGTH: 123
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDH3 G8A 6-B12

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
        35                  40                  45

Gly Val Ile Trp Thr Gly Gly Thr Asn Tyr Ala Ser Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
            100                 105                 110

Trp Gly Gln Gly Thr Leu Val Thr Val Ser Ser
        115                 120
```

```
<210> SEQ ID NO 122
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDH3 G8A 6-B12

<400> SEQUENCE: 122

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Phe Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys

<210> SEQ ID NO 123
<211> LENGTH: 251
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 scFv

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
        35                  40                  45

Gly Val Ile Trp Thr Gly Gly Gly Thr Asn Tyr Ala Ser Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160
```

Cys Lys Ser Ser Gln Ser Leu Leu Tyr Ser Ser Asn Gln Lys Asn Tyr
                165                 170                 175

Phe Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Ser Tyr Pro Tyr
225                 230                 235                 240

Thr Phe Gly Gln Gly Thr Lys Leu Glu Ile Lys
                245                 250

<210> SEQ ID NO 124
<211> LENGTH: 506
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 x I2C0 bispecific molecule

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
        35                  40                  45

Gly Val Ile Trp Thr Gly Gly Thr Asn Tyr Ala Ser Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Gln Lys Asn Tyr
                165                 170                 175

Phe Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Ser Tyr Pro Tyr
225                 230                 235                 240

Thr Phe Gly Gln Gly Thr Lys Leu Glu Ile Lys Ser Gly Gly Gly
                245                 250                 255

-continued

Ser Glu Val Gln Leu Val Glu Ser Gly Gly Leu Val Gln Pro Gly
            260                 265                 270

Gly Ser Leu Lys Leu Ser Cys Ala Ala Ser Gly Phe Thr Phe Asn Lys
        275                 280                 285

Tyr Ala Met Asn Trp Val Arg Gln Ala Pro Gly Lys Gly Leu Glu Trp
    290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
        355                 360                 365

Trp Ala Tyr Trp Gly Gln Gly Thr Leu Val Thr Val Ser Ser Gly Gly
    370                 375                 380

Gly Gly Ser Gly Gly Gly Ser Gly Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
        435                 440                 445

Gly Thr Lys Phe Leu Ala Pro Gly Thr Pro Ala Arg Phe Ser Gly Ser
    450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu
            500                 505

<210> SEQ ID NO 125
<211> LENGTH: 994
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 x I2C0 bispecific molecule HLE

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
        35                  40                  45

Gly Val Ile Trp Thr Gly Gly Thr Asn Tyr Ala Ser Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

```
Lys Ser Arg Gly Val Tyr Asp Phe Asp Gly Arg Gly Ala Met Asp Tyr
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Asp Ile Val Met Thr Gln
        130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Asn Gln Lys Asn Tyr
                165                 170                 175

Phe Ala Trp Tyr Gln Gln Lys Pro Gly Gln Pro Pro Lys Leu Leu Ile
                180                 185                 190

Tyr Trp Ala Ser Thr Arg Glu Ser Gly Val Pro Asp Arg Phe Ser Gly
            195                 200                 205

Ser Gly Ser Gly Thr Asp Phe Thr Leu Thr Ile Ser Ser Leu Gln Ala
        210                 215                 220

Glu Asp Val Ala Val Tyr Tyr Cys Gln Gln Tyr Tyr Ser Tyr Pro Tyr
225                 230                 235                 240

Thr Phe Gly Gln Gly Thr Lys Leu Glu Ile Lys Ser Gly Gly Gly Gly
                245                 250                 255

Ser Glu Val Gln Leu Val Glu Ser Gly Gly Gly Leu Val Gln Pro Gly
            260                 265                 270

Gly Ser Leu Lys Leu Ser Cys Ala Ala Ser Gly Phe Thr Phe Asn Lys
        275                 280                 285

Tyr Ala Met Asn Trp Val Arg Gln Ala Pro Gly Lys Gly Leu Glu Trp
            290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
        355                 360                 365

Trp Ala Tyr Trp Gly Gln Gly Thr Leu Val Thr Val Ser Ser Gly Gly
            370                 375                 380

Gly Gly Ser Gly Gly Gly Gly Ser Gly Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
        435                 440                 445

Gly Thr Lys Phe Leu Ala Pro Gly Thr Pro Ala Arg Phe Ser Gly Ser
            450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu Gly Gly Gly Gly Asp Lys
            500                 505                 510

Thr His Thr Cys Pro Pro Cys Pro Ala Pro Glu Leu Leu Gly Gly Pro
```

-continued

```
                515                 520                 525
Ser Val Phe Leu Phe Pro Pro Lys Pro Lys Asp Thr Leu Met Ile Ser
    530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
                565                 570                 575

Ala Lys Thr Lys Pro Cys Glu Glu Gln Tyr Gly Ser Thr Tyr Arg Cys
            580                 585                 590

Val Ser Val Leu Thr Val Leu His Gln Asp Trp Leu Asn Gly Lys Glu
                595                 600                 605

Tyr Lys Cys Lys Val Ser Asn Lys Ala Leu Pro Ala Pro Ile Glu Lys
            610                 615                 620

Thr Ile Ser Lys Ala Lys Gly Gln Pro Arg Glu Pro Gln Val Tyr Thr
625                 630                 635                 640

Leu Pro Pro Ser Arg Glu Glu Met Thr Lys Asn Gln Val Ser Leu Thr
                645                 650                 655

Cys Leu Val Lys Gly Phe Tyr Pro Ser Asp Ile Ala Val Glu Trp Glu
            660                 665                 670

Ser Asn Gly Gln Pro Glu Asn Asn Tyr Lys Thr Thr Pro Pro Val Leu
        675                 680                 685

Asp Ser Asp Gly Ser Phe Phe Leu Tyr Ser Lys Leu Thr Val Asp Lys
    690                 695                 700

Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
                725                 730                 735

Lys Gly Gly Gly Gly Ser Gly Gly Gly Ser Gly Gly Gly Gly Ser
            740                 745                 750

Gly Gly Gly Gly Ser Gly Gly Gly Ser Gly Gly Gly Gly Ser Asp
        755                 760                 765

Lys Thr His Thr Cys Pro Pro Cys Pro Ala Pro Glu Leu Leu Gly Gly
    770                 775                 780

Pro Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Cys Glu Glu Gln Tyr Gly Ser Thr Tyr Arg
        835                 840                 845

Cys Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Glu Glu Met Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940
```

-continued

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
                965                 970                 975

Glu Ala Leu His Asn His Tyr Thr Gln Lys Ser Leu Ser Leu Ser Pro
            980                 985                 990

Gly Lys

<210> SEQ ID NO 126
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR1 VH

<400> SEQUENCE: 126

Asn His Ile Ile His
1               5

<210> SEQ ID NO 127
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR2 VH

<400> SEQUENCE: 127

Tyr Ile Asn Pro Tyr Pro Gly Tyr His Ala Tyr Asn Glu Lys Phe Gln
1               5                   10                  15

Gly

<210> SEQ ID NO 128
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR3 VH

<400> SEQUENCE: 128

Asp Gly Tyr Tyr Arg Asp Thr Asp Val Leu Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR1 VL

<400> SEQUENCE: 129

Gln Ala Ser Gln Asp Ile Ser Asn Tyr Leu Asn
1               5                   10

```
<210> SEQ ID NO 130
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR2 VL

<400> SEQUENCE: 130

Tyr Thr Ser Arg Leu His Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR3 VL

<400> SEQUENCE: 131

Gln Gln Gly Asn Thr Leu Pro Trp Thr
1               5

<210> SEQ ID NO 132
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) VH

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser
        115                 120

<210> SEQ ID NO 133
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) VL
```

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Thr Gly Val Pro Ser Arg Phe Ser Gly
50                  55                  60

Ser Gly Ser Gly Thr Asp Phe Thr Phe Thr Ile Ser Ser Leu Glu Pro
65                  70                  75                  80

Glu Asp Ile Ala Thr Tyr Tyr Cys Gln Gln Gly Asn Thr Leu Pro Trp
                85                  90                  95

Thr Phe Gly Cys Gly Thr Lys Leu Glu Ile Lys
            100                 105

<210> SEQ ID NO 134
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) scFv

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
        195                 200                 205

Phe Thr Ile Ser Ser Leu Glu Pro Glu Asp Ile Ala Thr Tyr Tyr Cys
    210                 215                 220

Gln Gln Gly Asn Thr Leu Pro Trp Thr Phe Gly Cys Gly Thr Lys Leu

-continued

```
            225                 230                 235                 240

Glu Ile Lys

<210> SEQ ID NO 135
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) x I2C0 bispecific
      molecule

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
        195                 200                 205

Phe Thr Ile Ser Ser Leu Glu Pro Glu Asp Ile Ala Thr Tyr Tyr Cys
    210                 215                 220

Gln Gln Gly Asn Thr Leu Pro Trp Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
```

-continued

```
                325                 330                 335
Leu Lys Thr Glu Asp Thr Ala Val Tyr Tyr Cys Val Arg His Gly Asn
            340                 345                 350
Phe Gly Asn Ser Tyr Ile Ser Tyr Trp Ala Tyr Trp Gly Gln Gly Thr
            355                 360                 365
Leu Val Thr Val Ser Ser Gly Gly Gly Gly Ser Gly Gly Gly Gly Ser
370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
            405                 410                 415
Ala Val Thr Ser Gly Asn Tyr Pro Asn Trp Val Gln Gln Lys Pro Gly
            420                 425                 430
Gln Ala Pro Arg Gly Leu Ile Gly Gly Thr Lys Phe Leu Ala Pro Gly
            435                 440                 445
Thr Pro Ala Arg Phe Ser Gly Ser Leu Leu Gly Gly Lys Ala Ala Leu
        450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
            485                 490                 495
Val Leu
```

<210> SEQ ID NO 136
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) x I2C0-scFc bispecific molecule HLE

<400> SEQUENCE: 136

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn His
            20                  25                  30
Ile Ile His Trp Val Arg Gln Ala Pro Gly Gln Cys Leu Glu Trp Met
        35                  40                  45
Gly Tyr Ile Asn Pro Tyr Pro Gly Tyr His Ala Tyr Asn Glu Lys Phe
    50                  55                  60
Gln Gly Arg Ala Thr Met Thr Ser Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Gly Tyr Tyr Arg Asp Thr Asp Val Leu Asp Tyr Trp Gly
            100                 105                 110
Gln Gly Thr Leu Val Thr Val Ser Ser Gly Gly Gly Gly Ser Gly Gly
        115                 120                 125
Gly Gly Ser Gly Gly Gly Gly Ser Asp Ile Gln Met Thr Gln Ser Pro
    130                 135                 140
Ser Ser Leu Ser Ala Ser Val Gly Asp Arg Val Thr Ile Thr Cys Gln
145                 150                 155                 160
Ala Ser Gln Asp Ile Ser Asn Tyr Leu Asn Trp Tyr Gln Gln Lys Pro
```

```
                165                 170                 175
Gly Lys Ala Pro Lys Leu Leu Ile Tyr Tyr Thr Ser Arg Leu His Thr
                180                 185                 190

Gly Val Pro Ser Arg Phe Ser Gly Ser Gly Ser Gly Thr Asp Phe Thr
                195                 200                 205

Phe Thr Ile Ser Ser Leu Glu Pro Glu Asp Ile Ala Thr Tyr Tyr Cys
            210                 215                 220

Gln Gln Gly Asn Thr Leu Pro Trp Thr Phe Gly Cys Gly Thr Lys Val
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Gly Ser Gly Gly Gly Gly Ser
            370                 375                 380

Gly Gly Gly Gly Ser Gln Thr Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
            530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590
```

```
Gln Asp Trp Leu Asn Gly Lys Glu Tyr Lys Cys Lys Val Ser Asn Lys
            595                 600                 605
Ala Leu Pro Ala Pro Ile Glu Lys Thr Ile Ser Lys Ala Lys Gly Gln
610                 615                 620
Pro Arg Glu Pro Gln Val Tyr Thr Leu Pro Pro Ser Arg Glu Glu Met
625                 630                 635                 640
Thr Lys Asn Gln Val Ser Leu Thr Cys Leu Val Lys Gly Phe Tyr Pro
                645                 650                 655
Ser Asp Ile Ala Val Glu Trp Glu Ser Asn Gly Gln Pro Glu Asn Asn
            660                 665                 670
Tyr Lys Thr Thr Pro Pro Val Leu Asp Ser Asp Gly Ser Phe Phe Leu
        675                 680                 685
Tyr Ser Lys Leu Thr Val Asp Lys Ser Arg Trp Gln Gln Gly Asn Val
    690                 695                 700
Phe Ser Cys Ser Val Met His Glu Ala Leu His Asn His Tyr Thr Gln
705                 710                 715                 720
Lys Ser Leu Ser Leu Ser Pro Gly Lys Gly Gly Gly Ser Gly Gly
                725                 730                 735
Gly Gly Ser Gly Gly Gly Ser Gly Gly Gly Ser Gly Gly Gly
            740                 745                 750
Gly Ser Gly Gly Gly Ser Asp Lys Thr His Thr Cys Pro Pro Cys
        755                 760                 765
Pro Ala Pro Glu Leu Leu Gly Gly Pro Ser Val Phe Leu Phe Pro Pro
770                 775                 780
Lys Pro Lys Asp Thr Leu Met Ile Ser Arg Thr Pro Glu Val Thr Cys
785                 790                 795                 800
Val Val Val Asp Val Ser His Glu Asp Pro Glu Val Lys Phe Asn Trp
                805                 810                 815
Tyr Val Asp Gly Val Glu Val His Asn Ala Lys Thr Lys Pro Cys Glu
            820                 825                 830
Glu Gln Tyr Gly Ser Thr Tyr Arg Cys Val Ser Val Leu Thr Val Leu
        835                 840                 845
His Gln Asp Trp Leu Asn Gly Lys Glu Tyr Lys Cys Lys Val Ser Asn
    850                 855                 860
Lys Ala Leu Pro Ala Pro Ile Glu Lys Thr Ile Ser Lys Ala Lys Gly
865                 870                 875                 880
Gln Pro Arg Glu Pro Gln Val Tyr Thr Leu Pro Pro Ser Arg Glu Glu
                885                 890                 895
Met Thr Lys Asn Gln Val Ser Leu Thr Cys Leu Val Lys Gly Phe Tyr
            900                 905                 910
Pro Ser Asp Ile Ala Val Glu Trp Glu Ser Asn Gly Gln Pro Glu Asn
        915                 920                 925
Asn Tyr Lys Thr Thr Pro Pro Val Leu Asp Ser Asp Gly Ser Phe Phe
    930                 935                 940
Leu Tyr Ser Lys Leu Thr Val Asp Lys Ser Arg Trp Gln Gln Gly Asn
945                 950                 955                 960
Val Phe Ser Cys Ser Val Met His Glu Ala Leu His Asn His Tyr Thr
                965                 970                 975
Gln Lys Ser Leu Ser Leu Ser Pro Gly Lys
            980                 985

<210> SEQ ID NO 137
<211> LENGTH: 5
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR1

<400> SEQUENCE: 137

Asp Tyr Tyr Met Tyr
1               5

<210> SEQ ID NO 138
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR2

<400> SEQUENCE: 138

Ile Ile Ser Asp Ala Gly Tyr Tyr Thr Tyr Tyr Ser Asp Ile Ile Lys
1               5                   10                  15

Gly

<210> SEQ ID NO 139
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR3

<400> SEQUENCE: 139

Gly Phe Pro Leu Leu Arg His Gly Ala Met Asp Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR1

<400> SEQUENCE: 140

Lys Ala Ser Gln Asn Val Asp Ala Asn Val Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR2

<400> SEQUENCE: 141

Ser Ala Ser Tyr Val Tyr Trp
1               5
```

<210> SEQ ID NO 142
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR3

<400> SEQUENCE: 142

Gln Gln Tyr Asp Gln Gln Leu Ile Thr
1               5

<210> SEQ ID NO 143
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH

<400> SEQUENCE: 143

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
        115                 120

<210> SEQ ID NO 144
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ala Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

Ser Ala Ser Gly Thr Asp Phe Thr Leu Thr Ile Ser Ser Val Gln Ser

```
                65                  70                  75                  80
Glu Asp Phe Ala Thr Tyr Tyr Cys Gln Gln Tyr Asp Gln Gln Leu Ile
                    85                  90                  95

Thr Phe Gly Cys Gly Thr Lys Leu Glu Ile Lys
                100                 105

<210> SEQ ID NO 145
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC scFv

<400> SEQUENCE: 145

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
                20                  25                  30

Tyr Met Tyr Trp Val Arg Gln Ala Pro Gly Lys Cys Leu Glu Trp Val
            35                  40                  45

Ala Ile Ile Ser Asp Ala Gly Tyr Tyr Thr Tyr Tyr Ser Asp Ile Ile
        50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys

<210> SEQ ID NO 146
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 bispecific molecule
```

<400> SEQUENCE: 146

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

```
Ala Val Thr Ser Gly Asn Tyr Pro Asn Trp Val Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                485                 490                 495

Val Leu

<210> SEQ ID NO 147
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0-scFc bispecific HLE
      molecule

<400> SEQUENCE: 147

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255
```

```
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
370                 375                 380

Gly Gly Gly Ser Gln Thr Val Val Thr Gln Glu Pro Ser Leu Thr
385             390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670
```

Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
                725                 730                 735

Gly Gly Ser Gly Gly Gly Ser Gly Gly Gly Ser Gly Gly
            740                 745                 750

Gly Ser Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 148
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0-scFc_delGK bispecific
      HLE molecule

<400> SEQUENCE: 148

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

-continued

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
             85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
            210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

```
Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
```

```
865                 870                 875                 880
Arg Glu Pro Gln Val Tyr Thr Leu Pro Pro Ser Arg Glu Met Thr
                885                 890                 895
Lys Asn Gln Val Ser Leu Thr Cys Leu Val Lys Gly Phe Tyr Pro Ser
            900                 905                 910
Asp Ile Ala Val Glu Trp Glu Ser Asn Gly Gln Pro Glu Asn Asn Tyr
                915                 920                 925
Lys Thr Thr Pro Pro Val Leu Asp Ser Asp Gly Ser Phe Phe Leu Tyr
            930                 935                 940
Ser Lys Leu Thr Val Asp Lys Ser Arg Trp Gln Gln Gly Asn Val Phe
945                 950                 955                 960
Ser Cys Ser Val Met His Glu Ala Leu His Asn His Tyr Thr Gln Lys
                965                 970                 975
Ser Leu Ser Leu Ser Pro Gly Lys
            980

<210> SEQ ID NO 149
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 CC (103/43)-scFc
      bispecific molecule

<400> SEQUENCE: 149

Gln Val Gln Leu Val Glu Ser Gly Gly Gly Leu Val Lys Pro Gly Glu
1               5                   10                  15
Ser Leu Arg Leu Ser Cys Ala Ala Ser Gly Phe Thr Phe Ser Asp Tyr
            20                  25                  30
Tyr Met Tyr Trp Val Arg Gln Ala Pro Gly Lys Cys Leu Glu Trp Val
        35                  40                  45
Ala Ile Ile Ser Asp Ala Gly Tyr Tyr Thr Tyr Tyr Ser Asp Ile Ile
    50                  55                  60
Lys Gly Arg Phe Thr Ile Ser Arg Asp Asn Ala Lys Asn Ser Leu Tyr
65                  70                  75                  80
Leu Gln Met Asn Ser Leu Lys Ala Glu Asp Thr Ala Val Tyr Tyr Cys
                85                  90                  95
Ala Arg Gly Phe Pro Leu Leu Arg His Gly Ala Met Asp Tyr Trp Gly
            100                 105                 110
Gln Gly Thr Leu Val Thr Val Ser Ser Gly Gly Gly Gly Ser Gly Gly
        115                 120                 125
Gly Gly Ser Gly Gly Gly Ser Asp Ile Gln Met Thr Gln Ser Pro
    130                 135                 140
Ser Ser Leu Ser Ala Ser Val Gly Asp Arg Val Thr Ile Thr Cys Lys
145                 150                 155                 160
Ala Ser Gln Asn Val Asp Ala Asn Val Ala Trp Tyr Gln Gln Lys Pro
                165                 170                 175
Gly Gln Ala Pro Lys Ser Leu Ile Tyr Ser Ala Ser Tyr Val Tyr Trp
            180                 185                 190
Asp Val Pro Ser Arg Phe Ser Gly Ser Ala Ser Gly Thr Asp Phe Thr
        195                 200                 205
Leu Thr Ile Ser Ser Val Gln Ser Glu Asp Phe Ala Thr Tyr Tyr Cys
    210                 215                 220
```

```
Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
        355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu
```

<210> SEQ ID NO 150
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 CC (103/43)-scFc
    bispecific HLE molecule

<400> SEQUENCE: 150

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                 85                  90                  95

Ala Arg Gly Phe Pro Leu Leu Arg His Gly Ala Met Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Ser
    370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
                420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
```

-continued

```
                485                 490                 495
Val Leu Gly Gly Gly Asp Lys Thr His Thr Cys Pro Cys Pro
            500                 505                 510
Ala Pro Glu Leu Leu Gly Gly Pro Ser Val Phe Leu Phe Pro Pro Lys
            515                 520                 525
Pro Lys Asp Thr Leu Met Ile Ser Arg Thr Pro Glu Val Thr Cys Val
            530                 535                 540
Val Val Asp Val Ser His Glu Asp Pro Glu Val Lys Phe Asn Trp Tyr
545                 550                 555                 560
Val Asp Gly Val Glu Val His Asn Ala Lys Thr Lys Pro Cys Glu Glu
                565                 570                 575
Gln Tyr Gly Ser Thr Tyr Arg Cys Val Ser Val Leu Thr Val Leu His
            580                 585                 590
Gln Asp Trp Leu Asn Gly Lys Glu Tyr Lys Cys Lys Val Ser Asn Lys
            595                 600                 605
Ala Leu Pro Ala Pro Ile Glu Lys Thr Ile Ser Lys Ala Lys Gly Gln
            610                 615                 620
Pro Arg Glu Pro Gln Val Tyr Thr Leu Pro Pro Ser Arg Glu Glu Met
625                 630                 635                 640
Thr Lys Asn Gln Val Ser Leu Thr Cys Leu Val Lys Gly Phe Tyr Pro
                645                 650                 655
Ser Asp Ile Ala Val Glu Trp Glu Ser Asn Gly Gln Pro Glu Asn Asn
            660                 665                 670
Tyr Lys Thr Thr Pro Pro Val Leu Asp Ser Asp Gly Ser Phe Phe Leu
            675                 680                 685
Tyr Ser Lys Leu Thr Val Asp Lys Ser Arg Trp Gln Gln Gly Asn Val
            690                 695                 700
Phe Ser Cys Ser Val Met His Glu Ala Leu His Asn His Tyr Thr Gln
705                 710                 715                 720
Lys Ser Leu Ser Leu Ser Pro Gly Lys Gly Gly Gly Ser Gly Gly
                725                 730                 735
Gly Gly Ser Gly Gly Gly Gly Ser Gly Gly Gly Ser Gly Gly Gly
            740                 745                 750
Gly Ser Gly Gly Gly Gly Ser Asp Lys Thr His Thr Cys Pro Pro Cys
            755                 760                 765
Pro Ala Pro Glu Leu Leu Gly Gly Pro Ser Val Phe Leu Phe Pro Pro
            770                 775                 780
Lys Pro Lys Asp Thr Leu Met Ile Ser Arg Thr Pro Glu Val Thr Cys
785                 790                 795                 800
Val Val Val Asp Val Ser His Glu Asp Pro Glu Val Lys Phe Asn Trp
                805                 810                 815
Tyr Val Asp Gly Val Glu Val His Asn Ala Lys Thr Lys Pro Cys Glu
            820                 825                 830
Glu Gln Tyr Gly Ser Thr Tyr Arg Cys Val Ser Val Leu Thr Val Leu
            835                 840                 845
His Gln Asp Trp Leu Asn Gly Lys Glu Tyr Lys Cys Lys Val Ser Asn
            850                 855                 860
Lys Ala Leu Pro Ala Pro Ile Glu Lys Thr Ile Ser Lys Ala Lys Gly
865                 870                 875                 880
Gln Pro Arg Glu Pro Gln Val Tyr Thr Leu Pro Pro Ser Arg Glu Glu
                885                 890                 895
Met Thr Lys Asn Gln Val Ser Leu Thr Cys Leu Val Lys Gly Phe Tyr
                900                 905                 910
```

```
Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
        930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
        980                 985

<210> SEQ ID NO 151
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 CC (103/43)-scFc_delGK
      bispecific HLE molecule

<400> SEQUENCE: 151

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
```

```
                260                 265                 270
Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
            530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
            675                 680                 685
```

-continued

```
Tyr Ser Lys Leu Thr Val Asp Lys Ser Arg Trp Gln Gln Gly Asn Val
        690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
            725                 730                 735

Ser Gly Gly Gly Gly Ser Gly Gly Gly Ser Gly Gly Gly Gly Ser
            740                 745                 750

Gly Gly Gly Gly Ser Asp Lys Thr His Thr Cys Pro Pro Cys Pro Ala
            755                 760                 765

Pro Glu Leu Leu Gly Gly Pro Ser Val Phe Leu Phe Pro Pro Lys Pro
    770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
                820                 825                 830

Tyr Gly Ser Thr Tyr Arg Cys Val Ser Val Leu Thr Val Leu His Gln
            835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
            915                 920                 925

Lys Thr Thr Pro Pro Val Leu Asp Ser Asp Gly Ser Phe Phe Leu Tyr
        930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
            980

<210> SEQ ID NO 152
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR1

<400> SEQUENCE: 152

Asp Tyr Tyr Met Tyr
1               5

<210> SEQ ID NO 153
<211> LENGTH: 17
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR2

<400> SEQUENCE: 153

Ile Ile Ser Asp Gly Gly Tyr Tyr Thr Tyr Tyr Ser Asp Ile Ile Lys
1               5                   10                  15
Gly

<210> SEQ ID NO 154
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR3

<400> SEQUENCE: 154

Gly Phe Pro Leu Leu Arg His Gly Ala Met Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR1

<400> SEQUENCE: 155

Lys Ala Ser Gln Asn Val Asp Thr Asn Val Ala
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR2

<400> SEQUENCE: 156

Ser Ala Ser Tyr Val Tyr Trp
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR3

<400> SEQUENCE: 157

Gln Gln Tyr Asp Gln Gln Leu Ile Thr
1               5

<210> SEQ ID NO 158
```

```
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH

<400> SEQUENCE: 158
```

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
        115                 120

```
<210> SEQ ID NO 159
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL

<400> SEQUENCE: 159
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

Ser Ala Ser Gly Thr Asp Phe Thr Leu Thr Ile Ser Ser Val Gln Ser
65                  70                  75                  80

Glu Asp Phe Ala Thr Tyr Tyr Cys Gln Gln Tyr Asp Gln Gln Leu Ile
                85                  90                  95

Thr Phe Gly Gly Gly Thr Lys Leu Glu Ile Lys
            100                 105

```
<210> SEQ ID NO 160
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC scFv
```

<400> SEQUENCE: 160

```
Gln Val Gln Leu Val Glu Ser Gly Gly Leu Val Lys Pro Gly Glu
1               5                  10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
            35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
        210                 215                 220

Gln Gln Tyr Asp Gln Leu Ile Thr Phe Gly Gly Gly Thr Lys Leu
225                 230                 235                 240

Glu Ile Lys
```

<210> SEQ ID NO 161
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 bispecific molecule

<400> SEQUENCE: 161

```
Gln Val Gln Leu Val Glu Ser Gly Gly Gly Leu Val Lys Pro Gly Glu
1               5                  10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
            35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
```

```
                    85                  90                  95
Ala Arg Gly Phe Pro Leu Leu Arg His Gly Ala Met Asp Tyr Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
                180                 185                 190

Asp Val Pro Ser Arg Phe Ser Gly Ser Ala Ser Gly Thr Asp Phe Thr
                195                 200                 205

Leu Thr Ile Ser Ser Val Gln Ser Glu Asp Phe Ala Thr Tyr Tyr Cys
                210                 215                 220

Gln Gln Tyr Asp Gln Gln Leu Ile Thr Phe Gly Gly Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
                275                 280                 285

Ala Pro Gly Lys Gly Leu Glu Trp Val Ala Arg Ile Arg Ser Lys Tyr
                290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
                355                 360                 365

Leu Val Thr Val Ser Ser Gly Gly Gly Ser Gly Gly Gly Ser
                370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
                450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu
```

```
<210> SEQ ID NO 162
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific HLE
      molecule

<400> SEQUENCE: 162

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350
```

-continued

```
Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Ser
370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
                500                 505                 510

Ala Pro Glu Leu Leu Gly Gly Pro Ser Val Phe Leu Phe Pro Pro Lys
                515                 520                 525

Pro Lys Asp Thr Leu Met Ile Ser Arg Thr Pro Glu Val Thr Cys Val
            530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
                580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
            645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
            690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
                725                 730                 735

Gly Gly Ser Gly Gly Gly Ser Gly Gly Gly Ser Gly Gly
            740                 745                 750

Gly Ser Gly Gly Gly Gly Ser Asp Lys Thr His Thr Cys Pro Pro Cys
            755                 760                 765
```

```
Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                    805                 810                 815

Tyr Val Asp Gly Val Glu Val His Asn Ala Lys Thr Lys Pro Cys Glu
                820                 825                 830

Glu Gln Tyr Gly Ser Thr Tyr Arg Cys Val Ser Val Leu Thr Val Leu
            835                 840                 845

His Gln Asp Trp Leu Asn Gly Lys Glu Tyr Lys Cys Lys Val Ser Asn
850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 163
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc_delGK bispecific
      HLE molecule

<400> SEQUENCE: 163

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125
```

```
Gly Gly Ser Gly Gly Gly Ser Asp Ile Gln Met Thr Gln Ser Pro
130                 135                 140
Ser Ser Leu Ser Ala Ser Val Gly Asp Arg Val Thr Ile Thr Cys Lys
145                 150                 155                 160
Ala Ser Gln Asn Val Asp Thr Asn Val Ala Trp Tyr Gln Gln Lys Pro
                165                 170                 175
Gly Gln Ala Pro Lys Ser Leu Ile Tyr Ser Ala Ser Tyr Val Tyr Trp
                180                 185                 190
Asp Val Pro Ser Arg Phe Ser Gly Ser Ala Ser Gly Thr Asp Phe Thr
            195                 200                 205
Leu Thr Ile Ser Ser Val Gln Ser Glu Asp Phe Ala Thr Tyr Tyr Cys
        210                 215                 220
Gln Gln Tyr Asp Gln Gln Leu Ile Thr Phe Gly Gly Gly Thr Lys Leu
225                 230                 235                 240
Glu Ile Lys Ser Gly Gly Gly Ser Glu Val Gln Leu Val Glu Ser
                245                 250                 255
Gly Gly Gly Leu Val Gln Pro Gly Gly Ser Leu Lys Leu Ser Cys Ala
            260                 265                 270
Ala Ser Gly Phe Thr Phe Asn Lys Tyr Ala Met Asn Trp Val Arg Gln
        275                 280                 285
Ala Pro Gly Lys Gly Leu Glu Trp Val Ala Arg Ile Arg Ser Lys Tyr
290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
                325                 330                 335
Leu Lys Thr Glu Asp Thr Ala Val Tyr Tyr Cys Val Arg His Gly Asn
            340                 345                 350
Phe Gly Asn Ser Tyr Ile Ser Tyr Trp Ala Tyr Trp Gly Gln Gly Thr
        355                 360                 365
Leu Val Thr Val Ser Ser Gly Gly Gly Gly Ser Gly Gly Gly Gly Ser
370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
            420                 425                 430
Gln Ala Pro Arg Gly Leu Ile Gly Gly Thr Lys Phe Leu Ala Pro Gly
        435                 440                 445
Thr Pro Ala Arg Phe Ser Gly Ser Leu Leu Gly Gly Lys Ala Ala Leu
450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
                485                 490                 495
Val Leu Gly Gly Gly Gly Asp Lys Thr His Thr Cys Pro Pro Cys Pro
            500                 505                 510
Ala Pro Glu Leu Leu Gly Gly Pro Ser Val Phe Leu Phe Pro Pro Lys
        515                 520                 525
Pro Lys Asp Thr Leu Met Ile Ser Arg Thr Pro Glu Val Thr Cys Val
530                 535                 540
```

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
            565                 570                 575

Gln Tyr Gly Ser Thr Tyr Arg Cys Val Ser Val Leu Thr Val Leu His
                580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Ser Gly Gly Gly Ser Gly Gly Gly Gly Ser
            740                 745                 750

Gly Gly Gly Gly Ser Asp Lys Thr His Thr Cys Pro Pro Cys Pro Ala
            755                 760                 765

Pro Glu Leu Leu Gly Gly Pro Ser Val Phe Leu Phe Pro Pro Lys Pro
    770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
            805                 810                 815

Asp Gly Val Glu Val His Asn Ala Lys Thr Lys Pro Cys Glu Glu Gln
        820                 825                 830

Tyr Gly Ser Thr Tyr Arg Cys Val Ser Val Leu Thr Val Leu His Gln
    835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
    930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys

```
                    965             970             975
Ser Leu Ser Leu Ser Pro Gly Lys
            980
```

<210> SEQ ID NO 164
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
    bispecific molecule

<400> SEQUENCE: 164

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320
```

```
Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu

<210> SEQ ID NO 165
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific HLE molecule

<400> SEQUENCE: 165

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160
```

```
Ala Ser Gln Asn Val Asp Thr Asn Val Ala Trp Tyr Gln Gln Lys Pro
            165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
            210                 215                 220

Gln Gln Tyr Asp Gln Leu Ile Thr Phe Gly Gly Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
            530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
            565                 570                 575

Gln Tyr Gly Ser Thr Tyr Arg Cys Val Ser Val Leu Thr Val Leu His
```

```
              580               585               590
Gln Asp Trp Leu Asn Gly Lys Glu Tyr Lys Cys Lys Val Ser Asn Lys
            595               600               605
Ala Leu Pro Ala Pro Ile Glu Lys Thr Ile Ser Lys Ala Lys Gly Gln
        610               615               620
Pro Arg Glu Pro Gln Val Tyr Thr Leu Pro Pro Ser Arg Glu Glu Met
625               630               635               640
Thr Lys Asn Gln Val Ser Leu Thr Cys Leu Val Lys Gly Phe Tyr Pro
                645               650               655
Ser Asp Ile Ala Val Glu Trp Glu Ser Asn Gly Gln Pro Glu Asn Asn
            660               665               670
Tyr Lys Thr Thr Pro Pro Val Leu Asp Ser Asp Gly Ser Phe Phe Leu
        675               680               685
Tyr Ser Lys Leu Thr Val Asp Lys Ser Arg Trp Gln Gln Gly Asn Val
    690               695               700
Phe Ser Cys Ser Val Met His Glu Ala Leu His Asn His Tyr Thr Gln
705               710               715               720
Lys Ser Leu Ser Leu Ser Pro Gly Lys Gly Gly Gly Ser Gly Gly
                725               730               735
Gly Gly Ser Gly Gly Gly Ser Gly Gly Gly Ser Gly Gly
            740               745               750
Gly Ser Gly Gly Gly Ser Asp Lys Thr His Thr Cys Pro Pro Cys
        755               760               765
Pro Ala Pro Glu Leu Leu Gly Gly Pro Ser Val Phe Leu Phe Pro Pro
    770               775               780
Lys Pro Lys Asp Thr Leu Met Ile Ser Arg Thr Pro Glu Val Thr Cys
785               790               795               800
Val Val Val Asp Val Ser His Glu Asp Pro Glu Val Lys Phe Asn Trp
                805               810               815
Tyr Val Asp Gly Val Glu Val His Asn Ala Lys Thr Lys Pro Cys Glu
            820               825               830
Glu Gln Tyr Gly Ser Thr Tyr Arg Cys Val Ser Val Leu Thr Val Leu
        835               840               845
His Gln Asp Trp Leu Asn Gly Lys Glu Tyr Lys Cys Lys Val Ser Asn
    850               855               860
Lys Ala Leu Pro Ala Pro Ile Glu Lys Thr Ile Ser Lys Ala Lys Gly
865               870               875               880
Gln Pro Arg Glu Pro Gln Val Tyr Thr Leu Pro Pro Ser Arg Glu Glu
                885               890               895
Met Thr Lys Asn Gln Val Ser Leu Thr Cys Leu Val Lys Gly Phe Tyr
            900               905               910
Pro Ser Asp Ile Ala Val Glu Trp Glu Ser Asn Gly Gln Pro Glu Asn
        915               920               925
Asn Tyr Lys Thr Thr Pro Pro Val Leu Asp Ser Asp Gly Ser Phe Phe
    930               935               940
Leu Tyr Ser Lys Leu Thr Val Asp Lys Ser Arg Trp Gln Gln Gly Asn
945               950               955               960
Val Phe Ser Cys Ser Val Met His Glu Ala Leu His Asn His Tyr Thr
                965               970               975
Gln Lys Ser Leu Ser Leu Ser Pro Gly Lys
            980               985
```

<210> SEQ ID NO 166

```
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc_delGK
      bispecific HLE molecule

<400> SEQUENCE: 166
```

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr

```
                355                 360                 365
Leu Val Thr Val Ser Ser Gly Gly Gly Ser Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
    770                 775                 780
```

```
Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
            980

<210> SEQ ID NO 167
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR1

<400> SEQUENCE: 167

Asp Tyr Tyr Met Tyr
1               5

<210> SEQ ID NO 168
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR2

<400> SEQUENCE: 168

Ile Ile Ser Asp Gly Gly Tyr Tyr Thr Tyr Tyr Ser Asp Ile Ile Lys
1               5                   10                  15

Gly

<210> SEQ ID NO 169
<211> LENGTH: 12
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR3

<400> SEQUENCE: 169

Gly Phe Pro Leu Leu Arg His Gly Ala Met Asp Tyr
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR1

<400> SEQUENCE: 170

Lys Ala Ser Gln Asn Val Asp Thr Asn Val Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR2

<400> SEQUENCE: 171

Ser Ala Ser Tyr Val Tyr Trp
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR3

<400> SEQUENCE: 172

Gln Gln Tyr Asp Gln Gln Leu Ile Thr
1               5

<210> SEQ ID NO 173
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH

<400> SEQUENCE: 173

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
```

```
                    35                  40                  45

Ala Ile Ile Ser Asp Gly Gly Tyr Tyr Thr Tyr Tyr Ser Asp Ile Ile
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
            115                 120

<210> SEQ ID NO 174
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL

<400> SEQUENCE: 174

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

Ser Ala Ser Gly Thr Asp Phe Thr Leu Thr Ile Ser Ser Val Gln Ser
 65                  70                  75                  80

Glu Asp Phe Ala Thr Tyr Tyr Cys Gln Gln Tyr Asp Gln Gln Leu Ile
                85                  90                  95

Thr Phe Gly Cys Gly Thr Lys Leu Glu Ile Lys
            100                 105

<210> SEQ ID NO 175
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc scFv

<400> SEQUENCE: 175

Gln Val Gln Leu Val Glu Ser Gly Gly Gly Leu Val Lys Pro Gly Glu
 1               5                  10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
 65                  70                  75                  80
```

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
        210                 215                 220

Gln Gln Tyr Asp Gln Gln Leu Ile Thr Phe Gly Cys Gly Thr Lys Leu
225                 230                 235                 240

Glu Ile Lys

<210> SEQ ID NO 176
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific molecule

<400> SEQUENCE: 176

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp

```
            180                 185                 190
Asp Val Pro Ser Arg Phe Ser Gly Ser Ala Gly Thr Asp Phe Thr
            195                 200                 205

Leu Thr Ile Ser Ser Val Gln Ser Glu Asp Phe Ala Thr Tyr Tyr Cys
        210                 215                 220

Gln Gln Tyr Asp Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 177
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific HLE
      molecule

<400> SEQUENCE: 177

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
```

```
                    20                  25                  30
Tyr Met Tyr Trp Val Arg Gln Ala Pro Gly Lys Cys Leu Glu Trp Val
                35                  40                  45
Ala Ile Ile Ser Asp Gly Gly Tyr Thr Tyr Tyr Ser Asp Ile Ile
    50                  55                  60
Lys Gly Arg Phe Thr Ile Ser Arg Asp Asn Ala Lys Asn Ser Leu Tyr
65                  70                  75                  80
Leu Gln Met Asn Ser Leu Lys Ala Glu Asp Thr Ala Val Tyr Tyr Cys
                85                  90                  95
Ala Arg Gly Phe Pro Leu Leu Arg His Gly Ala Met Asp Tyr Trp Gly
                100                 105                 110
Gln Gly Thr Leu Val Thr Val Ser Ser Gly Gly Gly Ser Gly Gly
                115                 120                 125
Gly Gly Ser Gly Gly Gly Ser Asp Ile Gln Met Thr Gln Ser Pro
130                 135                 140
Ser Ser Leu Ser Ala Ser Val Gly Asp Arg Val Thr Ile Thr Cys Lys
145                 150                 155                 160
Ala Ser Gln Asn Val Asp Thr Asn Val Ala Trp Tyr Gln Gln Lys Pro
                165                 170                 175
Gly Gln Ala Pro Lys Ser Leu Ile Tyr Ser Ala Ser Tyr Val Tyr Trp
                180                 185                 190
Asp Val Pro Ser Arg Phe Ser Gly Ser Ala Ser Gly Thr Asp Phe Thr
                195                 200                 205
Leu Thr Ile Ser Ser Val Gln Ser Glu Asp Phe Ala Thr Tyr Tyr Cys
    210                 215                 220
Gln Gln Tyr Asp Gln Gln Leu Ile Thr Phe Gly Cys Gly Thr Lys Leu
225                 230                 235                 240
Glu Ile Lys Ser Gly Gly Gly Ser Glu Val Gln Leu Val Glu Ser
                245                 250                 255
Gly Gly Gly Leu Val Gln Pro Gly Gly Ser Leu Lys Leu Ser Cys Ala
                260                 265                 270
Ala Ser Gly Phe Thr Phe Asn Lys Tyr Ala Met Asn Trp Val Arg Gln
                275                 280                 285
Ala Pro Gly Lys Gly Leu Glu Trp Val Ala Arg Ile Arg Ser Lys Tyr
                290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
                325                 330                 335
Leu Lys Thr Glu Asp Thr Ala Val Tyr Tyr Cys Val Arg His Gly Asn
                340                 345                 350
Phe Gly Asn Ser Tyr Ile Ser Tyr Trp Ala Tyr Trp Gly Gln Gly Thr
                355                 360                 365
Leu Val Thr Val Ser Ser Gly Gly Gly Ser Gly Gly Gly Gly Ser
    370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
                420                 425                 430
Gln Ala Pro Arg Gly Leu Ile Gly Gly Thr Lys Phe Leu Ala Pro Gly
                435                 440                 445
```

-continued

```
Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
                725                 730                 735

Gly Gly Ser Gly Gly Gly Gly Ser Gly Gly Gly Ser Gly Gly Gly
            740                 745                 750

Gly Ser Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860
```

-continued

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 178
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc_delGK bispecific
      HLE molecule

<400> SEQUENCE: 178

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

```
Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Trp Gly Gln Gly Thr
    355                 360                 365

Leu Val Thr Val Ser Ser Gly Gly Gly Ser Gly Gly Gly Gly Ser
370                 375                 380

Gly Gly Gly Ser Gln Thr Val Val Thr Gln Glu Pro Ser Leu Thr
385             390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Gly Gly Gly Gly Asp Lys Thr His Thr Cys Pro Pro Cys Pro
        500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
            565                 570                 575

Gln Tyr Gly Ser Thr Tyr Arg Cys Val Ser Val Leu Thr Val Leu His
        580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640
```

```
Thr Lys Asn Gln Val Ser Leu Thr Cys Leu Val Lys Gly Phe Tyr Pro
            645                 650                 655
Ser Asp Ile Ala Val Glu Trp Glu Ser Asn Gly Gln Pro Glu Asn Asn
        660                 665                 670
Tyr Lys Thr Thr Pro Pro Val Leu Asp Ser Asp Gly Ser Phe Phe Leu
    675                 680                 685
Tyr Ser Lys Leu Thr Val Asp Lys Ser Arg Trp Gln Gln Gly Asn Val
690                 695                 700
Phe Ser Cys Ser Val Met His Glu Ala Leu His Asn His Tyr Thr Gln
705                 710                 715                 720
Lys Ser Leu Ser Leu Ser Pro Gly Gly Gly Gly Ser Gly Gly Gly Gly
            725                 730                 735
Ser Gly Gly Gly Gly Ser Gly Gly Gly Gly Ser Gly Gly Gly Gly Ser
            740                 745                 750
Gly Gly Gly Gly Ser Asp Lys Thr His Thr Cys Pro Pro Cys Pro Ala
            755                 760                 765
Pro Glu Leu Leu Gly Gly Pro Ser Val Phe Leu Phe Pro Pro Lys Pro
    770                 775                 780
Lys Asp Thr Leu Met Ile Ser Arg Thr Pro Glu Val Thr Cys Val Val
785                 790                 795                 800
Val Asp Val Ser His Glu Asp Pro Glu Val Lys Phe Asn Trp Tyr Val
            805                 810                 815
Asp Gly Val Glu Val His Asn Ala Lys Thr Lys Pro Cys Glu Glu Gln
            820                 825                 830
Tyr Gly Ser Thr Tyr Arg Cys Val Ser Val Leu Thr Val Leu His Gln
            835                 840                 845
Asp Trp Leu Asn Gly Lys Glu Tyr Lys Cys Lys Val Ser Asn Lys Ala
850                 855                 860
Leu Pro Ala Pro Ile Glu Lys Thr Ile Ser Lys Ala Lys Gly Gln Pro
865                 870                 875                 880
Arg Glu Pro Gln Val Tyr Thr Leu Pro Pro Ser Arg Glu Glu Met Thr
            885                 890                 895
Lys Asn Gln Val Ser Leu Thr Cys Leu Val Lys Gly Phe Tyr Pro Ser
            900                 905                 910
Asp Ile Ala Val Glu Trp Glu Ser Asn Gly Gln Pro Glu Asn Asn Tyr
            915                 920                 925
Lys Thr Thr Pro Pro Val Leu Asp Ser Asp Gly Ser Phe Phe Leu Tyr
    930                 935                 940
Ser Lys Leu Thr Val Asp Lys Ser Arg Trp Gln Gln Gly Asn Val Phe
945                 950                 955                 960
Ser Cys Ser Val Met His Glu Ala Leu His Asn His Tyr Thr Gln Lys
            965                 970                 975
Ser Leu Ser Leu Ser Pro Gly Lys
            980
```

<210> SEQ ID NO 179
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific molecule

<400> SEQUENCE: 179

-continued

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415
```

```
Ala Val Thr Ser Gly Asn Tyr Pro Asn Trp Val Gln Gln Lys Pro Gly
                420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 180
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific HLE molecule

<400> SEQUENCE: 180

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65              70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255
```

```
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
```

```
                675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly Gly
                725                 730                 735

Gly Gly Ser Gly Gly Gly Gly Ser Gly Gly Gly Ser Gly Gly Gly Gly
            740                 745                 750

Gly Ser Gly Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 181
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc_delGK
      bispecific HLE molecule

<400> SEQUENCE: 181

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30
```

-continued

```
Tyr Met Tyr Trp Val Arg Gln Ala Pro Gly Lys Cys Leu Glu Trp Val
         35                  40                  45

Ala Ile Ile Ser Asp Gly Gly Tyr Tyr Thr Tyr Tyr Ser Asp Ile Ile
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
             85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
         115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
```

```
              450                 455                 460
Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                    485                 490                 495

Val Leu Gly Gly Gly Asp Lys Thr His Thr Cys Pro Pro Cys Pro
                500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
        530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
                580                 585                 590

Gln Asp Trp Leu Asn Gly Lys Glu Tyr Lys Cys Lys Val Ser Asn Lys
                595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
                660                 665                 670

Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
        690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Ser Gly Gly Gly Gly Ser Gly Gly Gly Gly Ser
                740                 745                 750

Gly Gly Gly Gly Ser Asp Lys Thr His Thr Cys Pro Pro Cys Pro Ala
            755                 760                 765

Pro Glu Leu Leu Gly Gly Pro Ser Val Phe Leu Phe Pro Pro Lys Pro
770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
                820                 825                 830

Tyr Gly Ser Thr Tyr Arg Cys Val Ser Val Leu Thr Val Leu His Gln
            835                 840                 845

Asp Trp Leu Asn Gly Lys Glu Tyr Lys Cys Lys Val Ser Asn Lys Ala
        850                 855                 860

Leu Pro Ala Pro Ile Glu Lys Thr Ile Ser Lys Ala Lys Gly Gln Pro
865                 870                 875                 880
```

Arg Glu Pro Gln Val Tyr Thr Leu Pro Pro Ser Arg Glu Glu Met Thr
            885                 890                 895

Lys Asn Gln Val Ser Leu Thr Cys Leu Val Lys Gly Phe Tyr Pro Ser
        900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
    930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
            965                 970                 975

Ser Leu Ser Leu Ser Pro Gly Lys
            980

<210> SEQ ID NO 182
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG1 hinge

<400> SEQUENCE: 182

Asp Lys Thr His Thr Cys Pro Pro Cys Pro
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG2 subtype hinge

<400> SEQUENCE: 183

Glu Arg Lys Cys Cys Val Glu Cys Pro Pro Cys Pro
1               5                   10

<210> SEQ ID NO 184
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG3 subtype hinge

<400> SEQUENCE: 184

Glu Leu Lys Thr Pro Leu Asp Thr Thr His Thr Cys Pro Arg Cys Pro
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE

```
<223> OTHER INFORMATION: IgG3 subtype hinge

<400> SEQUENCE: 185

Glu Leu Lys Thr Pro Leu Gly Asp Thr Thr His Thr Cys Pro Arg Cys
1               5                   10                  15
Pro

<210> SEQ ID NO 186
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG4 subtype hinge

<400> SEQUENCE: 186

Glu Ser Lys Tyr Gly Pro Pro Cys Pro Ser Cys Pro
1               5                   10

<210> SEQ ID NO 187
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: G4S linker

<400> SEQUENCE: 187

Gly Gly Gly Gly Ser
1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: (G4S)2 linker

<400> SEQUENCE: 188

Gly Gly Gly Gly Ser Gly Gly Gly Gly Ser
1               5                   10

<210> SEQ ID NO 189
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: (G4S)3 linker

<400> SEQUENCE: 189

Gly Gly Gly Gly Ser Gly Gly Gly Gly Ser Gly Gly Gly Gly Ser
1               5                   10                  15

<210> SEQ ID NO 190
<211> LENGTH: 20
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: (G4S)4 linker

<400> SEQUENCE: 190

Gly Gly Gly Gly Ser Gly Gly Gly Gly Ser Gly Gly Gly Gly Ser Gly
1               5                   10                  15
Gly Gly Gly Ser
            20

<210> SEQ ID NO 191
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: (G4S)5 linker

<400> SEQUENCE: 191

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 192
<211> LENGTH: 30
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: (G4S)6 linker

<400> SEQUENCE: 192

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 193
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: (G4S)7 linker

<400> SEQUENCE: 193

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser
        35

<210> SEQ ID NO 194
<211> LENGTH: 40
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: (G4S)8 linker

<400> SEQUENCE: 194

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 195
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide linker

<400> SEQUENCE: 195

Pro Gly Gly Gly Gly Ser
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide linker

<400> SEQUENCE: 196

Pro Gly Gly Asp Gly Ser
1               5

<210> SEQ ID NO 197
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide linker

<400> SEQUENCE: 197

Ser Gly Gly Gly Gly Ser
1               5

<210> SEQ ID NO 198
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide linker

<400> SEQUENCE: 198

Gly Gly Gly Gly
1
```

<210> SEQ ID NO 199
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: hexa-histidine tag

<400> SEQUENCE: 199

His His His His His His
1               5

<210> SEQ ID NO 200
<211> LENGTH: 109
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3e binder VL

<400> SEQUENCE: 200

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 201
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3e binder VH

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

```
Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser
        115                 120                 125

<210> SEQ ID NO 202
<211> LENGTH: 249
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3e binder scFv

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

CONTINUOUS MANUFACTURING PROCESS FOR BISPECIFIC ANTIBODY PRODUCTS

TECHNICAL FIELD

This invention relates to methods of biotechnology, in particular to continuous manufacturing processes for the manufacture of bispecific antibodies.

BACKGROUND

Among the most quickly and promisingly developing therapeutics are protein-based pharmaceuticals which already have a significant role in almost every field of medicine and are among the fastest growing therapeutic agents in (pre)clinical development and as commercial products (Leader, Nature Reviews Drug Discovery 2008 Jan. 7, 21-39). In comparison to small chemical drugs, protein pharmaceuticals have high specificity and activity at relatively low concentrations, and typically provide for therapy of high impact diseases such as various cancers, autoimmune diseases, and metabolic disorders (Roberts, Trends Biotechnol. 2014 July; 32(7):372-80, Wang, Int J Pharm. 1999 Aug. 20; 185(2):129-88).

Protein-based pharmaceuticals, such as recombinant proteins, can now be obtained in high purity when first manufactured due to advances in commercial scale purification processes. However, proteins are only marginally stable and are highly susceptible to degradation even during upstream manufacturing, both chemical and physical. Chemical degradation refers to modifications involving covalent bonds, such as deamidation, oxidation, cleavage or formation of new disulfide bridges, hydrolysis, isomerization, or deglycosylation. Physical degradation includes protein unfolding, undesirable adsorption to surfaces, and aggregation. Dealing with these physical and chemical instabilities is one of the most challenging tasks in the development of protein pharmaceuticals (Chi et al., Pharm Res, Vol. 20, No. 9, September 2003, pp. 1325-1336, Roberts, Trends Biotechnol. 2014 July; 32(7):372-80).

Accordingly, despite the advances in manufacturing, new protein-based pharmaceuticals require new optimized manufacturing process in order to avoid product quality impact such as protein aggregation. This affects upstream manufacturing, downstream manufacturing, storage and application.

Such new protein-based pharmaceuticals comprise, for example, bispecific (monoclonal) antibodies. A bispecific antibody is an artificial protein that can simultaneously bind to two different types of antigen. They are known in several structural formats, and current applications have been explored for cancer immunotherapy and drug delivery (Fan, Gaowei; Wang, Zujian; Hao, Mingju; Li, Jinming (2015). "Bispecific antibodies and their applications". Journal of Hematology & Oncology. 8: 130).

In general, bispecific antibodies can be IgG-like, i.e. full length bispecific antibodies, or non-IgG-like bispecific antibodies, which are not full-length antibody constructs. Full length bispecific antibodies typically retain the traditional monoclonal antibody (mAb) structure of two Fab arms and one Fc region, except the two Fab sites bind different antigens. Non full-length bispecific antibodies lack an Fc region entirely. These include chemically linked Fabs, consisting of only the Fab regions, and various types of bivalent and trivalent single-chain variable fragments (scFvs). There are also fusion proteins mimicking the variable domains of two antibodies. The likely furthest developed of these newer formats are the bi-specific T-cell engagers (BiTE®) (Yang, Fa; Wen, Weihong; Qin, Weijun (2016). "Bispecific Antibodies as a Development Platform for New Concepts and Treatment Strategies". International Journal of Molecular Sciences. 18 (1): 48).

Bispecific molecules such as BiTE® antibody constructs are recombinant protein constructs made from two flexibly linked antibody derived binding domains. One binding domain of BiTE® antibody constructs is specific for a selected tumor-associated surface antigen on target cells; the second binding domain is specific for CD3, a subunit of the T cell receptor complex on T cells. By their particular design BiTE® antibody constructs are uniquely suited to transiently connect T cells with target cells and, at the same time, potently activate the inherent cytolytic potential of T cells against target cells. An important further development of the first generation of BiTE® antibody constructs (see WO 99/54440 and WO 2005/040220) developed into the clinic as AMG 103 and AMG 110 was the provision of bispecific antibody constructs binding to a context independent epitope at the N-terminus of the CD3ε chain (WO 2008/119567). BiTE® antibody constructs binding to this elected epitope do not only show cross-species specificity for human and *Callithrix jacchus, Saguinus oedipus* or *Saimiri sciureus* CDR chain, but also, due to recognizing this specific epitope instead of previously described epitopes for CD3 binders in bispecific T cell engaging molecules, do not unspecifically activate T cells to the same degree as observed for the previous generation of T cell engaging antibodies. This reduction in T cell activation was connected with less or reduced T cell redistribution in patients, which was identified as a risk for side effects.

Currently, bispecific antibodies are produced by fed batch culture manufacturing processes. Fed-batch culture is well known as an operational technique in biotechnological processes where one or more nutrients (substrates) are fed (supplied) to a bioreactor during cultivation and in which the product(s) remain in the bioreactor until the end of the run (Tsuneo Yamanè, Shoichi Shimizu: Fed-batch Techniques in Microbial Processes. (1984) Advances in Biochem Eng./Biotechnol, 30:147-194). Accordingly, the bispecific antibody products accumulate during the fed batch process and are prone to product quality loss, e.g. due to aggregation, clipping or certain chemical degradation reactions. Also, until the end of the run, no product can be obtained. In addition, process-related impurities such as host cell proteins (HCP) likewise accumulate in the bioreactor during a fed-batch process. Downstream removal of these impurities is often challenging and requires additional measures and resources to ensure end product quality. As each new run requires a new cell culture growing phase, overall productivity of a fed-batch is impaired by said required repeated growing phases. Further, in order to achieve sufficient product amount produced by fed-batch plants, large bioreactors are required which use large amounts of space and energy. Hence, there is a need for an improved upstream manufacturing process specifically for the production of bispecific antibodies, which both increases the product quantity and the product quality in order to provide sufficient product amounts at a commercial scale at such a quality that less product needs to be discarded in downstream processing. New process methods that provide even incremental improvements in recombinant protein production and recovery are valuable, given the expense of large scale cell culture processes and the growing demand for greater quantities of

SUMMARY

Surprisingly, an adapted continuous manufacturing process can be provided which both ensured improved bispecific antibody product quantity and the product quality. Even if continuous manufacturing processes for the production of proteins such as antibodies were known as such (e.g. Cattaneo et al., US 2017/0204446 A1), such processes were not geared to the specific needs of bispecific antibodies which have a tendency to aggregate, clip and chemically degrade already during upstream manufacturing process steps, thus resulting in lower product quantity and quality.

Hence, in one aspect, it is envisaged in the context of the present invention to provide a continuous upstream manufacturing process for the production of a bispecific antibody product comprising at least a first and a second binding domain, wherein the first binding domain binds to a different target than the second binding domain, the process comprising the steps of:
  (i) providing a liquid cell culture medium comprising at least one mammalian cell culture in a perfusion bioreactor, wherein the mammalian cell culture is capable of expressing the bispecific antibody product, and wherein the cells have a concentration of at least $0.5\times10^6$ cells/mL at inoculation in the perfusion bioreactor,
  (ii) growing the mammalian cell culture by applying a perfusion rate (D) to exchange the liquid cell culture medium in a preferably continuous manner, without removing the cells from bioreactor, wherein the perfusion rate initially corresponds to at least 0.4 vessel volume per day (vvd) and is then increased continuously, gradually or incrementally to at least 1 bioreactor volume, which is also understood herein as vessel volume per day (vvd), when a biomass set-point is reached, wherein the biomass set-point equals to a viable cell density (VCD) of at least $35\times10^6$ cells/mL,
  (iii) maintaining perfusion culture by applying the perfusion rate (D) to continuously or incrementally exchange the liquid cell culture medium, preferably without removing the cells from bioreactor, when the biomass set-point is reached, wherein the perfusion rate in step (iii) corresponds to at least 1 bioreactor volume, which is also understood herein as vessel volume per day (vvd), and
  (iv) optionally bleeding extra cells from the bioreactor to maintain the biomass set-point, wherein the bispecific antibody product concentration in the bioreactor is kept below 3.5 g/L by continuously harvesting the bispecific antibody product from the liquid cell culture medium throughout steps (ii) to (iv) and/or by adjusting D to the VCD.

According to said aspect, it is also envisaged in step (i) that the cells have a concentration of at least $1\times10^6$ cells/mL at inoculation in the bioreactor, According to said aspect, it is further envisaged in step (ii) that the biomass set-point equals to a VCD of at least $65\times10^6$ cells/mL.

According to said aspect, it is even more envisaged in step (ii) that the biomass set-point equals to a VCD of at least $71\times10^6$ cells/mL.

According to said aspect, it is also envisaged in step (ii) that the growing of the cell culture takes place for at least 4 days, preferably for at least 7 days, preferably for at least 12 days.

According to said aspect, it is further envisaged in step (ii) that the perfusion rate (D) is in the range from 0.4 to 7 vvd.

According to said aspect, it is further envisaged in step (ii) that the perfusion rate (D) is increased continuously, i.e. non-discretely.

According to said aspect, it is even more envisaged in step (iii) that the perfusion rate (D) is in the range from 1 to 7 vvd.

According to said aspect, it is also envisaged in step (iii) that the perfusion rate (D) is in the range from 2 to 6.4 vvd, preferably 2 vvd, most preferably 2.01 vvd.

According to said aspect, it is further envisaged in step (iii) that the perfusion rate (D) is a cell-specific perfusion rate (CSPR) in the range of 0.01 to 0.15 nL/cell-day (nL per cell per day), preferably in the range of 0.015 to 0.0315 nL/cell-day or in the range of 0.05 to 0.1 nL/cell-day.

According to said aspect, it is as well envisaged in steps (ii) to (iv) that the bispecific antibody product concentration is kept below 1.2 g/L, preferably below 0.5 g/L, most preferably below 0.12 g/L.

According to said aspect, it is also envisaged that the average residence time of the bispecific antibody product in the bioreactor before harvest after step (iii) or (iv), respectively, is at most 2 days, preferably at most 1 day, most preferably at most 0.5 days.

According to said aspect, it is also envisaged that the final IVCD is at least $10\times10^6$ cells-day/mL, preferably at least 12, 20 or $50\times10^6$ cells-day/mL, more preferably at least 100, 500 or even $1000\times10^6$ cells-day/mL.

According to said aspect, it is as well envisaged that the average HCCF productivity is at least 2 g/L of bioreactor volume, preferably at least 5, 10 or 15 g/L of bioreactor volume.

According to said aspect, it is also envisaged that the average HCCF daily productivity is at least 10 g/L of bioreactor volume per day, preferably at least 50 g/L of bioreactor volume per day, more preferably at least 100 or even at least 250 g/L of bioreactor volume per day.

According to said aspect, it is further envisaged that the percentile monomer content of the isolated bispecific antibody product is at least 50%, preferably at least 60%, more preferably at least 70%, 80%, 90%, 93% or even 95%.

According to said aspect, it is further envisaged that the percentile high molecular weight (HMW) species content of the isolated bispecific antibody product is at most 50%, preferably at most 40%, more preferably at most 30%, 20%, 10%, 7% or even 5%.

According to said aspect, a bispecific antibody product that is produced according to the present invention is characterized by an at least 60% reduction in host-cell protein content, in the first or second purification pool, compared to the same pool derived from a fed-batch process, preferably at least 65%, typically at least 68%, or even 75% to 86%.

According to said aspect, a bispecific antibody product that is produced according to the present invention is characterized by an at least 40% reduction in clipped protein levels, in the first or second purification pool, compared to the same pool derived from a fed-batch process, preferably at least 44%, typically at least 75% or even 97%.

According to said aspect, the percentile amount of product produced according to the present invention affected by clipping is at most 15% or 10%, preferably at most 7%, more preferably at most 6, 5, 4, 3, 2, or 1%, and most preferably at most 0.3%. The latter preferably applies to a bispecific antibody according to the present invention which is not a full-length antibody and preferably comprises a second domain comprising an amino acid sequence of the SEQ ID NO: 202.

According to said aspect, a bispecific antibody product that is produced according to the present invention is characterized by an at least 50% reduction in chemically-modified amino acids levels, preferably at least 65%, more preferably at least 68% or even at least 80% reduction in chemically-modified amino acids levels in the product, such as deamidated or isomerized product species, e.g. in the first or second purification pool, compared to the same pool derived from a fed-batch process.

According to said aspect, a bispecific antibody product that is produced according to the present invention is characterized by a percentile content of deamidated or isomerized product species of at most 2%, preferably at most 1%, more preferably at most 0.5% or even 0.1% compared to all product species.

According to said aspect, a bispecific antibody product that is produced according to the present invention is characterized by at least 25% reduction in high molecular weight species, i.e. constructs having a higher molecular weight than the pure product monomer, preferably at least 50% or even about 70% reduction in high molecular weight species, in the first or second purification pool, compared to the same pool derived from a fed-batch process.

According to said aspect, a bispecific antibody product that is produced according to the present invention is characterized by a reduction in acidic species levels, preferably by at least 30%, preferably at least 35, typically about 38 to 49%, typically in the first or second purification pool, when compared to the same pool derived from a fed-batch process.

According to said aspect, a bispecific antibody product that is produced according to the present invention is characterized by a percentile content of acidic product species of at most 15% compared to all product species, preferably at most 12%, more preferably at most 10%.

According to said aspect, it is as well envisaged that the bispecific antibody product is a bispecific full-length antibody, i.e. typically an antibody comprising 2 heavy and 2 light chains, or a non-full length bispecific antibody construct, including single chain bispecific antibody constructs.

According to said aspect, a bispecific full-length antibody is envisaged which first and/or second binding domain of the bispecific antibody construct binds to a target and/or an effector cell.

According to said aspect, a bispecific full-length antibody is envisaged which first and/or second binding domain of the bispecific antibody construct binds to T11A and/or to TNF-alpha.

According to said aspect, it is also envisaged that the bispecific antibody construct comprises a half-life extending moiety, preferably a Fc-based half-life extending moiety derived from an IgG antibody, most preferably a scFc half-life extending moiety.

According to said aspect, it is further envisaged that the bispecific antibody construct is a bispecific T-cell engager (BITE®).

According to said aspect, it is envisaged that the first binding domain of the bispecific antibody product binds to at least one target cell surface antigen selected from the group consisting of CD19, CD33, EGFRvIII, MSLN, CDH19, FLT3, DLL3, CDH3, BCMA and PSMA.

According to said aspect, it is further envisaged that the second binding domain of the bispecific antibody construct binds to a CD3 binding domain.

According to said aspect, it is also envisaged that the second binding domain comprises a VH region comprising CDR-H1, CDR-H2 and CDR-H3 and a VL region comprising CDR-L1, CDR-L2 and CDR-L3 selected from the group consisting of:
  (a) CDR-H1 as depicted in SEQ ID NO: 1, CDR-H2 as depicted in SEQ ID NO: 2, CDR-H3 as depicted in SEQ ID NO: 3, CDR-L1 as depicted in SEQ ID NO: 4, CDR-L2 as depicted in SEQ ID NO: 5 and CDR-L3 as depicted in SEQ ID NO: 6,
  (b) CDR-H1 as depicted in SEQ ID NO: 29, CDR-H2 as depicted in SEQ ID NO: 30, CDR-H3 as depicted in SEQ ID NO: 31, CDR-L1 as depicted in SEQ ID NO: 34, CDR-L2 as depicted in SEQ ID NO: 35 and CDR-L3 as depicted in SEQ ID NO: 36,
  (c) CDR-H1 as depicted in SEQ ID NO: 42, CDR-H2 as depicted in SEQ ID NO: 43, CDR-H3 as depicted in SEQ ID NO: 44, CDR-L1 as depicted in SEQ ID NO: 45, CDR-L2 as depicted in SEQ ID NO: 46 and CDR-L3 as depicted in SEQ ID NO: 47,
  (d) CDR-H1 as depicted in SEQ ID NO: 53, CDR-H2 as depicted in SEQ ID NO: 54, CDR-H3 as depicted in SEQ ID NO: 55, CDR-L1 as depicted in SEQ ID NO: 56, CDR-L2 as depicted in SEQ ID NO: 57 and CDR-L3 as depicted in SEQ ID NO: 58,
  (e) CDR-H1 as depicted in SEQ ID NO: 62, CDR-H2 as depicted in SEQ ID NO: 63, CDR-H3 as depicted in SEQ ID NO: 64, CDR-L1 as depicted in SEQ ID NO: 65, CDR-L2 as depicted in SEQ ID NO: 66 and CDR-L3 as depicted in SEQ ID NO: 67,
  (f) CDR-H1 as depicted in SEQ ID NO: 83, CDR-H2 as depicted in SEQ ID NO: 84, CDR-H3 as depicted in SEQ ID NO: 85, CDR-L1 as depicted in SEQ ID NO: 86, CDR-L2 as depicted in SEQ ID NO: 87 and CDR-L3 as depicted in SEQ ID NO: 88,
  (g) CDR-H1 as depicted in SEQ ID NO: 94, CDR-H2 as depicted in SEQ ID NO: 95, CDR-H3 as depicted in SEQ ID NO: 96, CDR-L1 as depicted in SEQ ID NO: 97, CDR-L2 as depicted in SEQ ID NO: 98 and CDR-L3 as depicted in SEQ ID NO: 99,
  (h) CDR-H1 as depicted in SEQ ID NO: 105, CDR-H2 as depicted in SEQ ID NO: 106, CDR-H3 as depicted in SEQ ID NO: 107, CDR-L1 as depicted in SEQ ID NO: 109, CDR-L2 as depicted in SEQ ID NO: 110 and CDR-L3 as depicted in SEQ ID NO: 111,
  (i) CDR-H1 as depicted in SEQ ID NO: 115, CDR-H2 as depicted in SEQ ID NO: 116, CDR-H3 as depicted in SEQ ID NO: 117, CDR-L1 as depicted in SEQ ID NO: 118, CDR-L2 as depicted in SEQ ID NO: 119 and CDR-L3 as depicted in SEQ ID NO: 120,
  (j) CDR-H1 as depicted in SEQ ID NO: 126, CDR-H2 as depicted in SEQ ID NO: 127, CDR-H3 as depicted in SEQ ID NO: 128, CDR-L1 as depicted in SEQ ID NO: 129, CDR-L2 as depicted in SEQ ID NO: 130 and CDR-L3 as depicted in SEQ ID NO: 131,
  (k) CDR-H1 as depicted in SEQ ID NO: 137, CDR-H2 as depicted in SEQ ID NO: 138, CDR-H3 as depicted in SEQ ID NO: 139, CDR-L1 as depicted in SEQ ID NO: 140, CDR-L2 as depicted in SEQ ID NO: 141 and CDR-L3 as depicted in SEQ ID NO: 142,
  (l) CDR-H1 as depicted in SEQ ID NO: 152, CDR-H2 as depicted in SEQ ID NO: 153, CDR-H3 as depicted in SEQ ID NO: 154, CDR-L1 as depicted in SEQ ID NO: 155, CDR-L2 as depicted in SEQ ID NO: 156 and CDR-L3 as depicted in SEQ ID NO: 157, and
  (m) CDR-H1 as depicted in SEQ ID NO: 167, CDR-H2 as depicted in SEQ ID NO: 168, CDR-H3 as depicted in SEQ ID NO: 169, CDR-L1 as depicted in SEQ ID NO: 170, CDR-L2 as depicted in SEQ ID NO: 171 and CDR-L3 as depicted in SEQ ID NO: 172.

According to said aspect, it is envisaged that the harvested bispecific antibody product is comprised in harvested cell culture fluid (HCCF).

According to said aspect, it is envisaged that the HCCF is obtained from step (ii) and (iii) or only from step (iii).

According to said aspect, it is envisaged that the HCCF is collected at room temperature, for example in 1, 2, 3, 4, 5, 6, 12 24, 36, 48, 72, 96, 120 and/or 144 hour increments or continuously and passed to downstream steps for further processing, e.g. capturing, the bispecific antibody product.

According to said aspect, it is envisaged that the downstream steps comprise capture chromatography, viral inactivation and/or polishing steps.

According to said aspect, it is envisaged that the perfusion culture is continuously running for at least 7 days, preferably for at least 14, 15, 16, 17, 18, 19, 20, 21, 22, 23, 24, 25, 26, 27 or 28 days, most preferably for at least 35 days by feeding at the defined cell-specific perfusion rate and bleeding extra cells from the bioreactor to maintain the biomass set-point.

In another aspect of the present invention, it is envisaged to provide a setup or apparatus to perform the continuous manufacturing method of the present invention as depicted in FIG. 1, comprising a perfusion bioreactor with at least a biomass control device, a DO control device and a level control device, and inlet with a perfusion flow rate regulating device, and an outlet with a cell retention device and a HCCF flow rate regulating device. The setup may comprise a perfusion medium which is pumped at a controlled perfusion flow rate (perfusion rate) into the bioreactor. Therein, oxygen level (DO), temperature, pH, biomass (capacitance) and fluid level (level) are controlled. Excess cells may be separated as cell bleed. Harvested cell culture fluid (HCCF) is obtained by separating fluid from the bioreactor by passing it through a cell retention device, which may comprise a 0.2 μm filter. Preferably, cell-free HCCF may be collected in a storage vessel before being passed to further downstream processing.

In another aspect of the present invention, a bispecific antibody product is envisaged, produced by the continuous upstream manufacturing process of the present invention.

In another aspect of the present invention, a hybrid method of fed batch and perfusion is envisaged which advantageously provides product characteristics of comparable quality as the herein presented, however, in a shorter period of time than CM. In turn, product quantity is lower and about comparable to FB. Preferably, the lower product concentration in the bioreactor results in better product quality as in a CM process according to the present invention. However, cell culture duration is minimized. Such a hybrid process according to the present invention comprises the process steps of (i) fed-batch from inoculation to about day 7, (ii) followed by a short duration of perfusion culture (comparable to CM) preferably using an alternating tangential flow (ATF) filtration system for harvest. The removal of the product is preferably performed in a similar way as a CM process according to the present invention in order to decreased product concentration and increased product quality.

DESCRIPTION OF THE FIGURES

FIG. 15 shows the comparison of product concentration and SEC HMW levels for permeate HCCF and bioreactor supernatant samples (from cell culture fluid) from CM processes for three BiTE® antibody constructs over the cell culture duration time (days). Samples are taken from bioreactor supernatant (⊖ open circles) or from the filter permeate HCCF (● closed circles).

DETAILED DESCRIPTION

Figure 1:
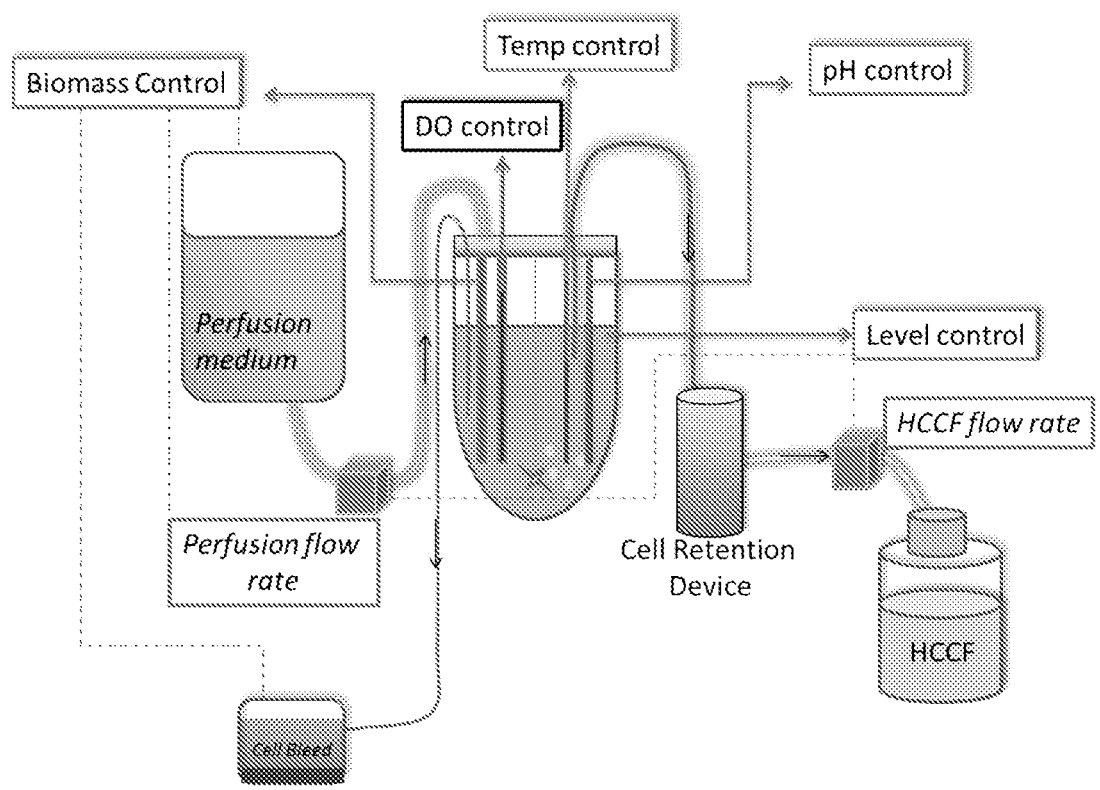
FIG. 1 shows one setup of the continuous manufacturing process according to the present invention. The setup comprises a perfusion medium which is pumped at a controlled perfusion flow rate (perfusion rate) into the bioreactor. Therein, oxygen level (DO), temperature, pH, biomass (capacitance) and fluid level (level) are controlled. Excess cells may be separated as cell bleed. Harvested cell culture fluid (HCCF) is obtained by separating fluid from the bioreactor by passing it through a cell retention device, which may comprise a 0.2 μm filter. Preferably, cell-free HCCF may be collected in a storage vessel before being passed to further downstream processing.

A continuous process for manufacturing therapeutic proteins, in particular bispecific antibodies is herein provided. The present invention is envisaged to gear the upstream process to the specific needs of manufacturing bispecific antibodies. Said upstream process does not only contribute to increased productivity and less requirement for space in comparison to standard fed batch manufacturing solutions known in the art. Even more, the present continues manufacturing process—preferably being a continues upstream manufacturing process—is specifically adapted for bispecific antibodies and is envisaged to result in higher product quality, i.e. less aggregated bispecific antibodies in terms of higher monomer content with respect to a fed batch manufacturing. Also, the present continuous manufacturing process advantageously provides less chemical modification, less clipping, less process-related impurities than a fed-batch manufacturing process known to the skilled person. As a particular manufacturing advantage, the output over time, based on the same cell type, also referred herein to as average HCCF daily productivity, is preferably increased at least 2-fold, preferably at least 3-fold, more preferably at least 4-fold and even more preferred at least 6-fold compared to a fed batch process known to the skilled person.

It was found that a particular low product concentration in the bioreactor decisively contributes to the avoidance of aggregates, i.e. to higher relative and/or absolute monomer concentrations of product. This is essential to ensure product quality and to enhance the overall economics of the process. The less aggregates are created upstream, the less non-quality product has to be removed downstream. A product concentration below 3.5 g/l is associated with less likelihood of aggregation. Product quality is even better if the maximum product concentration is kept below 1.2 g/l throughout the upstream process. Even more preferred is a product concentration below 0.5 or even 0.3 g/L. By ensuring a sufficiently high perfusion rate of 1 vvd or, preferably, at least 2 vvd or higher, economical favorable production rates of preferably aggregate-free product can be achieved. This applies to all bispecific antibody products, irrespective of being full length antibody or a non-full-length antibody such as (single chain) bispecific antibody constructs.

Another surprising aspect in the context of the present invention is the fact that an adaption of the perfusion rate with respect to the VCD is preferred for bispecific antibody products in order to obtain a favorable product quality and quantity. In this regard, the perfusion rate is continuously, gradually or incrementally increased after inoculation until the preferred set point is reached. Typically, said set point is reached when the biomass set-point equals to an average viable cell density (VCD) of at least 35×10^6 cells/mL, preferably at least 65×10^6 cells/mL, more preferably at least 71×10^6 cells/mL and most preferably at least 85×10^6 cells/mL. Typically the perfusion rate is set to a low value as long as the VCD is low with respect to the maximum VCD reached in the same process. For example, the perfusion rate may be as low as about 0.4 vvd when the VCD equals to about 0.5×10^6 cells. However, as the VCD increases due to cell growth in the bioreactor, the perfusion rate may for example be continuously, gradually or incrementally increased from 0.4 vvd to 2 vvd when a biomass set point of, for example, 35×10^6 cells/mL is reached. Preferably, the perfusion rate is increased the more, the higher the biomass set point is. For example, the vvd may be set to at least 2, preferably to at least 2.01, 3, 4, 5, 6, or even 6.4 when the biomass set point is, for example, at least 65×10^6 cells/mL, more preferably at least 71×10^6 cells/mL and most preferably at least 85×10^6 cells/mL.

Also preferably, the VCD is kept constant after the biomass set point is reached in step (iii) of the present invention, and, accordingly, the perfusion rate is likewise preferably kept constant. It is also envisaged in the context of the present invention that the perfusion rate is adjusted throughout the continuous manufacturing process depending on the continuously measured VCD. VCD is understood to be parameter that is easily accessible and reliable. Integrated viable cell density (IVCD) is understood herein as the area under the curve for VCD as a function of time Thereby, for example, a constant cell specific perfusion rate (CSPR, nL per cell per day) can preferably be uphold, which in turn, may contribute to a controlled product concentration in the bioreactor in order to avoid a negative impact on product quality.

In consequence, a controlled and preferably low product concentration—e.g. preferably below 1.2 g/l for full length bispecific antibodies, preferably below 0.4 g/l for HLE bispecific antibody constructs and preferably below 0.12 g/l for non-HLE bispecific antibody constructs according to the present invention—is ensured throughout the continuous upstream manufacturing process which results in less product being affected by aggregation, clipping or other chemical degradation.

The CSPR is understood in the context of the present invention as the ratio of the perfusion rate D (bioreactor volume per day) to the average VCD ($C_V$, i.e. the average number of viable cells per mL):

$$CSPR = \frac{D}{C_V}$$

It is also understood in the context of the present invention that a consistent microenvironment is preferably provided to the cells in the cell culture, regardless of the cell density. Accordingly, the medium is preferably exchanged at a rate proportional to the cell density. By applying a perfusion rate based on a preferred CSPR the perfusion rate is liked to the cell density.

In the context of the present invention, the CSPR may be applied automatically by a control station with online biomass measurement. This preferably allows minor and/or steady regulation of D in response to $C_V$ variations. Such steady, i.e. continuous, response may be preferred instead of step-wise, i.e. incremental or discrete, change of D. A minimum CSPR is that rate which delivers the minimum amount of nutrients meeting cell needs and supports high productivity. The application of the minimum CSPR or a CSPR close to the minimum CSPR is of particular practical importance at high cell densities, for example in high cell density cultures (HCDC). In the context of the present invention, a HCDC is, for example, directed to a cell culture having a VCD of at least 65×10^6 cells/mL, preferably at least 71×10^6 cells/mL or even at least 85×10^6 cells/mL. It is also envisaged that a HCDC may have a VCD of at least 100×10^6 cells/mL.

A typical minimum CSPR in the context of the present invention is 0.01 nl/cell-day Within the preferred boundaries common to all bispecific antibodies, some do have even more preferred values for best product quality. For example, in the context of the present invention, the CSPR for CD19×CD3 BiTE® antibody construct is preferably below 0.04 nl/cell-day, more preferably equal or below 0.028 nl/cell-day. For bispecific antibody constructs comprising a I2C domain (SEQ ID NO 26) targeting CD3, such as CD33×CD3 BiTE® antibody construct, the CSPR preferably is equal or below 0.028 nl/cell-day or at least 0.051 nl/cell-day, more preferably 0.06 to 0.1 nl/cell-day. For a full length bispecific antibody such as TNF-alpha×TL1A bispecific antibody, the CSPR preferably is equal or below 0.028 nl/cell-day or at least 0.051 nl/cell-day, more preferably 0.06 to 0.1 nl/cell-day.

In the context of the present invention, by "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate.

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. A preferred type of mammalian cells in the context of the present invention are GS-KO cells. Additional examples of mammalian cells are known in the art.

As used herein, the terms "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

Cell culture media include those that are typically employed in and/or are known for use with any cell culture process, such as, but not limited to, batch, extended batch, fed-batch and/or perfusion or continuous culturing of cells.

A "growth" cell culture medium or feed medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium or feed medium refers to a cell culture medium that is typically used in cell cultures during the transition when exponential growth is ending and during the subsequent transition and/or production phases when protein production takes over. Such cell culture medium is sufficiently complete to maintain a desired cell density, viability and/or product titer during this phase.

A "perfusion" cell culture medium or feed medium refers to a cell culture medium that is typically used in cell cultures that are maintained by perfusion or continuous culture methods and is sufficiently complete to support the cell culture during this process. Perfusion cell culture medium formulations may be richer or more concentrated than base cell culture medium formulations to accommodate the method used to remove the spent medium. Perfusion cell culture medium can be used during both the growth and production phases.

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" means the maintenance or proliferation of a mammalian cell under a controlled set of physical conditions.

The term "culture of mammalian cells" means a liquid culture medium containing a plurality of mammalian cells that is maintained or proliferated under a controlled set of physical conditions.

The term "liquid culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a bioreactor can be substantially free of mammalian cells.

A "bioreactor" in the context of the present invention refers to a vessel suitable to conduct a perfusion cell culture wherein at least the steps (i) to (iii) of the present invention take place. The bioreactor may be a disposable container, e.g. made of plastic material, or a reusable container, e.g. made of stainless steel.

The term "agitation" means stirring or otherwise moving a portion of liquid culture medium in a bioreactor. This is performed in order to, e.g., increase the dissolved 02 concentration in the liquid culture medium in a bioreactor. Agitation can be performed using any art known method, e.g., an instrument or propeller. Exemplary devices and methods that can be used to perform agitation of a portion of the liquid culture medium in a bioreactor are known in the art.

The term "continuous process" means a process which continuously feeds fluid through at least a part of the system. For example, in any of the exemplary continuous biological manufacturing systems described herein, a liquid culture medium containing a recombinant therapeutic protein is continuously fed into the system while it is in operation and a therapeutic protein drug substance is fed out of the system.

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "clipping" means the partial cleaving of expressed protein, usually by proteolysis.

The term "degradation" generally means the disintegration of a larger entity, such as a peptide or protein, into at least two smaller entities, whereof one entity may be significantly larger than the other entity or entities.

The term "deamidation" means any a chemical reaction in which an amide functional group in the side chain of an amino acid, typically asparagine or glutamine, is removed or converted to another functional group. Typically, asparagine is converted to aspartic acid or isoaspartic acid.

The term "aggregation" generally refers to the direct mutual attraction between molecules, e.g. via van der Waals forces or chemical bonding. In particular, aggregation is understood as proteins accumulating and clumping together. Aggregates may include amorphous aggregates, oligomers, and amyloid fibrils and are typically referred to as high molecular weight (HMW) species, i.e. molecules having a higher molecular weight than pure product molecules which are non-aggregated molecules, typically referred to herein also as low molecular weight (LMW) species or monomer.

Acidic species are typically understood herein to be comprised in variants which are commonly observed when antibodies are analyzed by charged based-separation techniques such as isoelectric focusing (IEF) gel electrophoresis, capillary isoelectric focusing (cIEF) gel electrophoresis, cation exchange chromatography (CEX) and anion exchange chromatography (AEX). These variants are referred to as acidic or basic species as compared with the main species. Acidic species are typically variants with lower apparent pI and basic species are variants with higher apparent pI when antibodies are analyzed using IEF based methods.

The term "residence time" typically refers to the time which a particular product molecule is present in a bioreactor, i.e. the time spanning from its biotechnological generation until its separation from the bioreactor lumen.

The "product quality" is typically assessed by the presence or absence of clipping, degradation, deamidation and/or aggregation. For example, a product (molecule) comprising a percentile content of HMW species below 40%, preferably below 35, or even 30, 25 or 20% may be considered as of preferred product quality. Also, preferred product quality is associated with the essential absence of residual Host Cell Protein (HCP) and the essential absence of clipping, degradation and deamidation, or with a significant reduction of HCP concentration, clipping, degradation and/or deamidation in comparison to a product manufactured by a process different than the process of the present invention, such as a fed-batch process. Methods known in the art to assess product quality in the context of the present invention comprise Cation Exchange-High Performance Chromatography for Charge Variant Analysis (CEX-HPLC), Tryptic Peptide Mapping for Chemical Modifications, Host Cell Protein (HCP) ELISA Reduced Capillary Electrophoresis-Sodium Dodecyl Sulfate (RCE-SDS), and Size Exclusion-High Performance Liquid Chromatography (SE-HPLC).

The term "antibody product" refers to "secreted protein" or "secreted recombinant protein" and means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term bispecific antibody product encompasses bispecific antibodies such as full length e.g. IgG-based antibodies as well as fragments therefor, which are typically referred to herein as bispecific antibody constructs.

The term "antibody construct" refers to a molecule in which the structure and/or function is/are based on the structure and/or function of an antibody, e.g., of a full-length or whole immunoglobulin molecule (typically comprising of two untruncated heavy and two light chains) and/or is/are drawn from the variable heavy chain (VH) and/or variable light chain (VL) domains of an antibody or fragment thereof. An antibody construct is hence capable of binding to its specific target or antigen. Furthermore, the domain which binds to its binding partner according to the present invention is understood herein as a binding domain of an antibody construct according to the invention. Typically, a binding domain according to the present invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region), preferably of all six CDRs. An alternative approach to define the minimal structure requirements of an antibody is the definition of the epitope of the antibody within the structure of the specific target, respectively, the protein domain of the target protein composing the epitope region (epitope cluster) or by reference to an specific antibody competing with the epitope of the defined antibody. The antibodies on which the constructs according to the invention are based include for example monoclonal, recombinant, chimeric, deimmunized, humanized and human antibodies.

The binding domain of an antibody construct according to the invention may e.g. comprise the above referred groups of CDRs. Preferably, those CDRs are comprised in the framework of an antibody light chain variable region (VL) and an antibody heavy chain variable region (VH); however, it does not have to comprise both. Fd fragments, for example, have two VH regions and often retain some antigen-binding function of the intact antigen-binding domain. Additional examples for the format of antibody fragments, antibody variants or binding domains include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv), the latter being preferred (for example, derived from an scFV-library). Examples for embodiments of antibody constructs according to the invention are e.g. described in WO 00/006605, WO 2005/040220, WO 2008/119567, WO 2010/037838, WO 2013/026837, WO 2013/026833, US 2014/0308285, US 2014/0302037, WO 2014/144722, WO 2014/151910, and WO 2015/048272.

Also within the definition of "binding domain" or "domain which binds" are fragments of full-length antibodies, such as VH, VHH, VL, (s)dAb, Fv, Fd, Fab, Fab', F(ab')2 or "r IgG" ("half antibody"). Antibody constructs according to the invention may also comprise modified fragments of antibodies, also called antibody variants, such as scFv, di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "multibodies" such as triabodies or tetrabodies, and single domain antibodies such as nanobodies or single variable domain antibodies comprising merely one variable domain, which might be VHH, VH or VL, that specifically bind an antigen or epitope independently of other V regions or domains.

As used herein, the terms "single-chain Fv," "single-chain antibodies" or "scFv" refer to single polypeptide chain antibody fragments that comprise the variable regions from both the heavy and light chains, but lack the constant regions. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041. In specific embodiments, single-chain antibodies can also be bispecific, multispecific, human, and/or humanized and/or synthetic.

Furthermore, the definition of the term "antibody construct" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter aha in Harlow and Lane, Antibodies a laboratory manual, CSHL Press (1988) and Using Antibodies: a laboratory manual, CSHL Press (1999), Kontermann and Dübel, Antibody Engineering, Springer, 2nd ed. 2010 and Little, Recombinant Antibodies for Immunotherapy, Cambridge University Press 2009.

The term "bispecific" as used herein refers to an antibody construct which is "at least bispecific", i.e., it comprises at least a first binding domain and a second binding domain, wherein the first binding domain binds to one antigen or target (e.g. the target cell surface antigen), and the second binding domain binds to another antigen or target (e.g. CD3). Accordingly, antibody constructs according to the invention comprise specificities for at least two different antigens or targets. For example, the first domain does preferably not bind to an extracellular epitope of CD3ε of one or more of the species as described herein. The term "target cell surface antigen" refers to an antigenic structure expressed by a cell and which is present at the cell surface such that it is accessible for an antibody construct as described herein. It may be a protein, preferably the extracellular portion of a protein, or a carbohydrate structure, preferably a carbohydrate structure of a protein, such as a glycoprotein. It is preferably a tumor antigen. The term "bispecific antibody construct" of the invention also encompasses multispecific antibody constructs such as trispecific antibody constructs, the latter ones including three binding domains, or constructs having more than three (e.g. four, five . . . ) specificities.

Given that the antibody constructs according to the invention are (at least) bispecific, they do not occur naturally and they are markedly different from naturally occurring products. A "bispecific" antibody construct or immunoglobulin is hence an artificial hybrid antibody or immunoglobulin having at least two distinct binding sides with different specificities. Bispecific antibody constructs can be produced by a variety of methods including fusion of hybridomas or linking of Fab' fragments. See, e.g., Songsivilai & Lachmann, Clin. Exp. Immunol. 79:315-321 (1990).

The at least two binding domains and the variable domains (VH/VL) of the antibody construct of the present invention may or may not comprise peptide linkers (spacer peptides). The term "peptide linker" comprises in accordance with the present invention an amino acid sequence by which the amino acid sequences of one (variable and/or binding) domain and another (variable and/or binding) domain of the antibody construct of the invention are linked with each other. The peptide linkers can also be used to fuse the third domain to the other domains of the antibody construct of the invention. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

The antibody constructs of the present invention are preferably "in vitro generated antibody constructs". This term refers to an antibody construct according to the above definition where all or part of the variable region (e.g., at least one CDR) is generated in a non-immune cell selection, e.g., an in vitro phage display, protein chip or any other method in which candidate sequences can be tested for their ability to bind to an antigen. This term thus preferably excludes sequences generated solely by genomic rearrangement in an immune cell in an animal. A "recombinant antibody" is an antibody made through the use of recombinant DNA technology or genetic engineering.

The term "monoclonal antibody" (mAb) or monoclonal antibody construct as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic side or determinant on the antigen, in contrast to conventional (polyclonal) antibody preparations which typically include different antibodies directed against different determinants (or epitopes). In addition to their specificity, the monoclonal antibodies are advantageous in that they are synthesized by the hybridoma culture, hence uncontaminated by other immunoglobulins. The modifier "monoclonal" indicates the character of the antibody as being obtained from a substantially homogeneous population of antibodies, and is not to be construed as requiring production of the antibody by any particular method.

For the preparation of monoclonal antibodies, any technique providing antibodies produced by continuous cell line cultures can be used. For example, monoclonal antibodies to be used may be made by the hybridoma method first described by Koehler et al., Nature, 256: 495 (1975), or may be made by recombinant DNA methods (see, e.g., U.S. Pat. No. 4,816,567). Examples for further techniques to produce human monoclonal antibodies include the trioma technique, the human B-cell hybridoma technique (Kozbor, Immunology Today 4 (1983), 72) and the EBV-hybridoma technique (Cole et al., Monoclonal Antibodies and Cancer Therapy, Alan R. Liss, Inc. (1985), 77-96).

Hybridomas can then be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the relevant antigen may be used as the immunogen, e.g., recombinant antigen, naturally occurring forms, any variants or fragments thereof, as well as an antigenic peptide thereof. Surface plasmon resonance as employed in the BIAcore system can be used to increase the efficiency of phage antibodies which bind to an epitope of a target cell surface antigen, (Schier, Human Antibodies Hybridomas 7 (1996), 97-105; Malmborg, J. Immunol. Methods 183 (1995), 7-13).

Another exemplary method of making monoclonal antibodies includes screening protein expression libraries, e.g., phage display or ribosome display libraries. Phage display is described, for example, in Ladner et al., U.S. Pat. No. 5,223,409; Smith (1985) Science 228:1315-1317, Clackson et al., Nature, 352: 624-628 (1991) and Marks et al., J. Mol. Biol., 222: 581-597 (1991).

In addition to the use of display libraries, the relevant antigen can be used to immunize a non-human animal, e.g., a rodent (such as a mouse, hamster, rabbit or rat). In one embodiment, the non-human animal includes at least a part of a human immunoglobulin gene. For example, it is possible to engineer mouse strains deficient in mouse antibody production with large fragments of the human Ig (immunoglobulin) loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO 96/33735.

A monoclonal antibody can also be obtained from a non-human animal, and then modified, e.g., humanized, deimmunized, rendered chimeric etc., using recombinant DNA techniques known in the art. Examples of modified antibody constructs include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. The in vitro affinity maturation has successfully been used to optimize antibodies, antibody constructs, and antibody fragments. Random mutations inside the CDRs are introduced using radiation, chemical mutagens or error-prone PCR. In addition, the genetic diversity can be increased by chain shuffling. Two or three rounds of mutation and selection using display methods like phage display usually results in antibody fragments with affinities in the low nanomolar range.

A preferred type of an amino acid substitutional variation of the antibody constructs involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sides (e.g. 6-7 sides) are mutated to generate all possible amino acid substitutions at each side. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sides for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., human target cell surface antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences. A variety of approaches for making chimeric antibodies have been described. See e.g., Morrison et al., Proc. Natl. Acad. Sci U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 0171496; EP 0173494; and GB 2177096.

An antibody, antibody construct, antibody fragment or antibody variant may also be modified by specific deletion of human T cell epitopes (a method called "deimmunization") by the methods disclosed for example in WO 98/52976 or WO 00/34317. Briefly, the heavy and light chain variable domains of an antibody can be analyzed for peptides that bind to MHC class II; these peptides represent potential T cell epitopes (as defined in WO 98/52976 and WO 00/34317). For detection of potential T cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences are disclosed e.g. in Tomlinson, et al. (1992) J. Mol. Biol. 227:776-798; Cook, G. P. et al. (1995) Immunol. Today Vol. 16 (5): 237-242; and Tomlinson et al. (1995) EMBO J. 14: 14:4628-4638. The V BASE directory provides a comprehensive directory of human immunoglobulin variable region sequences (compiled by Tomlinson, I A. et al. MRC Centre for Protein Engineering, Cambridge, UK). These sequences can be used as a source of human sequence, e.g., for framework regions and CDRs. Consensus human framework regions can also be used, for example as described in U.S. Pat. No. 6,300,064.

"Humanized" antibodies, antibody constructs, variants or fragments thereof (such as Fv, Fab, Fab', F(ab')2 or other antigen-binding subsequences of antibodies) are antibodies or immunoglobulins of mostly human sequences, which contain (a) minimal sequence(s) derived from non-human immunoglobulin. For the most part, humanized antibodies are human immunoglobulins (recipient antibody) in which residues from a hypervariable region (also CDR) of the recipient are replaced by residues from a hypervariable region of a non-human (e.g., rodent) species (donor antibody) such as mouse, rat, hamster or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

Humanized antibodies may also be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982, and EP 239 400).

The term "human antibody", "human antibody construct" and "human binding domain" includes antibodies, antibody constructs and binding domains having antibody regions such as variable and constant regions or domains which correspond substantially to human germline immunoglobulin sequences known in the art, including, for example, those described by Kabat et al. (1991) (loc. cit.). The human antibodies, antibody constructs or binding domains of the invention may include amino acid residues not encoded by human germline immunoglobulin sequences (e.g., mutations introduced by random or side-specific mutagenesis in vitro or by somatic mutation in vivo), for example in the CDRs, and in particular, in CDR3. The human antibodies, antibody constructs or binding domains can have at least one, two, three, four, five, or more positions replaced with an amino acid residue that is not encoded by the human germline immunoglobulin sequence. The definition of human antibodies, antibody constructs and binding domains as used herein, however, also contemplates "fully human antibodies", which include only non-artificially and/or genetically altered human sequences of antibodies as those can be derived by using technologies or systems such as the Xenomouse. Preferably, a "fully human antibody" does not include amino acid residues not encoded by human germline immunoglobulin sequences In some embodiments, the antibody constructs of the invention are "isolated" or "substantially pure" antibody constructs. "Isolated" or "substantially pure", when used to describe the antibody constructs disclosed herein, means an antibody construct that has been identified, separated and/or recovered from a component of its production environment. Preferably, the antibody construct is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The antibody constructs may e.g constitute at least about 5%, or at least about 50% by weight of the total protein in a given sample. It is understood that the isolated protein may constitute from 5% to 99.9% by weight of the total protein content, depending on the circumstances. The polypeptide may be made at a significantly higher concentration through the use of an inducible promoter or high expression promoter, such that it is made at increased concentration levels. The definition includes the production of an antibody construct in a wide variety of organisms and/or host cells that are known in the art. In preferred embodiments, the antibody construct will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody construct will be prepared by at least one purification step.

The term "binding domain" characterizes in connection with the present invention a domain which (specifically) binds to/interacts with/recognizes a given target epitope or a given target side on the target molecules (antigens), e.g. CD33 and CD3, respectively. The structure and function of the first binding domain (recognizing e.g. CD33), and preferably also the structure and/or function of the second binding domain (recognizing e.g. CD3), is/are based on the structure and/or function of an antibody, e.g. of a full-length or whole immunoglobulin molecule and/or is/are drawn from the variable heavy chain (VH) and/or variable light chain (VL) domains of an antibody or fragment thereof. Preferably the first binding domain is characterized by the presence of three light chain CDRs (i.e. CDR1, CDR2 and CDR3 of the VL region) and/or three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold.

According to the present invention, binding domains are in the form of one or more polypeptides. Such polypeptides may include proteinaceous parts and non-proteinaceous parts (e.g. chemical linkers or chemical cross-linking agents such as glutaraldehyde). Proteins (including fragments thereof, preferably biologically active fragments, and peptides, usually having less than 30 amino acids) comprise two or more amino acids coupled to each other via a covalent peptide bond (resulting in a chain of amino acids).

The term "polypeptide" as used herein describes a group of molecules, which usually consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

Preferably the binding domain which binds to the target cell surface antigen and/or the binding domain which binds to CD3ε is/are human binding domains. Antibodies and antibody constructs comprising at least one human binding domain avoid some of the problems associated with antibodies or antibody constructs that possess non-human such as rodent (e.g. murine, rat, hamster or rabbit) variable and/or constant regions. The presence of such rodent derived proteins can lead to the rapid clearance of the antibodies or antibody constructs or can lead to the generation of an immune response against the antibody or antibody construct by a patient. In order to avoid the use of rodent derived antibodies or antibody constructs, human or fully human antibodies/antibody constructs can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the use of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies or antibody constructs are expected to minimize the immunogenic and allergic responses intrinsic to mouse or mouse-derivatized mAbs and thus to increase the efficacy and safety of the administered antibodies/antibody constructs. The use of fully human antibodies or antibody constructs can be expected to provide a substantial advantage in the treatment of chronic and recurring human diseases, such as inflammation, autoimmunity, and cancer, which require repeated compound administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with the generation of the first Xeno-Mouse mouse strains (see Green et al. Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. The human Ig containing YACs proved to be compatible with the mouse system for both rearrangement and expression of antibodies and were capable of substituting for the inactivated mouse Ig genes. This was demonstrated by their ability to induce B cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620.

The production of the XenoMouse mice is further discussed and delineated in U.S. patent application Ser. No. 07/466,008, Ser. No. 07/610,515, Ser. No. 07/919,297, Ser. No. 07/922,649, Ser. No. 08/031,801, Ser. No. 08/112,848, Ser. No. 08/234,145, Ser. No. 08/376,279, Ser. No. 08/430,938, Ser. No. 08/464,584, Ser. No. 08/464,582, Ser. No. 08/463,191, Ser. No. 08/462,837, Ser. No. 08/486,853, Ser. No. 08/486,857, Ser. No. 08/486,859, Ser. No. 08/462,513, Ser. No. 08/724,752, and Ser. No. 08/759,620; and U.S. Pat. Nos. 6,162,963; 6,150,584; 6,114,598; 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998), EP 0 463 151 B1, WO 94/02602, WO 96/34096, WO 98/24893, WO 00/76310, and WO 03/47336.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg and Kay, U.S. Pat. Nos. 5,591,669 and 6,023,010 to Krimpenfort and Berns, U.S. Pat. Nos. 5,612,205; 5,721,367; and 5,789,215 to Berns et al., and U.S. Pat. No. 5,643,763 to Choi and Dunn, and GenPharm International U.S. patent application Ser. No. 07/574,748, Ser. No. 07/575,962, Ser. No. 07/810,279, Ser. No. 07/853,408, Ser. No. 07/904,068, Ser. No. 07/990,860, Ser. No. 08/053,131, Ser. No. 08/096,762, Ser. No. 08/155,301, Ser. No. 08/161, 739, Ser. No. 08/165,699, Ser. No. 08/209,741. See also EP 0 546 073 B1, WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al. (1992), Chen et al. (1993), Tuaillon et al. (1993), Choi et al. (1993), Lonberg et al. (1994), Taylor et al. (1994), and Tuaillon et al. (1995), Fishwild et al. (1996).

Kirin has also demonstrated the generation of human antibodies from mice in which, through microcell fusion, large pieces of chromosomes, or entire chromosomes, have been introduced. See European Patent Application Nos. 773 288 and 843 961. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996; 5,698,767; and 5,958,765.

Human anti-mouse antibody (HAMA) responses have led the industry to prepare chimeric or otherwise humanized antibodies. It is however expected that certain human anti-chimeric antibody (HACA) responses will be observed, particularly in chronic or multi-dose utilizations of the antibody. Thus, it would be desirable to provide antibody constructs comprising a human binding domain against the target cell surface antigen and a human binding domain against CD3ε in order to vitiate concerns and/or effects of HAMA or HACA response.

The terms "(specifically) binds to", (specifically) recognizes", "is (specifically) directed to", and "(specifically) reacts with" mean in accordance with this invention that a binding domain interacts or specifically interacts with a given epitope or a given target side on the target molecules (antigens), here: target cell surface antigen and CD3ε, respectively.

The term "epitope" refers to a side on an antigen to which a binding domain, such as an antibody or immunoglobulin, or a derivative, fragment or variant of an antibody or an immunoglobulin, specifically binds. An "epitope" is antigenic and thus the term epitope is sometimes also referred to herein as "antigenic structure" or "antigenic determinant". Thus, the binding domain is an "antigen interaction side". Said binding/interaction is also understood to define a "specific recognition".

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof (in the context of the present invention, the antigenic structure for one of the binding domains is comprised within the target cell surface antigen protein). For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

A method for epitope mapping is described in the following: When a region (a contiguous amino acid stretch) in the human target cell surface antigen protein is exchanged/replaced with its corresponding region of a non-human and non-primate target cell surface antigen (e.g., mouse target cell surface antigen, but others like chicken, rat, hamster, rabbit etc. might also be conceivable), a decrease in the binding of the binding domain is expected to occur, unless the binding domain is cross-reactive for the non-human, non-primate target cell surface antigen used. Said decrease is preferably at least 10%, 20%, 30%, 40%, or 50%; more preferably at least 60%, 70%, or 80%, and most preferably 90%, 95% or even 100% in comparison to the binding to the respective region in the human target cell surface antigen protein, whereby binding to the respective region in the human target cell surface antigen protein is set to be 100%. It is envisaged that the aforementioned human target cell surface antigen/non-human target cell surface antigen chimeras are expressed in CHO cells. It is also envisaged that the human target cell surface antigen/non-human target cell surface antigen chimeras are fused with a transmembrane domain and/or cytoplasmic domain of a different membrane-bound protein such as EpCAM.

In an alternative or additional method for epitope mapping, several truncated versions of the human target cell surface antigen extracellular domain can be generated in order to determine a specific region that is recognized by a binding domain. In these truncated versions, the different extracellular target cell surface antigen domains/sub-domains or regions are stepwise deleted, starting from the N-terminus. It is envisaged that the truncated target cell surface antigen versions may be expressed in CHO cells. It is also envisaged that the truncated target cell surface antigen versions may be fused with a transmembrane domain and/or cytoplasmic domain of a different membrane-bound protein such as EpCAM. It is also envisaged that the truncated target cell surface antigen versions may encompass a signal peptide domain at their N-terminus, for example a signal peptide derived from mouse IgG heavy chain signal peptide. It is furthermore envisaged that the truncated target cell surface antigen versions may encompass a v5 domain at their N-terminus (following the signal peptide) which allows verifying their correct expression on the cell surface. A decrease or a loss of binding is expected to occur with those truncated target cell surface antigen versions which do not encompass any more the target cell surface antigen region that is recognized by the binding domain. The decrease of binding is preferably at least 10%, 20%, 30%, 40%, 50%; more preferably at least 60%, 70%, 80%, and most preferably 90%, 95% or even 100%, whereby binding to the entire human target cell surface antigen protein (or its extracellular region or domain) is set to be 100.

A further method to determine the contribution of a specific residue of a target cell surface antigen to the recognition by an antibody construct or binding domain is alanine scanning (see e.g. Morrison K L & Weiss G A. Cur Opin Chem Biol. 2001 June; 5(3):302-7), where each residue to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired. Alanine scanning is a mature technology which has been used for a long period of time.

The interaction between the binding domain and the epitope or the region comprising the epitope implies that a binding domain exhibits appreciable affinity for the epitope/the region comprising the epitope on a particular protein or antigen (here: target cell surface antigen and CD3, respectively) and, generally, does not exhibit significant reactivity with proteins or antigens other than the target cell surface antigen or CD3. "Appreciable affinity" includes binding with an affinity of about $10^{-6}$ M (KD) or stronger. Preferably, binding is considered specific when the binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Whether a binding domain specifically reacts with or binds to a target can be tested readily by, inter alia, comparing the reaction of said binding domain with a target protein or antigen with the reaction of said binding domain with proteins or antigens other than the target cell surface antigen or CD3. Preferably, a binding domain of the invention does not essentially or substantially bind to proteins or antigens other than the target cell surface antigen or CD3 (i.e., the first binding domain is preferably not capable of binding to proteins other than the target cell surface antigen and the second binding domain is not capable of binding to proteins other than CD3). It is an envisaged characteristic of the antibody constructs according to the present invention to have superior affinity characteristics in comparison to other HLE formats. Such a superior affinity, in consequence, suggests a prolonged half-life in vivo. The longer half-life of the antibody constructs according to the present invention may reduce the duration and frequency of administration which typically contributes to improved patient compliance. This is of particular importance as the antibody constructs of the present invention are particularly beneficial for highly weakened or even multimorbide cancer patients.

The term "does not essentially/substantially bind" or "is not capable of binding" means that a binding domain of the present invention does not bind a protein or antigen other than the target cell surface antigen or CD3, i.e., does not show reactivity of more than 30%, preferably not more than 20%, more preferably not more than 10%, particularly preferably not more than 9%, 8%, 7%, 6% or 5% with proteins or antigens other than the target cell surface antigen or CD3, whereby binding to the target cell surface antigen or CD3, respectively, is set to be 100%.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-side with its specific antigen may result in a simple binding of said side to the antigen. Moreover, the specific interaction of the antigen-interaction-side with its specific antigen may alternatively or additionally result in the initiation of a signal, e.g. due to the induction of a change of the conformation of the antigen, an oligomerization of the antigen, etc.

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding side.

Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding side (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding side is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding side. H3, for example, can be as short as two amino acid residues or greater than 26 amino acids.

In a classical full-length antibody or immunoglobulin, each light (L) chain is linked to a heavy (H) chain by one covalent disulfide bond, while the two H chains are linked to each other by one or more disulfide bonds depending on the H chain isotype. The CH domain most proximal to VH is usually designated as CH1. The constant ("C") domains are not directly involved in antigen binding, but exhibit various effector functions, such as antibody-dependent, cell-mediated cytotoxicity and complement activation. The Fc region of an antibody is comprised within the heavy chain constant domains and is for example able to interact with cell surface located Fc receptors.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, CA, 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The term "Fc portion" or "Fc monomer" means in connection with this invention a polypeptide comprising at least one domain having the function of a CH2 domain and at least one domain having the function of a CH3 domain of an immunoglobulin molecule. As apparent from the term "Fc monomer", the polypeptide comprising those CH domains is a "polypeptide monomer". An Fc monomer can be a polypeptide comprising at least a fragment of the constant region of an immunoglobulin excluding the first constant region immunoglobulin domain of the heavy chain (CH1), but maintaining at least a functional part of one CH2 domain and a functional part of one CH3 domain, wherein the CH2 domain is amino terminal to the CH3 domain. In a preferred aspect of this definition, an Fc monomer can be a polypeptide constant region comprising a portion of the Ig-Fc hinge region, a CH2 region and a CH3 region, wherein the hinge region is amino terminal to the CH2 domain. It is envisaged that the hinge region of the present invention promotes dimerization. Such Fc polypeptide molecules can be obtained by papain digestion of an immunoglobulin region (of course resulting in a dimer of two Fc polypeptide), for example and not limitation. In another aspect of this definition, an Fc monomer can be a polypeptide region comprising a portion of a CH2 region and a CH3 region. Such Fc polypeptide molecules can be obtained by pepsin digestion of an immunoglobulin molecule, for example and not limitation. In one embodiment, the polypeptide sequence of an Fc monomer is substantially similar to an Fc polypeptide sequence of: an $IgG_1$ Fc region, an $IgG_2$ Fc region, an $IgG_3$ Fc region, an $IgG_4$ Fc region, an IgM Fc region, an IgA Fc region, an IgD Fc region and an IgE Fc region. (See, e.g., Padlan, Molecular Immunology, 31(3), 169-217 (1993)). Because there is some variation between immunoglobulins, and solely for clarity, Fc monomer refers to the last two heavy chain constant region immunoglobulin domains of IgA, IgD, and IgG, and the last three heavy chain constant region immunoglobulin domains of IgE and IgM. As mentioned, the Fc monomer can also include the flexible hinge N-terminal to these domains. For IgA and IgM, the Fc monomer may include the J chain. For IgG, the Fc portion comprises immunoglobulin domains CH2 and CH3 and the hinge between the first two domains and CH2. Although the boundaries of the Fc portion may vary an example for a human IgG heavy chain Fc portion comprising a functional hinge, CH2 and CH3 domain can be defined e.g. to comprise residues D231 (of the hinge domain—corresponding to D234 in Table 1 below)) to P476, respectively L476 (for $IgG_4$) of the carboxyl-terminus of the CH3 domain, wherein the numbering is according to Kabat. The two Fc portions or Fc monomers, which are fused to each other via a peptide linker define the third domain of the antibody construct of the invention, which may also be defined as scFc domain.

In one embodiment of the invention it is envisaged that a scFc domain as disclosed herein, respectively the Fc monomers fused to each other are comprised only in the third domain of the antibody construct.

In line with the present invention an IgG hinge region can be identified by analogy using the Kabat numbering as set forth in Table 1. In line with the above, it is envisaged that a hinge domain/region of the present invention comprises the amino acid residues corresponding to the $IgG_1$ sequence stretch of D234 to P243 according to the Kabat numbering. It is likewise envisaged that a hinge domain/region of the present invention comprises or consists of the IgG1 hinge sequence DKTHTCPPCP (SEQ ID NO: 182) (corresponding to the stretch D234 to P243 as shown in Table 1 below—variations of said sequence are also envisaged provided that the hinge region still promotes dimerization). In a preferred embodiment of the invention the glycosylation site at Kabat position 314 of the CH2 domains in the third domain of the antibody construct is removed by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321). It is also envisaged that the third domain of the antibody construct of the invention comprises or consists in an amino to carboxyl order: DKTHTCPPCP (SEQ ID NO: 182) (i.e. hinge) —CH2-CH3-linker-DKTHTCPPCP (SEQ ID NO: 182) (i.e. hinge) —CH2-CH3. The peptide linker of the aforementioned antibody construct is in a preferred embodiment characterized by the amino acid sequence Gly-Gly-Gly-Gly-Ser, i.e. Gly$_4$Ser (SEQ ID NO: 187), or polymers thereof, i.e. (Gly$_4$Ser)x, where x is an integer of 5 or greater (e.g. 5, 6, 7, 8 etc. or greater), 6 being preferred ((Gly4Ser)6). Said construct may further comprise the aforementioned substitutions N314X, preferably N314G, and/or the further substitutions V321C and R309C. In a preferred embodiment of the antibody constructs of the invention as defined herein before, it is envisaged that the second domain binds to an extracellular epitope of the human and/or the *Macaca* CD3ε chain.

TABLE 1

Kabat numbering of the amino acid residues of the hinge region

| IMGT numbering for the hinge | IgG$_1$ amino acid translation | Kabat numbering |
| --- | --- | --- |
| 1 | I | 226 |
| 2 | P | 227 |
| 3 | K | 228 |
| 4 | S | 232 |
| 5 | C | 233 |
| 6 | D | 234 |
| 7 | K | 235 |
| 8 | T | 236 |
| 9 | H | 237 |
| 10 | T | 238 |
| 11 | C | 239 |
| 12 | P | 240 |
| 13 | P | 241 |
| 14 | C | 242 |
| 15 | P | 243 |

In further embodiments of the present invention, the hinge domain/region comprises or consists of the IgG2 subtype hinge sequence ERKCCVECPPCP (SEQ ID NO: 183), the IgG3 subtype hinge sequence ELKTPLDTTHTCPRCP (SEQ ID NO: 184) or ELKTPLGDTTHTCPRCP (SEQ ID NO: 185), and/or the IgG4 subtype hinge sequence ESKYGPPCPSCP (SEQ ID NO: 186). The IgG1 subtype hinge sequence may be the following one EPKSCDKTHTCPPCP (as shown in Table 1 and SEQ ID NO: 183). These core hinge regions are thus also envisaged in the context of the present invention.

The location and sequence of the IgG CH2 and IgG CD3 domain can be identified by analogy using the Kabat numbering as set forth in Table 2:

TABLE 2

Kabat numbering of the amino acid residues of the IgG CH2 and CH3 region

| IgG subtype | CH2 aa translation | CH2 Kabat numbering | CH3 aa translation | CH3 Kabat numbering |
| --- | --- | --- | --- | --- |
| IgG$_1$ | APE . . . KAK | 244 . . . 360 | GQP . . . PGK | 361 . . . 478 |
| IgG$_2$ | APP . . . KTK | 244 . . . 360 | GQP . . . PGK | 361 . . . 478 |

TABLE 2-continued

Kabat numbering of the amino acid residues of the IgG CH2 and CH3 region

| IgG subtype | CH2 aa translation | CH2 Kabat numbering | CH3 aa translation | CH3 Kabat numbering |
| --- | --- | --- | --- | --- |
| IgG$_3$ | APE . . . KTK | 244 . . . 360 | GQP . . . PGK | 361 . . . 478 |
| IgG$_4$ | APE . . . KAK | 244 . . . 360 | GQP . . . LGK | 361 . . . 478 |

In one embodiment of the invention the emphasized bold amino acid residues in the CH3 domain of the first or both Fc monomers are deleted.

The peptide linker, by whom the polypeptide monomers ("Fc portion" or "Fc monomer") of the third domain are fused to each other, preferably comprises at least 25 amino acid residues (25, 26, 27, 28, 29, 30 etc.). More preferably, this peptide linker comprises at least 30 amino acid residues (30, 31, 32, 33, 34, 35 etc.). It is also preferred that the linker comprises up to 40 amino acid residues, more preferably up to 35 amino acid residues, most preferably exactly 30 amino acid residues. A preferred embodiment of such peptide linker is characterized by the amino acid sequence Gly-Gly-Gly-Gly-Ser, i.e. Gly$_4$Ser (SEQ ID NO: 187), or polymers thereof, i.e. (Gly$_4$Ser)x, where x is an integer of 5 or greater (e.g. 6, 7 or 8). Preferably the integer is 6 or 7, more preferably the integer is 6.

In the event that a linker is used to fuse the first domain to the second domain, or the first or second domain to the third domain, this linker is preferably of a length and sequence sufficient to ensure that each of the first and second domains can, independently from one another, retain their differential binding specificities. For peptide linkers which connect the at least two binding domains (or two variable domains) in the antibody construct of the invention, those peptide linkers are preferred which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A preferred embodiment of the peptide linker for a fusion the first and the second domain is depicted in SEQ ID NO:1. A preferred linker embodiment of the peptide linker for a fusion the second and the third domain is a (Gly)$_4$-linker, respectively G$_4$-linker.

A particularly preferred "single" amino acid in the context of one of the above described "peptide linker" is Gly. Accordingly, said peptide linker may consist of the single amino acid Gly. In a preferred embodiment of the invention a peptide linker is characterized by the amino acid sequence Gly-Gly-Gly-Gly-Ser, i.e. Gly$_4$Ser (SEQ ID NO: 187), or polymers thereof, i.e. (Gly$_4$Ser)x, where x is an integer of 1 or greater (e.g. 2 or 3). Preferred linkers are depicted in SEQ ID Nos: 1 to 12. The characteristics of said peptide linker, which comprise the absence of the promotion of secondary structures, are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which furthermore do not promote any secondary structures are preferred. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, New York, 2001).

In a preferred embodiment of the antibody construct or the present invention the first and second domain form an antibody construct in a format selected from the group consisting of (scFv)$_2$, scFv-single domain mAb, diabody and oligomers of any of the those formats According to a particularly preferred embodiment, and as documented in the appended examples, the first and the second domain of the antibody construct of the invention is a "bispecific single chain antibody construct", more preferably a bispecific "single chain Fv" (scFv). Although the two domains of the Fv fragment, VL and VH, are coded for by separate genes, they can be joined, using recombinant methods, by a synthetic linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are whole or full-length antibodies. A single-chain variable fragment (scFv) is hence a fusion protein of the variable region of the heavy chain (VH) and of the light chain (VL) of immunoglobulins, usually connected with a short linker peptide of about ten to about 25 amino acids, preferably about 15 to 20 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and introduction of the linker.

Bispecific single chain antibody constructs are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Loffler, Blood, (2000), 95, 6, 2098-2103, Bruhl, Immunol., (2001), 166, 2420-2426, Kipriyanov, J. Mol. Biol., (1999), 293, 41-56. Techniques described for the production of single chain antibodies (see, inter alia, U.S. Pat. No. 4,946,778, Kontermann and Dübel (2010), loc. Cit. and Little (2009), loc. Cit.) can be adapted to produce single chain antibody constructs specifically recognizing (an) elected target(s).

Bivalent (also called divalent) or bispecific single-chain variable fragments (bi-scFvs or di-scFvs having the format (scFv)$_2$ can be engineered by linking two scFv molecules (e.g. with linkers as described hereinbefore). If these two scFv molecules have the same binding specificity, the resulting (scFv)$_2$ molecule will preferably be called bivalent (i.e. it has two valences for the same target epitope). If the two scFv molecules have different binding specificities, the resulting (scFv)$_2$ molecule will preferably be called bispecific. The linking can be done by producing a single peptide chain with two VH regions and two VL regions, yielding tandem scFvs (see e.g. Kufer P. et al., (2004) Trends in Biotechnology 22(5):238-244). Another possibility is the creation of scFv molecules with linker peptides that are too short for the two variable regions to fold together (e.g. about five amino acids), forcing the scFvs to dimerize. This type is known as diabodies (see e.g. Hollinger, Philipp et al., (July 1993) Proceedings of the National Academy of Sciences of the United States of America 90 (14): 6444-8).

In line with this invention either the first, the second or the first and the second domain may comprise a single domain antibody, respectively the variable domain or at least the CDRs of a single domain antibody. Single domain antibodies comprise merely one (monomeric) antibody variable domain which is able to bind selectively to a specific antigen, independently of other V regions or domains. The first single domain antibodies were engineered from heavy chain antibodies found in camelids, and these are called V$_H$H fragments. Cartilaginous fishes also have heavy chain antibodies (IgNAR) from which single domain antibodies called V$_{NAR}$ fragments can be obtained. An alternative approach is to split the dimeric variable domains from common immunoglobulins e.g. from humans or rodents into monomers, hence obtaining VH or VL as a single domain Ab. Although most research into single domain antibodies is currently based on heavy chain variable domains, nanobodies derived from light chains have also been shown to bind specifically to target epitopes. Examples of single domain antibodies are called sdAb, nanobodies or single variable domain antibodies.

A (single domain mAb)$_2$ is hence a monoclonal antibody construct composed of (at least) two single domain monoclonal antibodies, which are individually selected from the group comprising V$_H$, V$_L$, V$_H$H and V$_{NAR}$. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

Whether or not an antibody construct competes for binding with another given antibody construct can be measured in a competition assay such as a competitive ELISA or a cell-based competition assay. Avidin-coupled microparticles (beads) can also be used. Similar to an avidin-coated ELISA plate, when reacted with a biotinylated protein, each of these beads can be used as a substrate on which an assay can be performed. Antigen is coated onto a bead and then precoated with the first antibody. The second antibody is added and any additional binding is determined. Possible means for the read-out includes flow cytometry.

T cells or T lymphocytes are a type of lymphocyte (itself a type of white blood cell) that play a central role in cell-mediated immunity. There are several subsets of T cells, each with a distinct function. T cells can be distinguished from other lymphocytes, such as B cells and NK cells, by the presence of a T cell receptor (TCR) on the cell surface. The TCR is responsible for recognizing antigens bound to major histocompatibility complex (MHC) molecules and is composed of two different protein chains. In 95% of the T cells, the TCR consists of an alpha (α) and beta (β) chain. When the TCR engages with antigenic peptide and MHC (peptide/MHC complex), the T lymphocyte is activated through a series of biochemical events mediated by associated enzymes, co-receptors, specialized adaptor molecules, and activated or released transcription factors.

The CD3 receptor complex is a protein complex and is composed of four chains. In mammals, the complex contains a CD3γ (gamma) chain, a CD3δ (delta) chain, and two CD3ε (epsilon) chains. These chains associate with the T cell receptor (TCR) and the so-called ζ (zeta) chain to form the T cell receptor CD3 complex and to generate an activation signal in T lymphocytes. The CD3γ (gamma), CD3δ (delta), and CD3ε (epsilon) chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signaling capacity of the TCR. The CD3 epsilon molecule is a polypeptide which in humans is encoded by the CD3E gene which resides on chromosome 11. The most preferred epitope of CD3 epsilon is comprised within amino acid residues 1-27 of the human CD3 epsilon extracellular domain. It is envisaged that antibody constructs according to the present invention typically and advantageously show less unspecific T cell activation, which is not desired in specific immunotherapy. This translates to a reduced risk of side effects.

The redirected lysis of target cells via the recruitment of T cells by a multispecific, at least bispecific, antibody construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

Cytotoxicity mediated by antibody constructs of the invention can be measured in various ways. Effector cells can be e.g. stimulated enriched (human) CD8 positive T cells or unstimulated (human) peripheral blood mononuclear cells (PBMC). If the target cells are of macaque origin or express or are transfected with macaque target cell surface antigen which is bound by the first domain, the effector cells should also be of macaque origin such as a macaque T cell line, e.g. 4119LnPx. The target cells should express (at least the extracellular domain of) the target cell surface antigen, e.g. human or macaque target cell surface antigen. Target cells can be a cell line (such as CHO) which is stably or transiently transfected with target cell surface antigen, e.g. human or macaque target cell surface antigen. Alternatively, the target cells can be a target cell surface antigen positive natural expresser cell line. Usually $EC_{50}$ values are expected to be lower with target cell lines expressing higher levels of target cell surface antigen on the cell surface. The effector to target cell (E:T) ratio is usually about 10:1, but can also vary. Cytotoxic activity of target cell surface antigenxCD3 bispecific antibody constructs can be measured in a $^{51}$Cr-release assay (incubation time of about 18 hours) or in a in a FACS-based cytotoxicity assay (incubation time of about 48 hours). Modifications of the assay incubation time (cytotoxic reaction) are also possible. Other methods of measuring cytotoxicity are well-known to the skilled person and comprise MTT or MTS assays, ATP-based assays including bioluminescent assays, the sulforhodamine B (SRB) assay, WST assay, clonogenic assay and the ECIS technology.

The cytotoxic activity mediated by target cell surface antigenxCD3 bispecific antibody constructs of the present invention is preferably measured in a cell-based cytotoxicity assay. It may also be measured in a $^{51}$Cr-release assay. It is represented by the $EC_{50}$ value, which corresponds to the half maximal effective concentration (concentration of the antibody construct which induces a cytotoxic response halfway between the baseline and maximum). Preferably, the $EC_{50}$ value of the target cell surface antigenxCD3 bispecific antibody constructs is ≤5000 pM or ≤4000 pM, more preferably ≤3000 pM or ≤2000 pM, even more preferably ≤1000 pM or ≤500 pM, even more preferably ≤400 pM or ≤300 pM, even more preferably ≤200 pM, even more preferably ≤100 pM, even more preferably ≤50 pM, even more preferably ≤20 pM or ≤10 pM, and most preferably ≤5 pM.

The above given $EC_{50}$ values can be measured in different assays. The skilled person is aware that an $EC_{50}$ value can be expected to be lower when stimulated/enriched $CD8^+$ T cells are used as effector cells, compared with unstimulated PBMC. It can furthermore be expected that the $EC_{50}$ values are lower when the target cells express a high number of the target cell surface antigen compared with a low target expression rat. For example, when stimulated/enriched human $CD8^+$ T cells are used as effector cells (and either target cell surface antigen transfected cells such as CHO cells or target cell surface antigen positive human cell lines are used as target cells), the $EC_{50}$ value of the target cell surface antigenxCD3 bispecific antibody construct is preferably ≤1000 pM, more preferably ≤500 pM, even more preferably ≤250 pM, even more preferably ≤100 pM, even more preferably ≤50 pM, even more preferably ≤10 pM, and most preferably ≤5 pM. When human PBMCs are used as effector cells, the $EC_{50}$ value of the target cell surface antigenxCD3 bispecific antibody construct is preferably ≤5000 pM or ≤4000 pM (in particular when the target cells are target cell surface antigen positive human cell lines), more preferably ≤2000 pM (in particular when the target cells are target cell surface antigen transfected cells such as CHO cells), more preferably ≤1000 pM or ≤500 pM, even more preferably ≤200 pM, even more preferably ≤150 pM, even more preferably ≤100 pM, and most preferably ≤50 pM, or lower. When a macaque T cell line such as LnPx4119 is used as effector cells, and a macaque target cell surface antigen transfected cell line such as CHO cells is used as target cell line, the $EC_{50}$ value of the target cell surface antigenxCD3 bispecific antibody construct is preferably ≤2000 pM or ≤1500 pM, more preferably ≤1000 pM or ≤500 pM, even more preferably ≤300 pM or ≤250 pM, even more preferably ≤100 pM, and most preferably ≤50 pM.

Preferably, the target cell surface antigenxCD3 bispecific antibody constructs of the present invention do not induce/mediate lysis or do not essentially induce/mediate lysis of target cell surface antigen negative cells such as CHO cells. The term "do not induce lysis", "do not essentially induce lysis", "do not mediate lysis" or "do not essentially mediate lysis" means that an antibody construct of the present invention does not induce or mediate lysis of more than 30%, preferably not more than 20%, more preferably not more than 10%, particularly preferably not more than 9%, 8%, 7%, 6% or 5% of target cell surface antigen negative cells, whereby lysis of a target cell surface antigen positive human cell line is set to be 100%. This usually applies for concentrations of the antibody construct of up to 500 nM. The skilled person knows how to measure cell lysis without further ado. Moreover, the present specification teaches specific instructions how to measure cell lysis.

The difference in cytotoxic activity between the monomeric and the dimeric isoform of individual target cell surface antigenxCD3 bispecific antibody constructs is referred to as "potency gap". This potency gap can e.g. be calculated as ratio between $EC_{50}$ values of the molecule's monomeric and dimeric form. Potency gaps of the target cell surface antigenxCD3 bispecific antibody constructs of the present invention are preferably ≤5, more preferably ≤4, even more preferably ≤3, even more preferably ≤2 and most preferably ≤1.

The first and/or the second (or any further) binding domain(s) of the antibody construct of the invention is/are preferably cross-species specific for members of the mammalian order of primates. Cross-species specific CD3 binding domains are, for example, described in WO 2008/119567. According to one embodiment, the first and/or second binding domain, in addition to binding to human target cell surface antigen and human CD3, respectively, will also bind to target cell surface antigen/CD3 of primates including (but not limited to) new world primates (such as

*Callithrix jacchus, Saguinus oedipus* or *Saimiri sciureus*), old world primates (such baboons and macaques), gibbons, and non-human homininae.

In one embodiment of the antibody construct of the invention the first domain binds to human target cell surface antigen and further binds to macaque target cell surface antigen, such as target cell surface antigen of *Macaca fascicularis*, and more preferably, to macaque target cell surface antigen expressed on the surface macaque cells. The affinity of the first binding domain for macaque target cell surface antigen is preferably ≤15 nM, more preferably ≤10 nM, even more preferably ≤5 nM, even more preferably ≤1 nM, even more preferably ≤0.5 nM, even more preferably ≤0.1 nM, and most preferably ≤0.05 nM or even ≤0.01 nM.

Preferably the affinity gap of the antibody constructs according to the invention for binding macaque target cell surface antigen versus human target cell surface antigen [ma target cell surface antigen:hu target cell surface antigen] (as determined e.g. by BiaCore or by Scatchard analysis) is <100, preferably <20, more preferably <15, further preferably <10, even more preferably <8, more preferably <6 and most preferably <2. Preferred ranges for the affinity gap of the antibody constructs according to the invention for binding macaque target cell surface antigen versus human target cell surface antigen are between 0.1 and 20, more preferably between 0.2 and 10, even more preferably between 0.3 and 6, even more preferably between 0.5 and 3 or between 0.5 and 2.5, and most preferably between 0.5 and 2 or between 0.6 and 2.

The second (binding) domain of the antibody construct of the invention binds to human CD3 epsilon and/or to *Macaca* CD3 epsilon. In a preferred embodiment the second domain further bind to *Callithrix jacchus*, *Saguinus oedipus* or *Saimiri sciureus* CD3 epsilon. *Callithrix jacchus* and *Saguinus 45yophil* are both new world primate belonging to the family of Callitrichidae, while *Saimiri sciureus* is a new world primate belonging to the family of Cebidae.

It is preferred for the antibody construct of the present invention that the second domain which binds to an extracellular epitope of the human and/or the *Macaca* CD3 on the comprises a VL region comprising CDR-L1, CDR-L2 and CDR-L3 selected from:
  (a) CDR-L1 as depicted in SEQ ID NO: 27 of WO 2008/119567, CDR-L2 as depicted in SEQ ID NO: 28 of WO 2008/119567 and CDR-L3 as depicted in SEQ ID NO: 29 of WO 2008/119567;
  (b) CDR-L1 as depicted in SEQ ID NO: 117 of WO 2008/119567, CDR-L2 as depicted in SEQ ID NO: 118 of WO 2008/119567 and CDR-L3 as depicted in SEQ ID NO: 119 of WO 2008/119567; and
  I CDR-L1 as depicted in SEQ ID NO: 153 of WO 2008/119567, CDR-L2 as depicted in SEQ ID NO: 154 of WO 2008/119567 and CDR-L3 as depicted in SEQ ID NO: 155 of WO 2008/119567.

In an also preferred embodiment of the antibody construct of the present invention, the second domain which binds to an extracellular epitope of the human and/or the *Macaca* CD3 epsilon chain comprises a VH region comprising CDR-H1, CDR-H2 and CDR-H3 selected from:
  (a) CDR-H1 as depicted in SEQ ID NO: 12 of WO 2008/119567, CDR-H2 as depicted in SEQ ID NO: 13 of WO 2008/119567 and CDR-H3 as depicted in SEQ ID NO: 14 of WO 2008/119567;
  (b) CDR-H1 as depicted in SEQ ID NO: 30 of WO 2008/119567, CDR-H2 as depicted in SEQ ID NO: 31 of WO 2008/119567 and CDR-H3 as depicted in SEQ ID NO: 32 of WO 2008/119567;
  I CDR-H1 as depicted in SEQ ID NO: 48 of WO 2008/119567, CDR-H2 as depicted in SEQ ID NO: 49 of WO 2008/119567 and CDR-H3 as depicted in SEQ ID NO: 50 of WO 2008/119567;
  (d) CDR-H1 as depicted in SEQ ID NO: 66 of WO 2008/119567, CDR-H2 as depicted in SEQ ID NO: 67 of WO 2008/119567 and CDR-H3 as depicted in SEQ ID NO: 68 of WO 2008/119567;
  I CDR-H1 as depicted in SEQ ID NO: 84 of WO 2008/119567, CDR-H2 as depicted in SEQ ID NO: 85 of WO 2008/119567 and CDR-H3 as depicted in SEQ ID NO: 86 of WO 2008/119567;
  (f) CDR-H1 as depicted in SEQ ID NO: 102 of WO 2008/119567, CDR-H2 as depicted in SEQ ID NO: 103 of WO 2008/119567 and CDR-H3 as depicted in SEQ ID NO: 104 of WO 2008/119567;
  (g) CDR-H1 as depicted in SEQ ID NO: 120 of WO 2008/119567, CDR-H2 as depicted in SEQ ID NO: 121 of WO 2008/119567 and CDR-H3 as depicted in SEQ ID NO: 122 of WO 2008/119567;
  (h) CDR-H1 as depicted in SEQ ID NO: 138 of WO 2008/119567, CDR-H2 as depicted in SEQ ID NO: 139 of WO 2008/119567 and CDR-H3 as depicted in SEQ ID NO: 140 of WO 2008/119567;
  (i) CDR-H1 as depicted in SEQ ID NO: 156 of WO 2008/119567, CDR-H2 as depicted in SEQ ID NO: 157 of WO 2008/119567 and CDR-H3 as depicted in SEQ ID NO: 158 of WO 2008/119567; and
  (j) CDR-H1 as depicted in SEQ ID NO: 174 of WO 2008/119567, CDR-H2 as depicted in SEQ ID NO: 175 of WO 2008/119567 and CDR-H3 as depicted in SEQ ID NO: 176 of WO 2008/119567.

In a preferred embodiment of the antibody construct of the invention the above described three groups of VL CDRs are combined with the above described ten groups of VH CDRs within the second binding domain to form (30) groups, each comprising CDR-L 1-3 and CDR-H1-3.

It is preferred for the antibody construct of the present invention that the second domain which binds to CD3 comprises a VL region selected from the group consisting of a VL region as depicted in SEQ ID NO: 17, 21, 35, 39, 53, 57, 71, 75, 89, 93, 107, 111, 125, 129, 143, 147, 161, 165, 179 or 183 of WO 2008/119567 or as depicted in SEQ ID NO: 200.

It is also preferred that the second domain which binds to CD3 comprises a VH region selected from the group consisting of a VH region as depicted in SEQ ID NO: 15, 19, 33, 37, 51, 55, 69, 73, 87, 91, 105, 109, 123, 127, 141, 145, 159, 163, 177 or 181 of WO 2008/119567 or as depicted in SEQ ID NO: 201.

More preferably, the antibody construct of the present invention is characterized by a second domain which binds to CD3 comprising a VL region and a VH region selected from the group consisting of:
  (a) a VL region as depicted in SEQ ID NO: 17 or 21 of WO 2008/119567 and a VH region as depicted in SEQ ID NO: 15 or 19 of WO 2008/119567;
  (b) a VL region as depicted in SEQ ID NO: 35 or 39 of WO 2008/119567 and a VH region as depicted in SEQ ID NO: 33 or 37 of WO 2008/119567;
  I a VL region as depicted in SEQ ID NO: 53 or 57 of WO 2008/119567 and a VH region as depicted in SEQ ID NO: 51 or 55 of WO 2008/119567;
  (d) a VL region as depicted in SEQ ID NO: 71 or 75 of WO 2008/119567 and a VH region as depicted in SEQ ID NO: 69 or 73 of WO 2008/119567;

I a VL region as depicted in SEQ ID NO: 89 or 93 of WO 2008/119567 and a VH region as depicted in SEQ ID NO: 87 or 91 of WO 2008/119567;

(f) a VL region as depicted in SEQ ID NO: 107 or 111 of WO 2008/119567 and a VH region as depicted in SEQ ID NO: 105 or 109 of WO 2008/119567;

(g) a VL region as depicted in SEQ ID NO: 125 or 129 of WO 2008/119567 and a VH region as depicted in SEQ ID NO: 123 or 127 of WO 2008/119567;

(h) a VL region as depicted in SEQ ID NO: 143 or 147 of WO 2008/119567 and a VH region as depicted in SEQ ID NO: 141 or 145 of WO 2008/119567;

(i) a VL region as depicted in SEQ ID NO: 161 or 165 of WO 2008/119567 and a VH region as depicted in SEQ ID NO: 159 or 163 of WO 2008/119567; and (j) a VL region as depicted in SEQ ID NO: 179 or 183 of WO 2008/119567 and a VH region as depicted in SEQ ID NO: 177 or 181 of WO 2008/119567.

Also preferred in connection with the antibody construct of the present invention is a second domain which binds to CD3 comprising a VL region as depicted in SEQ ID NO: 200 and a VH region as depicted in SEQ ID NO: 201.

According to a preferred embodiment of the antibody construct of the present invention, the first and/or the second domain have the following format: The pairs of VH regions and VL regions are in the format of a single chain antibody (scFv). The VH and VL regions are arranged in the order VH-VL or VL-VH. It is preferred that the VH-region is positioned N-terminally of a linker sequence, and the VL-region is positioned C-terminally of the linker sequence.

A preferred embodiment of the above described antibody construct of the present invention is characterized by the second domain which binds to CD3 comprising an amino acid sequence selected from the group consisting of SEQ ID Nos: 23, 25, 41, 43, 59, 61, 77, 79, 95, 97, 113, 115, 131, 133, 149, 151, 167, 169, 185 or 187 of WO 2008/119567 or depicted in SEQ ID NO: 202.

Covalent modifications of the antibody constructs are also included within the scope of this invention, and are generally, but not always, done post-translationally. For example, several types of covalent modifications of the antibody construct are introduced into the molecule by reacting specific amino acid residues of the antibody construct with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidazoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking the antibody constructs of the present invention to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates as described in U.S. Pat. Nos. 3,969,287; 3,691,016; 4,195,128; 4,247, 642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody construct is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the amino acid sequence of an antibody construct is preferably altered through changes at the DNA level, particularly by mutating the DNA encoding the polypeptide at preselected bases such that codons are generated that will translate into the desired amino acids.

Another means of increasing the number of carbohydrate moieties on the antibody construct is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, I aromatic residues such as those of phenylalanine, tyrosine, or tryptophan, or (f) the amide group of glutamine. These methods are described in WO 87/05330, and in Aplin and Wriston, 1981, CRC Crit. Rev. Biochem., pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Other modifications of the antibody construct are also contemplated herein. For example, another type of covalent modification of the antibody construct comprises linking the antibody construct to various non-proteinaceous polymers, including, but not limited to, various polyols such as polyethylene glycol, polypropylene glycol, polyoxyalkylenes, or copolymers of polyethylene glycol and polypropylene glycol, in the manner set forth in U.S. Pat. No. 4,640,835; 4,496,689; 4,301,144; 4,670,417; 4,791,192 or 4,179,337. In addition, as is known in the art, amino acid substitutions may be made in various positions within the antibody construct, e.g. in order to facilitate the addition of polymers such as PEG.

In some embodiments, the covalent modification of the antibody constructs of the invention comprises the addition of one or more labels. The labelling group may be coupled to the antibody construct via spacer arms of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to:

a) isotopic labels, which may be radioactive or heavy isotopes, such as radioisotopes or radionuclides (e.g., $^3$H, $^{14}$C, $^{15}$N, $^{35}$S, $^{89}$Zr, $^{90}$Y, $^{99}$Tc, $^{111}$In, $^{125}$I, $^{131}$I)

b) magnetic labels (e.g., magnetic particles)

c) redox active moieties d) optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluores or proteinaceous fluores e) enzymatic groups (e.g. horseradish peroxidase, β-galactosidase, luciferase, alkaline phosphatase)

f) biotinylated groups g) predetermined polypeptide epitopes recognized by a secondary reporter (e.g., leucine zipper pair sequences, binding sides for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, 5lyophilisat, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8$^{th}$ Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/

49019, U.S. Pat. Nos. 5,292,658; 5,418,155; 5,683,888; 5,741,668; 5,777,079; 5,804,387; 5,874,304; 5,876,995; 5,925,558).

The antibody construct of the invention may also comprise additional domains, which are e.g. helpful in the isolation of the molecule or relate to an adapted pharmacokinetic profile of the molecule. Domains helpful for the isolation of an antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All herein disclosed antibody constructs characterized by the identified CDRs may comprise a His-tag domain, which is generally known as a repeat of consecutive His residues in the amino acid sequence of a molecule, preferably of five, and more preferably of six His residues (hexa-histidine). The His-tag may be located e.g. at the N- or C-terminus of the antibody construct, preferably it is located at the C-terminus. Most preferably, a hexa-histidine tag (HHHHHH) (SEQ ID NO:199) is linked via peptide bond to the C-terminus of the antibody construct according to the invention. Additionally, a conjugate system of PLGA-PEG-PLGA may be combined with a poly-histidine tag for sustained release application and improved pharmacokinetic profile.

Amino acid sequence modifications of the antibody constructs described herein are also contemplated. For example, it may be desirable to improve the binding affinity and/or other biological properties of the antibody construct. Amino acid sequence variants of the antibody constructs are prepared by introducing appropriate nucleotide changes into the antibody constructs nucleic acid, or by peptide synthesis. All of the below described amino acid sequence modifications should result in an antibody construct which still retains the desired biological activity (binding to the target cell surface antigen and to CD3) of the unmodified parental molecule.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gin or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

Amino acid modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the antibody constructs, such as changing the number or position of glycosylation sites.

For example, 1, 2, 3, 4, 5, or 6 amino acids may be inserted, substituted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted, substituted or deleted in each of the FRs. Preferably, amino acid sequence insertions into the antibody construct include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. Corresponding modifications may also performed within the third domain of the antibody construct of the invention. An insertional variant of the antibody construct of the invention includes the fusion to the N-terminus or to the C-terminus of the antibody construct of an enzyme or the fusion to a polypeptide.

The sites of greatest interest for substitutional mutagenesis include (but are not limited to) the CDRs of the heavy and/or light chain, in particular the hypervariable regions, but FR alterations in the heavy and/or light chain are also contemplated. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for identification of certain residues or regions of the antibody constructs that are preferred locations for mutagenesis is called "alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions are then refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done using assays of antigen binding activities, such as the target cell surface antigen or CD3 binding.

Generally, if amino acids are substituted in one or more or all of the CDRs of the heavy and/or light chain, it is preferred that the then-obtained "substituted" sequence is at least 60% or 65%, more preferably 70% or 75%, even more preferably 80% or 85%, and particularly preferably 90% or 95% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the antibody construct may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions" listed in Table 3, below) is envisaged as long as the antibody construct retains its capability to bind to the target cell surface antigen via the first domain and to CD3, respectively CD3 epsilon, via the second domain and/or its CDRs have an identity to the then substituted sequence (at least 60% or 65%, more preferably 70% or 75%, even more preferably 80% or 85%, and particularly preferably 90% or 95% identical to the "original" CDR sequence).

Conservative substitutions are shown in Table 3 under the heading of "preferred substitutions". If such substitutions result in a change in biological activity, then more substantial changes, denominated "exemplary substitutions" in Table 3, or as further described below in reference to amino acid classes, may be introduced and the products screened for a desired characteristic.

TABLE 3

Amino acid substitutions

| Original | Exemplary Substitutions | Preferred Substitutions |
|---|---|---|
| Ala (A) | val, leu, ile | val |
| Arg I | lys, gln, asn | lys |
| Asn (N) | gln, his, asp, lys, arg | gln |
| Asp (D) | glu, asn | glu |
| Cys I | ser, ala | ser |
| Gln (Q) | asn, glu | asn |
| Glu I | asp, gln | Asp |
| Gly (G) | Ala | Ala |
| His (H) | asn, gln, lys, arg | Arg |
| Ile (I) | leu, val, met, ala, phe | Leu |
| Leu (L) | norleucine, ile, val, met, ala | Ile |
| Lys (K) | arg, gln, asn | Arg |
| Met (M) | leu, phe, ile | Leu |
| Phe (F) | leu, val, ile, ala, tyr | Tyr |
| Pro (P) | Ala | Ala |
| Ser (S) | Thr | Thr |
| Thr (T) | Ser | Ser |
| Trp (W) | tyr, phe | Tyr |
| Tyr (Y) | trp, phe, thr, ser | Phe |
| Val (V) | ile, leu, met, phe, ala | Leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr, asn, gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

For amino acid sequences, sequence identity and/or similarity is determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J Mol. Biol. 48:443, the search for similarity method of Pearson and Lipman, 1988, Proc. Nat. Acad. Sci. USA. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, Nucl. Acid Res. 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, J. Mol. Evol. 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, J. Mol. Biol. 215:403-410; Altschul et al., 1997, Nucleic Acids Res. 25:3389-3402; and Karin et al., 1993, Proc. Natl. Acad. Sci. U.S.A. 90:5873-5787. A particularly useful BLAST program is the WU-BLAST-2 program which was obtained from Altschul et al., 1996, Methods in Enzymology 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, Nucl. Acids Res. 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs or VH/VL sequences are at least 60% to the sequences depicted herein, and more typically with preferably increasing homologies or identities of at least 65% or 70%, more preferably at least 75% or 80%, even more preferably at least 85%, 90%, 91%, 92%, 93%, 94%, 95%, 96%, 97%, 98%, 99%, and almost 100%. In a similar manner, "percent (%) nucleic acid sequence identity"

with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs or VH/VL sequences and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Thus, a "variant CDR" or a "variant VH/VL region" is one with the specified homology, similarity, or identity to the parent CDR/VH/VL of the invention, and shares biological function, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR or VH/VL.

In one embodiment, the percentage of identity to human germline of the antibody constructs according to the invention is ≥70% or ≥75%, more preferably ≥80% or ≥85%, even more preferably ≥90%, and most preferably ≥91%, ≥92%, ≥93%, ≥94%, ≥95% or even ≥96%. Identity to human antibody germline gene products is thought to be an important feature to reduce the risk of therapeutic proteins to elicit an immune response against the drug in the patient during treatment. Hwang & Foote ("Immunogenicity of engineered antibodies"; Methods 36 (2005) 3-10) demonstrate that the reduction of non-human portions of drug antibody constructs leads to a decrease of risk to induce anti-drug antibodies in the patients during treatment. By comparing an exhaustive number of clinically evaluated antibody drugs and the respective immunogenicity data, the trend is shown that humanization of the V-regions of antibodies makes the protein less immunogenic (average 5.1% of patients) than antibodies carrying unaltered non-human V regions (average 23.59% of patients). A higher degree of identity to human sequences is hence desirable for V-region based protein therapeutics in the form of antibody constructs. For this purpose of determining the germline identity, the V-regions of VL can be aligned with the amino acid sequences of human germline V segments and J segments (http://vbase.mrc-cpe.cam.ac.uk/) using Vector NTI software and the amino acid sequence calculated by dividing the identical amino acid residues by the total number of amino acid residues of the VL in percent. The same can be for the VH segments (http://vbase.mrc-cpe.cam.ac.uk/) with the exception that the VH CDR3 may be excluded due to its high diversity and a lack of existing human germline VH CDR3 alignment partners. Recombinant techniques can then be used to increase sequence identity to human antibody germline genes.

In a further embodiment, the bispecific antibody constructs of the present invention exhibit high monomer yields under standard research scale conditions, e.g., in a standard two-step purification process. Preferably the monomer yield of the antibody constructs according to the invention is ≥0.25 mg/L supernatant, more preferably ≥0.5 mg/L, even more preferably ≥1 mg/L, and most preferably ≥3 mg/L supernatant.

Likewise, the yield of the dimeric antibody construct isoforms and hence the monomer percentage (i.e., monomer:(monomer+dimer)) of the antibody constructs can be determined. The productivity of monomeric and dimeric antibody constructs and the calculated monomer percentage can e.g. be obtained in the SEC purification step of culture supernatant from standardized research-scale production in roller bottles. In one embodiment, the monomer percentage of the antibody constructs is ≥80%, more preferably ≥85%, even more preferably ≥90%, and most preferably ≥95%.

In one embodiment, the antibody constructs have a preferred plasma stability (ratio of EC50 with plasma to EC50 w/o plasma) of ≤5 or ≤4, more preferably ≤3.5 or ≤3, even more preferably ≤2.5 or ≤2, and most preferably ≤1.5 or ≤1. The plasma stability of an antibody construct can be tested by incubation of the construct in human plasma at 37° C. for 24 hours followed by EC50 determination in a $^{51}$chromium release cytotoxicity assay. The effector cells in the cytotoxicity assay can be stimulated enriched human CD8 positive T cells. Target cells can e.g. be CHO cells transfected with the human target cell surface antigen. The effector to target cell (E:T) ratio can be chosen as 10:1. The human plasma pool used for this purpose is derived from the blood of healthy donors collected by EDTA coated syringes. Cellular components are removed by centrifugation and the upper plasma phase is collected and subsequently pooled. As control, antibody constructs are diluted immediately prior to the cytotoxicity assay in RPMI-1640 medium. The plasma stability is calculated as ratio of EC50 (after plasma incubation) to EC50 (control).

It is furthermore preferred that the monomer to dimer conversion of antibody constructs of the invention is low. The conversion can be measured under different conditions and analyzed by high performance size exclusion chromatography. For example, incubation of the monomeric isoforms of the antibody constructs can be carried out for 7 days at 37° C. and concentrations of e.g. 100 µg/ml or 250 µg/ml in an incubator. Under these conditions, it is preferred that the antibody constructs of the invention show a dimer percentage that is ≤5%, more preferably ≤4%, even more preferably ≤3%, even more preferably ≤2.5%, even more preferably ≤2%, even more preferably ≤1.5%, and most preferably ≤1% or ≤0.5% or even 0%.

It is also preferred that the bispecific antibody constructs of the present invention present with very low dimer conversion after a number of freeze/thaw cycles. For example, the antibody construct monomer is adjusted to a concentration of 250 µg/ml e.g. in generic formulation buffer and subjected to three freeze/thaw cycles (freezing at −80° C. for 30 min followed by thawing for 30 min at room temperature), followed by high performance SEC to determine the percentage of initially monomeric antibody construct, which had been converted into dimeric antibody construct. Preferably the dimer percentages of the bispecific antibody constructs are ≤5%, more preferably ≤4%, even more preferably ≤3%, even more preferably ≤2.5%, even more preferably ≤2%, even more preferably ≤1.5%, and most preferably ≤1% or even ≤0.5%, for example after three freeze/thaw cycles.

The bispecific antibody constructs of the present invention preferably show a favorable thermostability with aggregation temperatures ≥45° C. or ≥50° C., more preferably ≥52° C. or ≥54° C., even more preferably ≥56° C. or ≥57° C., and most preferably ≥58° C. or ≥59° C. The thermostability parameter can be determined in terms of antibody aggregation temperature as follows: Antibody solution at a concentration 250 µg/ml is transferred into a single use cuvette and placed in a Dynamic Light Scattering (DLS) device. The sample is heated from 40° C. to 70° C. at a heating rate of 0.5° C./min with constant acquisition of the measured radius. Increase of radius indicating melting of the protein and aggregation is used to calculate the aggregation temperature of the antibody.

Alternatively, temperature melting curves can be determined by Differential Scanning calorimetry (DSC) to determine intrinsic biophysical protein stabilities of the antibody constructs. These experiments are performed using a MicroCal LLC (Northampton, MA, U.S.A.) VP-DSC device. The energy uptake of a sample containing an antibody construct is recorded from 20° C. to 90° C. compared to a sample containing only the formulation buffer. The antibody constructs are adjusted to a final concentration of 250 µg/ml e.g. in SEC running buffer. For recording of the respective melting curve, the overall sample temperature is increased stepwise. At each temperature T energy uptake of the sample and the formulation buffer reference is recorded. The difference in energy uptake Cp (kcal/mole/° C.) of the sample minus the reference is plotted against the respective temperature. The melting temperature is defined as the temperature at the first maximum of energy uptake.

The target cell surface antigenxCD3 bispecific antibody constructs of the invention are also envisaged to have a turbidity (as measured by OD340 after concentration of purified monomeric antibody construct to 2.5 mg/ml and over night incubation) of ≤0.2, preferably of ≤0.15, more preferably of ≤0.12, even more preferably of ≤0.1, and most preferably of ≤0.08.

In a further embodiment the antibody construct according to the invention is stable at physiologic or slightly lower pH, i.e. about pH 7.4 to 6.0. The more tolerant the antibody construct behaves at unphysiologic pH such as about pH 6.0, the higher is the recovery of the antibody construct eluted from an ion exchange column relative to the total amount of loaded protein. Recovery of the antibody construct from an ion (e.g., cation) exchange column at about pH 6.0 is preferably ≥30%, more preferably ≥40%, more preferably ≥50%, even more preferably ≥60%, even more preferably ≥70%, even more preferably ≥80%, even more preferably ≥90%, even more preferably ≥95%, and most preferably ≥99%.

It is furthermore envisaged that the bispecific antibody constructs of the present invention exhibit therapeutic efficacy or anti-tumor activity. This can e.g. be assessed in a study as disclosed in the following example of an advanced stage human tumor xenograft model:

The skilled person knows how to modify or adapt certain parameters of this study, such as the number of injected tumor cells, the site of injection, the number of transplanted human T cells, the amount of bispecific antibody constructs to be administered, and the timelines, while still arriving at a meaningful and reproducible result. Preferably, the tumor growth inhibition T/C [%] is ≤70 or ≤60, more preferably ≤50 or ≤40, even more preferably ≤30 or ≤20 and most preferably ≤10 or ≤5 or even ≤2.5.

In a preferred embodiment of the antibody construct of the invention the antibody construct is a single chain antibody construct.

Also in a preferred embodiment of the antibody construct of the invention said third domain comprises in an amino to carboxyl order:

hinge-CH2-CH3-linker-hinge-CH2-CH3.

Also in one embodiment of the invention the CH2 domain of one or preferably each (both) polypeptide monomers of the third domain comprises an intra domain cysteine disulfide bridge. As known in the art the term "cysteine disulfide bridge" refers to a functional group with the general structure R—S—S—R. The linkage is also called an SS-bond or a disulfide bridge and is derived by the coupling of two thiol groups of cysteine residues. It is particularly preferred for the antibody construct of the invention that the cysteines forming the cysteine disulfide bridge in the mature antibody construct are introduced into the amino acid sequence of the CH2 domain corresponding to 309 and 321 (Kabat numbering).

In one embodiment of the invention a glycosylation site in Kabat position 314 of the CH2 domain is removed. It is preferred that this removal of the glycosylation site is achieved by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321).

It is assumed that the preferred features of the antibody construct of the invention compared e.g. to the bispecific heteroFc antibody construct known in the art (FIG. 1b) may be inter alia related to the introduction of the above described modifications in the CH2 domain. Thus, it is preferred for the construct of the invention that the CH2 domains in the third domain of the antibody construct of the invention comprise the intra domain cysteine disulfide bridge at Kabat positions 309 and 321 and/or the glycosylation site at Kabat position 314 is removed by a N314X substitution as above, preferably by a N314G substitution.

In a further preferred embodiment of the invention the CH2 domains in the third domain of the antibody construct of the invention comprise the intra domain cysteine disulfide bridge at Kabat positions 309 and 321 and the glycosylation site at Kabat position 314 is removed by a N314G substitution.

In one embodiment the invention provides an antibody construct, wherein:
(182) the first domain comprises two antibody variable domains and the second domain comprises two antibody variable domains;
(ii) the first domain comprises one antibody variable domain and the second domain comprises two antibody variable domains;
(iii) the first domain comprises two antibody variable domains and the second domain comprises one antibody variable domain; or
(iv) the first domain comprises one antibody variable domain and the second domain comprises one antibody variable domain.

Accordingly, the first and the second domain may be binding domains comprising each two antibody variable domains such as a VH and a VL domain. Examples for such binding domains comprising two antibody variable domains where described herein above and comprise e.g. Fv fragments, scFv fragments or Fab fragments described herein above. Alternatively either one or both of those binding domains may comprise only a single variable domain. Examples for such single domain binding domains where described herein above and comprise e.g. nanobodies or single variable domain antibodies comprising merely one variable domain, which might be VHH, VH or VL, that specifically bind an antigen or epitope independently of other V regions or domains.

In a preferred embodiment of the antibody construct of the invention first and second domain are fused to the third domain via a peptide linker. Preferred peptide linker have been described herein above and are characterized by the amino acid sequence Gly-Gly-Gly-Gly-Ser, i.e. Gly$_4$Ser (SEQ ID NO: 187), or polymers thereof, i.e. (Gly$_4$Ser)x, where x is an integer of 1 or greater (e.g. 2 or 3). A particularly preferred linker for the fusion of the first and second domain to the third domain is depicted in SEQ ID Nos: 1.

In a preferred embodiment the antibody construct of the invention is characterized to comprise in an amino to carboxyl order:
(a) the first domain;
(b) a peptide linker having an amino acid sequence selected from the group consisting of SEQ ID Nos: 187-189;
I the second domain;
(d) a peptide linker having an amino acid sequence selected from the group consisting of SEQ ID NO: 187, 188, 189, 195, 196, 197 and 198;
I the first polypeptide monomer of the third domain;
(f) a peptide linker having an amino acid sequence selected from the group consisting of SEQ ID Nos: 191, 192, 193 and 194; and
(g) the second polypeptide monomer of the third domain.

In one aspect of the invention the target cell surface antigen bound by the first domain is a tumor antigen, an antigen specific for an immunological disorder or a viral antigen. The term "tumor antigen" as used herein may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. Non-limiting examples of tumor antigens as used herein are CDH19, MSLN, DLL3, FLT3, EGFRvIII, CD33, CD19, CD20, CD70, BCMA and PSMA.

Further target cell surface antigens specific for an immunological disorder in the context of the present invention comprise, for example, TL1A and TNF-alpha. Said targets are preferably addressed by a bispecific antibody construct of the present invention, which is preferably a full length antibody. In a very preferred embodiment, an antibody of the present invention is a hetero IgG antibody.

In a preferred embodiment of the antibody construct of the invention the tumor antigen is selected from the group consisting of CDH19, MSLN, DLL3, FLT3, EGFRvIII, CD33, CD19, CD20, CD70, BCMA and PSMA.

In one aspect of the invention the antibody construct comprises in an amino to carboxyl order:
(a) the first domain having an amino acid sequence selected from the group consisting of SEQ ID Nos: 7, 8, 17, 27, 28, 37, 38, 39, 40, 41, 48, 49, 50, 51, 52, 59, 60, 61, 62, 63, 64, 71, 72, 73, 74, 75, 76, 77, 78, 79, 80, 81, 89, 90, 91, 92, 93, 100, 101, 102, 103, 104, 113, 114, 121, 122, 123, 124, 125, 131, 132, 133, 134, 135, 136, 143, 144, 145, 146, 147, 148, 149, 150, 151, 158, 159, 160, 161, 162, 163, 164, 165, 166, 173, 174, 175, 176, 177, 178, 179, 180, 181
(b) a peptide linker having an amino acid sequence selected from the group consisting of SEQ ID Nos: 187-189;
I the second domain having an amino acid sequence selected from the group consisting of SEQ ID Nos: SEQ ID Nos: 23, 25, 41, 43, 59, 61, 77, 79, 95, 97, 113, 115, 131, 133, 149, 151, 167, 169, 185 or 187 of WO 2008/119567 or of SEQ ID NO: 202;
(d) a peptide linker having an amino acid sequence selected from the group consisting of SEQ ID Nos: 187, 188, 189, 195, 196, 197 and 198;
I the first polypeptide monomer of the third domain having a polypeptide sequence selected from the group consisting of SEQ ID Nos: 17-24 of WO2017/134140;
(f) a peptide linker having an amino acid sequence selected from the group consisting of SEQ ID Nos: 191, 192, 193 and 194; and
(g) the second polypeptide monomer of the third domain having a polypeptide sequence selected from the group consisting of SEQ ID Nos: 17-24 of WO2017/134140.

In one aspect, the bispecific antibody construct of the invention is characterized by having an amino acid sequence selected from the group consisting of and being directed to the respective target cell surface antigen:
(a) SEQ ID Nos: 27, 28, 37 to 41; CD33
(b) SEQ ID Nos: each of 48 to 52; EGFRvIII
(c) SEQ ID Nos: each of 59 to 64; MSLN
(d) SEQ ID Nos: each of 71 to 82 CDH19
(e) SEQ ID Nos: each of 100 to 104 DLL3
(f) SEQ ID Nos: 7, 8, 17, 113 and 114 CD19
(g) SEQ ID Nos: each of 89 to 93 FLT3
(h) SEQ ID Nos: each of 121 to 125 CDH3
(i) SEQ ID Nos: each of 132 to 136 BCMA and
(j) SEQ ID Nos: each of 143 to 151, 158 to 166 and 173 to 181 PSMA The invention further provides a polynucleotide/nucleic acid molecule encoding an antibody construct of the invention. A polynucleotide is a biopolymer composed of 13 or more nucleotide monomers covalently bonded in a chain. DNA (such as cDNA) and RNA (such as mRNA) are examples of polynucleotides with distinct biological function. Nucleotides are organic molecules that serve as the monomers or subunits of nucleic acid molecules like DNA or RNA. The nucleic acid molecule or polynucleotide can be double stranded and single stranded, linear and circular. It is preferably comprised in a vector which is preferably comprised in a host cell. Said host cell is, e.g. after transformation or transfection with the vector or the polynucleotide of the invention, capable of expressing the antibody construct. For that purpose the polynucleotide or nucleic acid molecule is operatively linked with control sequences.

The genetic code is the set of rules by which information encoded within genetic material (nucleic acids) is translated into proteins. Biological decoding in living cells is accomplished by the ribosome which links amino acids in an order specified by mRNA, using tRNA molecules to carry amino acids and to read the mRNA three nucleotides at a time. The code defines how sequences of these nucleotide triplets, called codons, specify which amino acid will be added next during protein synthesis. With some exceptions, a three-nucleotide codon in a nucleic acid sequence specifies a single amino acid. Because the vast majority of genes are encoded with exactly the same code, this particular code is often referred to as the canonical or standard genetic code.

While the genetic code determines the protein sequence for a given coding region, other genomic regions can influence when and where these proteins are produced.

Furthermore, the invention provides a vector comprising a polynucleotide/nucleic acid molecule of the invention. A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding side. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding side is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density.

Moreover, the invention provides a host cell transformed or transfected with the polynucleotide/nucleic acid molecule or with the vector of the invention. As used herein, the terms "host cell" or "recipient cell" are intended to include any individual cell or cell culture that can be or has/have been recipients of vectors, exogenous nucleic acid molecules, and polynucleotides encoding the antibody construct of the present invention; and/or recipients of the antibody construct itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The antibody construct of the invention can be produced in bacteria. After expression, the antibody construct of the invention is isolated from the *E. coli* cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the antibody construct of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus; Yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger*.

Suitable host cells for the expression of glycosylated antibody construct of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be used as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/−DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCLS 1); TRI cells (Mather et al., Annals N.Y Acad. Sci. (1982) 383: 44-68); MRC 5 cells; FS4 cells; and a human hepatoma line (Hep G2).

In a further embodiment the invention provides a process for the production of an antibody construct of the invention, said process comprising culturing a host cell of the invention under conditions allowing the expression of the antibody construct of the invention and recovering the produced antibody construct from the culture.

As used herein, the term "culturing" refers to the in vitro maintenance, differentiation, growth, proliferation and/or propagation of cells under suitable conditions in a medium. The term "expression" includes any step involved in the production of an antibody construct of the invention including, but not limited to, transcription, post-transcriptional modification, translation, post-translational modification, and secretion.

When using recombinant techniques, the antibody construct can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody construct of the invention prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), 68yophili-focusing, SDS-PAGE, and ammonium sulfate precipitation are also available depending on the antibody to be recovered. Where the antibody construct of the invention comprises a CH3 domain, the Bakerbond ABX resin (J. T. Baker, Phillipsburg, NJ) is useful for purification.

Affinity chromatography is a preferred purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

Moreover, the invention provides a pharmaceutical composition comprising an antibody construct of the invention or an antibody construct produced according to the process of the invention. It is preferred for the pharmaceutical composition of the invention that the homogeneity of the antibody construct is ≥80%, more preferably ≥81%, ≥82%, ≥83%, ≥84%, or ≥85%, further preferably ≥86%, ≥87%, ≥88%, ≥89%, or ≥90%, still further preferably, ≥91%, ≥92%, ≥93%, ≥94%, or ≥95% and most preferably ≥96%, ≥97%, ≥98% or ≥99%.

As used herein, the term "pharmaceutical composition" relates to a composition which is suitable for administration to a patient, preferably a human patient. The particularly preferred pharmaceutical composition of this invention comprises one or a plurality of the antibody construct(s) of the invention, preferably in a therapeutically effective amount. Preferably, the pharmaceutical composition further comprises suitable formulations of one or more (pharmaceutically effective) carriers, stabilizers, excipients, diluents, solubilizers, surfactants, emulsifiers, preservatives and/or adjuvants. Acceptable constituents of the composition are preferably nontoxic to recipients at the dosages and concentrations employed. Pharmaceutical compositions of the invention include, but are not limited to, liquid, frozen, and lyophilized compositions.

The inventive compositions may comprise a pharmaceutically acceptable carrier. In general, as used herein, "pharmaceutically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with pharmaceutical administration, in particular with parenteral administration. The use of such media and agents in pharmaceutical compositions is well known in the art, and the compositions comprising such carriers can be formulated by well-known conventional methods.

Certain embodiments provide pharmaceutical compositions comprising the antibody construct of the invention and further one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In certain embodiments, the pharmaceutical composition may contain formulation materials for the purpose of modifying, maintaining or preserving, e.g., the pH, osmolarity, viscosity, clarity, color, isotonicity, odor, sterility, stability, rate of dissolution or release, adsorption or penetration of the composition (see, REMINGTON'S PHARMACEUTICAL SCIENCES, 18" Edition, (A. R. Genrmo, ed.), 1990, Mack Publishing Company). In such embodiments, suitable formulation materials may include, but are not limited to:

amino acids such as glycine, alanine, glutamine, asparagine, threonine, proline, 2-phenylalanine, including charged amino acids, preferably lysine, lysine acetate, arginine, glutamate and/or histidine antimicrobials such as antibacterial and antifungal agents antioxidants such as ascorbic acid, methionine, sodium 69yophili or sodium hydrogen-sulfite;

buffers, buffer systems and buffering agents which are used to maintain the composition at physiological pH or at a slightly lower pH; examples of buffers are borate, bicarbonate, Tris-HCl, citrates, phosphates or other organic acids, succinate, phosphate, and histidine; for example Tris buffer of about pH 7.0-8.5;

non-aqueous solvents such as propylene glycol, polyethylene glycol, vegetable oils such as olive oil, and injectable organic esters such as ethyl oleate;

aqueous carriers including water, alcoholic/aqueous solutions, emulsions or suspensions, including saline and buffered media;

biodegradable polymers such as polyesters;

bulking agents such as mannitol or glycine;

chelating agents such as ethylenediamine tetraacetic acid (EDTA);

isotonic and absorption delaying agents;

complexing agents such as caffeine, polyvinylpyrrolidone, beta-cyclodextrin or hydroxypropyl-beta-cyclodextrin)

fillers;

monosaccharides; disaccharides; and other carbohydrates (such as glucose, mannose or dextrins); carbohydrates may be non-reducing sugars, preferably trehalose, sucrose, octasulfate, sorbitol or xylitol;

(low molecular weight) proteins, polypeptides or proteinaceous carriers such as human or bovine serum albumin, gelatin or immunoglobulins, preferably of human origin;

coloring and flavouring agents;

sulfur containing reducing agents, such as glutathione, thioctic acid, sodium thioglycolate, thioglycerol, [alpha]-monothioglycerol, and sodium thio sulfate diluting agents;

emulsifying agents;

hydrophilic polymers such as polyvinylpyrrolidone)

salt-forming counter-ions such as sodium;

preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);

metal complexes such as Zn-protein complexes;

solvents and co-solvents (such as 70yophilis, propylene glycol or polyethylene glycol);

sugars and sugar alcohols, such as trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;

suspending agents;

surfactants or wetting agents such as pluronics, PEG, sorbitan esters, polysorbates such as polysorbate 20, polysorbate, triton, tromethamine, lecithin, cholesterol, tyloxapal; surfactants may be detergents, preferably with a molecular weight of >1.2 KD and/or a polyether, preferably with a molecular weight of >3 KD; non-limiting examples for preferred detergents are Tween 20, Tween 40, Tween 60, Tween 80 and Tween 85; non-limiting examples for preferred polyethers are PEG 3000, PEG 3350, PEG 4000 and PEG 5000;

stability enhancing agents such as sucrose or sorbitol;

tonicity enhancing agents such as alkali metal halides, preferably sodium or potassium chloride, mannitol sorbitol;

parenteral delivery vehicles including sodium chloride solution, Ringer's dextrose, dextrose and sodium chloride, lactated Ringer's, or fixed oils;

intravenous delivery vehicles including fluid and nutrient replenishers, electrolyte replenishers (such as those based on Ringer's dextrose).

It is evident to those skilled in the art that the different constituents of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

It is envisaged that the composition of the invention might comprise, in addition to the polypeptide of the invention defined herein, further biologically active agents, depending on the intended use of the composition. Such agents might be drugs acting on the gastro-intestinal system, drugs acting as cytostatica, drugs preventing 71yophilisatio, drugs inhibiting immunoreactions (e.g. corticosteroids), drugs modulating the inflammatory response, drugs acting on the circulatory system and/or agents such as cytokines known in the art. It is also envisaged that the antibody construct of the present invention is applied in a co-therapy, i.e., in combination with another anti-cancer medicament.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody construct of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, the antibody construct of the invention compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the antibody construct of the invention may be formulated as a lyophilizate using appropriate excipients such as sucrose.

When parenteral administration is contemplated, the therapeutic compositions for use in this invention may be provided in the form of a pyrogen-free, parenterally acceptable aqueous solution comprising the desired antibody construct of the invention in a pharmaceutically acceptable vehicle. A particularly suitable vehicle for parenteral injection is sterile distilled water in which the antibody construct of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody construct.

Additional pharmaceutical compositions will be evident to those skilled in the art, including formulations involving the antibody construct of the invention in sustained- or controlled-delivery/release formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949.

The antibody construct may also be entrapped in microcapsules prepared, for example, by coacervation techniques or by interfacial polymerization (for example, hydroxymethylcellulose or 72yophil-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16$^{th}$ edition, Oslo, A., Ed., (1980).

Pharmaceutical compositions used for in vivo administration are typically provided as sterile preparations. Sterilization can be accomplished by filtration through sterile filtration membranes. When the composition is lyophilized, sterilization using this method may be conducted either prior to or following 73yophilisation and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Another aspect of the invention includes self-buffering antibody construct of the invention formulations, which can be used as pharmaceutical compositions, as described in international patent application WO 06138181A2 (PCT/US2006/022599). A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution" in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions", Pharm Biotechnol. 13: 159-75 (2002), see particularly the parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic". Destabilizing solutes are referred to as "chaotropic". Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the antibody construct of the invention formulations in accordance with various embodiments of the invention as bulking agents, stabilizers, and antioxidants, as well as other standard uses. Lysine, proline, serine, and alanine can be used for stabilizing proteins in a formulation. Glycine is useful in 74yophilisation to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations. Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can 74yophili surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the antibody construct of the invention formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct of the invention formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard. Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the antibody construct of the invention formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized-dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

The antibody constructs disclosed herein may also be formulated as 76yophi-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4):1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above. It is an envisaged characteristic of the antibody constructs of the present invention provided with the specific FC modality that they comprise, for example, differences in pharmacokinetic behavior. A half-life extended targeting antibody construct according to the present invention preferably shows a surprisingly increased residence time in vivo in comparison to "canonical" non-HLE versions of said antibody construct.

"Half-life" means the time where 50% of an administered drug are eliminated through biological processes, e.g. metabolism, excretion, etc. By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of bispecific antibody constructs exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

In a preferred aspect of the invention the pharmaceutical composition is stable for at least four weeks at about −20° C. As apparent from the appended examples the quality of an antibody construct of the invention vs. the quality of corresponding state of the art antibody constructs may be tested using different systems. Those tests are understood to be in line with the "ICH Harmonised Tripartite Guideline: *Stability Testing of Biotechnological/Biological Products Q5C and Specifications: Test procedures and Acceptance Criteria for Biotech Biotechnological/Biological Products Q6B*" and, thus are elected to provide a stability-indicating profile that provides certainty that changes in the identity, purity and potency of the product are detected. It is well accepted that the term purity is a relative term. Due to the effect of glycosylation, deamidation, or other heterogeneities, the absolute purity of a biotechnological/biological product should be typically assessed by more than one method and the purity value derived is method-dependent. For the purpose of stability testing, tests for purity should focus on methods for determination of degradation products.

For the assessment of the quality of a pharmaceutical composition comprising an antibody construct of the invention may be analyzed e.g. by analyzing the content of soluble aggregates in a solution (HMWS per size exclusion). It is preferred that stability for at least four weeks at about −20° C. is characterized by a content of less than 1.5% HMWS, preferably by less than 1% HMWS.

A preferred Product Quality Analytical Method herein is Size Exclusion-High Performance Liquid Chromatography (SE-HPLC). SE-HPLC is typically performed using a size exclusion column and an UHPLC system, e.g. Waters BEH200 size exclusion column (4.6×150 mm, 1.7 μm) and Waters UHPLC system. The protein samples are injected neat and separated isocratically using a phosphate buffer e.g. containing NaCl salt (mobile phase was 100 mM sodium phosphate, 250 mM NaCl at pH 6.8) at a flow rate of e.g. 0.4 mL/min, and the eluent was monitored by UV absorbance at 280 nm. Typically, about 6 μg of sample is loaded.

Before the CM process is initiated, typically a vial containing CHO cells expressing the bispecific antibody construct is thawed. During scale-up, cells are resuspended in fresh selective growth medium at a targeted viable cell density (VCD). The culture volume is successively expanded in shake flasks or bioreactors to generate sufficient cell mass to ultimately inoculate a perfusion production bioreactor (e.g. 10 L or 50 L scale or more).

Once cells are inoculated into the production bioreactor at a concentration range as specified herein, there is an initial cell growth phase for a period of days, typically about 7 to 28 days, to increase cell density and biomass to a preferred set-point as described herein and as measured by a capacitance probe (Hamilton Bonaduz AG, Switzerland). Production bioreactor is controlled at a preferred pH, typically about 6 to 7.4, e.g. pH 6.85, dissolved oxygen of, for example, 64 mm Hg and about 36° C. Perfusion culture is initiated after a few days of the cell growth phase, typically on day 2, 3, 4, 5, 6, 7, 8, 9 or 10, preferably day 4, using an alternating tangential flow (ATF) filtration system (e.g. Refine Technologies, Hanover, NJ) with filters such as polyethersulfone 0.2-μm filters (e.g. GE Healthcare, Pittsburgh, PA), and a suitable chemically-defined perfusion medium at a VVD perfusion rate as described herein, e.g. at a 0.4 bioreactor VVD perfusion rate. Perfusion rate is typically increased gradually, e.g. from 0.4 VVD on day 4 to 2 VVD on day 12. Once biomass set-point is reached on the last day of gradual VVD increase, cell culture temperature is typically reduced, e.g. to 33.5° C., collection of HCCF started (i.e., cell-free permeate containing bispecific antibody construct), and perfusion culture continued for a period as described herein, e.g. at least 7, 14, 28 or 40 additional days, preferably at least 28 days, by feeding at a set perfusion rate, typically the highest VVD perfusion rate to which the gradual increase has led (i.e. the steady-state cell specific perfusion rate, CSPR, e.g. of 0.02-0.03 nL/cell-day), and bleeding extra cells to maintain the preferred biomass set-point. Cell density (measured by CDV, e.g. Nova Biomedical, Waltham, MA), metabolites (measured e.g. by NovaFlex, Nova Biomedical, Waltham, MA) and permeate titer (measured by HPLC analysis) are typically measured throughout the culture duration. The HCCF is collected preferably at room temperature continuously or in increments of, e.g. 6, 12, 24, 48, 72, 96, 120 or 144 hours, and processed forward to a protein-L capture chromatography. The eluate from protein-L, e.g. on days 26, 27, 34, 40, are analyzed for product quality attributes and process-related impurities using analytical cation exchange chromatography (CEX-HPLC), peptide mapping and/or HCP ELISA.

Tryptic Peptide Mapping for Chemical Modifications

Bispecific antibody construct protein samples are digested with a filter-based method using e.g. Millipore Microcon 30K device. The protein sample is added on the filter, centrifuged to remove the sample matrix, then denatured in e.g. 6 M guanidine hydrochloride (GuHCl) (e.g. Thermo Fisher Scientific, Rockford, IL) buffer containing methionine, reduced with e.g. 500 mM dithiothreitol (DTT) (e.g. Sigma-Aldrich, St. Louis, MO) at e.g. 37° C. for 30 min, and subsequently alkylated by incubation with e.g. 500 mM iodoacetic acid (IAA) (e.g. Sigma-Aldrich, St. Louis, MO) for e.g. 20 min in the dark at room temperature. Unreacted IAA is quenched by adding DTT. All the above steps occurred on the filter. Samples are subsequently buffer exchanged into the digestion buffer (e.g. 50 mM Tris, pH 7.8 containing Methionine) by centrifuging to remove any residual DTT and IAA. Trypsin digestion is performed on the filter e.g. for 1 hr at 37° C. using an enzyme to protein ratio of 1:20 (w/w). The digestion mixture is collected by centrifuging and then quenched e.g. by adding 8 M GuHCl in acetate buffer at pH 4.7.

The liquid chromatography-mass spectrometry (LC-MS) analysis is performed using a ultra-performance liquid chromatography (UPLC) system, e.g. Thermo U-3000, directly coupled with a Mass Spectrometer, e.g. Thermo Scientific Q-Exactive. The protein digests were separated by reversed phase using an Agilent Zorbax C18 RR HD column (2.1× 150 mm, 1.8 μm), with the column temperature maintained at 50° C. The mobile phase A consisted of 0.020% (v/v) formic acid (FA) in water, and the mobile phase B was 0.018% (v/v) FA in acetonitrile (I). Approximately 5 μg of the digested bispecific antibody construct is injected to the column. A gradient (e.g. 0.5 to 36% B over 145 min) is used to separate the peptides at a flow rate, e.g. of 0.2 mL/min. The eluted peptides are monitored by MS.

For peptide identification and modification analysis, a data-dependent tandem MS (MS/MS) experiment is typically utilized. A full scan is typically acquired, e.g. from 200 to 2000 m/z in the positive ion mode followed by e.g. 6 data-dependent MS/MS scans to identify the sequence of the peptide. The quantitation is based on mass spectrometry data of the selected ion monitoring using the equation below:

$$\text{Modification \%} = \frac{A_{modified}}{A_{modified} + A_{unmodified}} \times 100$$

Where Modification % is the level of the modified peptides, $A_{modified}$ is the extracted ion chromatogram area of modified peptide, $A_{unmodified}$ is the extracted ion chromatogram area of unmodified peptide.

Host Cell Protein (HCP) ELISA

A microtiter plate is coated with rabbit anti-HCP Immunoglobulin G (IgG) (Amgen, in-house antibody). After the plate is washed and blocked, the test samples, controls and HCP calibration standards are added to the plate and incubated. Unbound proteins are washed from the plate and pooled rabbit anti-HCP IgG-Biotin (Amgen, in-house antibody) is added to the plate and incubated. Following another wash, Streptavidin™ Horseradish Peroxidase conjugate (HRP-conjugate) (e.g. Amersham—GE, Buckinghamshire, UK) is added to the plate and incubated. The plate is washed a final time and the chromogenic substrate tetramethylbenzidine (TMB) (e.g. Kirkegaard and Perry Laboratories, Gaithersburg, MD) is added to plate. Color development is arrested with 1 M Phosphoric acid and the optical density is measured with a spectrophotometer.

A preferred formulation for the antibody construct as a pharmaceutical composition may e.g. comprise the components of a formulation as described below:

Formulation:
  potassium phosphate, L-arginine hydrochloride, trehalose, polysorbate 80 at pH 6.0

Other examples for the assessment of the stability of an antibody construct of the invention in form of a pharmaceutical composition are provided in the appended examples 4-12. In those examples embodiments of antibody constructs of the invention are tested with respect to different stress conditions in different pharmaceutical formulations and the results compared with other half-life extending (HLE) formats of bispecific T cell engaging antibody construct known from the art. In general, it is envisaged that antibody constructs provided with the specific FC modality according to the present invention are typically more stable over a broad range of stress conditions such as temperature and light stress, both compared to antibody constructs provided with different HLE formats and without any HLE format (e.g. "canonical" antibody constructs). Said temperature stability may relate both to decreased (below room temperature including freezing) and increased (above room temperature including temperatures up to or above body temperature) temperature. As the person skilled in the art will acknowledge, such improved stability with regard to stress, which is hardly avoidable in clinical practice, makes the antibody construct safer because less degradation products will occur in clinical practice. In consequence, said increased stability means increased safety.

One embodiment provides the antibody construct of the invention or the antibody construct produced according to the process of the invention for use in the prevention, treatment or amelioration of a proliferative disease, a tumorous disease, a viral disease or an immunological disorder.

The formulations described herein are useful as pharmaceutical compositions in the treatment, amelioration and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

The term "amelioration" as used herein refers to any improvement of the disease state of a patient having a tumor or cancer or a metastatic cancer as specified herein below, by the administration of an antibody construct according to the invention to a subject in need thereof. Such an improvement may also be seen as a slowing or stopping of the progression of the tumor or cancer or metastatic cancer of the patient. The term "prevention" as used herein means the avoidance of the occurrence or re-occurrence of a patient having a tumor or cancer or a metastatic cancer as specified herein below, by the administration of an antibody construct according to the invention to a subject in need thereof.

The term "disease" refers to any condition that would benefit from treatment with the antibody construct or the pharmaceutic composition described herein. This includes chronic and acute disorders or diseases including those pathological conditions that predispose the mammal to the disease in question.

A "neoplasm" is an abnormal growth of tissue, usually but not always forming a mass. When also forming a mass, it is commonly referred to as a "tumor". Neoplasms or tumors or can be benign, potentially malignant (pre-cancerous), or malignant. Malignant neoplasms are commonly called cancer. They usually invade and destroy the surrounding tissue and may form metastases, i.e., they spread to other parts, tissues or organs of the body. Hence, the term "metastatic cancer" encompasses metastases to other tissues or organs than the one of the original tumor. Lymphomas and leukemias are lymphoid neoplasms. For the purposes of the present invention, they are also encompassed by the terms "tumor" or "cancer".

The term "viral disease" describes diseases, which are the result of a viral infection of a subject.

The term "immunological disorder" as used herein describes in line with the common definition of this term immunological disorders such as autoimmune diseases, hypersensitivities, immune deficiencies.

In one embodiment the invention provides a method for the treatment or amelioration of a proliferative disease, a tumorous disease, a viral disease or an immunological disorder, comprising the step of administering to a subject in need thereof the antibody construct of the invention, or produced according to the process of the invention.

The terms "subject in need" or those "in need of treatment" includes those already with the disorder, as well as those in which the disorder is to be prevented. The subject in need or "patient" includes human and other mammalian subjects that receive either prophylactic or therapeutic treatment.

The antibody construct of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration include, but are not limited to topical routes (such as epicutaneous, inhalational, nasal, 83yophilisa, auricular/aural, vaginal, mucosal);

enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions and the antibody construct of this invention are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447,233; 4,486,194; 4,487,603; 4,596,556; 4,790,824; 4,941,880; 5,064,413; 5,312,335; 5,312,335; 5,383,851; and 5,399,163.

In particular, the present invention provides for an uninterrupted administration of the suitable composition. As a non-limiting example, uninterrupted or substantially uninterrupted, i.e. continuous administration may be realized by a small pump system worn by the patient for metering the influx of therapeutic agent into the body of the patient. The pharmaceutical composition comprising the antibody construct of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the antibody constructs of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may also be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to 84yophilisation.

The compositions of the present invention can be administered to the subject at a suitable dose which can be determined e.g. by dose escalating studies by administration of increasing doses of the antibody construct of the invention exhibiting cross-species specificity described herein to non-chimpanzee primates, for instance macaques. As set forth above, the antibody construct of the invention exhibiting cross-species specificity described herein can be advantageously used in identical form in preclinical testing in non-chimpanzee primates and as drug in humans. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts or doses effective for this use will depend on the condition to be treated (the indication), the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted according to the judgment of the attending physician such that it can be administered to the patient once or over a series of administrations, and in order to obtain the optimal therapeutic effect.

A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of an antibody construct of the invention preferably results in a decrease in severity of disease symptoms, an increase in frequency or duration of disease symptom-free periods or a prevention of impairment or disability due to the disease affliction. For treating target cell antigen-expressing tumors, a therapeutically effective amount of the antibody construct of the invention, e.g. an anti-target cell antigen/anti-CD3 antibody construct, preferably inhibits cell growth or tumor growth by at least about 20%, at least about 40%, at least about 50%, at least about 60%, at least about 70%, at least about 80%, or at least about 90% relative to untreated patients. The ability of a compound to inhibit tumor growth may be evaluated in an animal model predictive of efficacy The pharmaceutical composition can be administered as a sole therapeutic or in combination with additional therapies such as anti-cancer therapies as needed, e.g. other proteinaceous and non-proteinaceous drugs. These drugs may be administered simultaneously with the composition comprising the antibody construct of the invention as defined herein or separately before or after administration of said antibody construct in timely defined intervals and doses.

The term "effective and non-toxic dose" as used herein refers to a tolerable dose of an inventive antibody construct which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI- CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

Finally, the invention provides a kit comprising an antibody construct of the invention or produced according to the process of the invention, a pharmaceutical composition of the invention, a polynucleotide of the invention, a vector of the invention and/or a host cell of the invention.

In the context of the present invention, the term "kit" means two or more components—one of which corresponding to the antibody construct, the pharmaceutical composition, the vector or the host cell of the invention—packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material (preferably waterproof, e.g. plastic or glass) containing the antibody construct or the pharmaceutical composition of the present invention in an appropriate dosage for administration (see above). The kit may additionally contain directions for use (e.g. in the form of a leaflet or instruction manual), means for administering the antibody construct of the present invention such as a syringe, pump, infuser or the like, means for reconstituting the antibody construct of the invention and/or means for diluting the antibody construct of the invention.

The invention also provides kits for a single-dose administration unit. The kit of the invention may also contain a first recipient comprising a dried/lyophilized antibody construct and a second recipient comprising an aqueous formulation. In certain embodiments of this invention, kits containing single-chambered and multi-chambered pre-filled syringes (e.g., liquid syringes and lyosyringes) are provided.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following examples, offered for illustrative purposes only. The examples are not intended to limit the scope of the present invention in any way.

Example 1: Comparison of Fed Batch Vs. Continuous Manufacturing Mode for the Production of CD19×CD3 BiTE® Antibody Construct CD19×CD3 BiTE® Antibody Construct Fed-Batch Process (FB)

The FB process was initiated by thawing a vial containing Chinese hamster ovary (CHO) cells expressing the CD19× CD3 BiTE® antibody construct. During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (2 L or 500 L scale).

Once cells were inoculated into the production bioreactor at a cell density of $1.5 \times 10^6$ cells/mL, the culture was fed a defined amount of proprietary chemically-defined feed medium on days 2, 5, 7, 9, 11 and 13. Culture was maintained at pH 6.85, dissolved oxygen of 64 mm Hg and 36° C., with a temperature shift to 33.5° C. on approximately day 7. Cell density (CDV, Nova Biomedical, Waltham, MA), metabolites (NovaFlex, Nova Biomedical, Waltham, MA) and titer (HPLC analysis) mere measured throughout the culture duration. After 15 days of production, harvest and clarification were performed via centrifugation and filtration to produce harvested cell culture fluid (HCCF), which was processed forward to a protein-L capture chromatography and the eluate analyzed for product quality attributes and process-related impurities using analytical cation exchange chromatography (CEX-HPLC), peptide mapping and host cell protein (HCP) ELISA.

CD19×CD3 BiTE® Antibody Construct Continuous Manufacturing Process (CM)

Before, the CM process was initiated a vial containing CHO cells expressing the CD19×CD3 BiTE® antibody construct was thawed. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (10 L or 50 L scale).

Once cells were inoculated into the production bioreactor at $0.7 \times 10^6$ cells/mL, there was an initial cell growth phase for 12 days to increase cell density and biomass to a set-point of 70 pF/cm ($60$-$80 \times 10^6$ cells/mL) as measured by a capacitance probe (Hamilton Bonaduz AG, Switzerland). Production bioreactor was controlled at pH 6.85, dissolved oxygen of 64 mm Hg and 36° C. Perfusion culture was initiated on day 4 of the cell growth phase using an alternating tangential flow (ATF) filtration system (Refine Technologies, Hanover, NJ) with polyethersulfone 0.2-µm filters (GE Healthcare, Pittsburgh, PA), and a proprietary chemically-defined perfusion medium at a 0.4 bioreactor volumes per day (VVD) perfusion rate. Perfusion rate was increased gradually from 0.4 VVD on day 4 to 2 VVD on day 12. Once biomass set-point was reached on day 12, cell culture temperature was reduced to 33.5° C., collection of HCCF started (i.e., cell-free permeate containing CD19×CD3 BiTE® antibody construct), and perfusion culture continued for 28 additional days by feeding at 2 VVD perfusion rate (steady-state cell specific perfusion rate, CSPR, of 0.02-0.03 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. The HCCF was collected at room temperature in 24 hour increments and processed forward to a protein-L capture chromatography. The eluate from protein-L on days 26, 27, 34, 40 were analyzed for product quality attributes and process-related impurities using analytical cation exchange chromatography (CEX-HPLC), peptide mapping and HCP ELISA.

Figure 2:
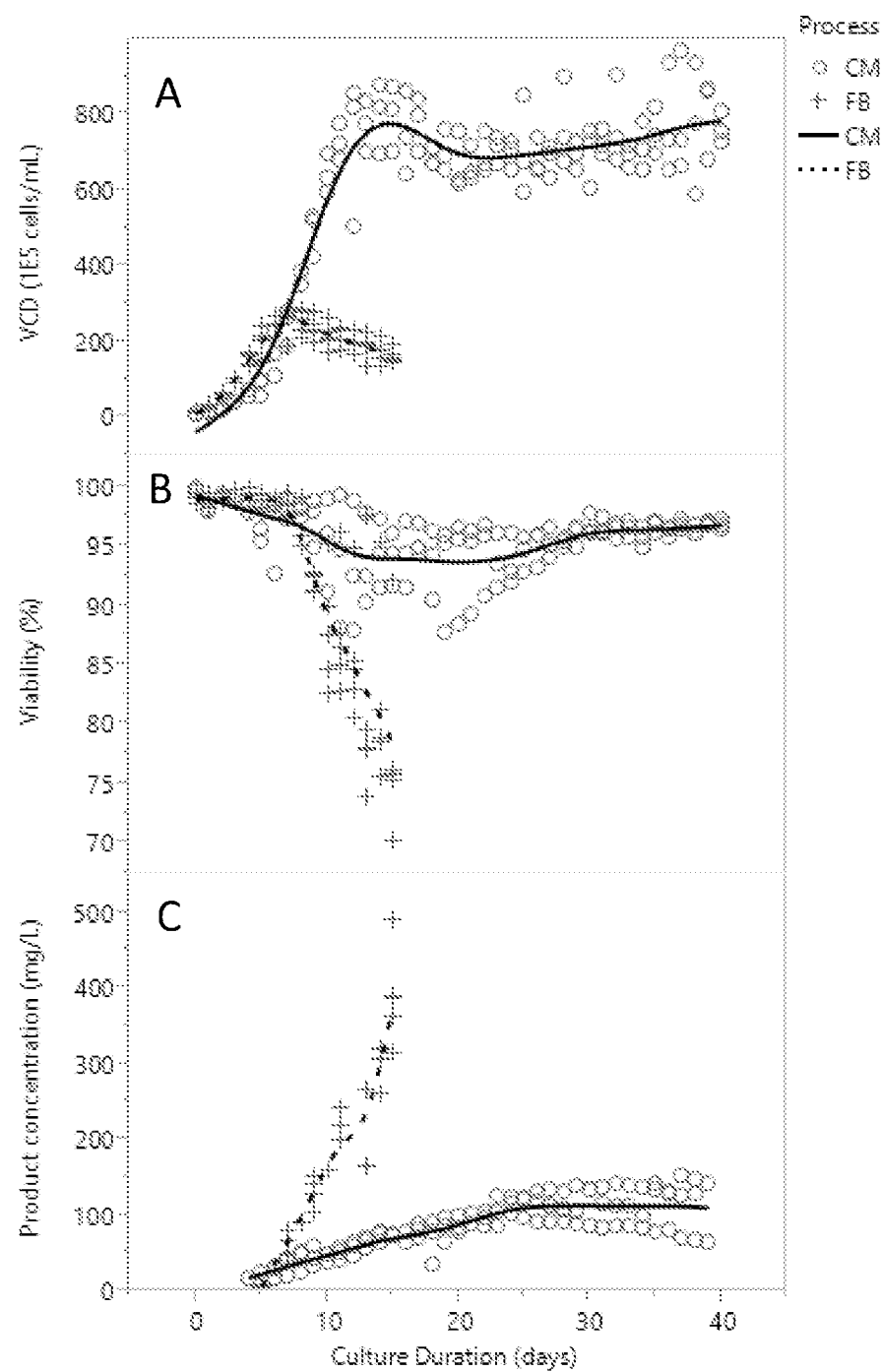
FIG. 2 shows the viable cell density (VCD) ($10^5$ cells/mL) as a function of culture time (A), the percentile viability of cells of the culture cell line as a function of culture time (B) and the product concentration (mg/L) as a function of culture time (C) with regard to fed batch ("+") and continuous manufacturing (open circles) of CD19XCD3 BITE® ANTIBODY CONSTRUCT, respectively. The solid line represents the mean of CM values, the dotted line the mean of fed-batch values, respectively. Same CHO cell line derived from GS-KO host was used for both process formats.

Cell culture performance (FIG. 2, Table 4), product quality attributes and process-related impurity levels (Table 4) of the CD19×CD3 BiTE® antibody construct CM were improved as compared to the CD19×CD3 BiTE® antibody construct FB process. Higher volumetric productivity, less chemical and physical product degradation and lower process-related impurities were demonstrated with the CD19×CD3 BiTE® antibody construct upstream CM process. The normalized values indicated in Table 4 correspond to the average of all the absolute numbers divided by the average of all the absolute numbers in FB; for FB this correspond to 1; for CM is one number corresponding to the ratio described.

Product Quality Analytical Methods

Cation Exchange-High Performance Chromatography for Charge Variant Analysis (CEX-HPLC)

Weak cation exchange (CEX) separation was performed using a Thermo Scientific™ ProPac WCX-10 column (4.0× 250 mm, 10 µm) and Agilent HPLC 1100 series. The protein samples were diluted to 22.5 µg/mL using formulation buffer and then conditioned with 2-(N-morpholino) ethanesulfonic (MES) buffer (pH 5.8) prior to the loading and separated at set temperature of 30° C. using an increasing gradient of NaCl. The mobile phase A was 20 mM MES at pH 5.8, and mobile phase B was 20 mM MES and 1.0 M NaCl at pH 5.8. A linear gradient was performed from 7% B to 54% B in 55 min at a flow rate of 0.5 mL/min. Approximately 1.5 µg of sample was injected and the signal was monitored with FL detection (excitation at 280 nm, emission at 345 nm).

Tryptic Peptide Mapping for Chemical Modifications

CD19×CD3 BiTE® antibody construct protein samples were digested with a filter-based method using Millipore Microcon 30K device. The protein sample was added on the filter, centrifuged to remove the sample matrix, then denatured in 6 M guanidine hydrochloride (GuHCl) (Thermo Fisher Scientific, Rockford, IL) buffer containing methionine, reduced with 500 mM dithiothreitol (DTT) (Sigma-Aldrich, St. Louis, MO) at 37° C. for 30 min, and subsequently alkylated by incubation with 500 mM iodoacetic acid (IAA) (Sigma-Aldrich, St. Louis, MO) for 20 min in the dark at room temperature. Unreacted IAA was quenched by adding DTT. All the above steps occurred on the filter. Samples were subsequently buffer exchanged into the digestion buffer (50 mM Tris, pH 7.8 containing Methionine) by centrifuging to remove any residual DTT and IAA. Trypsin digestion was performed on the filter for 1 hr at 37° C. using an enzyme to protein ratio of 1:20 (w/w). The digestion mixture was collected by centrifuging and then quenched by adding 8 M GuHCl in acetate buffer at pH 4.7.

The liquid chromatography-mass spectrometry (LC-MS) analysis was performed using a Thermo U-3000 ultra-performance liquid chromatography (UPLC) system directly coupled with a Thermo Scientific Q-Exactive Mass Spectrometer.

The protein digests were separated by reversed phase using an Agilent Zorbax C18 RR HD column (2.1×150 mm, 1.8 µm), with the column temperature maintained at 50° C. The mobile phase A consisted of 0.020% (v/v) formic acid (FA) in water, and the mobile phase B was 0.018% (v/v) FA in acetonitrile (I). Approximately 5 µg of the digested CD19×CD3 BiTE® antibody construct was injected to the column. A gradient (0.5 to 36% B over 145 min) was used to separate the peptides at a flow rate of 0.2 mL/min. The eluted peptides were monitored by MS.

For peptide identification and modification analysis, a data-dependent tandem MS (MS/MS) experiment was utilized. A full scan was acquired from 200 to 2000 m/z in the positive ion mode followed by 6 data-dependent MS/MS scans to identify the sequence of the peptide. The quantitation was based on mass spectrometry data of the selected ion monitoring using the equation below:

$$\text{Modification \%} = \frac{A_{modified}}{A_{modified} + A_{unmodified}} \times 100$$

Where Modification % is the level of the modified peptides, $A_{modified}$ is the extracted ion chromatogram area of modified peptide, $A_{unmodified}$ is the extracted ion chromatogram area of unmodified peptide.

Host Cell Protein (HCP) ELISA

A microtiter plate is coated with rabbit anti-HCP Immunoglobulin G (IgG) (Amgen, in-house antibody). After the plate is washed and blocked, the test samples, controls and HCP calibration standards are added to the plate and incubated. Unbound proteins are washed from the plate and pooled rabbit anti-HCP IgG-Biotin (Amgen, in-house antibody) is added to the plate and incubated. Following another wash, Streptavidin™ Horseradish Peroxidase conjugate (HRP-conjugate) (Amersham—GE, Buckinghamshire, UK) is added to the plate and incubated. The plate is washed a final time and the chromogenic substrate tetramethylbenzidine (TMB) (Kirkegaard and Perry Laboratories, Gaithersburg, MD) is added to plate. Color development is arrested with 1 M Phosphoric acid and the optical density is measured with a spectrophotometer.

TABLE 4

Comparison of CD19 × CD3 BiTE ® antibody construct CM process versus FB process using same CHO cell line derived from GS-KO host. IVCD is understood herein and in the context of the present invention as integrated viable cell density.

| Process Parameter | CD19 × CD3 BiTE ® antibody construct FB Process | CD19 × CD3 BiTE ® antibody construct CM Process |
|---|---|---|
| Cell Culture Metrics | | |
| 4 runs at 2 L and 1 run at 500 L for FB; 2 runs at 10 L and 1 run at 50 L for CM. Both absolute numbers and normalized to FB (in brackets) are provided | | |
| Production culture duration (days) | 15 [1] | 40 [2.67] |
| Final IVCD ($10^6$ cells-day/mL) | 254.2 [1[ | 2298.3 [9.04[ |
| Average HCCF productivity (g/L of bioreactor volume) | 0.31 [1[ | 5.07 [16.34] |
| Average HCCF daily productivity (mg/L of bioreactor volume/day) | 20.8 [1] | 129.0 [6.21] |
| Product Quality Attributes | | |
| 2 capture eluates analyzed for FB; 4 capture eluates (days 26, 27, 34, 40) analyzed for CM. Both absolute numbers and normalized average to FB average (in brackets) are provided | | |
| Histidine-tag clipped species in capture eluate as measured in acidic peaks in CEX-HPLC (%) | 28; 21 [1] | 6; 6; 6; 6 [0.24] |
| D32 isomerization by peptide mapping in capture eluate (%) | 2.2; 2.0 [1] | 0.6; 0.6; 0.8; 0.7 [0.32] |
| Process-related Impurities | | |
| 2 capture eluates analyzed for FB; 4 capture eluates (days 26, 27, 34, 40) analyzed for CM. Both absolute numbers and normalized average to FB average (in brackets) are provided | | |
| Host cell protein in capture eluate (ppm) | 885; 1292 [1] | 185; 138; 145; 129 [0.14] |

Example 2: Comparison of Fed Batch Vs. Continuous Manufacturing Mode for the Production of EGFRvIIIxCD3 BiTE® Antibody Construct EGFRvIIIxCD3 BiTE® Antibody Construct Fed-Batch Process (FB)

The FB process was initiated by thawing a vial containing CHO cells expressing the EGFRvIIIxCD3 BiTE® antibody construct. During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (2 L scale). Once cells were inoculated into the production bioreactor at a cell density of $1.0 \times 10^6$ cells/mL, the culture was fed a defined amount of proprietary chemically-defined feed medium on days 3, 6 and 8. Culture was maintained at pH 6.9, dissolved oxygen of 64 mm Hg and 36° C. constant. Cell density (CDV, Nova Biomedical, Waltham, MA), metabolites (NovaFlex, Nova Biomedical, Waltham, MA) and titer (HPLC analysis) mere measured throughout the culture duration. After 12 days of production, cell culture supernatant was purified with immobilized metal affinity chromatography (IMAC) and the eluate analyzed for product quality attributes using size exclusion chromatography (SE-HPLC).

EGFRvIIIxCD3 BiTE® Antibody Construct Continuous Manufacturing Process (CM)

The CM process was initiated by thawing a vial containing CHO cells expressing the EGFRvIIIxCD3 BiTE® antibody construct. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (2 L scale).

Once cells were inoculated into the production bioreactor at $5-10 \times 10^6$ cells/mL, there was an initial cell growth phase for approximately 6 days to increase cell density and biomass to a set-point of 80 pF/cm ($60-80 \times 10^6$ cells/mL) as measured by a capacitance probe (Hamilton Bonaduz AG, Switzerland). Production bioreactor was controlled at pH 6.9, dissolved oxygen of 64 mm Hg and 36° C. Perfusion culture was initiated on approximately day 1 of the cell growth phase using an alternating tangential flow (ATF) filtration system (Refine Technologies, Hanover, NJ) with polyethersulfone 0.2-µm filters (GE Healthcare, Pittsburgh, PA), and a proprietary chemically-defined perfusion medium at a 0.5 VVD perfusion rate. Perfusion rate was increased gradually from 0.5 VVD on day 1 to 2 VVD on day 4. Once biomass set-point was reached on approximately day 6, collection of HCCF started (i.e., cell-free permeate containing EGFRvIIIxCD3 BiTE® antibody construct, and perfusion culture was continued for 29 additional days by feeding at 2 VVD perfusion rate (steady-state CSPR of 0.02-0.03 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. Permeate samples from days 5, 10, 15, 20, 25, 30 and 35 were purified with immobilized metal affinity chromatography (IMAC) and the eluate analyzed for product quality attributes using size exclusion chromatography (SE-HPLC). The normalized values indicated in Table 5 correspond to the average of all the absolute numbers divided by the average of all the absolute numbers in FB; for FB this correspond to 1; for CM is one number corresponding to the ratio described.

Figure 3:
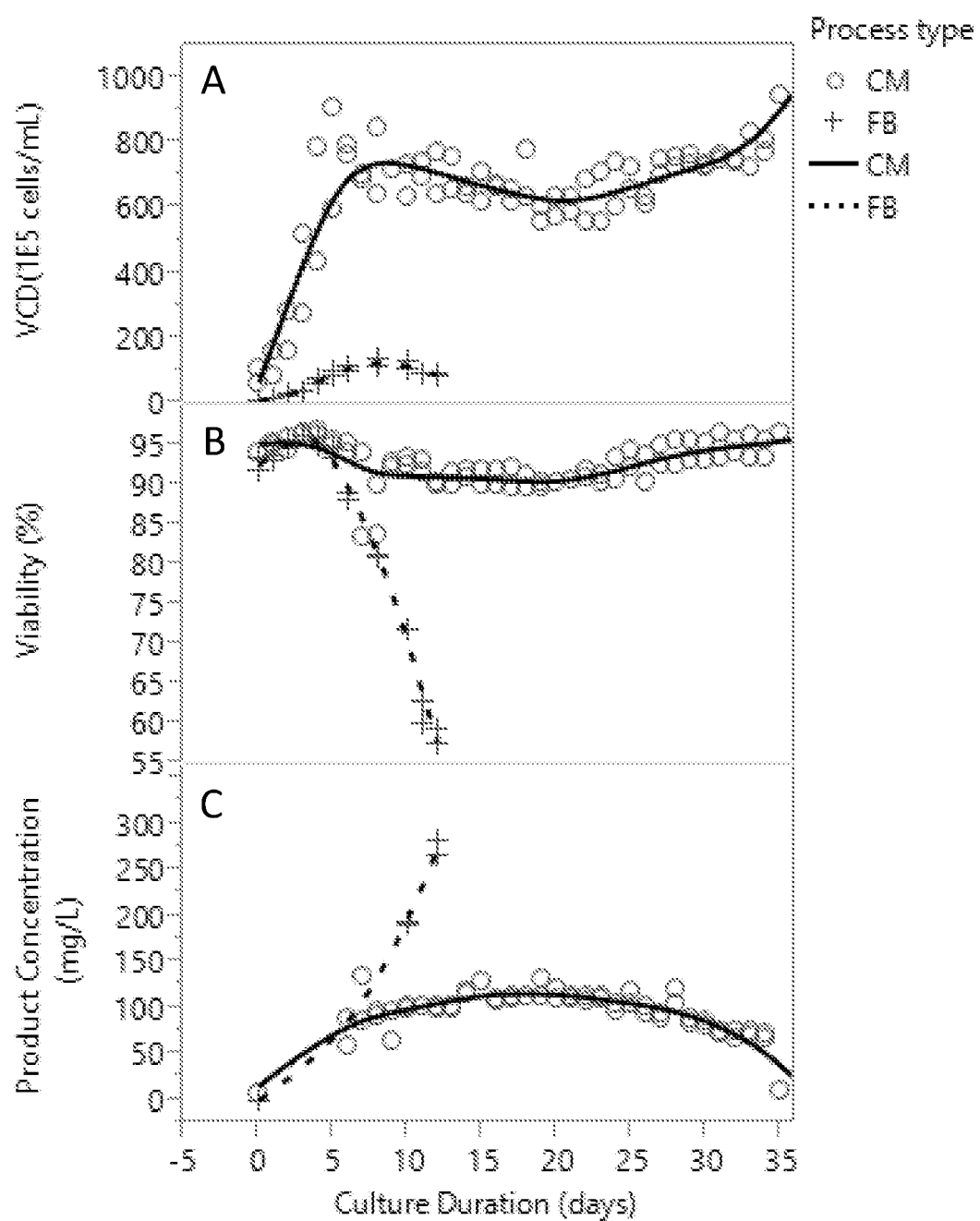
FIG. 3 shows the viable cell density (VCD) ($10^5$ cells/mL) as a function of culture time (A), the percentile viability of cells of the culture cell line as a function of culture time (B) and the product concentration (mg/L) as a function of culture time (C) with regard to fed batch ("+") and continuous manufacturing (open circles) of EGFRvIIIxCD3 BiTE® antibody construct, respectively. The solid line represents the mean of CM values, the dotted line the mean of fed-batch values, respectively. Same CHO cell line derived from DHFR deficient host was used for both process formats.
Figure 4:
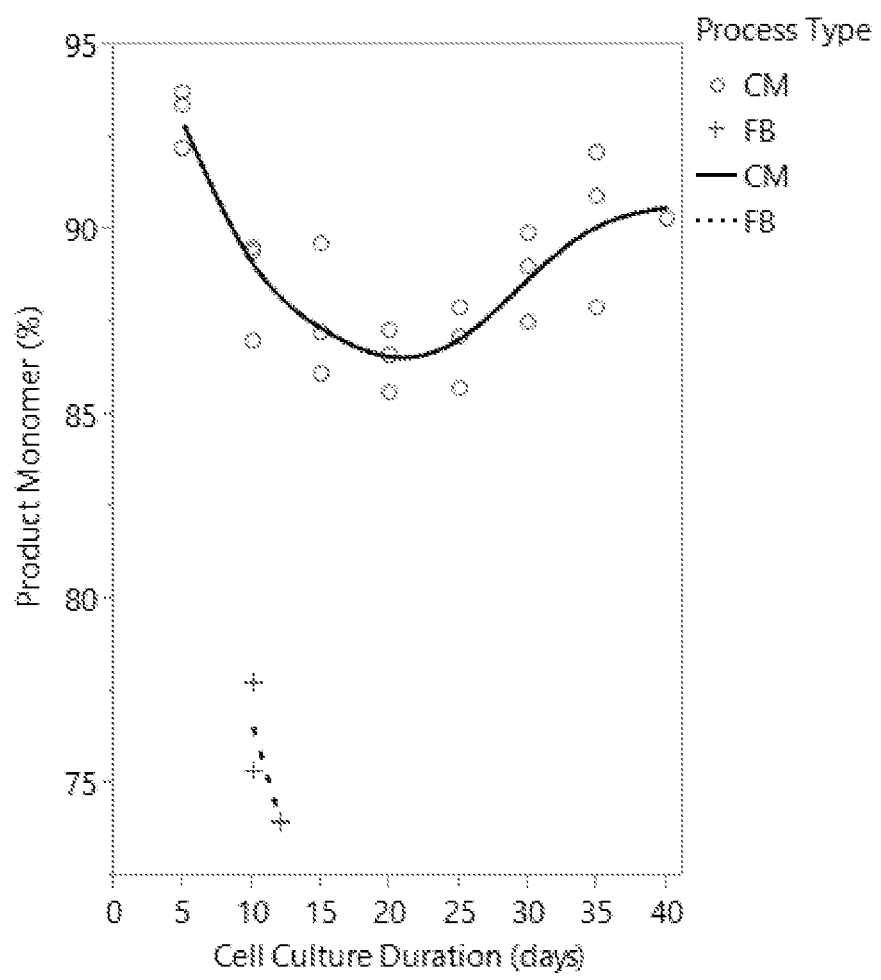
FIG. 4 shows the EGFRvIIIxCD3 BiTE® antibody construct product monomer (%) in CM permeate (open circles) and FB supernatant ("+") samples. The solid line represents the mean of CM values, the dotted line the mean of fed-batch values, respectively.

Cell culture performance (FIG. 3, Table 5) and product quality attributes (Table 5) of the EGFRvIIIxCD3 BiTE® antibody construct CM process were improved as compared to the EGFRvIIIxCD3 BiTE® antibody construct FB process using the same CHO cell line. In particular, the lower concentration in the CM process permeate correlated with lower high molecular weight (HMW) species levels and higher product monomer as compared to the FB process (FIG. 4). Higher volumetric productivity with less physical product degradation was demonstrated with the EGFRvIIIxCD3 BiTE® antibody construct upstream CM process.

As Product Quality Analytical Methods
Size Exclusion-High Performance Liquid Chromatography (SE-HPLC)

SE-HPLC was performed using a Waters BEH200 size exclusion column (4.6×150 mm, 1.7 μm) and Waters UHPLC system. The protein samples were injected neat and separated isocratically using a phosphate buffer containing NaCl salt (mobile phase was 100 mM sodium phosphate, 250 mM NaCl at pH 6.8) at a flow rate of 0.4 mL/min, and the eluent was monitored by UV absorbance at 280 nm. Approximately 6 μg of sample was loaded.

TABLE 5

Comparison of EGFRvIIIxCD3 BiTE ® antibody construct CM process versus FB process using same CHO cell line derived from DHFR deficient host

| Process Parameter | EGFRvIIIxCD3 BiTE ® antibody construct FB Process | EGFRvIIIxCD3 BiTE ® antibody construct CM Process |
|---|---|---|
| Cell Culture Metrics | | |
| 2 runs at 2 L for FB; 2 runs at 2 L for CM. Both absolute numbers and normalized to FB (in brackets) are provided | | |
| Production culture duration (days) | 12 [1] | 36 [2.96] |
| Final IVCD ($10^6$ cells-day/mL) | 95.5 [1] | 2013.5 [21.08] |
| Average HCCF productivity (g/L of bioreactor volume) | 0.28 [1] | 4.4 [15.97] |
| Average HCCF daily productivity (mg/L of bioreactor volume/day) | 22.96 [1] | 124.0 [5.40] |
| Product Quality Attributes | | |
| 2 capture eluates analyzed for FB; 14 capture eluates (days 5, 10, 15, 20, 25, 30 and 35 from 2 runs) analyzed for CM. Both absolute numbers and normalized average to FB average (in brackets) are provided | | |
| HMW in capture eluate (%) | 24.1; 23.4 [1] | 6.6; 7.1; 8.5; 7.6; 5.8; 5.7; 2.6; 6.3; 8.9; 7.4; 8.4; 6.9; 6.7; 4.6 [0.28] |

Example 3: Comparison of Fed Batch Vs. Continuous Manufacturing Mode for the Production of TNF-AlphaxTL1A Bispecific Antibody TNF-AlphaxTL1A Bispecific Antibody Fed-Batch Process (FB)

The FB process was initiated by thawing a vial containing CHO cells expressing the TNF-alphaxTL1A bispecific antibody (full length). During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (2 L scale).

Once cells were inoculated into the production bioreactor at a cell density of $1.0 \times 10^6$ cells/mL, the culture was fed a defined amount of proprietary chemically-defined feed medium on days 3, 6 and 8. Culture was maintained at pH 6.9, dissolved oxygen of 64 mm Hg and 36° C. constant. Cell density (CDV, Nova Biomedical, Waltham, MA), metabolites (NovaFlex, Nova Biomedical, Waltham, MA) and titer (HPLC analysis) mere measured throughout the culture duration. After 12 days of production, harvest and clarification were performed via centrifugation and filtration to produce harvested cell culture fluid (HCCF), which was processed forward to a protein-A capture chromatography followed by a strong-cation exchange (CEX) chromatographic step with a NaCl gradient elution. The CEX eluate was analyzed for product quality attributes and process-related impurities using reduced capillary electrophoresis-sodium dodecyl sulfate (RCE-SDS), analytical cation exchange chromatography (CEX-HPLC), peptide mapping and host cell protein (HCP) ELISA.

TNF-AlphaxTL1A Bispecific Antibody Continuous Manufacturing Process (CM)

The CM process was initiated by thawing a vial containing CHO cells expressing the TNF-alphaxTL1A bispecific antibody. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (2 L scale).

Once cells were inoculated into the production bioreactor at $5 \times 10^6$ cells/mL, there was an initial cell growth phase for 6 days to increase cell density and biomass to a set-point of 80 pF/cm ($60-80 \times 10^6$ cells/mL) as measured by a capacitance probe (Hamilton Bonaduz AG, Switzerland). Production bioreactor was controlled at pH 6.9, dissolved oxygen of 64 mm Hg and 36° C. Perfusion culture was initiated on day 1 of the cell growth phase using an alternating tangential flow (ATF) filtration system (Refine Technologies, Hanover, NJ) with polyethersulfone 0.2-μm filters (GE Healthcare, Pittsburgh, PA), and a proprietary chemically-defined perfusion medium at a 0.5 VVD perfusion rate. Perfusion rate was increased gradually from 0.5 VVD on day 1 to 2 VVD on day 6. Once biomass set-point was reached on day 6, collection of HCCF started (i.e., cell-free permeate containing TNF-alphaxTL1A bispecific antibody), and perfusion culture was continued for 28 additional days by feeding at 2 VVD perfusion rate (steady-state CSPR of 0.02-0.03 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. HCCF was collected from day 8 to day 10 and from day 29 to day 31 and processed forward to a protein-A capture chromatography followed by a strong-cation exchange (CEX) chromatographic step with a NaCl gradient elution. The CEX eluate was analyzed for product quality attributes and process-related impurities using reduced capillary electrophoresis-sodium dodecyl sulfate (RCE-SDS), analytical cation exchange chromatography (CEX-HPLC), peptide mapping and host cell protein (HCP) ELISA. The normalized values indicated in Table 6 correspond to the average of all the absolute numbers divided by the average of all the absolute numbers in FB; for FB this correspond to 1; for CM is one number corresponding to the ratio described.

Figure 5:
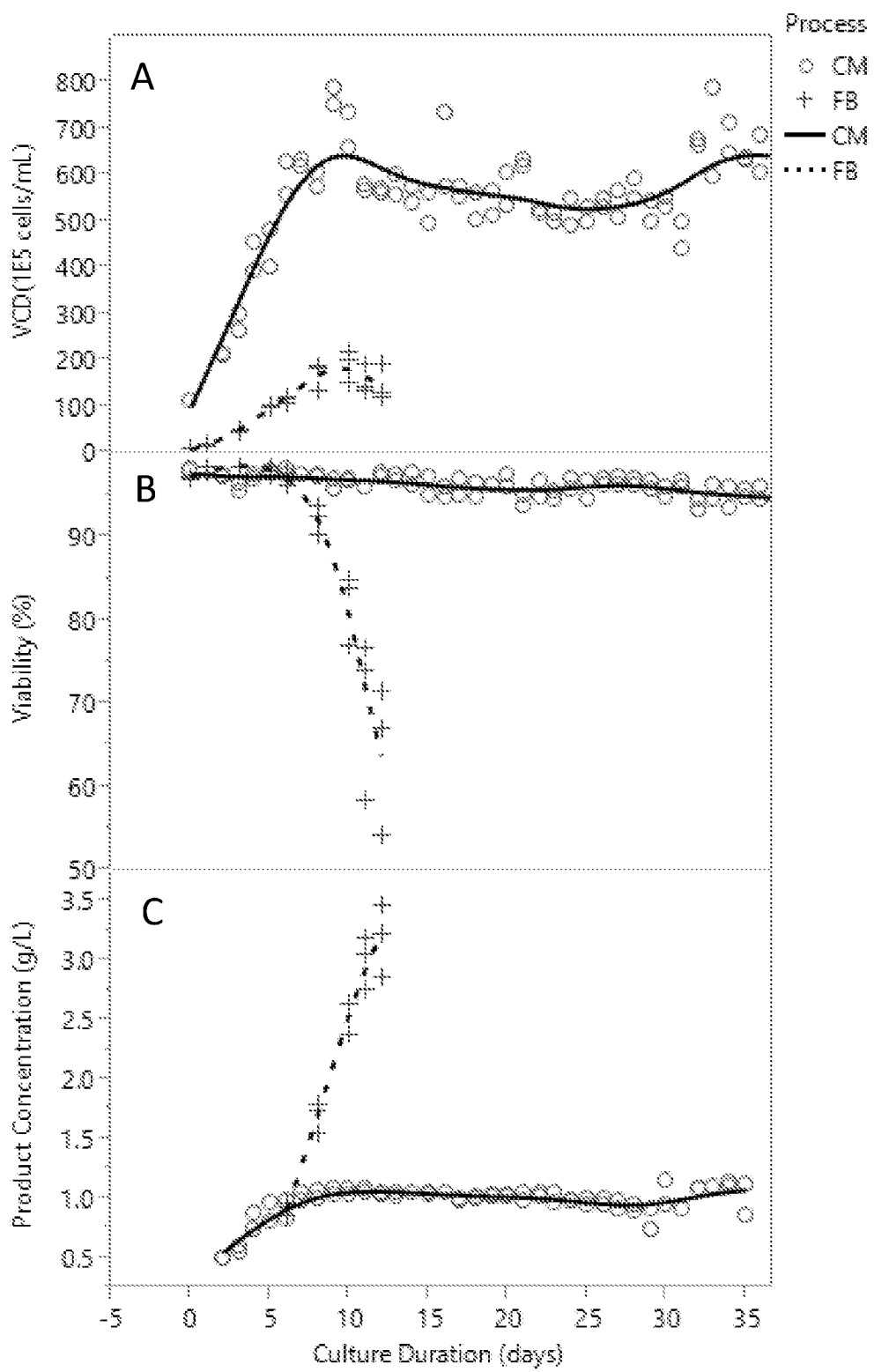
FIG. 5 shows the viable cell density (VCD) ($10^5$ cells/mL) as a function of culture time (A), the percentile viability of cells of the culture cell line as a function of culture time (B) and the product concentration (mg/L) as a function of culture time (C) with regard to fed batch ("+") and continuous manufacturing (open circles) of TNF-alphaxTL1A bispecific antibody, respectively. The solid line represents the mean of CM values, the dotted line the mean of fed-batch values, respectively. Same CHO cell line derived from DHFR deficient host was used for both process formats.

Cell culture performance (FIG. 5, Table 6), product quality attributes and process-related impurities (Table 6) of the TNF-alpha×TL1A bispecific antibody CM process were improved as compared to the TNF-alpha×TL1A bispecific antibody FB process. Higher volumetric productivity, less chemical and physical product degradation and lower process-related impurities were demonstrated with the TNF-alpha×TL1A bispecific antibody upstream CM process.

Product Quality Analytical Methods

Cation Exchange-High Performance Chromatography for Charge Variant Analysis (CEX-HPLC)

Strong cation exchange (CEX) separation was performed using a YMC-BioPro SP-F; 100×4.6 mm I.D; 5 µm column and Agilent HPLC 1100 series. The protein samples were diluted to 3.0 mg/mL using mobile phase A prior to the loading and separated at set temperature of 25° C. using an increasing gradient of NaCl. The mobile phase A was 20 mM Sodium Phosphate at pH 6.9, and mobile phase B was 20 mM Sodium Phosphate and 0.5 M NaCl at pH 6.9. A linear gradient was performed from 2% B to 25% B in 10 minutes at a flow rate of 0.6 mL/min. Approximately 90 µg of sample was injected and the signal was monitored with UV detection at 280 nm.

Reduced Capillary Electrophoresis-Sodium Dodecyl Sulfate (RCE-SDS)

The reduced CE-SDS was performed on Beckman Coulter ProteomeLab PA800 PLUS CE system. The protein samples were diluted to 0.5 mg/mL with water and then reduced with β-mercaptoethanol (β-ME) in Beckman SDS sample buffer at 70° C. for 10 min (Beckman Coulter, Brea, CA). The reduced and denatured protein samples were electrokinetically injected (5 kV for 20 sec) into a bare fused silica capillary (50 µm ID×30.0 cm effective length), separated using SDS gel buffer (separation at 15 kV for 30 min), and detection was obtained using UV at 220 nm by a photodiode array detector.

Tryptic Peptide Mapping

TNF-alpha×TL1A bispecific antibody protein sample is diluted in water to a working volume of 3 mg/mL, then denatured in 4 M GuHCl buffer containing ethylenediaminetetraacetic acid (EDTA), reduced with 500 mM DTT at 37° C. for 30 minutes, and subsequently alkylated by incubation with 500 mM IAA for 20 minutes in the dark at room temperature. Unreacted IAA was quenched by adding DTT. Samples were desalted and buffer exchanged into the digestion buffer (50 mM Tris, pH 7.8 containing methionine) with the NAP-5 column by gravity flow (GE Healthcare, UK). Trypsin digestion was performed at a 1:10 ratio and incubated at 37° C. for 35 minutes. The digestion was quenched using 10% formic acid.

The liquid chromatography-mass spectrometry (LC-MS) analysis was performed using a Waters Acquity series equipped with a binary pump, column heating compartment, auto-injector and auto-sampler with temperature control, directly coupled with a Thermo-Scientific Q-Exactive Plus Mass Spectrometer.

The protein digests were separate by reversed phase using an Agilent Zorbax C18 RR HD column (2.1×150 mm, 1.8 um), with the column temperature maintained at 50° C. The mobile phase A consisted of 0.1% formic acid in water and the mobile phase B was 0.1% formic acid in acetonitrile. A gradient (1% to 36% B over 79 minutes) was used to separate the peptides at flow rate of 0.25 mL/min. The eluted peptides were monitored by MS.

For peptide identification and modification analysis, a data-dependent tandem MS (MS/MS) experiment was utilized. A full scan was acquired from 200-2000 m/z in the positive mode followed by 8 data-dependent MS/MS scans to identify the sequence of the peptide. The quantitation was based on mass spectrometry data of the selected ion monitoring using the equation below:

$$\text{Modification \%} = \frac{A_{modified}}{A_{modified} + A_{unmodified}} \times 100$$

Where Modification % is the level of the modified peptides, $A_{modified}$ is the extracted ion chromatogram area of modified peptide, $A_{unmodified}$ is the extracted ion chromatogram area of unmodified peptide.

Host Cell Protein (HCP) ELISA

A microtiter plate is coated with rabbit anti-HCP Immunoglobulin G (IgG) (Amgen, in-house antibody). After the plate is washed and blocked, the test samples, controls and HCP calibration standards are added to the plate and incubated. Unbound proteins are washed from the plate and pooled rabbit anti-HCP IgG-Biotin (Amgen, in-house antibody) is added to the plate and incubated. Following another wash, Streptavidin™ Horseradish Peroxidase conjugate (HRP-conjugate) (Amersham—GE, Buckinghamshire, UK) is added to the plate and incubated. The plate is washed a final time and the chromogenic substrate tetramethylbenzidine (TMB) (Kirkegaard and Perry Laboratories, Gaithersburg, MD) is added to plate. Color development is arrested with 1 M Phosphoric acid and the optical density is measured with a spectrophotometer.

TABLE 6

Comparison of TNF-alpha × TL1A bispecific antibody CM process versus FB process using same CHO cell line derived from DHFR deficient host

| Process Parameter | TNF-alpha × TL1A bispecific antibody FB Process | TNF-alpha × TL1A bispecific antibody CM Process |
|---|---|---|
| Cell Culture Metrics | | |
| 2 runs at 2 L for FB; 2 runs at 2 L for CM. Both absolute numbers and normalized to FB (in brackets) are provided | | |
| Production culture duration (days) | 12 [1] | 35 [2.92] |
| Final IVCD ($10^6$ cells-day/mL) | 125.0 [1] | 1729.0 [13.83] |
| Average HCCF productivity (g/L of bioreactor volume) | 2.93 [1] | 49.1 [16.74] |
| Average HCCF daily productivity (g/L of bioreactor volume/day) | 0.25 [1] | 1.41 [5.70] |
| Product Quality Attributes | | |
| One purified pool (proA and CEX purification) analyzed for FB; 2 purified pools (proA and CEX purification) analyzed for CM (collected from day 8 to day 10 and from day 29 to day 31 in cell culture). Both absolute numbers and normalized average to FB average (in brackets) are provided | | |
| CDR clipped species by RCE-SDS in CEX eluate (%) | 1.2 [1] | 0.3; 0.3 [0.25] |
| Acidic peak by CEX-HPLC in CEX eluate (%) | 16.5 [1] | 9.3; 11.3 [0.62] |

TABLE 6-continued

Comparison of TNF-alpha × TL1A bispecific
antibody CM process versus FB process using
same CHO cell line derived from DHFR deficient host

| Process Parameter | TNF-alpha × TL1A bispecific antibody FB Process | TNF-alpha × TL1A bispecific antibody CM Process |
|---|---|---|
| Fc deamidation by peptide mapping in CEX eluate (%) | 0.6 [1] | 0.1; 0.1 [0.17] |
| Process-related Impurities | | |
| One purified pool (proA and CEX purification) analyzed for FB; 2 purified pools (proA and CEX purification) analyzed for CM (collected from day 8 to day 10 and from day 29 to day 31 in cell culture). Both absolute numbers and normalized average to FB average (in brackets) are provided | | |
| Host cell protein in CEX eluate (ppm) | 253 [1] | 66; 63 [0.25] |

Example 4: Comparison of Fed Batch Vs. Continuous Manufacturing Mode for the Production of CD33×CD3 BiTE® Antibody Construct CD33×CD3 BiTE® Antibody Construct Fed-Batch Process (FB)

The FB process was initiated by thawing a vial containing CHO cells (clone A) expressing the CD33×CD3 BiTE® antibody construct. During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (2 L scale).

Once cells were inoculated into the production bioreactor at a cell density of $1.0 \times 10^6$ cells/mL, the culture was fed a defined amount of proprietary chemically-defined feed medium on days 3, 6, 8 and 10. Culture was maintained at pH 6.9, dissolved oxygen of 64 mm Hg and 36° C. constant. Cell density (CDV, Nova Biomedical, Waltham, MA), metabolites (NovaFlex, Nova Biomedical, Waltham, MA) and titer (HPLC analysis) mere measured throughout the culture duration. After 12 days of production, cell culture supernatant was purified with immobilized metal affinity chromatography (IMAC) and the eluate analyzed for product quality attributes using size exclusion chromatography (SE-HPLC).

CD33×CD3 BiTE® Antibody Construct Continuous Manufacturing Process (CM)

The CM process was initiated by thawing a vial containing CHO cells expressing the CD33×CD3 BiTE® antibody construct. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (2 L scale).

Cells were inoculated into the production bioreactor at $1 \times 10^6$ cells/mL and four subsequent stages of perfusion culture were studied with increasing biomass set points (Table 7) as measured by a capacitance probe (Hamilton Bonaduz AG, Switzerland). Production bioreactor was controlled at pH 6.9, dissolved oxygen of 64 mm Hg and 36° C. Perfusion culture was initiated on day 3 using an alternating tangential flow (ATF) filtration system (Refine Technologies, Hanover, NJ) with polyethersulfone 750 kDa filter (GE Healthcare, Pittsburgh, PA), and a proprietary chemically-defined perfusion medium at a 1 VVD perfusion rate. Perfusion rate was maintained constant at 1 VVD for the duration of the perfusion culture, whereas biomass set-points were gradually increased to achieve four different CSPRs (Table 7). Collection of HCCF started on day 4 (i.e., cell-free permeate containing CD33×CD3 BiTE® antibody construct), and perfusion culture was continued to day 25 by feeding at 1 VVD perfusion rate and bleeding extra cells to maintain the four biomass set-points accordingly. Cell density (CDV, Nova Biomedical, Waltham, MA), metabolites (NovaFlex, Nova Biomedical, Waltham, MA) and permeate titer (HPLC analysis) were measured throughout the culture duration. Daily permeate samples were purified with immobilized metal affinity chromatography (IMAC) and the eluate analyzed for product quality attributes using size exclusion chromatography (SE-HPLC).

Figure 6:
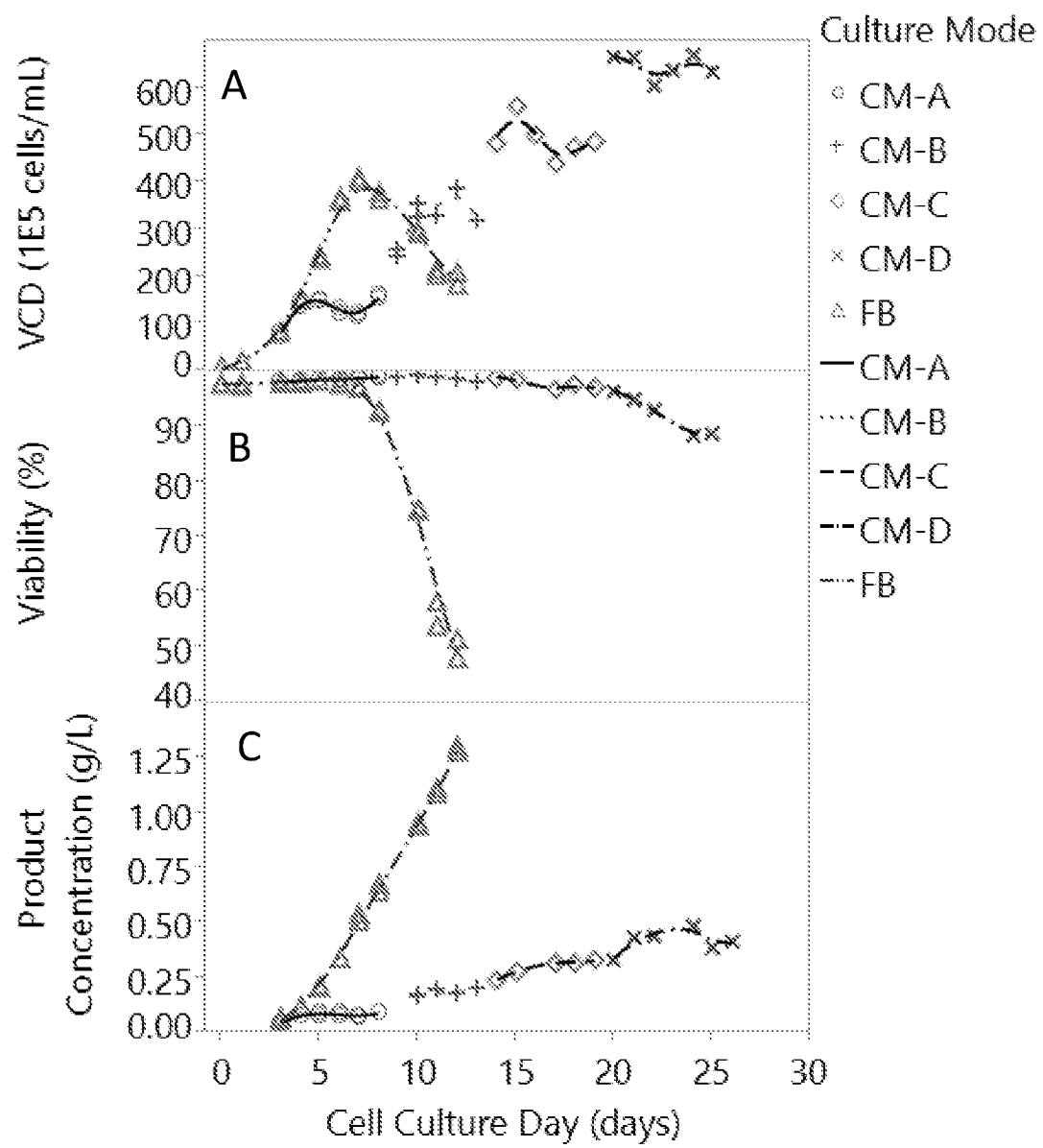
FIG. 6 shows the viable cell density (VCD) ($10^5$ cells/mL) (A) as a function of culture time (A), the percentile viability of cells of the culture cell line as a function of culture time (B) and the product concentration (mg/L) as a function of culture time (C) with regard to fed batch (open triangles) and continuous manufacturing (CM-A: ○; CM-B: +, CM-C: ◇; CM-D: x) of CD33xCD3 BiTE® antibody construct, respectively. The VCD set points under continuous manufacturing were 12.8*$10^5$ (CM-A), 32.0*$10^5$ (CM-B), 49.2*$10^5$ (CM-C) and 64.8*$10^5$ (CM-D) cells points, respectively, to achieve four different product concentrations. Means of each process are indicated by solid, dashed or dotted lines, respectively. Same CHO cell line (clone A) derived from GS-KO host was used for both process formats.
Figure 7:
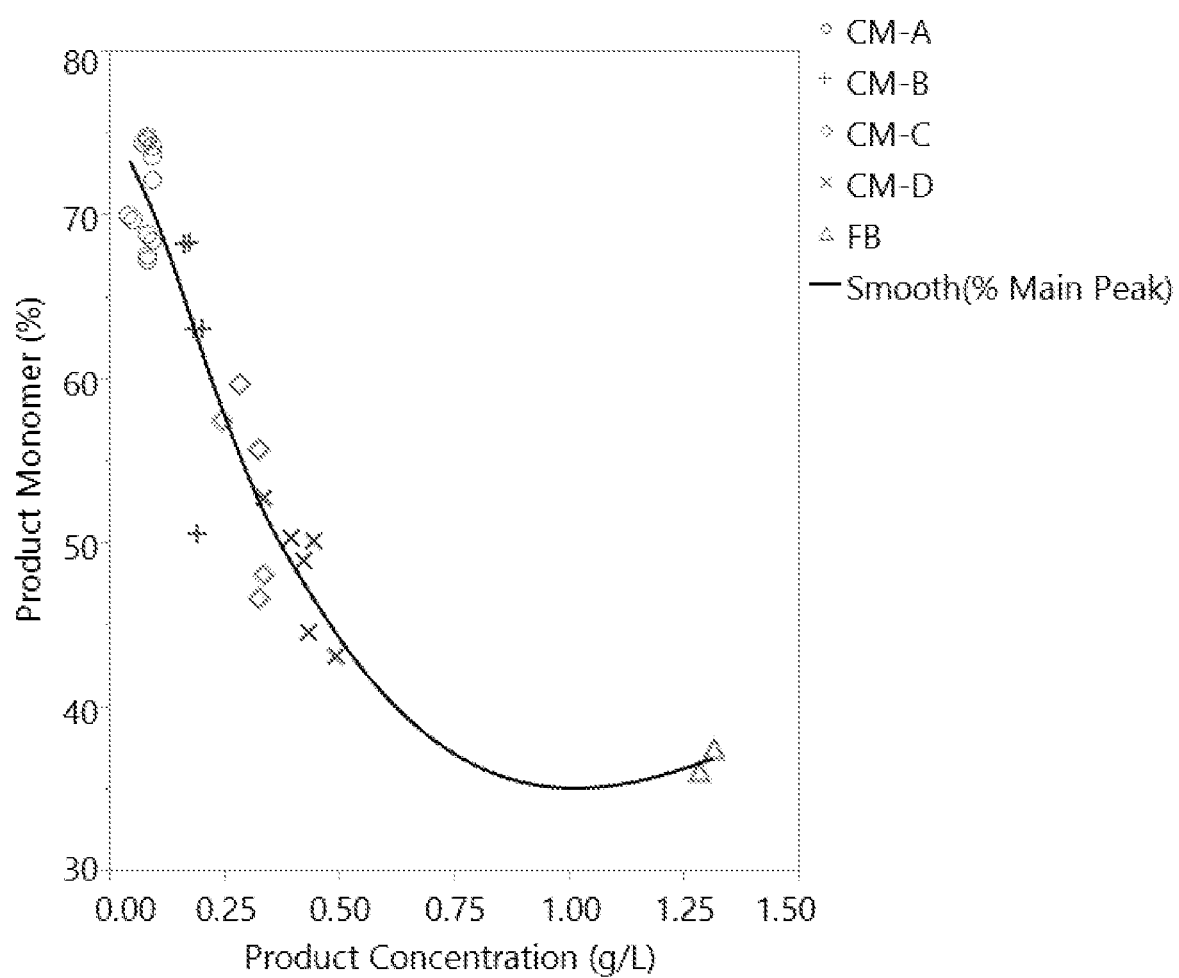
FIG. 7 shows the product monomer (%) of CD33xCD3 BiTE® antibody construct as a function of product concentration in CM permeate and FB supernatant samples. The CM processed included four different biomass set-points (CM-A: ○; CM-B: +, CM-C: ◇; CM-D: x) to achieve four different product concentrations.
Figure 8:
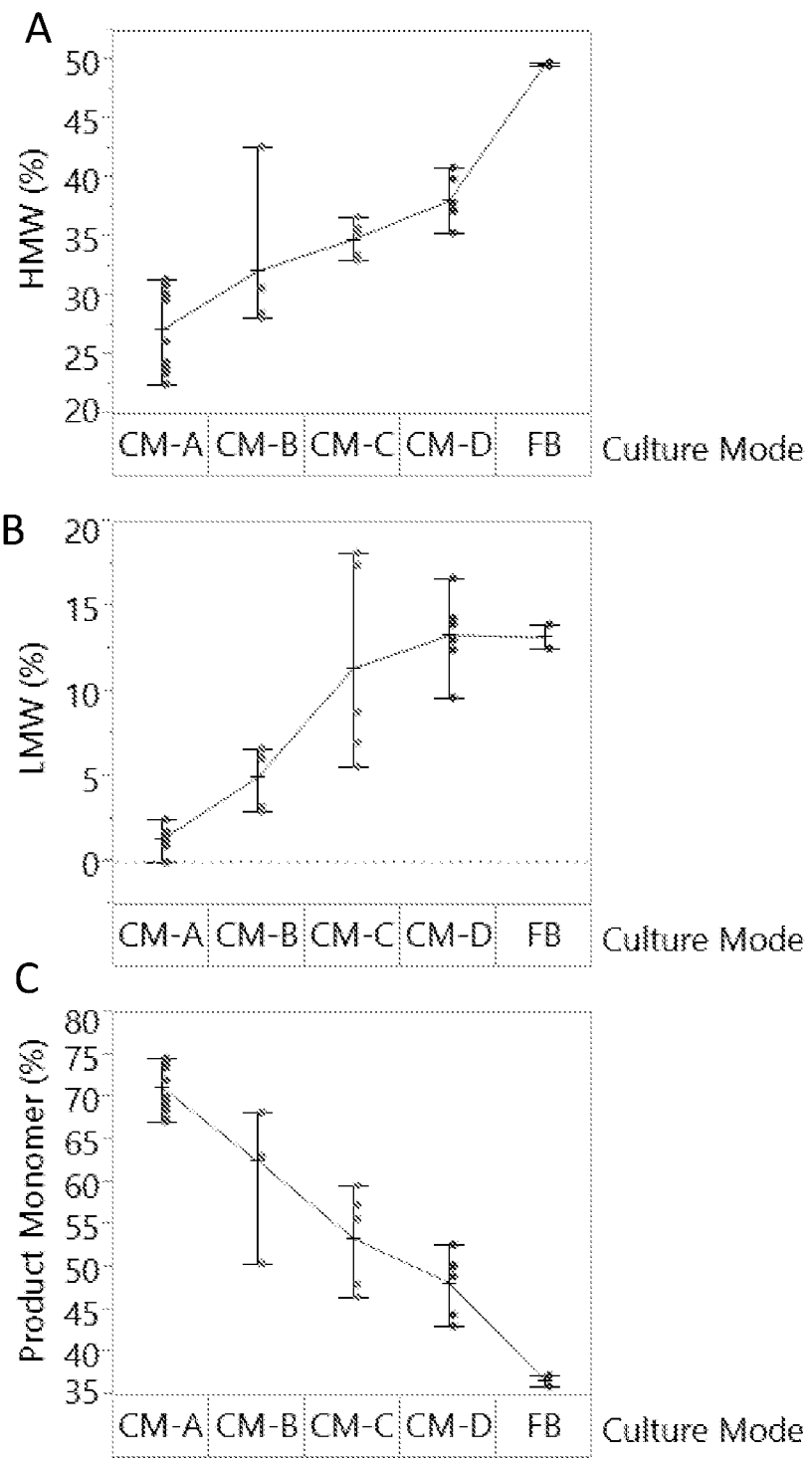
FIG. 8 shows the percentile high molecular weight fraction (A), the percentile low molecular weight fraction (B) and the percentile main peak fraction (C) for CD33×CD3 BiTE® antibody construct (clone A) produced either by fed batch (FB) or by a continuous manufacturing (CM-x) with VCD set points of 12.8*10^5 (CM-A), 32.0*10^5 (CM-B), 49.2*10^5 (CM-C) and 64.8*10^5 (CM-D) cells, respectively, to achieve four different concentrations. Same CHO cell line (clone A) derived from GS-KO host was used for both process formats.
Figure 9:
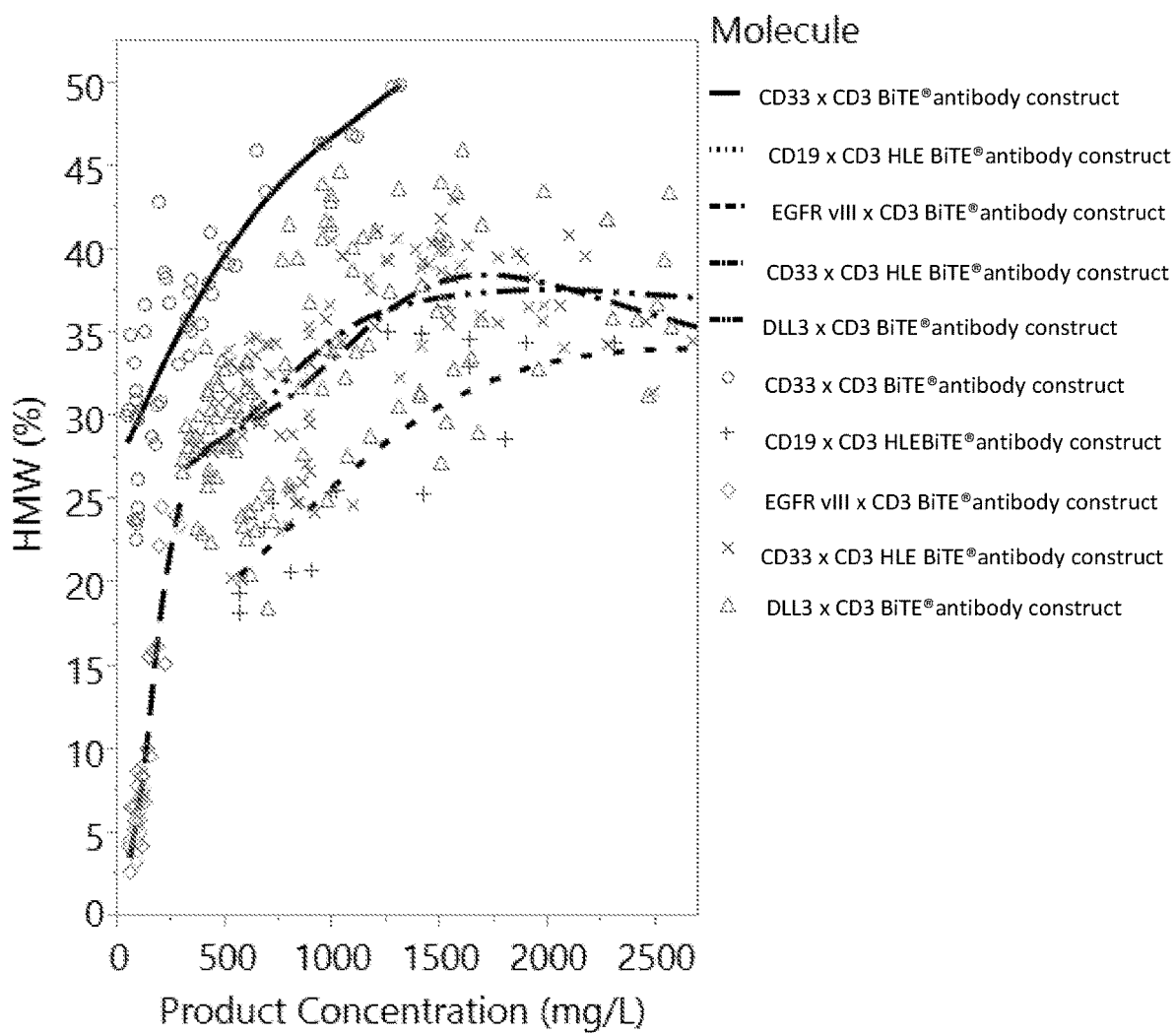
FIG. 9 shows Correlation of increased high molecular weight (HMW, %) with increased product concentration for five bispecific antibody products CD33×CD3 BiTE® antibody construct, CD19×CD3 HLE BiTE® antibody construct, EGFRvIIIxCD3 BiTE® antibody construct, CD19× CD3 HLE BiTE® antibody construct and DLL3×CD3 BiTE® antibody construct.

Product concentration of the CD33×CD3 BiTE® antibody construct CM process was lower than CD33×CD3 BiTE® antibody construct FB process (FIG. 6). Increased VCD in CM increased product concentration and volumetric productivity as measured in daily monomer mass (Table 8). However, lower product concentration correlated with higher monomer levels and lower HMW (FIGS. 7 and 8). This correlation is found in several BiTE products (FIG. 9). Even more, higher cell-specific perfusion rates and corresponding lower product concentration correlated with decreased CD33×CD3 BiTE® antibody construct aggregation. To both maximize percent monomer and daily monomer mass with increased VCD, a higher perfusion rate of 6.4 VVD and VCD of $64.8 \times 10^6$ cells/mL can be used (Table 7).

Product Quality Analytical Methods

Size Exclusion-High Performance Liquid Chromatography (SE-HPLC)

SE-HPLC was performed using a Waters BEH200 size exclusion column (4.6×150 mm, 1.7 μm) and Waters UHPLC system. The protein samples were injected neat and separated isocratically using a phosphate buffer containing NaCl salt (mobile phase was 100 mM sodium phosphate, 250 mM NaCl at pH 6.8) at a flow rate of 0.4 mL/min, and the eluent was monitored by UV absorbance at 280 nm. Approximately 6 μg of sample was loaded.

TABLE 7

Process conditions for CD33 × CD3 BiTE ® antibody construct FB and
CM processes using same CHO cell line derived from GS-KO host

| CD33 × CD3 BiTE ® antibody construct Process Name | Process Type | Target Biomass (pF/cm) | Average VCD ($10^6$ cells/mL) | Perfusion Rate (VVD) | CSPR (nL/cell-day) |
|---|---|---|---|---|---|
| Fed-batch | Fed-batch | Not applicable | Not applicable | Not applicable | Not applicable |

TABLE 7-continued

Process conditions for CD33 × CD3 BiTE ® antibody construct FB and
CM processes using same CHO cell line derived from GS-KO host

| CD33 × CD3 BiTE ® antibody construct Process Name | Process Type | Target Biomass (pF/cm) | Average VCD (10⁶ cells/mL) | Perfusion Rate (VVD) | CSPR (nL/cell-day) |
|---|---|---|---|---|---|
| CM-A | Perfusion | 10 | 12.8 | 1 | 0.078 |
| CM-B | Perfusion | 35 | 32.0 | 1 | 0.031 |
| CM-C | Perfusion | 60 | 49.2 | 1 | 0.020 |
| CM-D | Perfusion | 80 | 64.8 | 1 | 0.015 |

TABLE 8

CD33 × CD3 BiTE ® antibody construct Monomer Productivity
Calculations for FB and CM processes using same CHO cell line derived from GS-KO host.

| Process | VCD (e6 cells/mL) | Perfusion Rate (VVD) | CSPR (nL/cell-day) | FB D12 Titer (g/L) | Daily Titer (g/L) | Monomer (%) | Monomer Concentration (Titer × % Monomer) (g/L) | D12 HCCF Volume (Bioreactor volume) | Daily HCCF volume (Bioreactor volume/day) | Daily Monomer Mass per 1 BR volume (g/day) |
|---|---|---|---|---|---|---|---|---|---|---|
| FB | N/A | N/A | N/A | 1.25 | N/A | 39 | 0.49 | 1 | N/A | 0.04 |
| CM-A | 12.8 | 1.0 | 0.078 | N/A | 0.08 | 70 | 0.06 | N/A | 0.3 | 0.02 |
| CM-B | 32.0 | 1.0 | 0.031 | N/A | 0.18 | 61 | 0.11 | N/A | 0.4 | 0.04 |
| CM-C | 49.2 | 1.0 | 0.020 | N/A | 0.35 | 52 | 0.18 | N/A | 0.6 | 0.10 |
| CM-D | 64.8 | 1.0 | 0.015 | N/A | 0.53 | 44 | 0.23 | N/A | 0.9 | 0.20 |
| CM with High Monomer & High VCD[#] | 64.8 | 6.4 | 0.100 | N/A | 0.08 | 70 | 0.06 | N/A | 6.3 | 0.37 |

[#]Calculated productivities based on same product monomer in CM-A and same titer as in CM-D divided by 6.4;
N/A = not applicable

Example 5: Further Comparison of Fed Batch Vs. Continuous Manufacturing Mode for the Production of CD33×CD3 BiTE® Antibody Construct CD33×CD3 BiTE antibody construct Fed-Batch Process (FB)

The FB process was initiated by thawing a vial containing Chinese hamster ovary (CHO) cells expressing the CD33× CD3 BiTE® antibody construct (clone B). During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (3 L scale).

Once cells were inoculated into the production bioreactor at a cell density of 0.8×10⁶ cells/mL, the culture was fed a defined amount of proprietary chemically-defined feed medium on days 3, 6 and 8. Culture was maintained at pH 6.9, dissolved oxygen of 48 mm Hg and 36° C. Cell density (CDV, Nova Biomedical, Waltham, MA), metabolites (NovaFlex, Nova Biomedical, Waltham, MA) and titer (HPLC analysis) mere measured throughout the culture duration. At the end of production, harvest and clarification were performed to produce harvested cell culture fluid (HCCF), which was processed forward to a protein-L capture chromatography and the eluate analyzed for product quality attributes using size exclusion chromatography (SE-HPLC).

CD33×CD3 BiTE® Antibody Construct Continuous Manufacturing Process (CM)

The CM process was initiated by thawing a vial containing CHO cells expressing the CD33×CD3 BiTE® antibody construct (clone B). During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (3 L scale).

Once cells were inoculated into the production bioreactor at 0.7×10⁶ cells/mL, there was an initial cell growth phase for 12 days to increase cell density and biomass to a set-point of 70 pF/cm (70–90×10⁶ cells/mL) as measured by a capacitance probe (Hamilton Bonaduz AG, Switzerland). Production bioreactor was controlled at pH 6.85, dissolved oxygen of 64 mm Hg and 36° C. Perfusion culture was initiated on day 4 of the cell growth phase using an alternating tangential flow (ATF) filtration system (Refine Technologies, Hanover, NJ) with polyethersulfone 0.2-μm filters (GE Healthcare, Pittsburgh, PA), and a proprietary chemically-defined perfusion medium at a 0.5 bioreactor volumes per day (VVD) perfusion rate. Perfusion rate was increased gradually from 0.5 VVD on day 4 to 1.8 VVD on day 8. Once biomass set-point was reached, cell culture temperature was reduced to 33.0° C., collection of HCCF started on day 12 (i.e., cell-free permeate containing CD33×CD3 BiTE® antibody construct), and perfusion culture continued for 30 additional days by feeding at 2 VVD perfusion rate (steady-state cell specific perfusion rate, CSPR, of 0.02-0.03 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. The HCCF was collected at room temperature in 24 hour increments and processed forward to a protein-L capture chromatography. The eluate from protein-L were analyzed for product quality attributes using size exclusion chromatography (SE-HPLC). The normalized values indicated in Table 9 correspond to the average of all the absolute numbers divided by the average of all the absolute numbers in FB; for FB this correspond to 1; for CM is one number corresponding to the ratio described.

Figure 10:
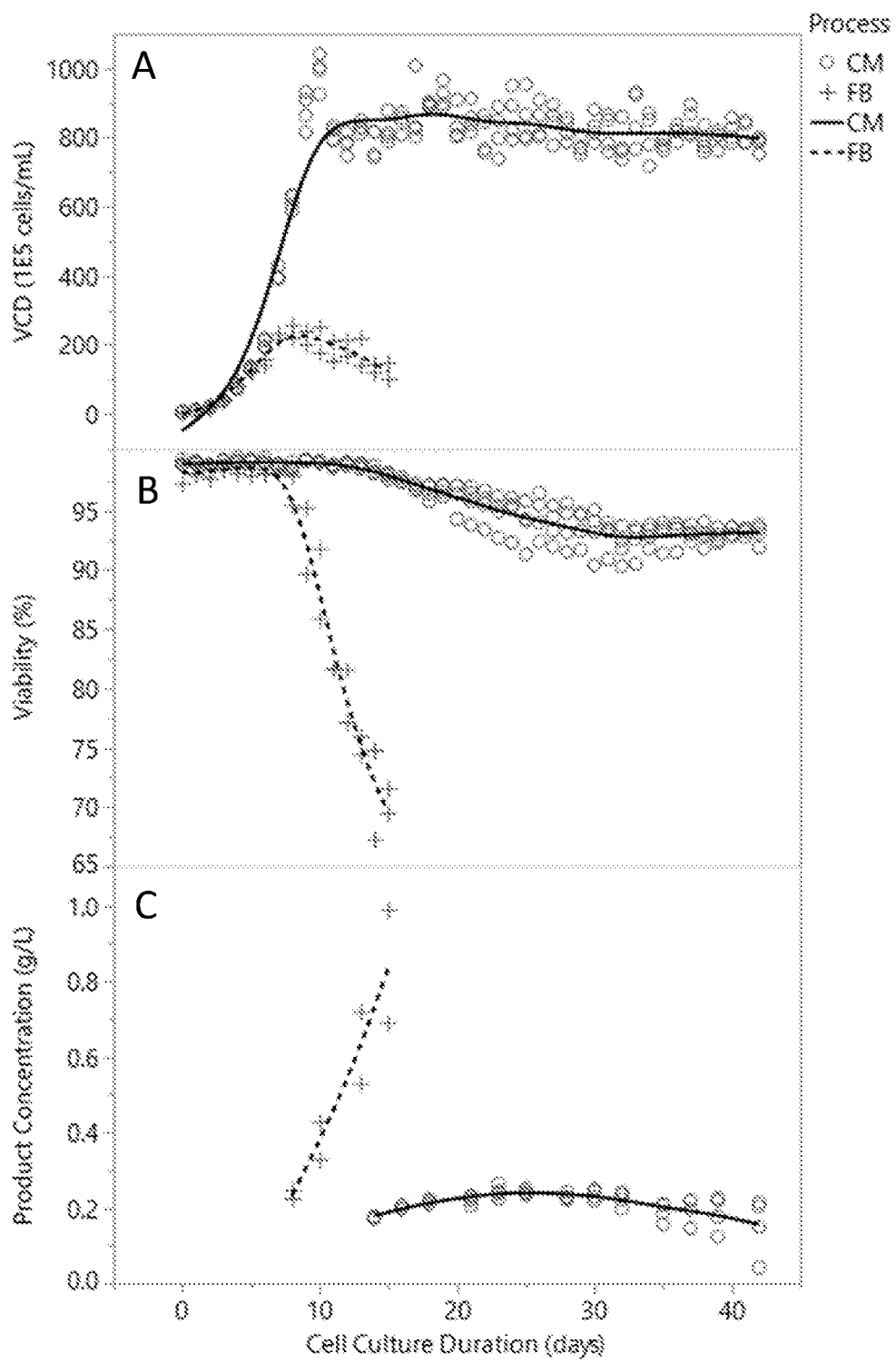
FIG. 10 shows the comparison of CD33×CD3 BiTE® antibody construct (CHO cell line clone B) FB and CM processes. (A) viable cell density as a function of culture time; (B) viability as a function of culture time; (C) product concentration as a function of culture time

Cell culture performance (FIG. 10, Table 9) and product quality attributes levels (FIG. 11, Table 9) of the CD33×CD3 BiTE® antibody construct CM were improved as compared to the CD33×CD3 BiTE® antibody construct FB process. Higher volumetric productivity, less chemical and physical product degradation were demonstrated with the CD33×CD3 BiTE® antibody construct upstream CM process.

Product Quality Analytical Methods
Size Exclusion-High Performance Liquid Chromatography (SE-HPLC)

SE-HPLC was performed using a Waters BEH200 size exclusion column (4.6×150 mm, 1.7 µm) and Waters UHPLC system. The protein samples were injected neat and separated isocratically using a phosphate buffer containing NaCl salt (mobile phase was 100 mM sodium phosphate, 250 mM NaCl at pH 6.8) at a flow rate of 0.4 mL/min, and the eluent was monitored by UV absorbance at 280 nm. Approximately 6 µg of sample was loaded.

TABLE 9

Comparison of CD33 × CD3 BiTE ® antibody construct CM process versus FB process using the same CHO cell line (clone B) derived from GS-KO host. IVCD is understood herein and in the context of the present invention as integrated viable cell density.

Figure 11:
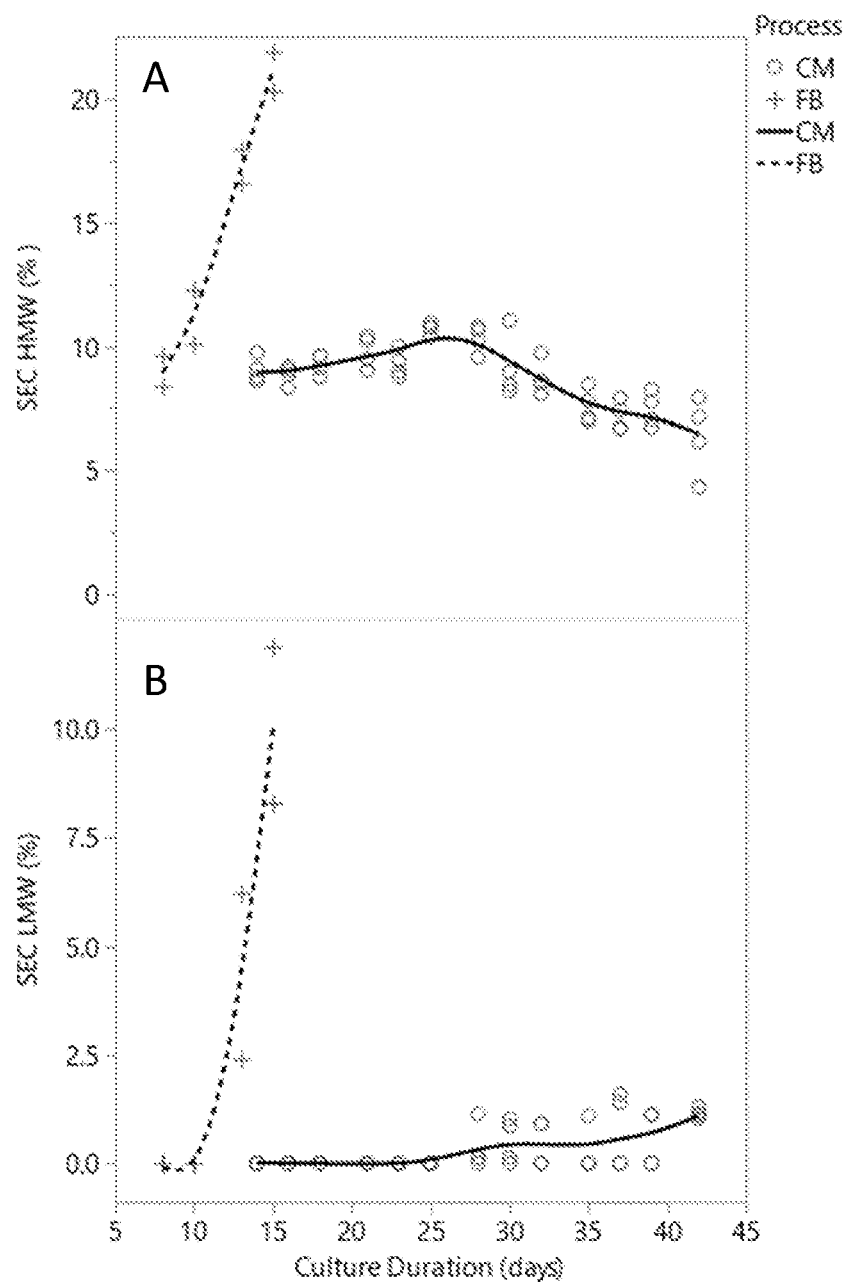
FIG. 11 shows the comparison of CD33×CD3 BiTE® antibody construct (clone B) SEC high molecular weight (HMW) and low molecular weight (LMW) in FB and CM processes.

| Process Parameter | CD33 × CD3 BiTE ® antibody construct FB Process | CD33 × CD3 BiTE ® antibody construct CM Process |
| --- | --- | --- |
| Cell Culture Metrics | | |
| 2 runs at 3 L for FB; 4 runs at 3 L for CM. Both absolute numbers and normalized to FB (in brackets) are provided | | |
| Production culture duration (days) | 15 [1] | 42 [2.8] |
| Final IVCD ($10^6$ cells-day/mL) | 212 [1] | 2937 [13.9] |
| Average HCCF productivity (g/L of bioreactor volume) | 0.6 [1] | 11.9 [21.0] |
| Average HCCF daily productivity (mg/L of bioreactor volume/day) | 42 [1] | 284 [6.8] |
| Product Quality Attributes | | |
| 2 capture eluates analyzed for FB; 13 capture eluates (days 14, 16, 18, 21, 23, 25, 28, 30, 32, 35, 37, 39, 42) analyzed for CM for 4 runs (FIG. 11). Both absolute average numbers and normalized average to FB average (in brackets) are provided | | |
| HMW in capture eluate (%) | 21.1 [1] | 8.8 [0.41] |
| LMW in capture eluate (%) | 10.1 [1] | 0.3 [0.03] |

Example 6: Comparison of Traditional 15-Day Fed Batch Vs. Hybrid 10-Day Fed Batch Mode for the Production of CD33×CD3 BiTE® Antibody Construct To benefit of the lower product concentration and better product quality from a CM process but minimize culture duration, a hybrid fed-batch process was tested. For this, the process was fed-batch from inoculation to day 7, followed by a short duration perfusion culture using an alternating tangential flow (ATF) filtration system for harvest. The removal of the product in a similar way to a CM process decreased product concentration and increased product quality.

CD33×CD3 BiTE® Antibody Construct Traditional 15-Day Fed-Batch Process (Traditional FB)

The FB process was initiated by thawing a vial containing Chinese hamster ovary (CHO) cells expressing the CD33×CD3 BiTE® antibody construct (clone B). During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (3 L scale).

Once cells were inoculated into the production bioreactor at a cell density of $0.8 \times 10^6$ cells/mL, the culture was fed a defined amount of proprietary chemically-defined feed medium on days 3, 6 and 8. Culture was maintained at pH 6.9, dissolved oxygen of 48 mm Hg and 36° C. Cell density (CDV, Nova Biomedical, Waltham, MA), metabolites (NovaFlex, Nova Biomedical, Waltham, MA) and titer (HPLC analysis) mere measured throughout the culture duration. At various duration of production (10 day or 15 day), centrifugation-based harvest and clarification were performed to produce harvested cell culture fluid (HCCF), which was processed forward to a protein-L capture chromatography and the eluate analyzed for product quality attributes using size exclusion chromatography (SE-HPLC) and cation exchange chromatography (CEX-HPLC).

CD33×CD3 BiTE® Antibody Construct Hybrid 10-Day Fed-Batch Process (Hybrid FB)

The hybrid FB process used the same scale-up and production conditions and sampling as traditional FB. For the 3 day, 1 VVD microfiltration hybrid FB process (hybrid-3D-1VVD), the culture was fed a defined amount of proprietary chemically-defined feed medium on days 3 and 6. On day 7, the culture was perfused with proprietary chemically-defined perfusion medium at 1 vessel volume per day (1 VVD) for 3 days using an alternating tangential flow (ATF) filtration system (Refine Technologies, Hanover, NJ) with polyethersulfone 750 kDa filters (GE Healthcare, Pittsburgh, PA). The CD33×CD3 BiTE antibody product was permeated through the filter and collected as HCCF during days 7 to 10. The HCCF was processed forward to a protein-L capture chromatography and the eluate analyzed for product quality attributes using size exclusion chromatography (SE-HPLC) and cation exchange chromatography (CEX-HPLC). The normalized values indicated in Table 10 correspond to the average of all the absolute numbers divided by the average of all the absolute numbers in FB; for FB this correspond to 1; for CM is one number corresponding to the ratio described.

Figure 12:
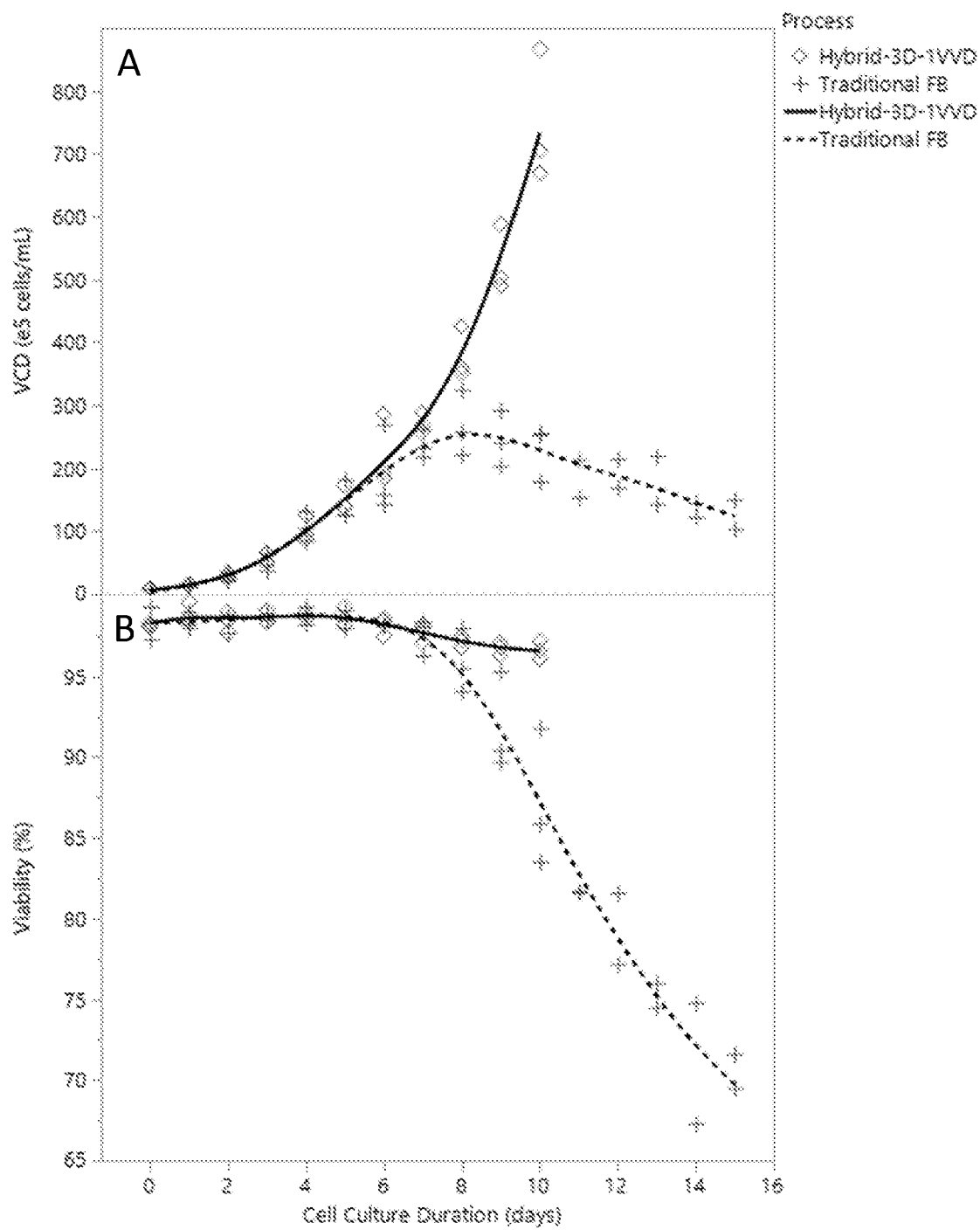
FIG. 12 shows the comparison of CD33×CD3 BiTE® antibody construct (clone B) hybrid-3D-1VVD 10-day and traditional FB processes. (A) viable cell density as a function of culture time; (B) viability as a function of culture time.

Cell culture performance (FIG. 12, Table 10) and product quality attributes levels (Table 10) of the CD33×CD3 BiTE® antibody construct hybrid-3D-1VVD process were improved as compared to the CD33×CD3 BiTE® antibody construct traditional 15-day FB process. The hybrid-3D-1VVD 10-day FB demonstrated similar volumetric productivity as the traditional 15-day FB process, however, the former had shorter duration, higher daily volumetric productivity and better product quality (Table 10). In particular, lower HCCF concentration with less product aggregation, and less chemical and physical product degradation were demonstrated with the CD33×CD3 BiTE antibody construct hybrid-3D-1VVD 10-day FB process.

Product Quality Analytical Methods
Size Exclusion-High Performance Liquid Chromatography (SE-HPLC)

SE-HPLC was performed using a Waters BEH200 size exclusion column (4.6×150 mm, 1.7 µm) and Waters UHPLC system. The protein samples were injected neat and separated isocratically using a phosphate buffer containing NaCl salt (mobile phase was 100 mM sodium phosphate, 250 mM NaCl at pH 6.8) at a flow rate of 0.4 mL/min, and the eluent was monitored by UV absorbance at 280 nm. Approximately 6 µg of sample was loaded.

Cation Exchange-High Performance Chromatography for Charge Variant Analysis (CEX-HPLC)

Weak cation exchange (CEX) separation was performed using a Waters Protein-Pak Hi Res CM 4.6×100 mm column and Waters Ultrahigh Performance Liquid Chromatography (UHPLC) system. The protein samples were preconditioned with formulation buffer 10 mM Potassium Phosphate, 8% Sucrose, 0.01% (w/v) Polysorbate 80, 1% (w/v) Captisol (pH 6.1±0.04) prior to the loading. The samples were separated at set temperature of 26° C., at a flow rate of 0. mL/min, under various gradients of three mobile phases (A, B, and C). The mobile phase A was 50 mM Sodium Phosphate at pH 6.0, mobile phase B was 50 mM Tris-HCl, 250 mM Sodium Chloride at pH 8.0, and mobile phase C was 50 mM Tris-HCl, 500 mM Sodium Chloride at pH 8.0. Approximately 8.0 µg of sample was injected and the signal was monitored with FLD detection (excitation at 280 nm, emission at 345 nm).

TABLE 10

Comparison of CD33 × CD3 BiTE ® antibody construct traditional 15-day FB process versus hybrid 10-day FB process (hybrid-3D-1VVD) using same CHO cell line (clone B) derived from GS-KO host. IVCD is understood herein and in the context of the present invention as integrated viable cell density.

| Process Parameter | CD33 × CD3 BiTE ® antibody construct Traditional FB Process | | CD33 × CD3 BiTE ® antibody construct hybrid-3D-1VVD |
|---|---|---|---|
| | 10-Day | 15-Day | 10-day FB Process |
| Cell Culture Metrics | | | |
| 3 runs at 3 L for 10-day traditional FB; 2 runs for 15-day traditional FB; 3 runs at 3 L for hybrid-3D-1VVD. Both absolute numbers and normalized to 15-day traditional FB (in brackets) are provided | | | |
| Production culture duration (days) | 10 [0.67] | 15 [1] | 10 [0.67] |
| Final IVCD ($10^6$ cells-day/mL) | 140.4 [0.66] | 211.6 [1] | 212.9 [1.01] |
| Average HCCF concentration (g/L) | 0.43 [0.52] | 0.84 [1] | 0.18 [0.21] |
| Average HCCF productivity (g/L of bioreactor volume) | 0.42 [0.67] | 0.62 [1] | 0.61 [1] |
| Average HCCF daily productivity (mg/L/day) | 42 [1] | 42 [1] | 61 [1.45] |
| Product Quality Attributes | | | |
| 3 capture eluates analyzed for 10-day traditional FB; 2 capture eluates analyzed for 15-day traditional FB; 3 capture elutes analyzed for hybrid-3D-1VVD. Both absolute average numbers and normalized average to 15-day traditional FB average (in brackets) are provided | | | |
| SEC-HMW in capture eluate (%) | 9.3 [0.44] | 21.1 [1] | 5.4 [0.25] |
| SEC-LMW in capture eluate (%) | 0 [0] | 10.1 [1] | 0 [0] |
| CEX-HPLC- Acidic in capture elute (%) | 17.4 | Not measured | 9.0 |

Example 7: Comparison of Fed Batch Vs. Continuous Manufacturing Mode for the Production of BCMA×CD3 BiTE®-HLE BCMA×CD3 BITE®-HLE Fed-Batch Process (FB)

The FB process was initiated by thawing a vial containing Chinese hamster ovary (CHO) cells expressing the BCMA×CD3 BiTE®-HLE. During scale-up, cells were resuspended in fresh selective growth medium at a targeted viable cell density (VCD). The culture volume was successively expanded in shake flasks to generate sufficient cell mass to ultimately inoculate a production fed-batch bioreactor (2 L scale).

Once cells were inoculated into the production bioreactor at a cell density of $1.0 \times 10^6$ cells/mL, the culture was fed a defined amount of proprietary chemically-defined feed medium on days 3, 6, and 8. Culture was maintained at pH 6.9, dissolved oxygen of 64 mm Hg and 36° C., with a temperature shift to 34° C. on approximately day 6. Cell density (CDV, Nova Biomedical, Waltham, MA), metabolites (NovaFlex, Nova Biomedical, Waltham, MA) and titer (HPLC analysis) mere measured throughout the culture duration. After 12 days of production, harvest and clarification were performed via centrifugation and filtration to produce harvested cell culture fluid (HCCF), which was processed forward to a protein-A capture chromatography and the eluate analyzed for product quality attributes and process-related impurities using analytical cation exchange chromatography (CEX-HPLC), peptide mapping, reduced capillary electrophoresis-sodium dodecyl sulfate, reduced host cell protein (HCP) ELISA and DNA (qPCR).

BCMA×CD3 BITE®-HLE Continuous Manufacturing Process (CM)

The CM process was initiated by thawing a vial containing CHO cells expressing the BCMA×CD3 BiTE®-HLE. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (10 L or 50 L scale).

Once cells were inoculated into the production bioreactor at $0.7 \times 10^6$ cells/mL, there was an initial cell growth phase for 12 days to increase cell density and biomass to a set-point of 70 pF/cm ($40-60 \times 10^6$ cells/mL) as measured by a capacitance probe (Hamilton Bonaduz AG, Switzerland). Production bioreactor was controlled at pH 6.9, dissolved oxygen of 64 mm Hg and 36° C. Perfusion culture was initiated on day 4 of the cell growth phase using an alternating tangential flow (ATF) filtration system (Refine Technologies, Hanover, NJ) with polyethersulfone 0.2-µm filters (GE Healthcare, Pittsburgh, PA), and a proprietary chemically-defined perfusion medium at a 0.4 bioreactor volumes per day (VVD) perfusion rate. Perfusion rate was increased gradually from 0.4 VVD on day 4 to 2 VVD on day 12. Once biomass set-point was reached on day 12, cell culture temperature was reduced to 34° C., collection of HCCF started (i.e., cell-free permeate containing BCMA×CD3 BITE®-HLE), and perfusion culture continued for 28 additional days by feeding at 2 VVD perfusion rate (steady-state cell specific perfusion rate, CSPR, of 0.03-0.05 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. The HCCF was collected at room temperature in 24 hour increments and processed forward to a protein-A capture chromatography. The eluate from protein-A on days 19 and 40 (day 7 and day 28 from steady-state) were analyzed for product quality attributes and process-related impurities using analytical cation exchange chromatography (CEX-HPLC), peptide mapping, reduced capillary electrophoresis-sodium dodecyl sulfate, reduced host cell protein (HCP) ELISA and DNA (qPCR).

Figure 13:
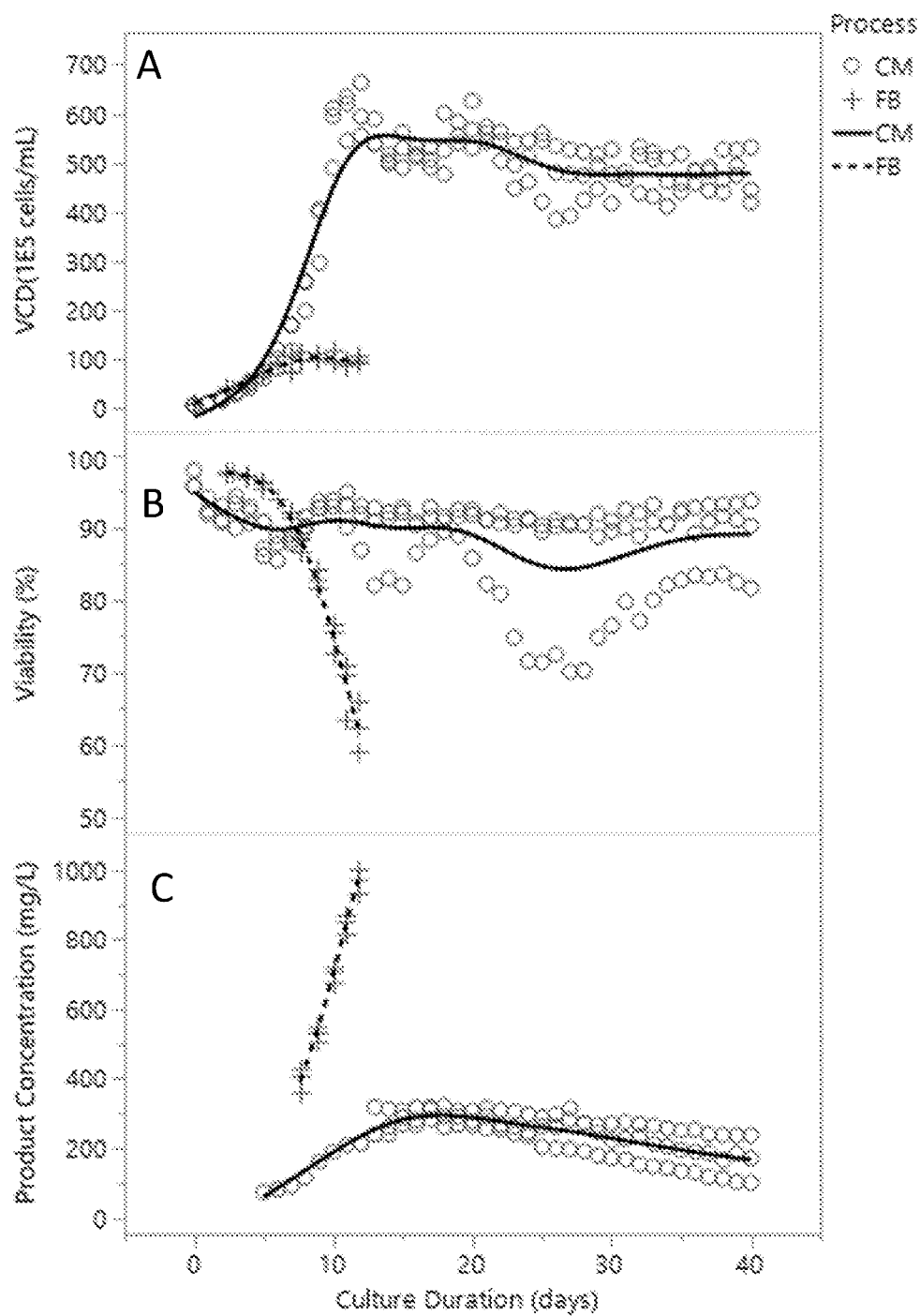
FIG. 13 shows the comparison of BCMAxCD3 BiTE®-HLE antibody construct FB and CM processes. (A) viable cell density as a function of culture time; (B) viability as a function of culture time; (C) product concentration as a function of culture time.

Cell culture performance (FIG. 13, Table 11), product quality attributes and process-related impurity levels (Table 11) of the BCMAxCD3 BITE®-HLE CM were improved as compared to the BCMAxCD3 BITE®-HLE FB process. Higher volumetric productivity, less chemical and physical product degradation and lower process-related impurities were demonstrated with the BCMAxCD3 BITE®-HLE upstream CM process. The normalized values indicated in Table 11 correspond to the average of all the absolute numbers divided by the average of all the absolute numbers in FB; for FB this correspond to 1; for CM is one number corresponding to the ratio described.

Product Quality Analytical Methods
Cation Exchange-High Performance Chromatography for Charge Variant Analysis (CEX-HPLC)

Weak cation exchange (CEX) separation was performed using a Thermo Scientific™ ProPac WCX-10 column (4.0× 250 mm, 10 µm) and Agilent HPLC 1100 series. The protein samples were diluted to 500 µg/mL with mobile phase A and separated at set temperature of 30° C. using an increasing gradient of NaCl. The mobile phase A was 50 mM Sodium Phosphate at pH 6.0, and mobile phase B was 50 mM Sodium Phosphate, 500 mM NaCl at pH 6.0. A linear gradient was performed from 10% B to 40% B in 50 min at a flow rate of 0.5 mL/min. Approximately 50 µg of sample was injected and the signal was monitored with UV detection at 220 nm by a variable wavelength detector.

Tryptin/Elastase Peptide Mapping for Chemical Modifications

Protein samples were digested with a filter-based method using Millipore Microcon 30K device. The protein sample was added on the filter, centrifuged to remove the sample matrix, then denatured in 6 M guanidine hydrochloride (GuHCl) (Thermo Fisher Scientific; Rockford, IL) buffer containing methionine, reduced with 37.5 mM dithiothreitol (DTT) (Sigma-Aldrich; St. Louis, MO) at 37° C. for 30 min, and subsequently alkylated by incubation with 87.5 mM iodoacetic acid (IAA) (Sigma-Aldrich; St. Louis, MO) for 20 min in the dark at room temperature. Unreacted IAA was quenched by adding DTT. All the above steps occurred on the filter. Samples were subsequently buffer exchanged into the digestion buffer (50 mM Tris, pH 7.8 containing Methionine) by centrifuging to remove any residual DTT and IAA. Trypsin digestion was performed on the filter for 1 hr at 37° C. using an enzyme to protein ratio of 1:20 (w/w). Small tryptic digest was collected by centrifuging and large tryptic digest was subjected to elastase digestion performed on filter for 30 min at 37° C. using an enzyme to protein ratio of 1:20 (w/w). The digestion mixture was collected by centrifuging and then quenched by adding 8 M GuHCl in 250 mM acetate buffer at pH 4.7.

The liquid chromatography-mass spectrometry (LC-MS) analysis was performed using an Agilent 1260 Infinity II high performance liquid chromatography (HPLC) system directly coupled with a Thermo Scientific Q-Exactive Mass Spectrometer.

The protein digests were separated by reversed phase using an Water Acquity UPLC peptide BEH C18 column (2.1×150 mm, 1.7 µm), with the column temperature maintained at 50° C. The mobile phase A consisted of 0.10% (v/v) formic acid (FA) in water, and the mobile phase B was 0.1% (v/v) FA in acetonitrile (ACN). Approximately 6.25 µg of the digested protein was injected to the column. A gradient (1 to 36% B over 78 min) was used to separate the peptides at a flow rate of 0.25 mL/min. The eluted peptides were monitored by MS.

For peptide identification and modification analysis, a data-dependent tandem MS (MS/MS) experiment was utilized. A full scan was acquired from 200 to 2000 m/z in the positive ion mode followed by 5 data-dependent MS/MS scans to identify the sequence of the peptide. The quantitation was based on mass spectrometry data of the selected ion monitoring using the equation below:

Equation 1.

$$\text{Modification \%} = \frac{A_{modified}}{A_{modified} + A_{unmodified}} \times 100$$

Where Modification % is the level of the modified peptides, $A_{modified}$ is the extracted ion chromatogram area of modified peptide, $A_{unmodified}$ is the extracted ion chromatogram area of unmodified peptide.

Reduced Capillary Electrophoresis-Sodium Dodecyl Sulfate (Reduced CE-SDS)

The reduced CE-SDS was performed on Beckman Coulter ProteomeLab PA800 PLUS CE system. The protein samples were diluted to 0.5 mg/mL with water and then reduced with β-mercaptoethanol (β-ME) in Beckman SDS sample buffer at 70° C. for 10 min (Beckman Coulter, Brea, CA). The reduced and denatured protein samples were electrokinetically injected (5 kV for 20 sec) into a bare fused silica capillary (50 µm ID×30.0 cm effective length), separated using SDS gel buffer (separation at 15 kV for 40 min), and detection was obtained using UV at 220 nm by a photodiode array detector.

Host Cell Protein (HCP) ELISA

A microtiter plate is coated with rabbit anti-HCP Immunoglobulin G (IgG) (Amgen, in-house antibody). After the plate is washed and blocked, the test samples, controls and HCP calibration standards are added to the plate and incubated. Unbound proteins are washed from the plate and pooled rabbit anti-HCP IgG-Biotin (Amgen, in-house antibody) is added to the plate and incubated. Following another wash, Streptavidin™ Horseradish Peroxidase conjugate (HRP-conjugate) (Amersham—GE; Buckinghamshire, UK) is added to the plate and incubated. The plate is washed a final time and the chromogenic substrate tetramethylbenzidine (TMB) (Kirkegaard and Perry Laboratories; Gaithersburg, MD) is added to plate. Color development is arrested with 1 M Phosphoric acid and the optical density is measured with a spectrophotometer.

DNA Method (qPCR)

Samples were prepared by digestion with Proteinase K followed by DNA extraction and isopropyl alcohol precipitation. Primers were designed to amplify a CHO-cell specific repetitive DNA sequence (referred to as Rep A), and a specific probe was designed to anneal between them. The probe is labeled with the fluorescent reporter dye FAM (6-carboxyfluorescein) at its 5' end and the quencher dye TAMRA (6-carboxytetramethylrhodamine) at its 3' end. When the annealed probe is intact, the fluorescence of the reporter dye is quenched by the proximity of the quencher dye. During the extension phase of each PCR cycle the Taq DNA polymerase cleaves the annealed probe, releasing the reporter dye from the probe resulting in an increase in fluorescence. This increase in fluorescence is directly proportional to the amount of amplified target DNA present in the reaction and is continually monitored throughout the PCR reaction by the real-time PCR instrument. Within the exponential phase of amplification, the quantity of product sequence is proportional to the starting quantity of DNA. A standard curve of known quantities of genomic DNA isolated from CHO cells is used to correlate the level of fluorescence to concentrations of genomic DNA in the original sample.

TABLE 11

Comparison of BCMA × CD3 BiTE(R)-HLE
CM process versus FB process using same
CHO cell line derived from DHFR deficient host

| Process Parameter | BCMA × CD3 BITE(R)-HLE FB Process | BCMA × CD3 BITE(R)-HLE CM Process |
|---|---|---|
| Cell Culture Metrics | | |
| 3 runs at 2 L for FB; 2 runs at 10 L and 1 run at 50 L for CM. Both absolute numbers and normalized to FB (in brackets) are provided | | |
| Production culture duration (days) | 12 [1] | 40 [3.39] |
| Final IVCD ($10^6$ cells-day/mL) | 85 [1] | 1673 [19.66] |
| Average HCCF productivity (g/L of bioreactor volume) | 0.92 [1] | 12.19 [13.24] |
| Average HCCF daily productivity (mg/L of bioreactor volume/day) | 78.0 [1] | 304.8 [3.91] |
| Product Quality Attributes | | |
| 3 capture eluates analyzed for FB (2 L); 2 capture eluates (days 19 and 40) analyzed for CM (50 L). Both absolute numbers and normalized average to FB average (in brackets) are provided | | |
| Acidic peaks in CEX-HPLC in capture eluate (%) | 7.6; 7.3; 8.7 [1] | 3.7; 4.3 [0.51] |
| Protein clips by rCE in capture eluate (%) | 6.0; 5.5; 5.5 [1] | 1.9; 2.0 [0.34] |
| CDR Asn352 deamidation by peptide mapping in capture eluate (%) | 2.2; 2.0; 2.1 [1] | 0.4; 0.6 [0.25] |
| CDR Asn355 deamidation by peptide mapping in capture eluate (%) | 6.2; 5.8; 6.1 [1] | 1.2; 1.6 [0.23] |
| Process-related Impurities | | |
| 3 capture eluates analyzed for FB (2 L); 2 capture eluates (days 19 and 40) analyzed for CM (50 L). Both absolute numbers and normalized average to FB average (in brackets) are provided | | |
| DNA by qPCR in capture eluate (pg/mg) | 1260.2; 1101.3; 1010.0 [1] | <12.4; <16.1 [<0.01] |
| Host cell protein in capture eluate (ppm) | 957; 1231; 452 [1] | 418; 144 [0.32] |

Example 8: Comparison of Fed Batch Vs. Continuous Manufacturing Mode for the Production of DLL3×CD3 BiTE®-HLE DLL3×CD3 BITE®-HLE Fed-Batch Process (FB)

The FB process was initiated by thawing a vial containing CHO cells expressing the DLL3×CD3 BiTE®-HLE. During scale-up, cells were resuspended in fresh selective growth medium at a targeted viable cell density (VCD). The culture volume was successively expanded in shake flasks or bioreactors to generate sufficient cell mass to ultimately inoculate a production fed-batch bioreactor (2 L scale).

Once cells were inoculated into the production bioreactor at a cell density of $1.0 \times 10^6$ cells/mL, the culture was fed a defined amount of proprietary chemically-defined feed medium on days 3, 6 and 8. Culture was maintained at pH 6.9, dissolved oxygen of 64 mm Hg and 36° C. constant. Cell density (CDV, Nova Biomedical, Waltham, MA), metabolites (NovaFlex, Nova Biomedical, Waltham, MA) and titer (HPLC analysis) mere measured throughout the culture duration. After 12 days of production, cell culture supernatant was purified with protein-A chromatography and the eluate analyzed for product quality attributes using size exclusion chromatography (SE-HPLC).

DLL3×CD3 BITE®-HLE Continuous Manufacturing Process (CM)

The CM process was initiated by thawing a vial containing CHO cells expressing the DLL3×CD3 BiTE®-HLE. During scale-up, cells were resuspended in fresh selective growth medium at a targeted viable cell density (VCD). The culture volume was successively expanded in shake flasks or bioreactors to generate sufficient cell mass to ultimately inoculate a perfusion production bioreactor (2 L scale).

Once cells were inoculated into the production bioreactor at $1.5 \ 10^6$ cells/mL, there was an initial cell growth phase for approximately 10 days to increase cell density and biomass to a set-point of 70 pF/cm ($40\text{-}60 \times 10^6$ cells/mL) as measured by a capacitance probe (Hamilton Bonaduz AG, Switzerland). Production bioreactor was controlled at pH 6.9, dissolved oxygen of 64 mm Hg and 36° C. Perfusion culture was initiated on approximately day 3 of the cell growth phase using an alternating tangential flow (ATF) filtration system (Refine Technologies, Hanover, NJ) with polyethersulfone 0.2-µm filters (GE Healthcare, Pittsburgh, PA), and a proprietary chemically-defined perfusion medium at a 0.5 VVD perfusion rate. Perfusion rate was increased gradually from 0.5 VVD on day 3 to 2 VVD on day 10. Once biomass set-point was reached on approximately day 10, collection of HCCF started (i.e., cell-free permeate containing DLL3×CD3 BiTE®-HLE), and perfusion culture was continued for 13 additional days by feeding at 2 VVD perfusion rate (steady-state CSPR of 0.03-0.05 nL/cell-day), and bleeding extra cells to maintain the biomass set-point. Cell density (CDV, Nova Biomedical, Waltham, MA), metabolites (NovaFlex, Nova Biomedical, Waltham, MA) and permeate titer (HPLC analysis) were measured throughout the culture duration. Permeate samples from days 10 to day 23 were purified with protein-A chromatography and the eluate analyzed for product quality attributes using size exclusion chromatography (SE-HPLC).

Figure 14:
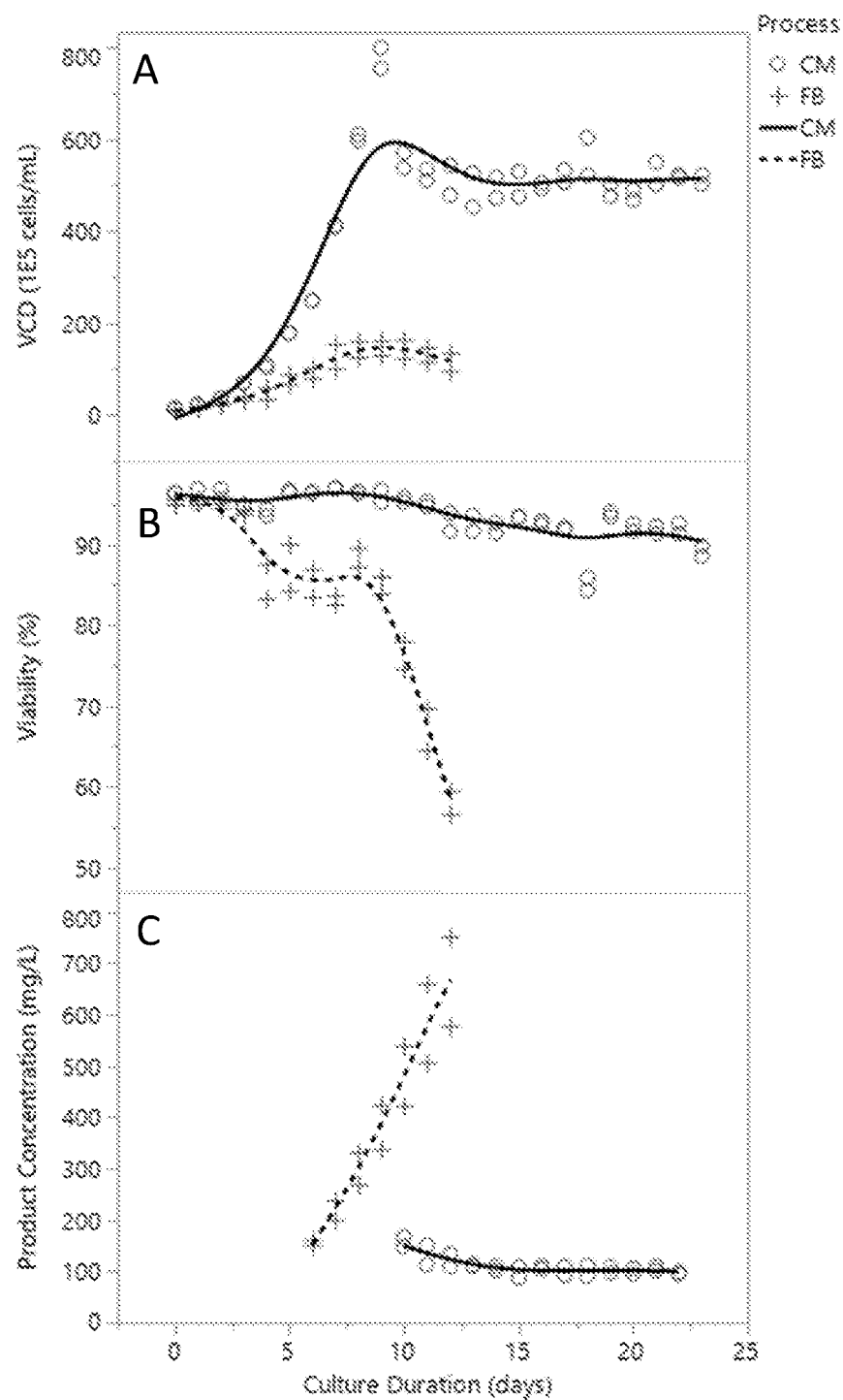
FIG. 14 shows the comparison of DLL3×CD3 BiTE®-HLE FB and CM processes. (A) viable cell density as a function of culture time; (B) viability as a function of culture time; (C) product concentration as a function of culture time.

Cell culture performance (FIG. 14, Table 12) and product quality attributes (Table 12) of the DLL3×CD3 BITE®-HLE CM process were improved as compared to the DLL3×CD3 BITE®-HLE FB process using the same CHO cell line. The normalized values represented in Table 12 correspond to the average of all the absolute numbers divided by the average of all the absolute numbers in FB; for FB this correspond to 1; for CM is one number corresponding to the ratio described. Higher volumetric productivity with less physical product degradation or aggregation was demonstrated with the DLL3×CD3 BITE®-HLE upstream CM process. For DLL3×CD3 BITE®-HLE CM and other BiTE® CM processes, the ATF filtration harvest process per se is beneficial in producing permeate HCCF that has both lower concentration and lower HMW species as compared to the cell culture fluid retained in the bioreactor (FIG. 15).

Product Quality Analytical Methods
Size Exclusion-High Performance Liquid Chromatography (SE-HPLC)

SE-HPLC was performed using a Waters BEH200 size exclusion column (4.6×150 mm, 1.7 µm) and Waters UHPLC system. The protein samples were injected neat and separated isocratically using a phosphate buffer containing NaCl salt (mobile phase was 100 mM sodium phosphate, 250 mM NaCl at pH 6.8) at a flow rate of 0.4 mL/min, and the eluent was monitored by UV absorbance at 220 nm. Approximately 10 µg of sample was loaded.

Reduced Capillary Electrophoresis-Sodium Dodecyl Sulfate (Reduced CE-SDS)

The reduced CE-SDS was performed on Beckman Coulter ProteomeLab PA800 PLUS CE system. The protein samples were diluted to 1.0 mg/mL with formulation buffer and then reduced with β-mercaptoethanol (β-ME) in Beckman SDS sample buffer at 70° C. for 10 min (Beckman Coulter, Brea, CA) for a final concentration of 0.48 mg/mL. The reduced and denatured protein samples were electrokinetically injected (10 kV for 30 sec) into a bare fused silica capillary (50 μm ID×20.0 cm effective length), separated using SDS gel buffer (separation at 15 kV for 40 min), and detection was obtained using UV at 220 nm by a photodiode array detector.

TABLE 12

Comparison of DLL3 × CD3 BiTE(R)-HLE CM process versus FB process using same CHO cell line derived from DHFR deficient host

| Process Parameter | DLL3 × CD3 BITE(R)-HLE FB Process | DLL3 × CD3 BITE(R)-HLE CM Process |
|---|---|---|
| Cell Culture Metrics | | |
| 2 runs at 2 L for FB; 2 runs at 2 L for CM. Both absolute numbers and normalized to FB (in brackets) are provided. The values for a 38 day process were calculated based on the trends from the experimental 23 day process tested | | |
| Production culture duration (days) | 12 [1] | 23 [1.9] 38 [3.2] |
| Final IVCD ($10^6$ cells-day/mL) | 105.56 [1] | 939.22 [8.9] 1604.50 [15.2] |
| Average HCCF productivity (g/L of bioreactor volume) | 0.63 [1] | 2.75 [4.3] 5.50 [8.7] |
| Average HCCF daily productivity (mg/L of bioreactor volume/day) | 52.66 [1] | 119.49 [2.3] 144.65 [2.9] |
| Product Quality Attributes | | |
| 2 capture eluates analyzed for FB (2 L); 9-13 capture eluates (days 10 to day 23 from 2 runs) analyzed for CM. Both absolute numbers and normalized average to FB average (in brackets) are provided | | |
| Protein clips by rCE in capture eluate (%) | 3.7; 3.7 [1] | 2.4; 1.0; 2.7; 1.1; 2.6; 1.3; 2.7; 2.6; 2.4 [0.57] |
| HMW by SEC in capture eluate (%) | 33.4; 32.6 [1] | 26.5; 27.5; 26.0; 24.4; 23.1; 20.3; 20.2; 29.5; 24.3; 27.4; 23.7; 25.2; 19.9 [0.74] |

---

The invention claimed is:

1. A continuous upstream manufacturing process for the production of a bispecific antibody product comprising at least a first and a second binding domain, wherein the first binding domain binds to a different target than the second binding domain, wherein the bispecific antibody product is a non-full length bispecific antibody construct, and wherein the bispecific antibody product is a bispecific T-cell engager antibody construct, the process comprising the steps, in order, of:

(i) providing a liquid cell culture medium comprising at least one mammalian cell culture in a perfusion bioreactor, wherein the mammalian cell culture is expressing the bispecific antibody product, and wherein the cells have a concentration of at least 0.4×10⁶ cells/mL at inoculation in the perfusion bioreactor, (ii) growing the mammalian cell culture by applying a perfusion rate (D) to exchange the liquid cell culture medium in a continuous manner, without removing the cells from bioreactor, wherein the perfusion rate initially corresponds to at least 0.4 vessel volume per day (vvd) and is then increased continuously, gradually or incrementally to at least 2 vvd reaching a biomass set-point, wherein the biomass set-point equals to a viable cell density (VCD) of at least 35×10⁶ cells/mL, (iii) maintaining perfusion culture by applying the perfusion rate (D) to continuously or incrementally exchange the liquid cell culture medium, wherein the perfusion rate in step (iii) is in the range from 2 to 6.4 vvd, and wherein the perfusion rate (D) is a cell-specific perfusion rate (CSPR) in the range of 0.01 to 0.15 nL per cell per day (nL/cell/day), and (iv) bleeding extra cells from the bioreactor to maintain the biomass set-point, wherein the bispecific antibody product concentration in the bioreactor is kept below 0.3 g/L by continuously harvesting the bispecific antibody product from the liquid cell culture medium throughout steps (ii) to (iv).

2. The process according to claim 1, wherein in step (i) the cells have a concentration of at least 1×10⁶ cells/mL at inoculation in the bioreactor.

3. The process according to claim 1, wherein in step (ii) the biomass set-point equals to a VCD of at least 71×10⁶ cells/mL.

4. The process according to claim 1, wherein in step (ii) the growing of the cell culture takes place for at least 4 days.

5. The process according to claim 1, wherein in step (ii) the initial or increased perfusion rate (D) is in the range from 0.4 to 7 vvd.

6. The process according to claim 1, wherein in step (iii) the perfusion rate (D) is 2.01 vvd.

7. The process according to claim 1, wherein in step (iii) the perfusion rate (D) is a cell-specific perfusion rate (CSPR) in the range of 0.015 to 0.035 nL/cell/day or in the range of 0.051 to 0.1 nL/cell/day.

8. The process according to claim 1, wherein in step (iv) the bispecific antibody product concentration is kept below 0.12 g/L.

9. The process according to claim 1, wherein the residence time of the bispecific antibody product in the bioreactor before harvest in step (iv) is at most 2 days.

10. The process according to claim 1, wherein the percentile monomer content of the isolated bispecific antibody is at least 80%.

11. The process according to claim 1, wherein the first and/or second binding domain binds to a target and/or an effector cell, and wherein the first and the second binding domain of the bispecific antibody construct each comprise two VH and VL domains.

12. The process according to claim 1, wherein the bispecific antibody construct comprises a half-life extending third domain comprising a hinge-CH2-CH3-linker-hinge-CH2-CH3 in an amino to carboxyl order.

13. The process according to claim 1, wherein the first binding domain of the bispecific antibody product binds to at least one target cell surface antigen selected from the group consisting of CD19, CD33, EGFRvIII, MSLN, CDH19, FLT3, DLL3, CDH3, BCMA and PSMA.

14. The process according to claim 1, wherein the second binding domain of the bispecific antibody product binds to CD3.

15. The process according to claim 1, wherein the first binding domain comprises a VH region comprising CDR-H1, CDR-H2 and CDR-H3 and a VL region comprising CDR-L1, CDR-L2 and CDR-L3 selected from the group consisting of:

(a) CDR-H1 as depicted in SEQ ID NO: 1, CDR-H2 as depicted in SEQ ID NO: 2, CDR-H3 as depicted in SEQ ID NO: 3, CDR-L1 as depicted in SEQ ID NO: 4, CDR-L2 as depicted in SEQ ID NO: 5 and CDR-L3 as depicted in SEQ ID NO: 6, (b) CDR-H1 as depicted in SEQ ID NO: 29, CDR-H2 as depicted in SEQ ID NO: 30, CDR-H3 as depicted in SEQ ID NO: 31, CDR-L1 as depicted in SEQ ID NO: 34, CDR-L2 as depicted in SEQ ID NO: 35 and CDR-L3 as depicted in SEQ ID NO: 36, (c) CDR-H1 as depicted in SEQ ID NO: 42, CDR-H2 as depicted in SEQ ID NO: 43, CDR-H3 as depicted in SEQ ID NO: 44, CDR-L1 as depicted in SEQ ID NO: 45, CDR-L2 as depicted in SEQ ID NO: 46 and CDR-L3 as depicted in SEQ ID NO: 47, (d) CDR-H1 as depicted in SEQ ID NO: 53, CDR-H2 as depicted in SEQ ID NO: 54, CDR-H3 as depicted in SEQ ID NO: 55, CDR-L1 as depicted in SEQ ID NO: 56, CDR-L2 as depicted in SEQ ID NO: 57 and CDR-L3 as depicted in SEQ ID NO: 58, (e) CDR-H1 as depicted in SEQ ID NO: 65, CDR-H2 as depicted in SEQ ID NO: 66, CDR-H3 as depicted in SEQ ID NO: 67, CDR-L1 as depicted in SEQ ID NO: 68, CDR-L2 as depicted in SEQ ID NO: 69 and CDR-L3 as depicted in SEQ ID NO: 70, (f) CDR-H1 as depicted in SEQ ID NO: 83, CDR-H2 as depicted in SEQ ID NO: 84, CDR-H3 as depicted in SEQ ID NO: 85, CDR-L1 as depicted in SEQ ID NO: 86, CDR-L2 as depicted in SEQ ID NO: 87 and CDR-L3 as depicted in SEQ ID NO: 88, (g) CDR-H1 as depicted in SEQ ID NO: 94, CDR-H2 as depicted in SEQ ID NO: 95, CDR-H3 as depicted in SEQ ID NO: 96, CDR-L1 as depicted in SEQ ID NO: 97, CDR-L2 as depicted in SEQ ID NO: 98 and CDR-L3 as depicted in SEQ ID NO: 99, (h) CDR-H1 as depicted in SEQ ID NO: 105, CDR-H2 as depicted in SEQ ID NO: 106, CDR-H3 as depicted in SEQ ID NO: 107, CDR-L1 as depicted in SEQ ID NO: 109, CDR-L2 as depicted in SEQ ID NO: 110 and CDR-L3 as depicted in SEQ ID NO: 111, (i) CDR-H1 as depicted in SEQ ID NO: 115, CDR-H2 as depicted in SEQ ID NO: 116, CDR-H3 as depicted in SEQ ID NO: 117, CDR-L1 as depicted in SEQ ID NO: 118, CDR-L2 as depicted in SEQ ID NO: 119 and CDR-L3 as depicted in SEQ ID NO: 120, (j) CDR-H1 as depicted in SEQ ID NO: 126, CDR-H2 as depicted in SEQ ID NO: 127, CDR-H3 as depicted in SEQ ID NO: 128, CDR-L1 as depicted in SEQ ID NO: 129, CDR-L2 as depicted in SEQ ID NO: 130 and CDR-L3 as depicted in SEQ ID NO: 131, (k) CDR-H1 as depicted in SEQ ID NO: 137, CDR-H2 as depicted in SEQ ID NO: 138, CDR-H3 as depicted in SEQ ID NO: 139, CDR-L1 as depicted in SEQ ID NO: 140, CDR-L2 as depicted in SEQ ID NO: 141 and CDR-L3 as depicted in SEQ ID NO: 142, (l) CDR-H1 as depicted in SEQ ID NO: 152, CDR-H2 as depicted in SEQ ID NO: 153, CDR-H3 as depicted in SEQ ID NO: 154, CDR-L1 as depicted in SEQ ID NO: 155, CDR-L2 as depicted in SEQ ID NO: 156 and CDR-L3 as depicted in SEQ ID NO: 157, and (m) CDR-H1 as depicted in SEQ ID NO: 167, CDR-H2 as depicted in SEQ ID NO: 168, CDR-H3 as depicted in SEQ ID NO: 169, CDR-L1 as depicted in SEQ ID NO: 170, CDR-L2 as depicted in SEQ ID NO: 171 and CDR-L3 as depicted in SEQ ID NO: 172.

16. The process according to claim 1, wherein the harvested bispecific antibody product is comprised in harvested cell culture fluid (HCCF).

17. The process according to claim 1, wherein the HCCF is collected at room temperature in 1, 2, 3, 4, 5, 6, 7, 8, 9, 10, 11, 12, 24, 36, 48, 72, 96, 120, or 144 hour increments or continuously and passed to downstream steps for further processing the bispecific antibody product.

18. The process according to claim 17, wherein the downstream steps comprise capture chromatography, viral inactivation, and/or polishing steps.

19. The process according to claim 1, wherein the perfusion culture is continuously running for at least 7 days by feeding at the defined cell-specific perfusion rate and bleeding extra cells from the bioreactor to maintain the biomass set-point.

20. The process according to claim 1, wherein the bispecific antibody product is a single chain antibody construct.

21. The process according to claim 1, wherein the bispecific antibody product comprises in an amino to carboxyl order:
(a) the first domain;
(b) a peptide linker having an amino acid sequence selected from the group consisting of SEQ ID Nos: 187-189;
(c) the second domain;
(d) a peptide linker having an amino acid sequence selected from the group consisting of SEQ ID NO: 187, 188, 189, 195, 196, 197 and 198;
(e) the first polypeptide monomer of a third domain;
(f) a peptide linker having an amino acid sequence selected from the group consisting of SEQ ID Nos: 191, 192, 193 and 194; and
(g) the second polypeptide monomer of the first domain.

22. The process according to claim 1, wherein the first binding domain of the bispecific antibody product binds to at least one tumor antigen.

23. The process according to claim 1, wherein the biomass set-point equals to a viable cell density (VCD) of at least $65 \times 10^6$ cells/mL.

* * * * *

UNITED STATES PATENT AND TRADEMARK OFFICE
CERTIFICATE OF CORRECTION

PATENT NO. : 12,227,571 B2
APPLICATION NO. : 16/770441
DATED : February 18, 2025
INVENTOR(S) : Chetan Goudar et al.

Page 1 of 1

It is certified that error appears in the above-identified patent and that said Letters Patent is hereby corrected as shown below:

In the Claims

At Column 373, Line 15, "and/or" should be -- or --.

Signed and Sealed this
Second Day of September, 2025

Coke Morgan Stewart
*Acting Director of the United States Patent and Trademark Office*